United States Patent
Lear

(10) Patent No.: US 10,327,762 B2
(45) Date of Patent: Jun. 25, 2019

(54) SUTURE LOCKS

(71) Applicant: JULVIA Technologies, Inc., Corvallis, OR (US)

(72) Inventor: William Lear, Corvallis, OR (US)

(73) Assignee: SUTUREGARD Medical, Inc., Portland, OR (US)

(*) Notice: Subject to any disclaimer, the term of this patent is extended or adjusted under 35 U.S.C. 154(b) by 43 days.

(21) Appl. No.: 14/990,715

(22) Filed: Jan. 7, 2016

(65) Prior Publication Data

US 2017/0014124 A1    Jan. 19, 2017

Related U.S. Application Data

(60) Provisional application No. 62/193,764, filed on Jul. 17, 2015, provisional application No. 62/221,410, filed on Sep. 21, 2015.

(51) Int. Cl.
  *A61B 17/04* (2006.01)

(52) U.S. Cl.
  CPC ................. *A61B 17/0487* (2013.01)

(58) Field of Classification Search
  CPC ............ A61B 17/06; A61B 2017/0464; A61B 2017/045; A61B 2017/0454; A61B 17/0401–17/0466; A61B 17/122–17/1227; A61B 17/0487–2017/049; A61B 17/08–2017/086; Y10T 24/44–24/44991
  See application file for complete search history.

(56) References Cited

U.S. PATENT DOCUMENTS

| | | | | |
|---|---|---|---|---|
| 784,018 | A * | 2/1905 | Witherbee | A61B 17/04 606/233 |
| 815,264 | A * | 3/1906 | Chambers | A61B 17/0466 606/233 |
| 3,705,586 | A * | 12/1972 | Sarracino | A61B 17/122 24/543 |
| 3,931,821 | A * | 1/1976 | Kletschka | A61B 17/0466 24/129 R |
| 3,934,592 | A * | 1/1976 | Wolvek | A61B 17/0466 606/233 |
| 4,291,698 | A | 9/1981 | Fuchs et al. | |
| D277,785 | S | 2/1985 | Green | |

(Continued)

OTHER PUBLICATIONS

B. Braun Sutures, Product Brochure—Ventrofil® [online] 4 pages. Retrieved on Apr. 7, 2016. <http://www.bbraun.com/cps/rde/xchg/bbraun-com/hs.xsl/products.html?prid=PRID00000789>.

(Continued)

*Primary Examiner* — Elizabeth Houston
*Assistant Examiner* — Charles M Wei
(74) *Attorney, Agent, or Firm* — Wei & Sleman LLP

(57) ABSTRACT

A suture securing device includes a body connected to an arm by a hinge and is useable to secure a suture without requiring the tying of a knot. The body includes a bottom surface that contacts a patient's skin when in use, an eversion recess formed in the bottom surface, and a first gripping surface. The arm is connected to the body by the hinge and includes a second gripping surface that contacts at least a portion of the first gripping surface when the hinge is in the closed configuration. The device may also include an engagement structure configured to secure the arm to the body in the closed configuration.

22 Claims, 93 Drawing Sheets

(56) References Cited

U.S. PATENT DOCUMENTS

| | | | |
|---|---|---|---|
| 4,519,392 A * | 5/1985 | Lingua | A61B 17/11 606/151 |
| D283,642 S | 4/1986 | Gravener et al. | |
| 5,078,731 A | 1/1992 | Hayhurst | |
| 5,160,339 A | 11/1992 | Chen et al. | |
| 5,234,449 A * | 8/1993 | Bruker | A61B 17/122 227/902 |
| 5,282,832 A | 2/1994 | Toso et al. | |
| 5,330,442 A * | 7/1994 | Green | A61B 17/0487 606/151 |
| 5,363,539 A * | 11/1994 | Tisol | F16L 3/2235 24/339 |
| 5,389,082 A * | 2/1995 | Baugues | A61M 5/1418 128/DIG. 26 |
| 5,409,499 A | 4/1995 | Yi | |
| 5,474,572 A * | 12/1995 | Hayhurst | A61B 17/0487 606/151 |
| 5,645,553 A | 7/1997 | Kolesa et al. | |
| 5,810,853 A * | 9/1998 | Yoon | A61B 17/0487 606/151 |
| 6,015,428 A | 1/2000 | Pagedas | |
| 6,200,329 B1 | 3/2001 | Fung et al. | |
| 6,434,803 B1 * | 8/2002 | Spong | A47G 25/145 24/30.5 P |
| 6,471,715 B1 | 10/2002 | Weiss | |
| 6,508,829 B1 | 1/2003 | Levinson et al. | |
| 7,001,412 B2 * | 2/2006 | Gallagher | A61B 17/0487 606/151 |
| 7,300,541 B2 | 11/2007 | Crombie et al. | |
| 7,316,696 B2 | 1/2008 | Wilson, Jr. et al. | |
| 7,326,223 B2 | 2/2008 | Wilson, Jr. | |
| 8,353,919 B2 | 1/2013 | Lee et al. | |
| 8,465,504 B2 * | 6/2013 | Mohamed | A61B 17/0469 606/144 |
| 8,740,937 B2 | 6/2014 | Surti | |
| 8,764,778 B2 | 7/2014 | Yeretsian | |
| 9,078,645 B2 | 7/2015 | Conklin et al. | |
| 9,079,006 B1 | 7/2015 | Ovcharchyn et al. | |
| 9,084,596 B2 | 7/2015 | Stanley et al. | |
| 9,107,655 B2 | 8/2015 | Stanley | |
| 2003/0229377 A1 | 12/2003 | Tong | |
| 2007/0276417 A1 | 11/2007 | Mendes, Jr. et al. | |
| 2008/0033487 A1 * | 2/2008 | Schwartz | A61B 17/0401 606/232 |
| 2010/0256676 A1 | 10/2010 | Hay et al. | |
| 2012/0158054 A1 * | 6/2012 | Stupak | A61B 17/0057 606/233 |
| 2012/0184991 A1 | 7/2012 | Paraschac et al. | |
| 2013/0079820 A1 | 3/2013 | Stanley | |
| 2013/0296930 A1 * | 11/2013 | Belson | A61B 17/08 606/216 |
| 2014/0018829 A1 | 1/2014 | Patani | |
| 2014/0243862 A1 | 8/2014 | Bagaoisan et al. | |
| 2014/0277124 A1 | 9/2014 | Rosenthal et al. | |
| 2015/0240852 A1 | 8/2015 | Eaves, III | |
| 2015/0250470 A1 | 9/2015 | Vargas | |
| 2016/0106415 A1 * | 4/2016 | Mohamed | A61B 17/0469 606/144 |
| 2017/0071596 A1 * | 3/2017 | Lear | A61B 17/0466 |

OTHER PUBLICATIONS

Product Tutorial—TopClosure®. [online] 3 pages. Retrieved on Apr. 11, 2016. <http://www.topclosure.com/productTutorial.aspx>.

* cited by examiner

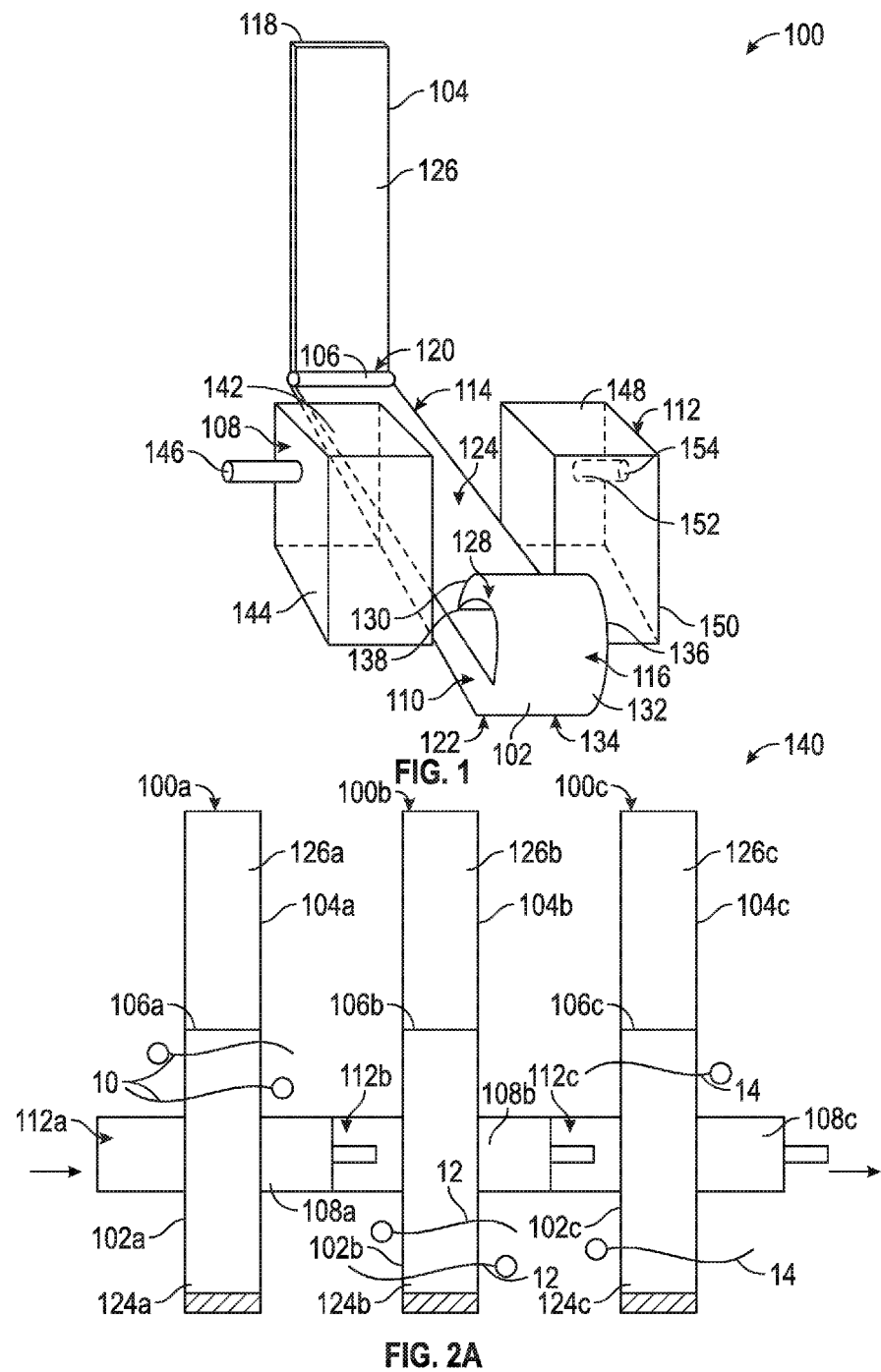

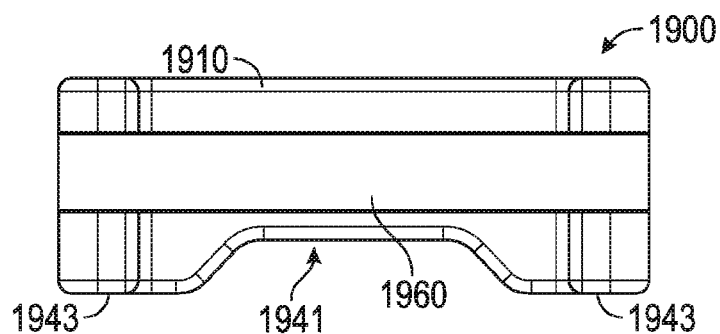
FIG. 19E
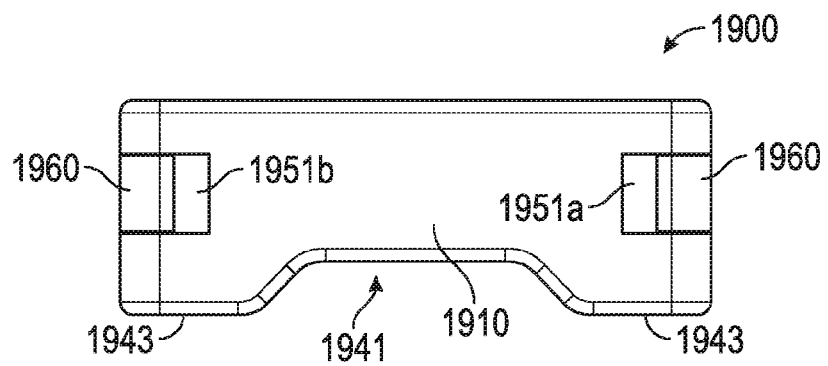
FIG. 19F
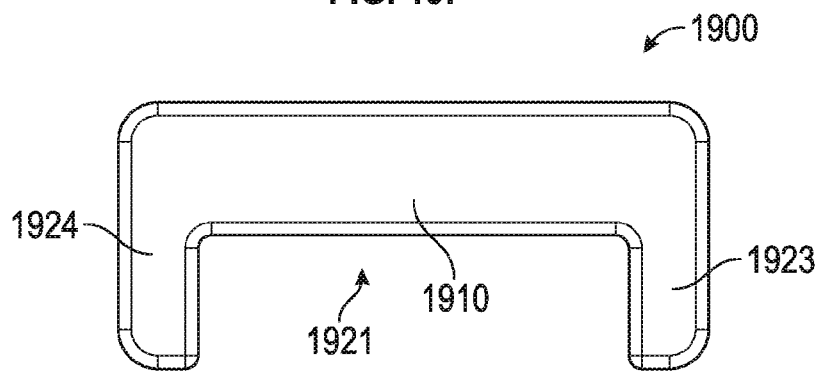
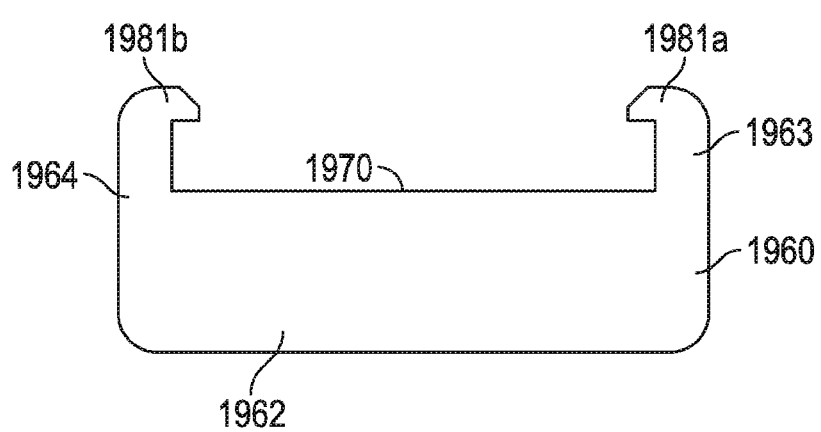
FIG. 19G

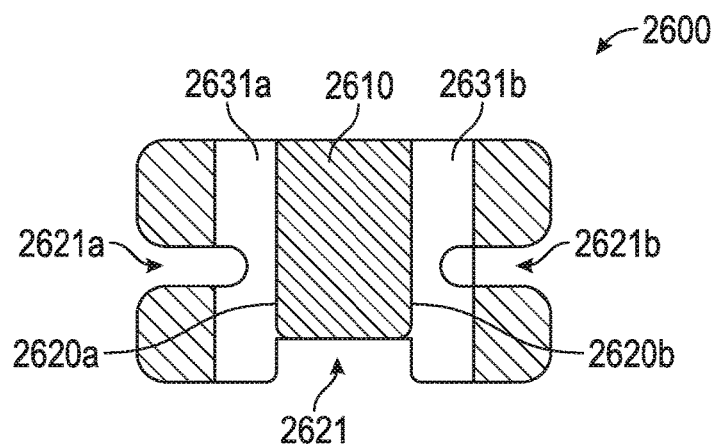
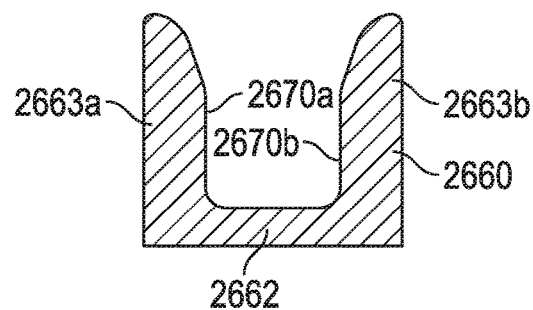
FIG. 26C
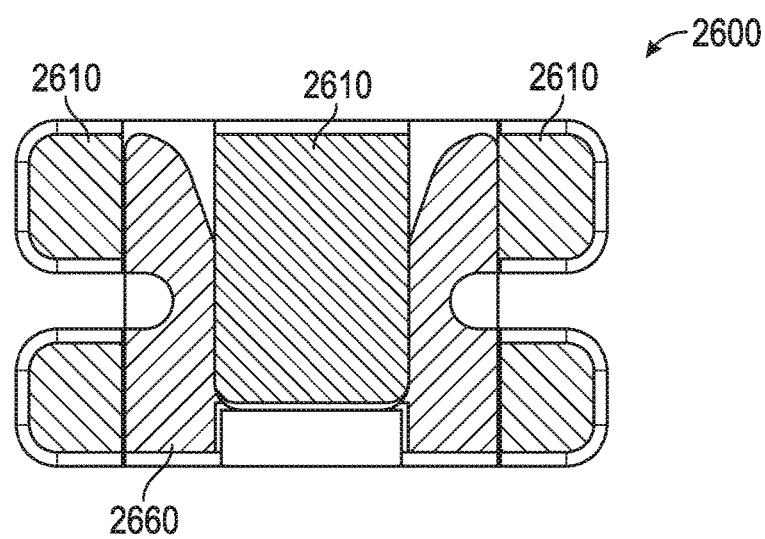
FIG. 26D

SUTURE LOCKS

INCORPORATION BY REFERENCE TO ANY PRIORITY APPLICATIONS

This application claims priority to U.S. Provisional Application No. 62/221,410, filed Sep. 21, 2015, and U.S. Provisional Application No. 62/193,764, filed Jul. 17, 2015, each of which is incorporated by reference in its entirety. Any and all applications for which a foreign or domestic priority claim is identified in the Application Data Sheet as filed with the present application are hereby incorporated by reference under 37 C.F.R. § 1.57.

BACKGROUND

Field of the Disclosure

The present disclosure relates generally to devices, systems, and methods for securing sutures. In particular, the suture securing devices, systems, and methods described herein may be used, in some embodiments, to secure a suture without requiring the tying of a knot and/or to elevate an external portion of a suture above a patient's skin, among other purposes.

Description of Related Art

Sutures are stitches used to close open wounds and/or surgical incisions of a patient. A medical practitioner generally uses a needle with an attached thread to substantially sew two adjacent sections of skin together to close the wound or incision. Surgical knots are often used to secure the sutures and ensure proper healing. However, effective surgical knots can be difficult to tie, thereby potentially allowing reopening of the wound or incision. Further, the patient may be at risk of infection if the wound or incision reopens. In another example, sutures and surgical knots contacting the skin can be inflammatory and/or become "ingrown" and actually impede healing of the wound or incision. Further, eversion of the wound edges is a desirable feature of a wound closure. However, current technologies require considerable operator skill to achieve wound eversion.

SUMMARY OF CERTAIN INVENTIVE ASPECTS

Disclosed herein are suture securing devices, systems, and methods that may be used to secure a suture without requiring the tying of a knot and/or to elevate an external portion of a suture above a patient's skin.

In a first aspect, a suture securing device is disclosed. The suture securing device includes a base having a bottom surface, at least a portion of the bottom surface configured to contact a patient's skin when in use, an eversion recess formed in the bottom surface, and a top surface opposite the bottom surface. The suture securing device also includes an arm connected to the base by a hinge. The hinge may have an open configuration and a closed configuration. In the closed configuration the arm may be folded on top of the base. The arm may have a contacting surface that contacts at least a portion of the top surface of the base when the hinge is in the closed configuration. The suture securing device may also include an engagement structure for securing the arm to the base when the hinge is in the closed configuration. In some embodiments, when the hinge is in the closed configuration external portions of a thread of a mattress suture are secured between the top surface of the base and the contacting surface of the arm.

The base may comprise an elongate shape configured to extend across a wound, and the mattress suture may be a horizontal mattress suture. In some embodiments, when the hinge is in the closed configuration, a first external portion of the horizontal mattress suture is secured between the base and the arm on a first side of the eversion recess and a second portion of the horizontal mattress suture is secured between the base and the arm on a second side of the eversion recess. In some embodiments, the mattress sutures may be a vertical mattress suture. The base may further include a bulge extending from the top surface. The arm may further include two ridges extending substantially in parallel from the contacting surface. In some embodiments, when the hinge is in the closed configuration the bulge is received between the two ridges.

The suture securing device may also include at least one nub extending from a top surface of the ridge, and at least one recess formed in the contacting surface. The at least one recess may be configured to receive the at least one nub in the closed configuration. The at least one nub may include three nubs, and the at least one recess may include three recesses. One or more notches may be formed in the bulge.

In some embodiments, the base further includes two tracks extending from top surface on opposite sides of the bulge. In some embodiments, the device also include a first tab extending outwardly from a first end of the base and a second tab extending outwardly from a second end of the base, the second end opposite the first end, and wherein each of the first tab and the second tab include a hole extending therethrough. In some embodiments, one of the first tab or the second tab includes a male adapter extending therefrom, and the other of the first tab or the second tab includes a female adapter extending therefrom. In some embodiments, the engagement structure comprises a protrusion formed at a free end of the arm and a corresponding opening formed in the body, the recess positioned on the body such that, in the closed configuration, the protrusion extends into the opening. In some embodiments, the hinge comprises a living hinge. In some embodiments, one or more holes extend laterally through the bulge. In use, the suture may be threaded through the hole to help position the device.

In a second aspect, another suture securing device is disclosed. The suture securing device includes a body having a bottom surface, at least a portion of the bottom surface configured to contact a patient's skin when in use, and an eversion recess formed in the bottom surface, and a first gripping surface. In some embodiments, the first gripping surface is oriented substantially perpendicular to the bottom surface. An arm is connected to the body by a hinge having an open configuration and a closed configuration. The arm includes a second gripping surface with at least a portion of the second gripping surface configured to contact at least a portion of the first gripping surface when the hinge is in the closed configuration. The suture securing device may also include an engagement structure configured to secure the arm to the body in the closed configuration. When the hinge is in the closed configuration, external portions of a thread of a simple interrupted suture are secured between the first gripping surface and the second gripping surface.

In a third aspect, a suture securing device is disclosed. The suture securing device includes a first piece having a bottom surface configured to contact a patient's skin when in use, a top surface opposite the bottom surface, and a hole extending therethrough. The suture securing device also include a second piece connected to the first piece by a hinge, the hinge having an open configuration and a closed configuration. In the closed configuration the second piece is folded on top of the first piece. The second piece includes a contacting surface that contacts at least a portion of the top surface of the first piece when the hinge is in the closed configuration. In some embodiments, when the hinge is in the closed configuration, an external portion of a thread of a subcutaneous suture is secured between the top surface of the first piece and the contacting surface of the second piece. In some embodiments, each of the first piece and the second piece are substantially circular. In some embodiments, a diameter of the first piece is larger than a diameter of the second piece. In some embodiments, the first piece further comprises an outer ring and an inner ring extending from the top surface, the second piece further comprise an outer ring and an inner ring extending from the top surface, and, in the closed configuration, the outer and inner rings of the first piece mate with the outer and inner rings of the second piece. In some embodiments, further comprises one or more tabs extending outwardly from first piece.

In some embodiments, the suture securing device may include one or more arms attached to the body by one or more hinges. In some embodiments, the hinges may be omitted. In these embodiments, the arm (or arms) is not attached to the body, and may be described a clip (or clip) that is insertable into the body. The arm(s) and/or clip(s) may engage with one or more sides of the body, including the top, bottom, front, back, left, right or bottom sides.

The suture securing devices and systems described throughout this disclosure are useable to secure a suture without requiring the tying of a knot. In some embodiments the suture is secured through friction, bending of the suture around features of a suture securing device, and/or interference fits with a suture securing device. Additionally, these devices may eliminate or reduce the likelihood that a suture will become ingrown. In some embodiments, this is accomplished by eliminating or reducing the portion of the suture that contacts the surface of the patient's skin. In some embodiments, the suture, when secured by a suture securing device as described herein, may be left in place for longer than traditional knot-tied sutures. For example, a suture may remain in place for up to six, or more, weeks.

The suture securing device may be used with any type of suturing technique, including, for example, simple interrupted sutures, horizontal or vertical mattress sutures, and subcutaneous sutures. In some instances, multiple suture securing devices may be used in conjunction with multiple sutures to close a wound or incision.

BRIEF DESCRIPTION OF THE DRAWINGS

The features and advantages of the suture securing devices, systems, and methods described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. The drawings may not be drawn to scale.

FIG. 1 is an isometric view of an embodiment of a suture securing device.

FIG. 2A is a top plan view of three of the suture securing devices shown in FIG. 1 connected to form an interconnected chain.

FIGS. 12A and 12B are perspective views of the first embodiment of the suture securing device in an open configuration and a closed configuration, respectively.

FIGS. 12K through 12P show front, back, top, bottom, and first and second side views of the first embodiment of the suture securing device in the closed configuration, respectively.

FIGS. 13A and 13B are perspective views of the second embodiment of the suture securing device in an open configuration and a closed configuration, respectively.

FIGS. 13K through 13P show front, back, top, bottom, and first and second side views of the second embodiment of the suture securing device in the closed configuration, respectively.

FIGS. 14A and 14B are perspective views of the third embodiment of the suture securing device in an open configuration and a closed configuration, respectively.

FIGS. 14K through 14P show front, back, top, bottom, and first and second side views of the third embodiment of the suture securing device in the closed configuration, respectively.

FIGS. 15A and 15B are perspective views of the fourth embodiment of the suture securing device in an open configuration and a closed configuration, respectively.

FIGS. 15K through 15P show front, back, top, bottom, and first and second side views of the fourth embodiment of the suture securing device in the closed configuration, respectively.

FIGS. 16A and 16B are perspective views of the fifth embodiment of the suture securing device in an open configuration and a closed configuration, respectively.

FIGS. 16K through 16P show front, back, top, bottom, and first and second side views of the fifth embodiment of the suture securing device in the closed configuration, respectively.

FIGS. 17A and 17B are perspective views of the sixth embodiment of the suture securing device in an open configuration and a closed configuration, respectively.

FIGS. 17K through 17P show front, back, top, bottom, and first and second side views of the fifth embodiment of the suture securing device in the closed configuration, respectively.

FIGS. 18A and 18B are perspective views of the seventh embodiment of the suture securing device in an open configuration and a closed configuration, respectively.

FIGS. 18K through 18P show front, back, top, bottom, and first and second side views of the seventh embodiment of the suture securing device in the closed configuration, respectively.

FIGS. 19A and 19B are perspective views of the eighth embodiment of the suture securing device in an open configuration and a closed configuration, respectively.

FIGS. 19E through 19J show front, back, top, bottom, and first and second side views of the eighth embodiment of the suture securing device in the open configuration, respectively.

FIGS. 19K through 19P show front, back, top, bottom, and first and second side views of the eighth embodiment of the suture securing device in the closed configuration, respectively.

FIGS. 20A and 20B are perspective views of the ninth embodiment of the suture securing device in an open configuration and a closed configuration, respectively.

FIGS. 20K through 20P show front, back, top, bottom, and first and second side views of the ninth embodiment of the suture securing device in the closed configuration, respectively.

FIGS. 21A and 21B are perspective views of the tenth embodiment of the suture securing device in an open configuration and a closed configuration, respectively.

FIGS. 21K through 21P show front, back, top, bottom, and first and second side views of the tenth embodiment of the suture securing device in the closed configuration, respectively.

FIGS. 22A and 22B show perspective views the eleventh embodiment of the suture securing device in an open and closed configuration, respectively.

FIGS. 22C and 22B show perspective views the eleventh embodiment of the suture securing device in use with a simple interrupted suture, in the open and closed configuration, respectively.

FIGS. 26A-D illustrate another embodiment of a suture securing device configured for use with a simple interrupted suture. The suture securing device includes a clip that is insertable into a body. The body surrounds the clip. FIGS. 26A and 26B are perspective views of the suture securing device in an open configuration and a closed configuration, respectively. FIGS. 26C and 26D are cross-sectional views of the suture securing device in the open and closed configurations, respectively.

FIGS. 27A and 27B are perspective views of the suture securing device in an open configuration and a closed configuration, respectively. FIGS. 27C and 27D are cross-sectional views of the suture securing device in the open and closed configurations, respectively.

DETAILED DESCRIPTION OF CERTAIN INVENTIVE EMBODIMENTS

Figure 2B:
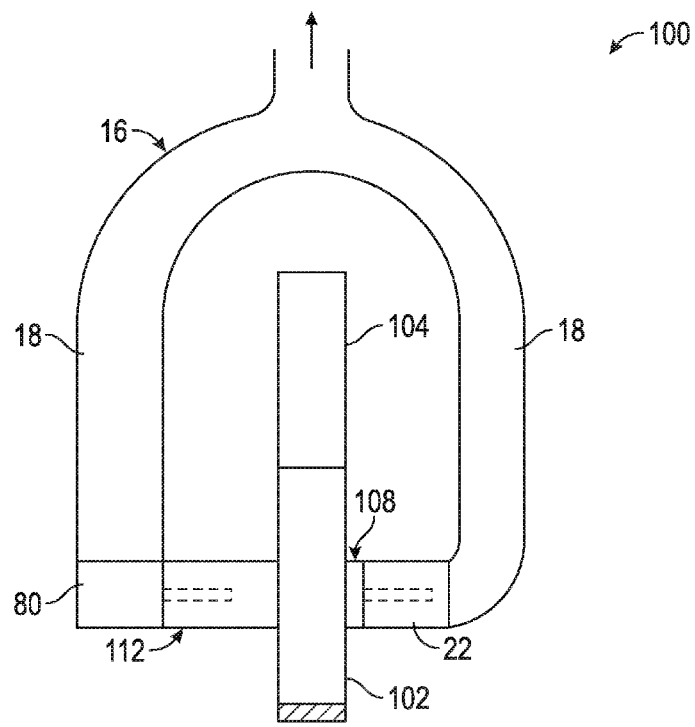
FIG. 2B is a side elevation view of the suture securing device shown in FIG. 1, depicting an external device attached to the suture securing device.

The suture securing devices, systems, and methods described herein may be used to secure a suture without requiring the tying of a knot, reduce or eliminate the likelihood that a suture will become inflamed, infected, and/or ingrown, and increase the length of time that the suture can remain in place, among other purposes. These and other advantages will become more fully apparent to one of skill in the art upon consideration and review of this disclosure. While this disclosure describes various detailed embodiments, it is not intended to be limited to only the illustrated and described embodiments. The disclosed embodiments may be varied, modified, and altered without departing from the scope of the inventions described herein. Further, while many variations are contemplated for different applications and design considerations, for the sake of brevity each and every contemplated variation is not individually described.

The following discussion presents detailed descriptions of the several embodiments of suture securing devices shown in the figures. As previously noted, these embodiments are not intended to be limiting, and modifications, variations, combinations, etc., are possible and within the scope of this disclosure. Related features in the embodiments may be identical, similar, or dissimilar in different embodiments.

In many instances in this disclosure, a particular embodiment of suture securing device may be described for use with a particular type of suturing technique, for example, simple interrupted sutures, horizontal or vertical mattress sutures, or subcutaneous sutures. However, a particular embodiment so described need not be limited to use with only that particular suturing technique. That is, each of the suture securing devices described herein may be used (or may be modified for use) with any type of suturing technique, even if not explicitly described.

With reference to FIGS. 1-9, various embodiments of several related suture securing devices will now be described. The features of any of these embodiments may be combined with any other suture securing device described throughout this application. These example suture securing devices function to retain sutures and limit reopening of a wound or incision. Further, the example suture securing devices function to retain a position of the suture securing device on the patient's skin. Additionally or alternatively, these example suture securing devices can be used to retain a position of other suture securing devices relative to each other.

As shown in FIG. 1, a suture securing device 100 includes a base 102 attached to a moveable arm 104 via a hinge 106. The suture securing device 100 further includes a first matable partner 108 attached to a first longitudinal edge 110 of base 102 and a second matable partner 112 attached to a second longitudinal edge 114 of base 102. Further, suture securing device 100 includes a locking mechanism 116 configured to engage a lip edge 118 of the arm 104. Specifically, hinge 106 is located on a first lateral edge 120 of base 102, while the locking mechanism 116 is located on a second opposing lateral edge 122. Additionally or alternatively, in other examples, the first and second matable partners can be attached at the lateral ends of the suture securing device. In even other examples, the suture securing device can exclude the first and second matable partners.

As stated above, the base 102 and the arm 104 are closeable for retaining a suture therebetween. Accordingly, as can be seen in FIGS. 1 and 2A, base 102 and arm 104 include gripping surfaces on a top surface 124 of base 102 and a bottom surface 126 of arm 104 (for example, surfaces 124a, 126a, 124b, 126b, and 124c, 126c in FIG. 2A) configured to grasp and retain suture threads, such as suture threads 10, 12, and 14 shown in FIG. 2. In some examples, the gripping surfaces are textured surfaces included the same material the suture securing device body (for example, base 102, arm 104, etc.). The material can be any sturdy and resilient material, such as plastic resin (for example, polypropylene, polyethylene, acrylonitrile butadiene styrene (ABS), high impact polystyrene (HIPS), poly vinyl chloride (PVC), polycarbonate, thermoplastic elastomers, Polybutylene terephthalate, enthylene vinyl acetate, nylon and low-density polyethylene, linear low-density polyethylene, etc.). In other examples, the gripping surfaces can be formed of or include a different material with a greater friction coefficient than the clamp body (for example, rubber, latex, nitrile, etc.). In these other examples, the gripping surfaces can be smooth or textured.

In order to retain a position of the suture threads, gripping surface 126 is compressed against gripping surface 124 by closing arm 104 (in other words, pivoting arm 104 around hinge 106). Locking mechanism 116 is configured to maintain a closed position of arm 104. In the present example, locking mechanism 116 includes a hooked portion 128 have a curved inner wall 130 that is attached to a vertical wall 132. A first end 134 of vertical wall 132 is attached to and/or coextensive with lateral edge 122, while hooked portion 128 is attached to a second end 136 of vertical wall 132.

As the suture securing device body (for example, base 102 including locking mechanism 116, arm 104 including lip edge 118, etc.) includes a resilient material, arm 104 and vertical wall 132 can be slightly elastically deformed (in other words, the arm can be bent and the vertical wall moved outwardly) as lip edge 118 is slid over curved inner wall 130. After lip edge 118 is slid past an end of hooked portion 128, arm 104 and vertical wall 132 elastically return to their original shapes. Further, a "closed" position of arm 104 is maintained as lip edge 118 is abutted to and/or engages with a lip edge 138 of hooked portion 128.

In some examples, the arm can be permanently "closed" after engagement with the locking mechanism. In other examples, the arm can be releasable after engagement with the locking mechanism. In other words, the arm can be released from the hook portion to return the arm to an "open" position, such as the position shown in FIG. 1. It will be appreciated that in alternate examples the locking mechanism can have a different configuration. In one specific alternate example, the arm can include a pin with a distal flange at a region proximal to lip edge that can be snap-fitted into a receiving hole proximal to the second lateral edge of the base. It will be further appreciated that the locking mechanism can have any known or yet to be discovered locking mechanism.

As described above, the suture securing device 100 further includes first matable partner 108 attached to first longitudinal edge 110 of base 102 and second matable partner 112 attached to second longitudinal edge 114 of base 102. The first and second matable partners are configured to be matable to the second and first matable partner, respectively, of adjacent suture securing devices. FIG. 2A shows an example of an interconnected suture securing device chain 140, including mated suture securing devices 100a, 100b, and 100c (having an identical configurations to suture securing device 100). It will be appreciated that in other examples an interconnected suture securing device chain can include more or fewer suture securing devices (for example, two, four, five, etc.).

As can be seen in FIGS. 1-2B, first matable partner 108 includes cuboid body 142 having an outer face 144. A pin 146 is outwardly projected from outer surface 144. Further, second matable partner 112 includes a cuboid body 148 having an outer face 150. A channel 152 is disposed in cuboid body 148 and has an outer opening 154 in outer face 150.

Channel 152 is configured to receive a pin of an adjacent suture securing device, while pin 146 is configured to be received by a channel of an adjacent suture securing device. Accordingly, matable partner 108 is a "male" partner, while matable partner 112 is a "female" partner. In the example of suture securing device chain 140, male partner 108a is mated to female partner 112b and male partner 108b is mated to female partner 112c. Further, female partner 112a and male partner 108c are unmated partners that are available for mating to other suture securing devices.

Interconnectability of suture securing devices through matable partners attached to either side of the suture securing device has the advantages that complex (for example, jagged) wounds and/or longer incisions can more easily be closed than with conventional suture methods and techniques. As can be seen in FIG. 2A, sutures 10, 12, 14 can be received in a variety of locations on the interconnected suture securing device chain 140. Specifically, suture 10 disposed on base 102a on a side of matable partners 112a and 108a proximal to hinge 106a, suture 12 are disposed on base 102b on a side of matable partners 112b and 108b that is distal relative to hinge 106b, and suture 14 have one end of the suture disposed on base 102c on a side of matable partners 112c and 108c proximal to hinge 106c and a second end of the suture disposed on base 102c on a side of matable partners 112c and 108c that is distal relative to hinge 106c. Closing of the wound and/or incision can be assisted as the suture securing devices retain a position of each suture and interconnection of the suture securing devices retains a position of the clamps relative to each other.

The matable partners have the further advantage that they can facilitate attachment of a suture securing device and/or an interconnected suture securing device chain to other devices. For example, as depicted in FIG. 2B, a clamp placement device 16 is attachable to suture securing device 100 for setting a position of the suture securing device on the patient. Device 16 includes a pair of arms 18 that are attachable to opposing longitudinal sides of suture securing device 100. A distal end of one of arms 18 includes a male connector for releasable connection to matable partner 112 (in other words, the female partner) and a distal end of the other of arms 18 includes a female connector for releasable connection to matable partner 108 (in other words, the male partner). Device 18 can be made from a resilient material and/or can be a mechanical pincer device for engagement with and release of suture securing device 100.

Additionally or alternatively, other devices can be connectable to the suture securing device and/or suture securing device chain. For example, a suture securing device and/or an interconnected suture securing device chain can be attached to medical devices, such as IV catheters, central venous and arterial catheters, urinary catheters, chest tubes, and/or dressings. It will be appreciated that the suture securing device and/or the interconnected suture lock chain can be connected to any medical device adapted with matable connectors that is known or yet to be discovered. The principles described above in reference the suture securing device 100 can be incorporated into any of the suture securing devices described throughout this disclosure.

Turning attention to FIGS. 3A-5C, another embodiment of a suture securing device, suture securing device 200, is shown. Suture securing device 200 includes many similar or identical features to suture securing device 100. Thus, for the sake of brevity, each feature of suture securing device 200 will not be redundantly explained. Rather, key distinctions between suture securing devices 100 and 200 will be described in detail and the reader should reference the discussion above for features substantially similar between the two suture securing devices. This is true throughout this application and will not be repeated in each instance.

Figure 3A:
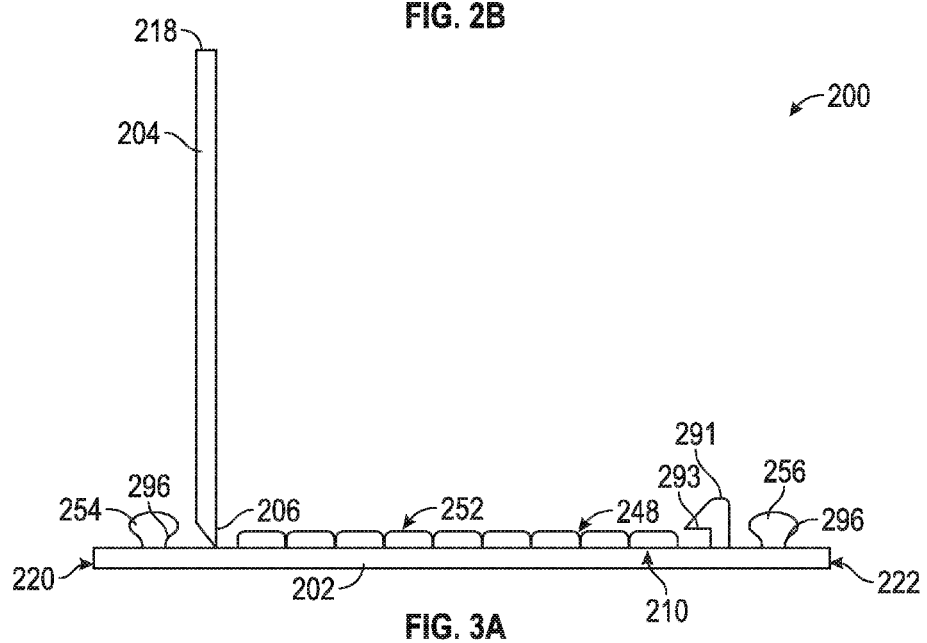
FIGS. 3A-3C are side elevation and top plan views, respectively, of another embodiment of a suture securing device including single wing extensions and an arrangement of teeth.
Figure 3B:
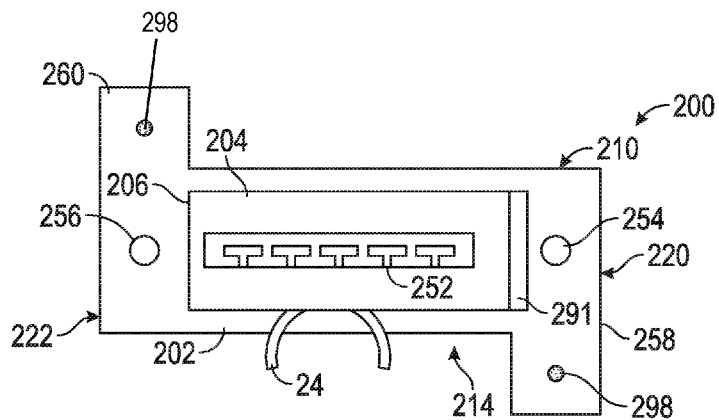
Figure 3C:
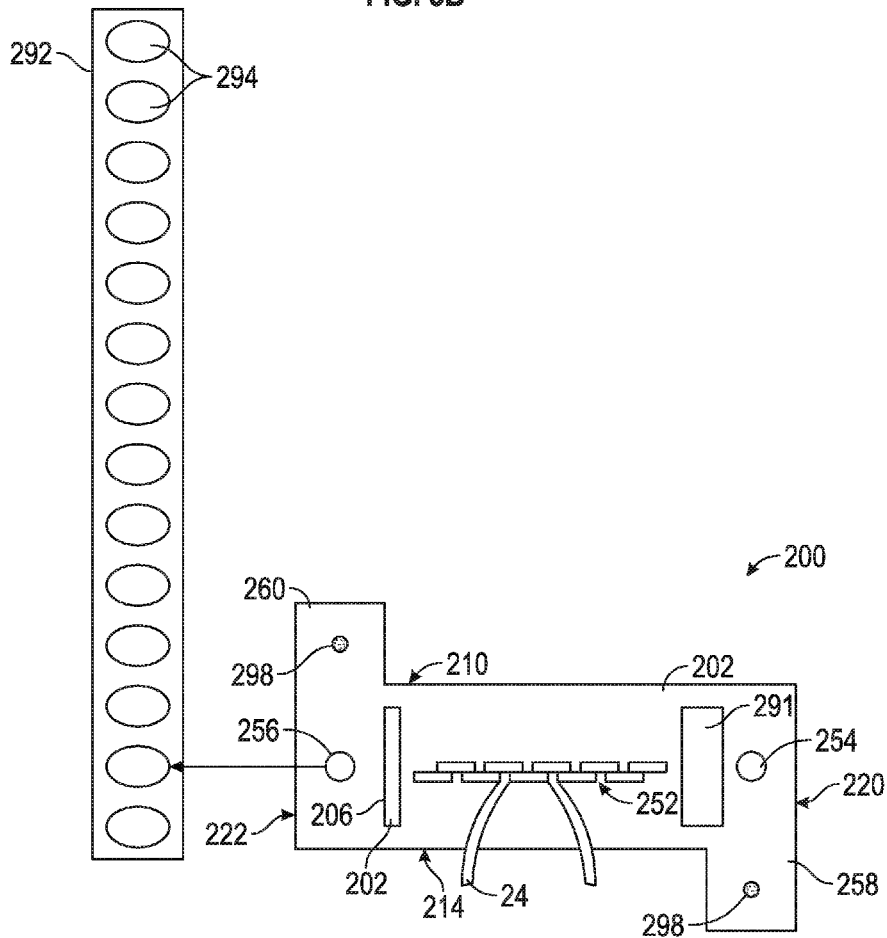

As can be seen in FIGS. 3A-3C, suture securing device 200 includes a base 202 attached to a moveable arm 204 via a hinge 206. Suture clamp 200 further includes teeth 252 disposed on a top surface 248 of base 202, pegs 254 and 256 disposed on top surface 248 of base 202 proximal to opposing lateral edges 220 and 222, respectively, and single wing extensions 258 and 260 disposed on opposing longitudinal edges 210 and 214 of base 202.

Specifically, single wing extension 258 is extended outwardly from longitudinal edge 210 proximal to lateral edge 220 and single wing extension 260 is outwardly extended from longitudinal edge 214 proximal to lateral edge 222. The single wing extensions provide additional stability for maintaining a position of the suture securing device on the skin. Furthermore, suture securing device 200 includes a locking mechanism 216 having a different configuration than locking mechanism 116 of suture securing device 100 (described in detail below).

Figure 4A:
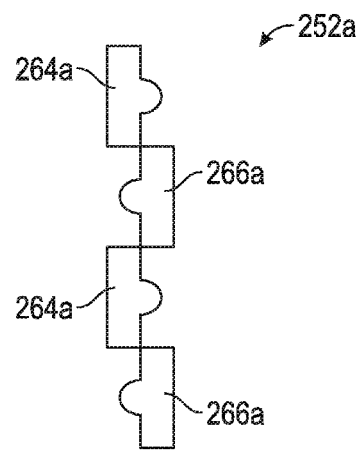
FIGS. 4A-4C are top plan, perspective, and cross sectional views, respectively, of a first example configuration for teeth of the embodiment of the suture securing device shown in FIGS. 3A-3C.
Figure 4B:
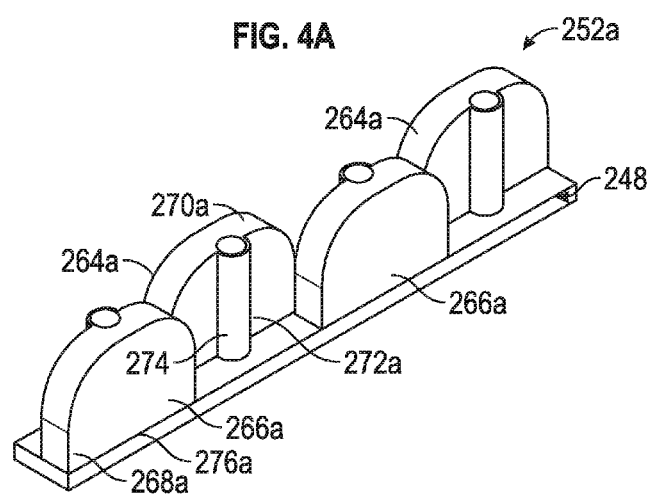
Figure 4C:
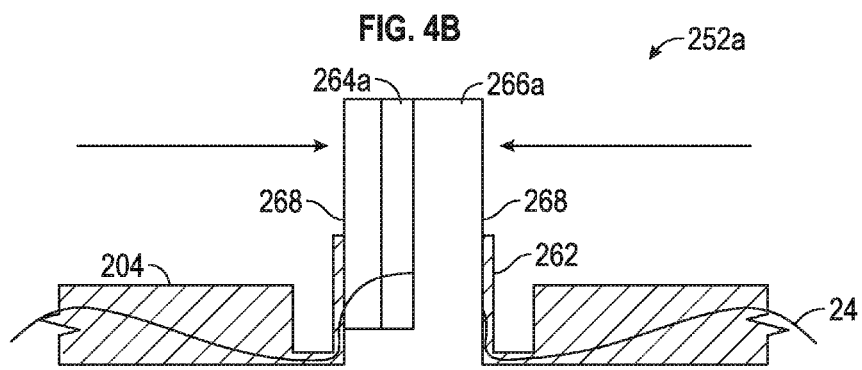

As stated above, base 202 and arm 204 are closeable for retaining a suture therebetween. Accordingly, as can be seen in FIGS. 3A-3C, teeth 252 on top surface 248 are configured to receive sutures between adjacent teeth, such as suture 24. Detailed views of teeth 252 are shown in FIGS. 4A-4C. Teeth 252 are formed of or include a resilient material and are further configured to engage with and be compressed by a window 262 (shown in FIGS. 3B and 5B) in arm 204 for locking of the suture securing device. Accordingly, teeth 252 and window 262 include locking mechanism 216. The suture securing device body (for example, base 202, arm 204, teeth 252, etc.) can be formed of or include any sturdy and resilient material as described above in reference to suture securing device 100.

As depicted in FIGS. 4A-4C, teeth 252a (in other words, a first example of teeth 252) include rows of opposing teeth 264a and 266a. Teeth 264a and 266a alternating and are offset relative to adjacent teeth. Further, corners of adjacent teeth are in contact with each other, but are non-overlapping. In other words, there is no space between the row of teeth 264a and the row of teeth 266a.

Each of teeth 264a and 266a has a substantially similar structure. Specifically, each of the teeth has a flat outer wall 268, a curved top wall 270, a substantially flat inner wall 272 having a vertical half cylinder 274 extended over the height of the inner wall, and a base 276 that is attached to top surface 248. As shown in FIG. 4C, suture 24 can be intertwined, placed, and/or woven between teeth 264a and 266a. Opposing teeth 264a and 266a can be compressed towards each other when window 262 is fitted over the teeth, thereby retaining, compressing, and/or trapping suture 24 between the teeth and locking a closed position of suture securing device 200. It will be appreciated that in some examples the teeth releasably lock the closed position of the suture securing device.

Figure 5A:
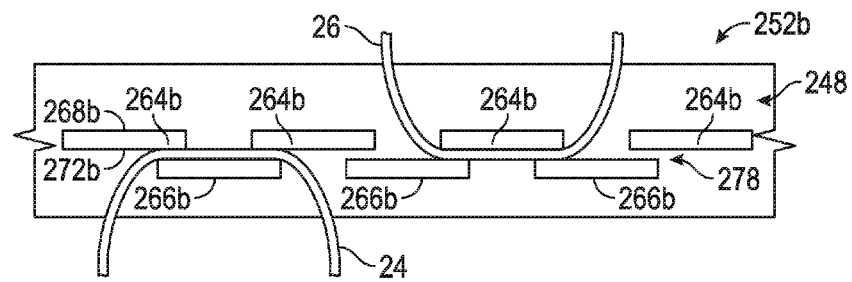
FIGS. 5A and 5B are top plan and isometric views, respectively, of a second example configuration for teeth of the embodiment of the suture securing device shown in FIGS. 3A-3C.
Figure 5B:
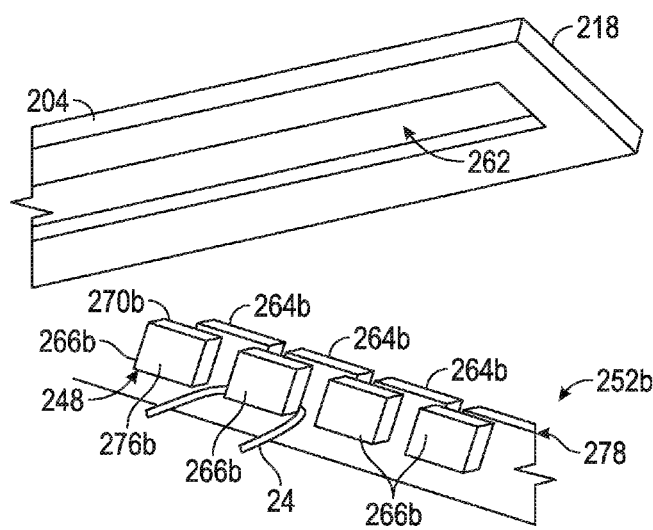

Turning to FIGS. 5A-5B, teeth 252b (in other words, a second example of teeth 252) include rows of opposing teeth 264b and 266b. Teeth 264b and 266b alternating and are offset relative to adjacent teeth. Further, corners of adjacent teeth are overlapping, but not in contact with each other. In other words, there is a space 278 between the row of teeth 264b and the row of teeth 266b.

Each of teeth 264b and 266b has a substantially similar structure. Specifically, each of the teeth has a flat outer wall 268b, a flat top wall 270b, a flat inner wall 272b, and a base 276b that is attached to top surface 248. As shown in FIG. 5B, suture 24 can be intertwined, placed, and/or woven between teeth 264b and 266b. Further, additional sutures, such as suture 26, can be intertwined, placed, and/or woven between teeth 264b and 266b. Opposing teeth 264b and 266b can be compressed towards each other when window 262 is fitted over the teeth, thereby retaining, compressing, and/or trapping sutures 24 and 26 between the teeth and locking a closed position of suture securing device 200. It will be appreciated that in some examples the teeth releasably lock the closed position of the suture securing device.

Figure 5C:
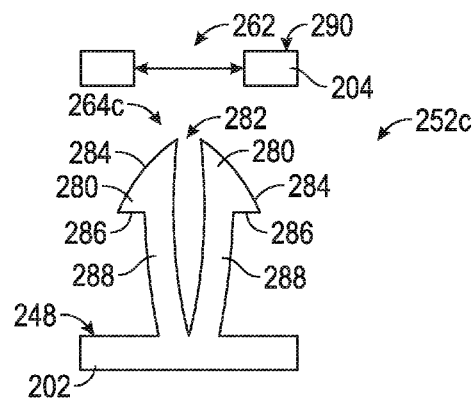
FIG. 5C is a side elevation view of a third example configuration for teeth of the embodiment of the suture securing device shown in FIGS. 3A-3C.

FIG. 5C shows a third example of teeth 252, teeth 252c, including a single row of teeth 264c. Only one of teeth 264c is shown in FIG. 5C, however, it will be appreciated that teeth 252c include a plurality of teeth 264c in the row of teeth. Each of teeth 264c has a substantially similar structure. Specifically, each of teeth 264c has a flexible two-pronged structure including prongs 280 with a space 282 between the prongs. Each of the prongs includes a sloped top wall 284 and an outer flange 286 at a top portion of a stem 288, which is attached to top surface 248.

Although not specifically shown, one or more sutures can be intertwined, placed, and/or woven between prongs 280. Prongs 280 are compressed towards each other (closing space 282) when window 262 is fitted over the teeth, thereby retaining, compressing, and/or trapping one or more sutures between the teeth. Further, flanges 286 can engage with a top surface 290 of arm 204 in order to lock a closed position of suture securing device 200. It will be appreciated that in some examples the teeth releasably lock the closed position of the suture securing device.

Returning to FIGS. 3B and 3C, locking mechanism 216 further includes a clasp 291 proximal to lateral edge 222. Clasp 291 includes a flange 293 for engaging with a lip edge 218 of arm 204. In some examples, the clasp is releasable for releasable attachment to the lip edge. In other examples, the clasp is non-releasable. In the example of the teeth 252c, the clasp can be excluded.

Further, differently from suture securing device 100, suture securing device 200 can be joined to adjacent suture securing devices via connecting strip 292 including a plurality of holes 294. Each of holes 294 can be fitted over one of pegs 254 and 256. Each of pegs 254 and 256 includes an annular flange 296 at a top end of the peg that can engage with strip 292 to allow releasable or non-releasable attachment of the strip to the pegs. Accordingly, adjacent suture securing devices 200 are interconnectable via strips 292.

It will be appreciated that the strips can be connected at adjacent pegs on both sides of the suture securing devices and the strips allow "step-wise" attachment between adjacent suture securing devices. Interconnectability of suture securing devices through attachment of strips to pegs at either side of the suture securing device has the advantages that complex (for example, jagged) wounds and/or longer incisions can more easily be closed than with conventional suture methods and techniques and/or can facilitate attachment of a suture securing device and/or an interconnected suture securing devices to other devices, such as those described above in reference to suture securing device 100. A position of the suture securing devices can optionally be further secured by sewing a suture through one or more of holes 298 located in wings 258 and 260.

Turning attention to FIGS. 6A-7B, another example of a suture securing device 300 is shown. Suture securing device 300 includes many similar or identical features to suture securing devices 100 and 200, as well as others described throughout this application.

Figure 6A:
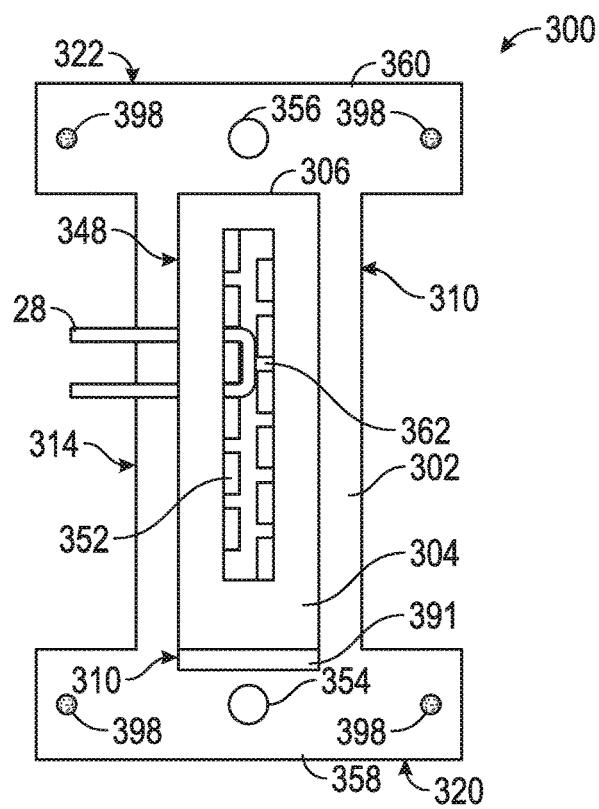
FIGS. 6A and 6B are top plan views of another embodiment of a suture securing device that includes double wing extensions and an arrangement of teeth.
Figure 6B:
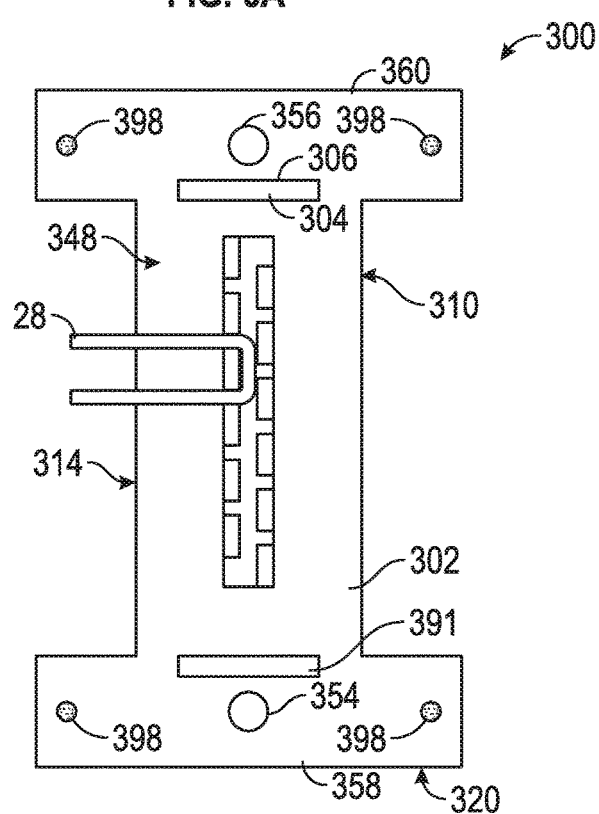

As can be seen in FIGS. 6A-6B, suture securing device 300 includes a base 302 attached to a moveable arm 304 via a hinge 306. Suture clamp 300 further includes teeth 352 disposed on a top surface 348 of base 302, pegs 354 and 356 disposed on top surface 348 of base 302 proximal to opposing lateral edges 320 and 322, respectively, and double wing extensions 358 and 360 disposed on opposing longitudinal edges 310 and 314 of base 302.

Specifically, double wing extension 358 is outwardly extended from longitudinal edges 310 and 314 proximal to lateral edge 320 and double wing extension 360 is outwardly extended from longitudinal edges 310 and 314 proximal to lateral edge 322. The double wing extensions provide additional stability for maintaining a position of the suture securing device on the skin. Furthermore, suture securing device 300 includes a locking mechanism 316 having a different configuration than locking mechanism 116 of suture securing device 100, but is substantially similar to locking mechanism 216 described above.

As stated above, base 302 and arm 304 are closeable for retaining a suture therebetween. Accordingly, as can be seen in FIGS. 6A and 6B, teeth 352 on top surface 348 are configured to receive sutures between adjacent teeth, such as suture 28. Teeth 352 are formed or comprised of or include a resilient material and are further configured to engage with and be compressed by a window 362 (shown in FIG. 6A) in arm 304 for locking of the suture securing device. Accordingly, teeth 352 and window 362 include locking mechanism 316. The suture securing device body (for example, base 302, arm 304, teeth 352, etc.) can be formed of any known or yet to be discovered sturdy and resilient material, such as those described above in reference to previously described embodiments. It will be appreciated that teeth 352 can have any of the example configurations described above in reference to teeth 252 (for example, teeth 252a, teeth 252b, and teeth 252c).

Similar to suture securing device 200, locking mechanism 316 further includes a clasp 391 proximal to lateral edge 322. Although not specifically shown, clasp 391 is includes a flange for engaging with a lip edge 318 of arm 304. In some examples, the clasp is releasable for releasable attachment to the lip edge. In other examples, the clasp is non-releasable. In the example of teeth similar to teeth 252c, the clasp can be excluded.

Also similar to suture securing device 200, suture securing device 300 can be joined to adjacent suture securing devices via connecting strips including a plurality of holes (in other words, a connecting strip substantially identical to connecting strip 292 shown in FIGS. 3A and 3B). Each of the holes can be fitted over one of pegs 354 and 356. Although not specifically shown, each of pegs 354 and 356 includes an annular flange at a top end of the peg that can engage with a connecting strip to allow releasable or non-releasable attachment of the strip to the pegs. Accordingly, adjacent clamps 300 are interconnectable via connecting strips, such as connecting strip 292.

Figure 7A:
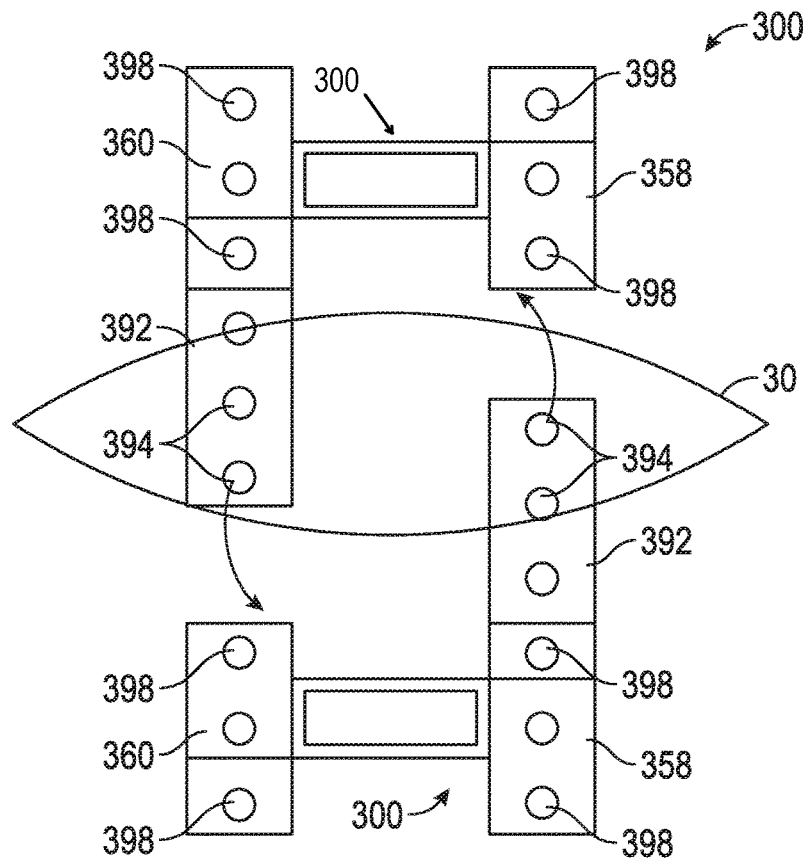
FIGS. 7A and 7B are top plan and side elevation views, respectively, of an embodiment of connecting strips for the suture securing device shown in FIGS. 6A and 6B.
Figure 7B:
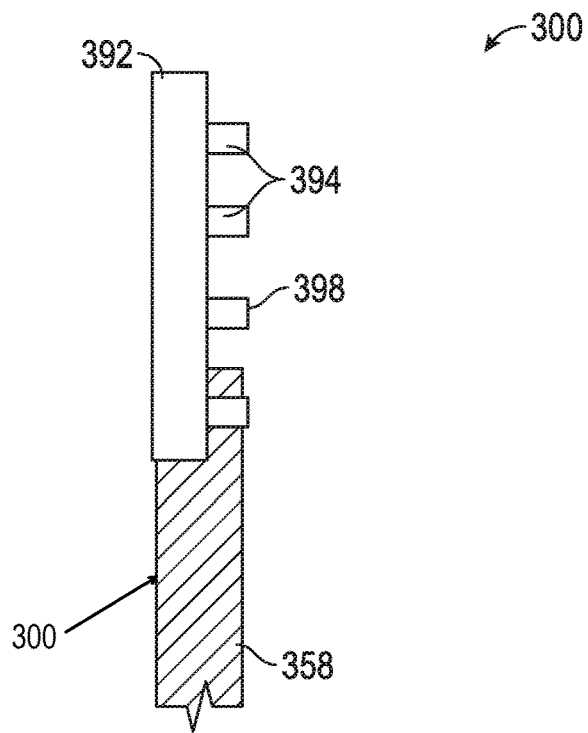

Additionally or alternatively, as depicted in FIGS. 7A and 7B, suture securing devices 300 can be joined to adjacent suture securing devices via connecting strips 392 including a plurality of projections 394. Each of projections 394 can be fitted into one of holes 398. Although not specifically shown, each of projections 394 can include an annular flange at a top end of the projection that can engage with suture securing device base (in other words, wing extensions 358 or 360) to allow releasable or non-releasable attachment of the strip to the holes. Accordingly, adjacent clamps 300 are additionally or alternatively interconnectable via connecting strips, such as connecting strip 392.

It will be appreciated that the connecting strips can be connected at adjacent pegs or holes on both sides of the suture securing devices and the strips allow "step-wise" attachment between adjacent suture securing devices and/or "step-wise" closure of the wound, such as wound 30 shown in FIG. 7A.

Interconnectability of suture securing devices through attachment of strips to pegs at either side of the suture securing device has the advantages that complex (for example, jagged) wounds and/or longer incisions can more easily be closed than with conventional suture methods and techniques and/or can facilitate attachment of a suture securing device and/or an interconnected suture securing devices to other devices, such as those described above in reference to suture securing device 100. A position of the suture securing devices can optionally be further secured by sewing a suture through one or more of holes 398 located in wings 358 and 360.

Figure 8:
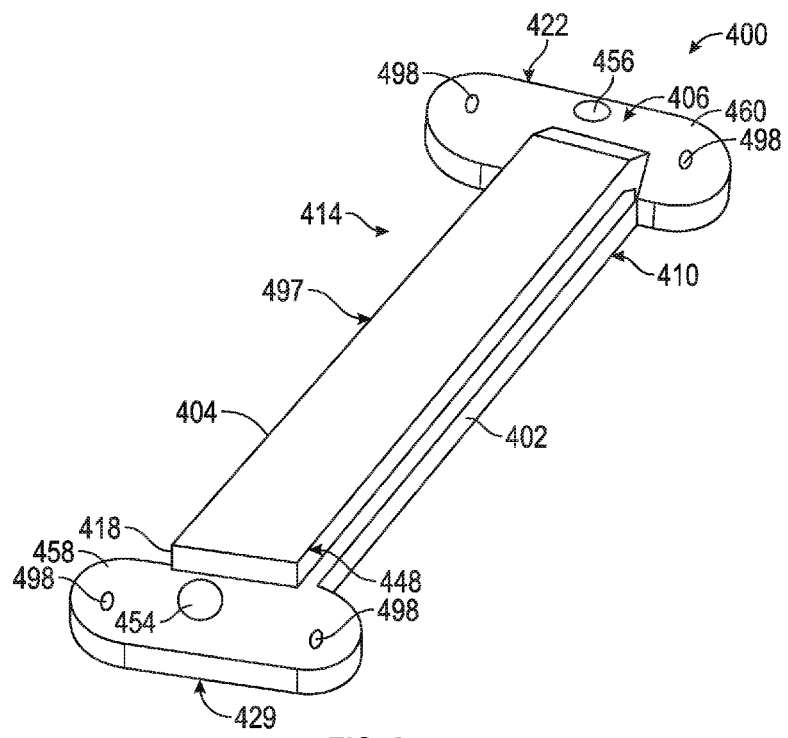
FIG. 8 is an isometric view of another embodiment of a suture securing device including a flat top surface and an elevated bottom surface.
Figure 9:
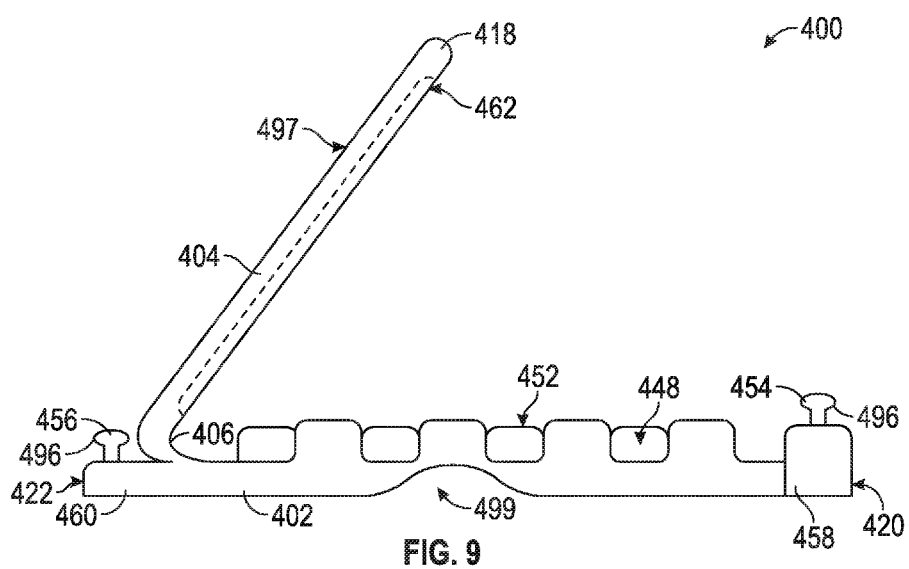
FIG. 9 is a side elevation view of the suture securing device shown in FIG. 8.

Turning attention to FIGS. 8 and 9, another example of a suture securing device 400 is shown. As can be seen in FIGS. 8 and 9, suture securing device 400 includes a base 402 attached to a moveable arm 404 via a hinge 406. Suture securing device 400 further includes teeth 452 disposed on a top surface 448 of base 402, pegs 454 and 456 disposed on top surface 448 of base 402 proximal to opposing lateral edges 420 and 422, respectively, and double wing extensions 458 and 460 disposed on opposing longitudinal edges 410 and 414 of base 402. Specifically, double wing extension 458 is outwardly extended from longitudinal edges 410 and 414 proximal to lateral edge 420 and double wing extension 460 is outwardly extended from longitudinal edges 410 and 414 proximal to lateral edge 422. The double wing extensions provide additional stability for maintaining a position of the suture securing device on the skin. Furthermore, suture securing device 400 includes a locking mechanism 416 having a different configuration than locking mechanism 116 of suture securing device 100, but is substantially similar to locking mechanisms 216 and 316 described above.

As stated above, base 402 and arm 404 are closeable for retaining a suture therebetween. Accordingly, as can be seen in FIG. 9, teeth 452 on top surface 448 are configured to receive sutures between adjacent teeth. Teeth 452 are formed or comprised of a resilient material and are further configured to engage with and be compressed by a depression 462 in arm 404 for locking of the suture securing device. Accordingly, teeth 452 and window 462 include locking mechanism 416. The suture securing device body (for example, base 402, arm 404, teeth 452, etc.) can be formed of any known or yet to be discovered sturdy and resilient material, such as those previously listed. It will be appreciated that teeth 452 can have any of the example configurations described above in reference to teeth 252 (for example, teeth 252a, teeth 252b, and teeth 252c).

Though not specifically shown, similar to suture securing devices 200 and 300, locking mechanism 416 can further include a clasp proximal to lateral edge 422. The clasp can include a flange for engaging with a lip edge 418 of arm 404. In some examples, the clasp is releasable for releasable attachment to the lip edge. In other examples, the clasp is non-releasable. In the example of teeth similar to teeth 252c, the clasp can be excluded.

Also similar to suture securing devices 200 and 300, suture securing device 400 can be joined to adjacent suture securing devices via connecting strips including a plurality of holes (in other words, a connecting strip substantially identical to connecting strip 292 shown in FIGS. 3A and 3B). Each of the holes can be fitted over one of pegs 454 and 456. Each of pegs 454 and 456 includes an annular flange 496 at a top end of the peg that can engage with a connecting strip to allow releasable or non-releasable attachment of the strip to the pegs. Accordingly, adjacent clamps 400 are interconnectable via connecting strips, such as connecting strip 292.

Additionally or alternatively, suture securing devices 400 can be joined to adjacent suture securing devices via connecting strips, such as connecting strip 392 shown in FIGS. 7A and 7B, including a plurality of projections. Each of the projections can be fitted into one of holes 498. Each of the projections can include an annular flange at a top end of the projection that can engage with suture securing device base (in other words, wing extensions 458 or 460) to allow releasable or non-releasable attachment of the strip to the holes. Accordingly, adjacent clamps 400 are additionally or alternatively interconnectable via connecting strips, such as connecting strip 392. A position of the suture securing devices can optionally be further secured by sewing a suture through one or more of holes 498 located in wings 458 and 460.

Differently from the previously explained example suture securing devices, suture securing device 400 includes a flat top surface 497 on arm 404 and an elevated bottom surface 499 on base 402. The flat top surface can be a location of printing and or labeling (for example, patterns, logos, coloration, stickers, etc.). The elevated bottom surface 499 can facilitate eversion of the suture securing device against the skin of the patient, allowing movement and preventing tearing of the sutures. The purpose of the elevated surface 499 is to create eversion.

Figure 10A:
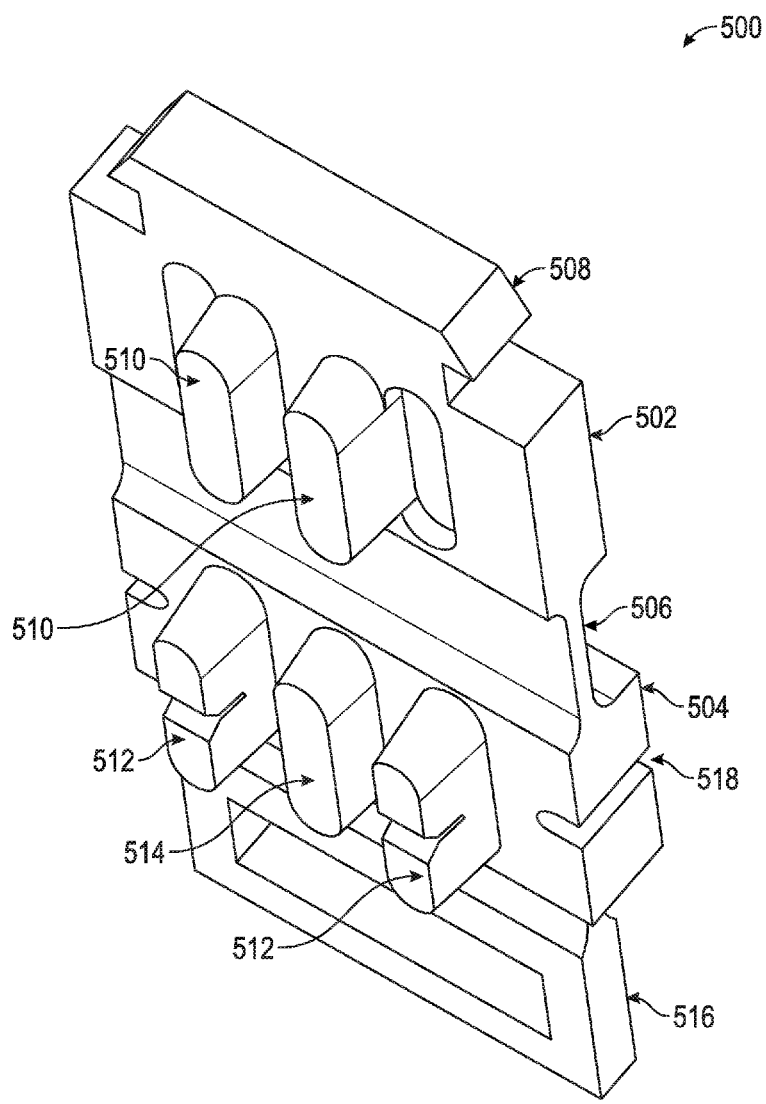
FIG. 10A is a perspective view of another embodiment of a suture securing device.

FIG. 10A is a perspective view of another embodiment of a suture securing device 500. As illustrated in FIG. 10A, the suture securing device 500 includes a first piece 502 (upper arm), a second piece 504 (lower arm) and a first hinge 506. The first hinge 506 is illustrated in FIG. 10A in an open position. The first piece also includes an attachment piece 508, which will be discussed below.

The first piece 502 includes dual protrusions 510 on a front surface. The second piece 504 includes plurality of protrusions on a front surface. The front surface of the second piece 504 includes a middle protrusion 514 surrounded by two protrusions 512. The two protrusions 512 each include a notch. When the first hinge 506 is in a closed position, the first piece 502 folds over the second piece 504. The dual protrusions 510 of the first piece 502 will engage with the plurality of protrusions on the first surface of the second piece 504. One of the dual protrusions 510 will fit between the middle protrusion 514 and one of the two protrusions 512 and the other of the dual protrusions 510 will fit between the middle protrusion 514 and the other of the two protrusions 512.

Additionally, the second piece 504 is attached to a locking piece 516 via a second hinge 598. The locking piece 516 includes a hole attachment 515. When the first hinge 506 is in the closed position the locking piece 516 folds on the second hinge 598 to an engagement position where the receiver attachment 515 receives the attachment piece 508 and locks the first piece 502 to the second piece 504. A notch 518 is located on either side of the second piece 504. The notch 518 provides a pathway through which sutures may be placed.

Figure 10B:
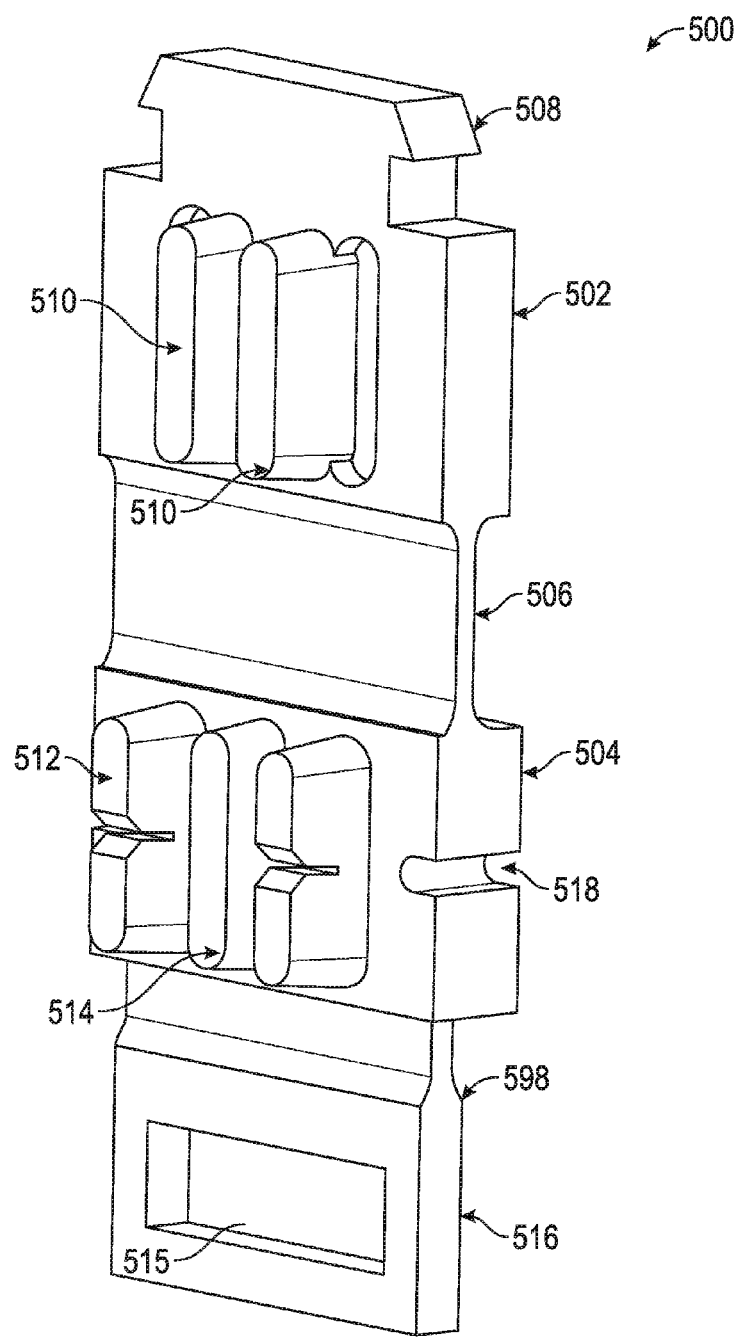
FIG. 10B is a different perspective view of the suture securing device of FIG. 10A.
Figure 10C:
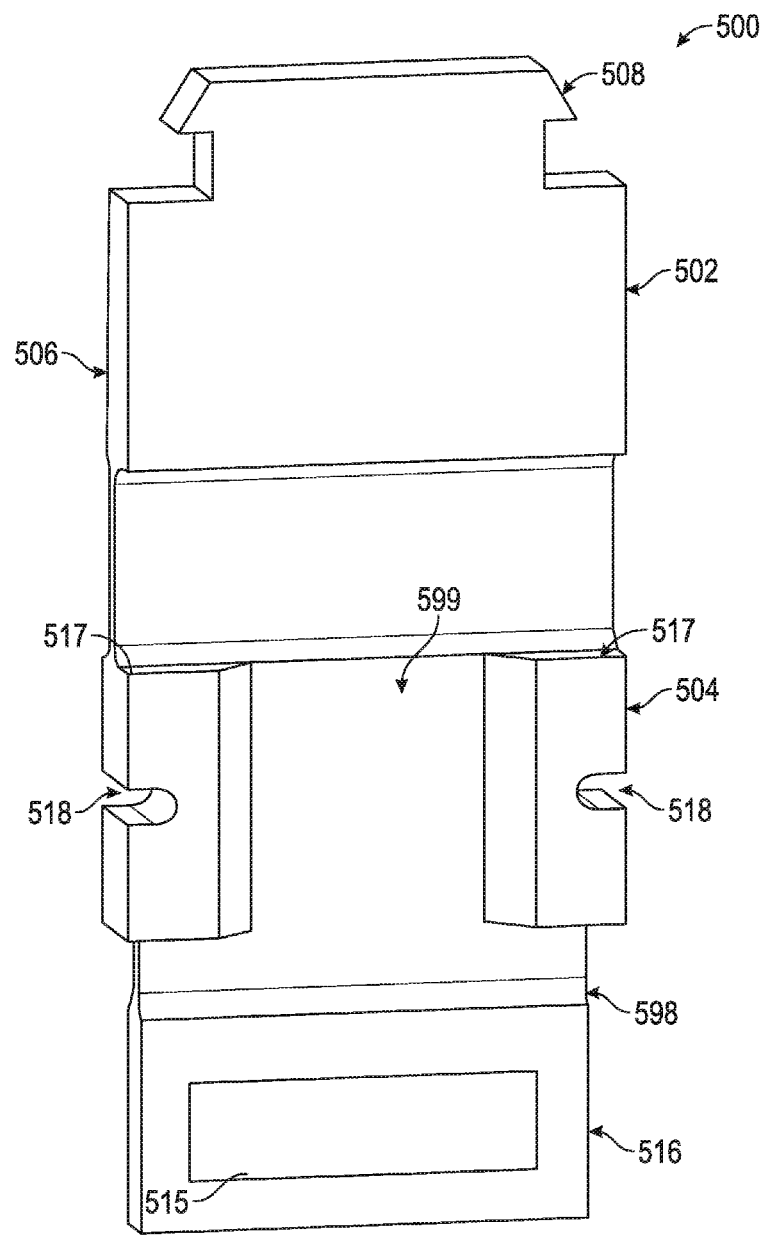
FIG. 10C is a back view of the suture securing device of FIG. 10A.

FIG. 10B is a different perspective view of the suture securing device 500 of FIG. 10A. FIG. 10C is a back view of the suture securing device or suture lock of FIG. 10A. FIG. 10C illustrates a raised feature 517 on the second side of the second piece 504. The raised feature 517 on either side of the second piece 504 each include the notch 518. Between each raised feature 517 is a concave feature 599. The concave feature 599 may be a trench that is configured to facilitate wound eversion. In some embodiments, the concave feature 500 may be configured to create a space for wound eversion and may or may not contact the wound. In other words, after sutures are properly applied to a wound, either edge of the healing wound will be placed and held together such that a convex bulge is made. The convex bulge will mate with the concave feature 599 of the suture lock 500. Thus, with the suture securing device 500, the concave feature 599 is positioned to be substantially parallel to the direction of the wound when coupled to a simple interrupted suture.

Figure 11A:
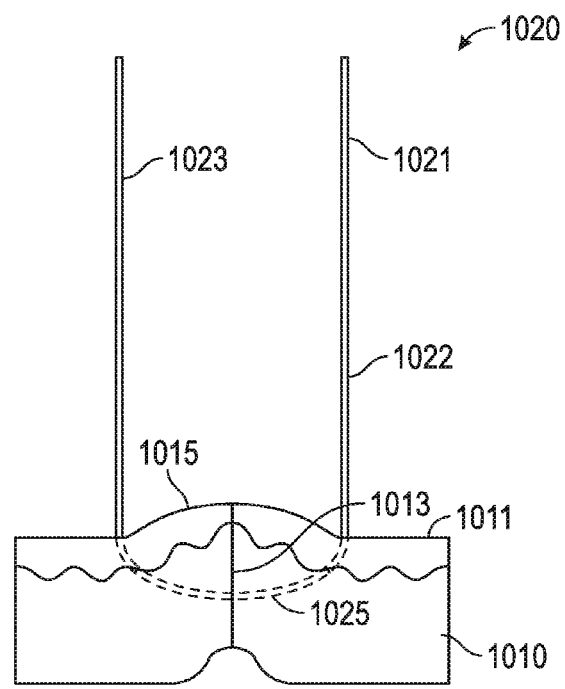
FIGS. 11A and 11B illustrate views of a single unsecured simple interrupted suture.
Figure 11B:
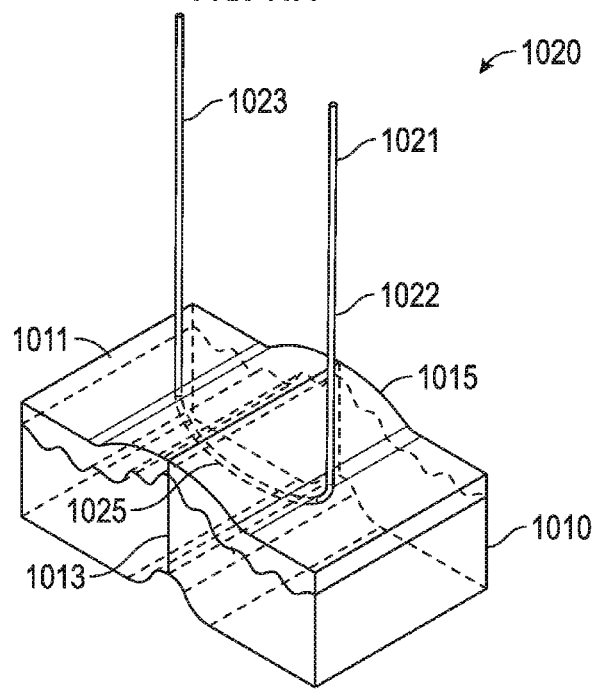

FIGS. 11A and 11B illustrate views of a single unsecured simple interrupted suture 1020: FIG. 11A shows a front view and FIG. 11B shows a perspective view. FIGS. 11A and 11B also show an example section of a patient's skin 1010, having a surface 1011 and a wound or incision 1013. To fully illustrate the simple interrupted suture 1020, the section of the patient's skin 1010 is illustrated as transparent so that the portion of the simple interrupted suture 1020 internal to the patient is visible. The simple interrupted suture 1020 is used to close the wound 1013. Simple interrupted suture 1020 includes a suture material, herein referred to as a thread 1020, which is stitched through the incision 1013 such that opposite sides of the incision can be drawn together, closing the incision 1013. As seen in FIG. 11A, the simple interrupted suture 1020 can create a section of skin eversion 1015, seen as a raised portion of the skin surface 1011. The suture 1020 is formed with the thread 1022 such that it includes a first external portion 1021, a second external portion 1023, and an internal portion 1025. The suture material or thread 1022 can potentially be any type of suture material. For example, suitable suture materials may include either absorbable and/or non-absorbable material. Some specific suture materials may include, for example, nylon, polypropylene, or polybutylester. Other suitable suture materials known in the art might also be used.

In FIGS. 11A and 11B, the simple interrupted suture 1020 is "unsecured" because nothing is included to secure the first and second external portions 1021, 1023 of the thread 1022 to hold the simple interrupted suture 1020 in place. Commonly, the simple interrupted suture 1020 is "secured" by tying the first and second external portions 1021, 1023 of the thread 1022 with one of a number of surgical knots. This secures the simple interrupted suture 1020; however, the knot generally rests directly on the skin surface 1011. Further, the knot may be difficult to tie. These and other problems with the conventional method for securing a simple interrupted suture 1020 can be remedied by the use of the suture securing devices described below. FIGS. 12A through 27N illustrate various embodiments of suture securing devices configured for use with simple interrupted sutures 1020 as shown in FIGS. 11A and 11B. Although these embodiments are specifically described in reference to use with a simple interrupted suture, they may also be used (or modified for use) with other types of sutures and suturing techniques.

Figure 12A:
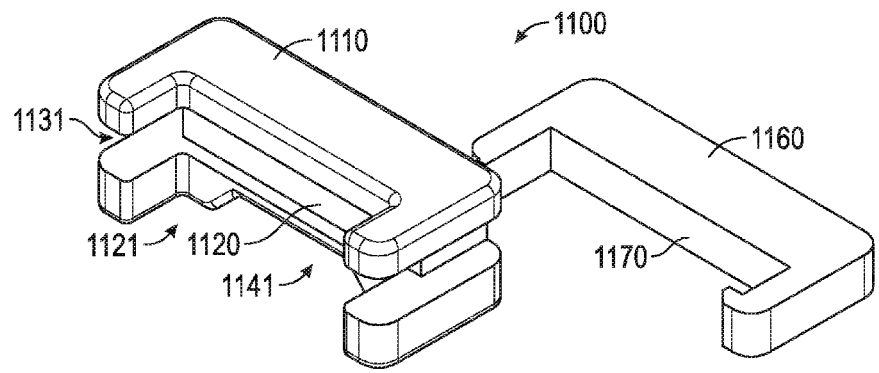
FIGS. 12A through 12P illustrate various views of a first embodiment of a suture securing device for securing a simple interrupted suture. The first embodiment includes a body configured to be positioned across a patient's wound or incision and an arm attached to the body by a hinge. The hinge allows the suture securing device to be transitioned between an open configuration and a closed configuration. In the open configuration the suture securing device can be positioned around exposed portions of the suture. In the closed configuration, the suture is secured between the arm and the body.
Figure 12B:
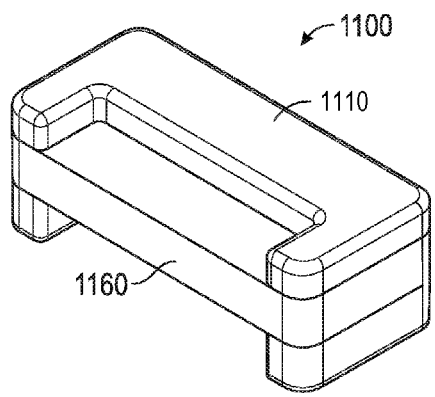
Figure 12C:
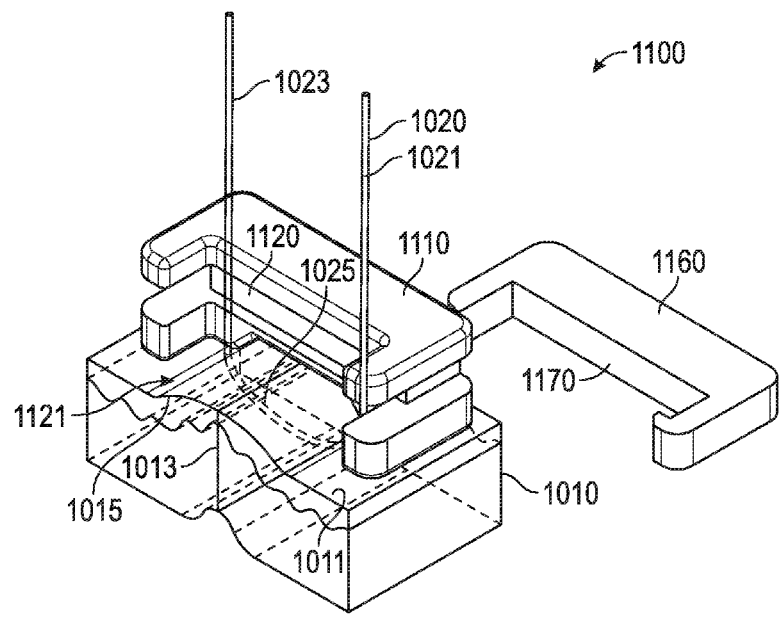
FIGS. 12C and 12D are perspective views of the first embodiment of the suture securing device shown in use, positioned on a patient's skin and securing a simple interrupted suture.
Figure 12D:
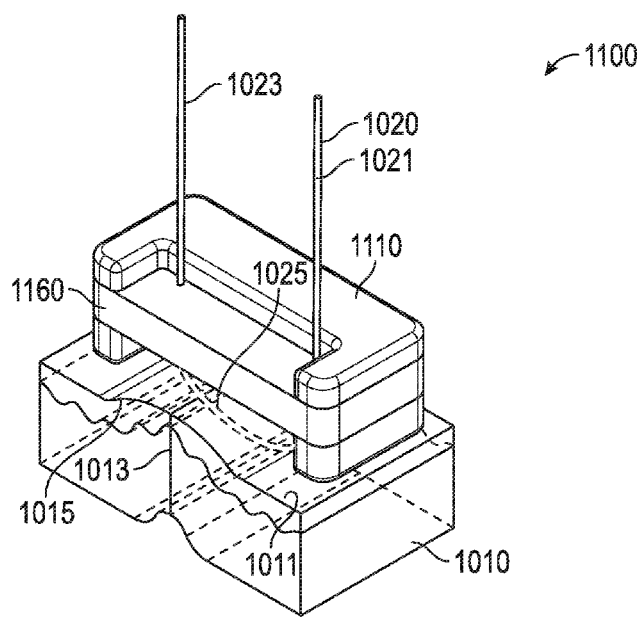
Figure 12E:
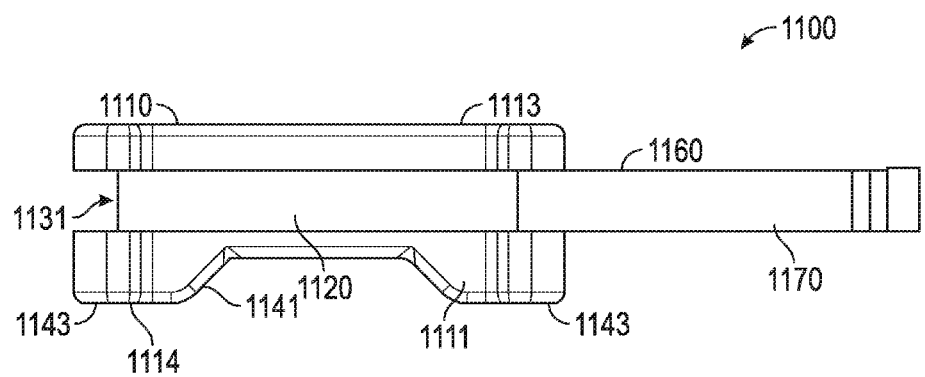
FIGS. 12E through 12J show front, back, top, bottom, and first and second side views of the first embodiment of the suture securing device in the open configuration, respectively.
Figure 12F:
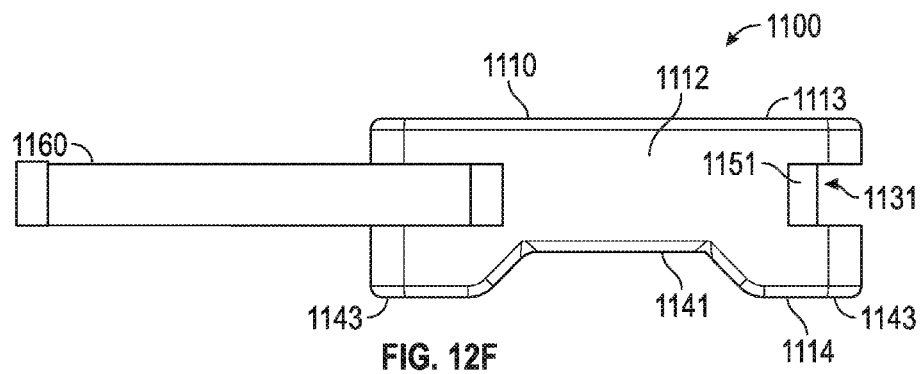
Figure 12G:
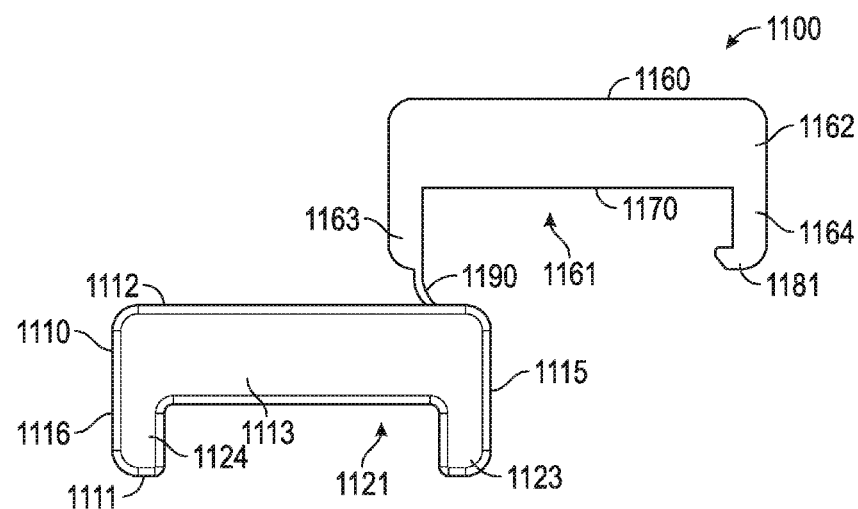
Figure 12H:
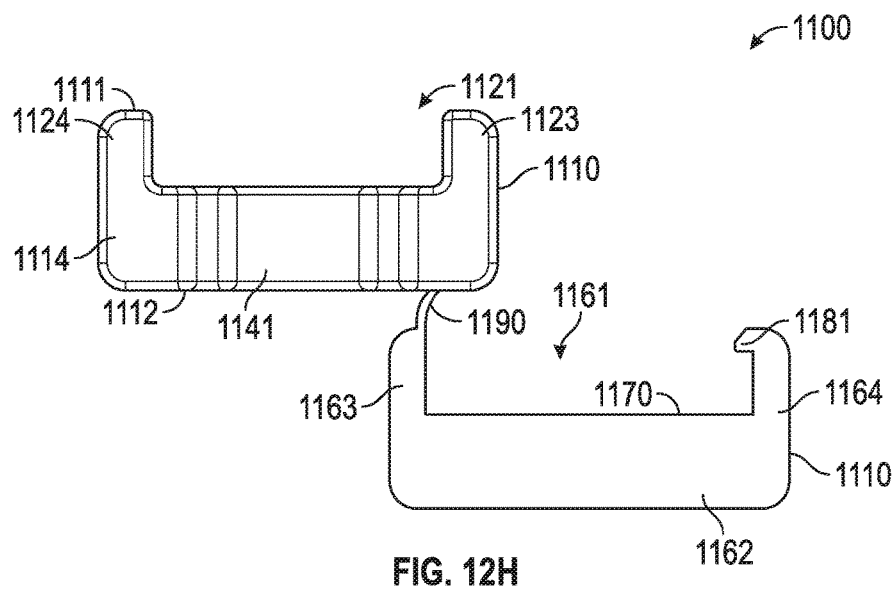
Figure 12I:
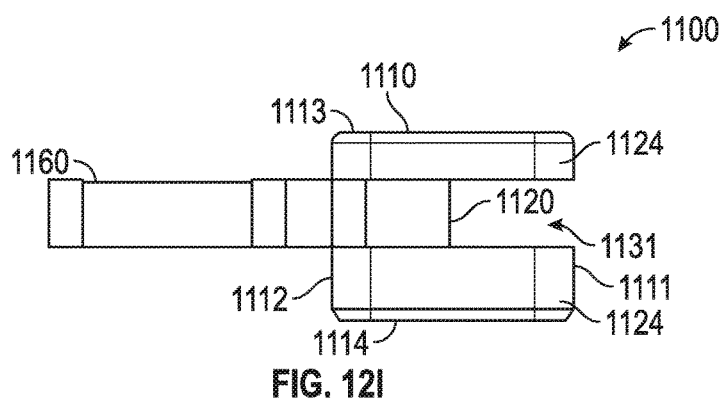
Figure 12J:
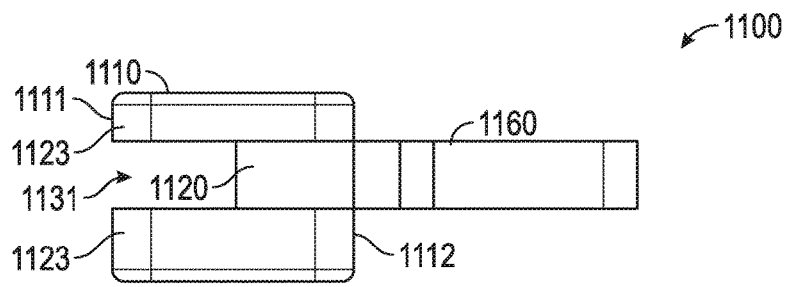
Figure 12K:
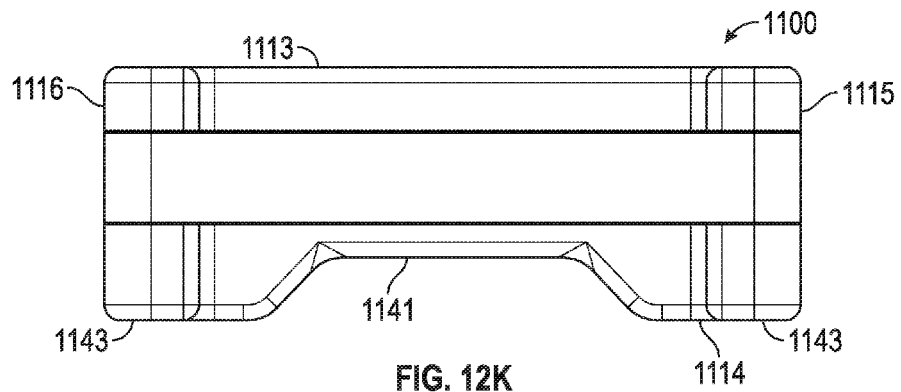
Figure 12L:
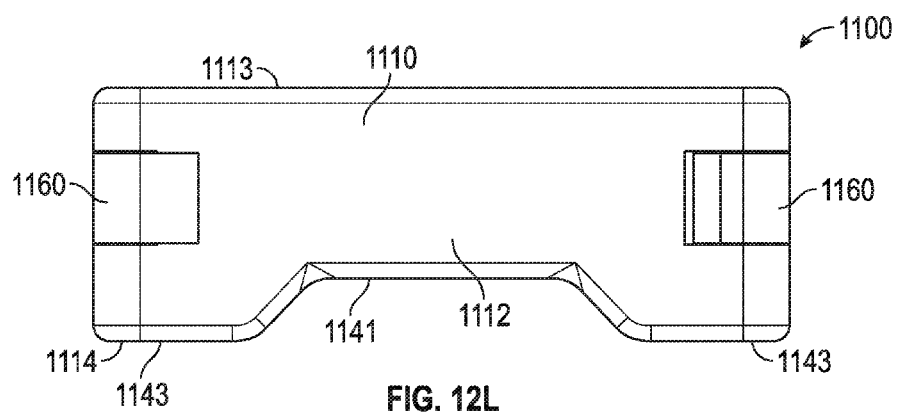
Figure 12M:
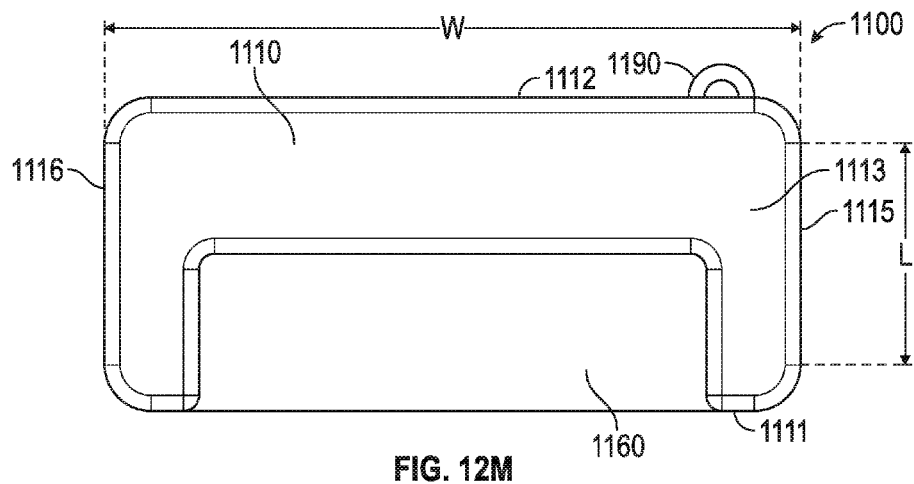
Figure 12N:
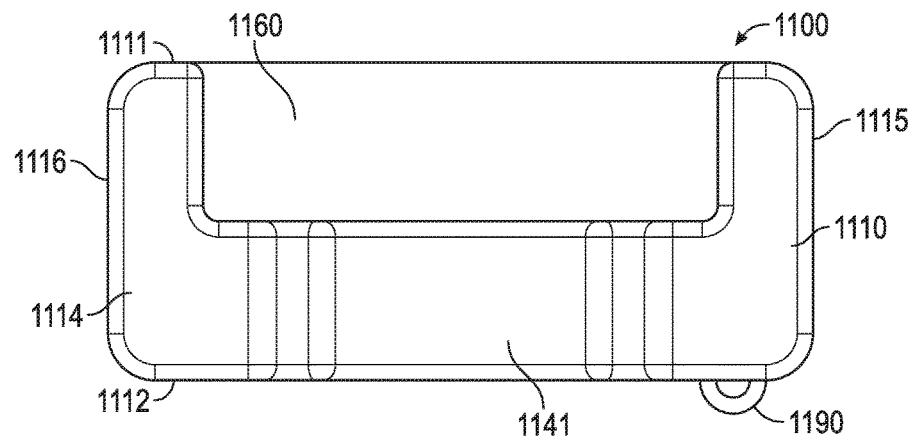
Figure 12O:
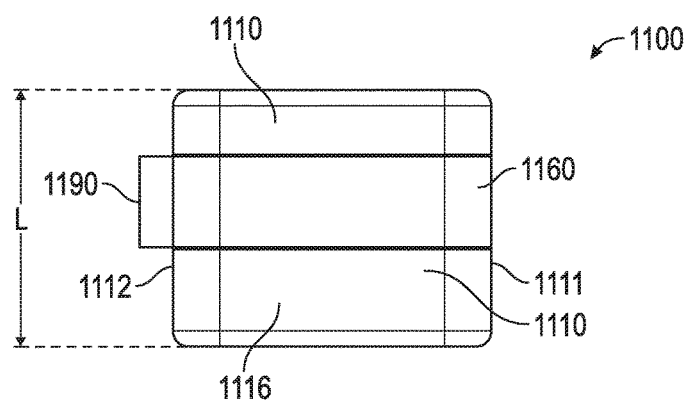
Figure 12P:
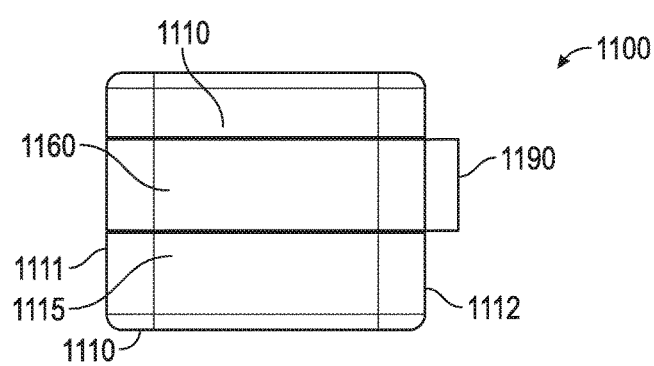

FIGS. 12A through 12P illustrate various views of a first embodiment of a suture securing device 1100 for securing a simple interrupted suture 1020. The first embodiment includes a body 1110 configured to be positioned across a patient's wound or incision 1013 and an arm 1160 attached to the body 1110 by a hinge 1190. The hinge 1190 allows the suture securing device 1100 to be transitioned between an open configuration and a closed configuration. In the open configuration the suture securing device 1100 can be positioned around exposed the portions 1021, 1023 of the suture 1020. In the closed configuration, the suture 1020 is secured between the arm 1110 and the body 1110. FIGS. 12A and 12B are perspective views of the first embodiment of the suture securing device 1100 in an open configuration and a closed configuration, respectively. FIGS. 12C and 12D are perspective views of the first embodiment of the suture securing device 1100 shown in use, positioned on a patient's skin 1010 and securing a simple interrupted suture 1020. FIGS. 12E through 12J show front, back, top, bottom, and first and second side views, respectively, of the first embodiment of the suture securing device 1100 in the open configuration. FIGS. 12K through 12P show front, back, top, bottom, and first and second side views, respectively, of the first embodiment of the suture securing device 1100 in the closed configuration. The open configuration illustrated in the figures is merely provided as an example, and the relative positioning of the components of the suture securing device 1100, for example, the relative position of the body 1110 to the arm 1160, may be varied in the open position. In other words, although the arm 1160 is illustrated as opened to approximately 180 degrees relative to the body 1110 in the figures, in some embodiments, the arm 1160 may open to less than or greater than 180 degrees.

As noted above, the suture securing device 1100 includes a body 1110 and an arm 1160. The body 1110 and the arm 1160 are connected by a hinge 1190. The hinge 1190 can be seen in, for example, FIGS. 12G and 12M. The hinge 1190 is configured to allow the arm 1160 to rotate relative to the body 1110, for example between the open configuration and the closed configuration. In general, in the open configuration, the arm 1160 is positioned away from the body 1110, and, in the closed position, at least a portion of the arm 1160 is positioned proximal to or in contact with the body 1110. As will be described in greater detail below, the suture securing device 1100 may be positioned on a patient's skin 1010 proximal to a suture 1020 in the open configuration, and then transitioned to the closed configuration to secure the suture 1020. In the illustrated embodiment, the hinge 1190 is connected to the body 1110 on a back surface 1112 of the body 1110. However, in some embodiments, the hinge 1190 may connect to the body 1110 on other surfaces and/or locations of the body 1110. In some embodiments, the hinge 1190 may be a living or compliant hinge. A living or compliant hinge may be integrally formed with the body 1110 and/or the arm 1160. In some embodiments, a mechanical hinge may be used.

The body 1110 includes a first gripping surface 1120, and the arm 1160 includes a second gripping surface 1170. The first gripping surface 1120 and the second gripping surface 1170 are positioned on the body 1110 and the arm 1160, respectively, such that, when the suture securing device 1100 is in the closed configuration, the first gripping surface 1120 contacts the second gripping surface 1170. In the closed configuration, the suture 1020 can be securely held between the first and second gripping surfaces 1120, 1170. For example, in use, suture securing device 1100 can be positioned on the patient's skin 1010 in the open configuration so that the external portions 1021, 1023 of the suture 1020 are adjacent to the first gripping surface 1120, as shown in FIG. 12C. The suture securing device 1100 can then be transitioned to the closed configuration by rotating the arm 1160 toward the body 1110 until the second gripping surface 1170 of the arm 1160 contacts the first gripping surface 1120 of the body 1110. As shown in FIG. 12D, in this configuration, the external portions 1021, 1023 of the suture 1020 are thus captured between the first gripping surface 1120 and the second gripping surface 1170, and the suture 1020 is secured. In some embodiments, the gripping surfaces 1120, 1170 include the same material as the body 1110 and/or arm 1160. In other embodiments, the gripping surfaces 1120, 1170 can be comprised of a different material with a greater friction coefficient than that of the body 1110 and/or arm 1160, for example, rubber, latex, nitrile, etc. In some embodiments, the gripping surfaces 1120, 1170 can be smooth, textured, or include other features that increase the ability of the suture securing device 1100 to retain the suture 1020. For example, one of the gripping surfaces 1120, 1170 may include one or more ridges or protrusions extending therefrom, while the other of the gripping surfaces 1120, 1170 may include corresponding grooves or recesses that are configured in size, shape, and position to mate with the corresponding ridges or protrusions.

In the illustrated embodiment, the body 1110 (or the suture securing device when in the closed configuration) is generally shaped as a rectangular prism. The body 1110 includes a front surface 1111, a back surface 1112, a top surface 1113, a bottom surface 1114, a first side surface 1115, and a second side surface 1116. Although many of these surfaces are illustrated as planar, this need not be the case in all embodiments. Similarly, although many of these surfaces are illustrated as positioned orthogonally relative to adjacent surfaces, this need not be the case in all embodiments. Various other shapes for the body 1110 are possible.

As seen, for example, in FIG. 12G, the body 1110 includes a front opening 1121. The front opening 1121 extends generally into the body 1110 from the front surface 1111 partway toward the back surface 1112. The front opening 1121 also extends entirely through the body 1110 from the top surface 1113 to the bottom surface 1114. On opposite side surfaces 1115, 1116 of the body 1110, the front opening is defined by members 1123 and 1124 which extend outwardly from the body 1110. Thus, with the front opening 1121 and the members 1123 and 1124, the body 1110 may be described as having a C-shape, as best seen in the top and bottom views of FIGS. 12G and 12H. In some instances, the front opening 1121 may be used to help position the suture securing device 1100 relative to the suture 1020. For example, with the suture securing device 1100 in the open position, the suture securing device 1100 can be positioned such that the external portions 1021, 1023 of the suture are positioned within the front opening 1121, as shown in FIG. 12C. The front opening 1121 and members 1123, 1124 may help to maintain the suture securing device 1100 and suture 1020 in position until the suture securing device is transitioned to the closed configuration. In other words, the body 1110 may have a substantially C-shaped profile when viewed from the top or bottom, and the external portions 1021, 1023 of the suture 1020 may be positioned within the opening of the C (in other words, front opening 1121).

As best seen in the front and back views of FIGS. 12E, 12F, 12K, and 12L, the bottom surface 1114 of the body 1110 includes an eversion recess 1141. The eversion recess 1141 may be configured as an indentation or opening extending into the body 1110 from the bottom surface 1114. The eversion recess 1141 may also be considered as a channel extending through the body 1110 from the front surface 1111 to the back surface 1112. A longitudinal axis of the eversion recess 1141 may be configured so as to be aligned with an incision or wound 1013 when the suture securing device 1100 is in use. The eversion recess 1141 creates a space below the suture securing device 1100 to accommodate skin eversion 1015 (as seen in FIGS. 11A and 11B) that may be present at the wound or incision closure. For example, as shown in FIGS. 12C and 12D, the suture securing device 1100 may be positioned across a wound or incision 1013, so that the bottom surface 1114 of the suture securing device 1100 rests on the surface 1011 of the patient's skin 1010 on opposite sides of the wound or incision 1013. The eversion recess 1141 may be positioned substantially directly above the wound or incision 1013 so as to accommodate skin eversion 1015. In some embodiments, the eversion recess 1141 may be omitted.

The bottom surface 1114 may be considered to have feet 1143 on opposite sides of the eversion recess 1141. The feet 1943 may be the portions of the suture securing device 1100 that contact the surface 1011 of the patient's skin 1010. In some embodiments, the feet 1943 and/or bottom surface 1114 may include a treated undersurface having adhesive, anti-bacterial, medicaments, and/or other agents for transfer to the patient's skin underlying the suture securing device to aid in positioning and/or retention of the suture securing device 1100, assist in healing, and/or reduce scarring, among other purposes.

The body 1110 also includes a channel 1131 configured to receive the arm 1160 in the closed configuration. The channel 1131 is formed as an opening which extends partway into the body 1110 from the front surface 1111 and the first and second side surfaces 1115, 1116. The channel 1131 is likely best seen in FIGS. 12E, 12F, 12I, and 12J. As shown, the channel 1131 is positioned between the top surface 1113 and the bottom surface 1114 and generally runs parallel to each. As shown in the side views of FIGS. 12I and 12J, the channel 1131 bisects the members 1123 and 1124, dividing each into two separate protrusions on each side of the suture securing device 1100. The first gripping surface 1120 is positioned within the body 1110 and at least partially defines the end of the channel 1131 in one direction: for example, the first gripping surface 1120 defines the end or depth of the channel 1131 extending into the body 1110 from the front surface 1111. In the illustrated embodiment, the channel 1131 is configured such that, in the closed configuration, the arm 1160 is substantially received within the body 1110 as shown, for example, in FIGS. 12B, 12D and 12K through 12P. Accordingly, the depth of the channel 1131 extending from the front surface 1111 and the first and second side surfaces 1115, 1116 may be chosen to correspond to the dimensions and shape of the arm 1160 as will be described in greater detail below. Similarly, the thickness of the channel 1131 may be chosen to correspond to the thickness of the arm 1160. In the illustrated embodiment, the depth of the channel 1131 extending into the body 1110 from the front surface 1111 is greater than the depth of the front opening 1121. Thus, a cross-sectional shape bisecting the body 1110 between the first and second side surfaces 1115, 1116 may also be substantially C-shaped. In some embodiments, the arm is received within the opening of the C. In the closed configuration this may cause the suture 1020 to serpentine through the body 1110, following this C-shape. This may further help to retain the suture 1020 within the suture securing device 1100 in the closed configuration. In some embodiments, the channel 1131 may be omitted or may be configured to only partially receive the arm 1160 within the body 1110.

In the illustrated embodiment, the arm 1160 includes a front member 1162 and two side members 1163 and 1164, as seen, for example, in FIG. 12G. The front member 1162 is configured to extend across the width of the suture securing device 1100. The front member 1162 also includes the second gripping surface 1170. The side members 1163 and 1164 extend as protrusions from the front member 1162 on opposite ends of the arm 1160. Accordingly, in the illustrated embodiment, the arm 1160 is substantially C-shaped, and the second gripping surface 1170 is positioned within the interior of the C. The shape of the arm 1160 may be configured so as to fit within the channel 1131 of the body 1110 described above, such that the arm 1160 may be substantially completely positioned within the body 1110 in the closed configuration. Accordingly, the front portion 1162 can be sized so as to fit within the channel 1131 extending into the body 1110 from the front surface 1111 of the body 1110. The front portion may further be configured such that the second gripping surface 1170 contacts the first gripping surface 1120 in the closed configuration. Similarly, the side members 1162, 1163 may be sized so as to fit within the channel 1131 extending into the side surfaces 1115, 1116 of the body 1110. In this way, the arm 1160 may be configured to mate with the body 1110. It will be appreciated, however, that other shapes for the arm 1160 are possible and within the scope of this disclosure.

In the illustrated embodiment, the hinge 1190 attaches to the arm 1160 at a first of the side members 1163 of the arm 1160. The second of the side members 1164 includes an engagement structure 1181 configured to correspond to and engage with a corresponding engagement structure 1151 of the body 1110. The engagement structures 1151, 1181 may cooperate to secure the arm 1160 to the body 1110 in the closed configuration. In some embodiments, the arm 1160 can be permanently locked into the closed configuration with the body 1110 after mating the engagement structures 1151, 1181. In other embodiments, the engagement structures 1151, 1181 can be configured to releasably engage, such that the arm can releasably engage the body 1110 and the suture securing device can be alternatively and repeatedly transitioned between the open and closed configuration. Releasable engagement of the engagement structures 1151, 1181 may allow for repositioning and/or tensioning adjustment of the suture 1020 over time. In the illustrated embodiment, the engagement structure 1181 on the arm 1160 includes a hooked structure, and the engagement structure 1151 of the body 1110 includes a recess. The suture securing device 1100 can thus be secured in the closed configuration by catching the hooked structure within the recess. The hooked structure and the recess may be configured for a compliant snap fit. That is, the hooked member, the side member 1164, or side of the recess may be configured to deform slightly to allow for engagement and/or disengagement. In some embodiments, these features may be reversed, such that the arm 1160 includes the recess and the body 1110 includes the hooked structure. Further, other possible engagement structures 1151, 1181 are possible and within the scope of this disclosure.

The suture securing device 1100 may be formed partially or entirely from any sturdy and resilient material, such as plastic resin, for example, polypropylene, polyethylene, acrylonitrile butadiene styrene (ABS), high impact polystyrene (HIPS), poly vinyl chloride (PVC), polycarbonate, thermoplastic elastomers, Polybutylene terephthalate, ethylene vinyl acetate, nylon and low-density polyethylene, linear low-density polyethylene, etc. In some embodiments, the body 1110, arm 1160, and hinge 1190 may be formed as a single unitary part, while in other embodiments, these parts may be formed separately and then joined together.

The suture securing device 1100 may have a width W, thickness T, and length L as illustrated in FIGS. 12M and 12O. In some embodiments, the width W may be between 1 mm to 15 mm. In some embodiments, the thickness T may be between 0.5 mm to 10 mm. In some embodiments, the length L may be between 5 mm to 60 mm. However, these ranges are merely provided as examples and may be adjusted to adapt the suture securing device 1100 for any particular application.

As previously described, the suture securing device 1100 secures the external portions 1021, 1023 of the suture between first and second gripping surfaces 1120, 1170. Accordingly, the suture securing device 1100 may be used to secure a suture 1020 without requiring the external portions 1021, 1023 to be tied into a knot. In some embodiments, the suture securing device 1100 may be used in conjunction with a knot, and the external portions 1021, 1023 of the suture 1020 extending beyond the suture securing device 1100 may be tied into a knot over the suture securing device 1100. Additionally, as best seen in FIGS. 12C and 12D, the suture securing device 1100 secures the external portions 1021, 1023 of the suture 1020 in a position at which they extend substantially orthogonally to the surface 1011 of the patient's skin 1010. Thus, the suture securing device reduces or eliminates the need for any portion of the suture 1020 rest directly on the surface of the skin as is common with convention suture securing techniques like knot tying. This may eliminate or reduce the likelihood that the suture 1020 will become ingrown as the wound or incision heals. Further, because the likelihood that the suture 1020 will be become ingrown is reduced when the suture securing device 1100 is used, the suture 1020 can remain in place for longer. For example, traditional sutures secured with knots may be removed after around two weeks to prevent them from becoming ingrown, even though the wound may not be entirely healed. In contrast, sutures secured with the suture securing device 1100 may remain in place for longer, for example up to six weeks, which may allow for more complete healing of the wound or incision.

Figure 13A:
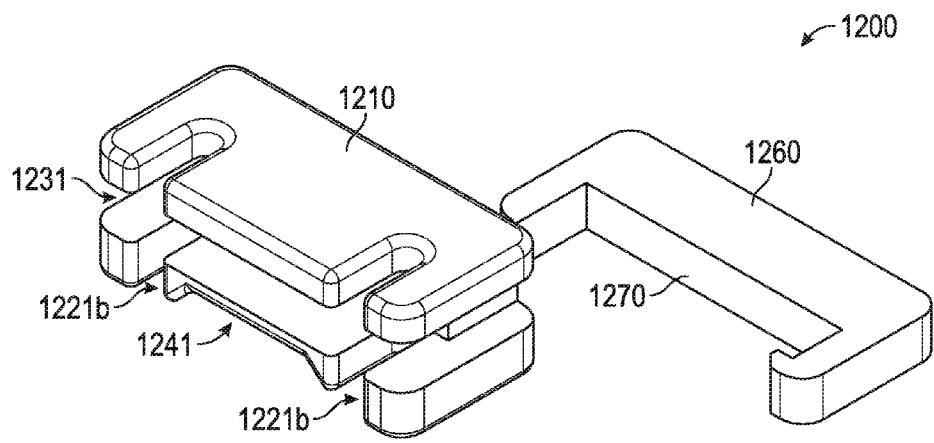
FIGS. 13A through 13P illustrate various views of a second embodiment of a suture securing device for securing a simple interrupted suture. Similar to the first embodiment of FIG. 2A, the second embodiment includes a body configured to be positioned across a patient's wound or incision and an arm attached to the body by a hinge. However, in the second embodiment, the body includes individual slots extending through the front of the body for receiving the external strands of the suture.
Figure 13B:
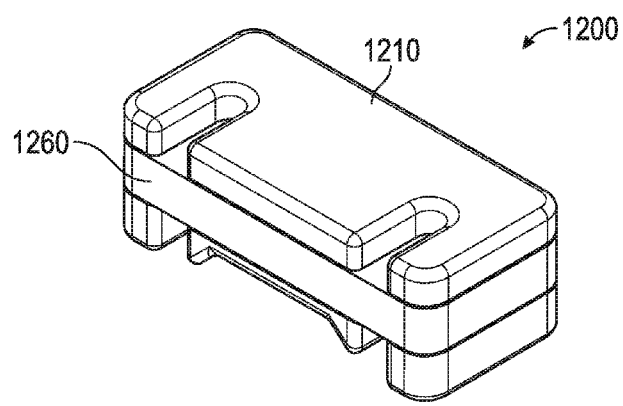
Figure 13C:
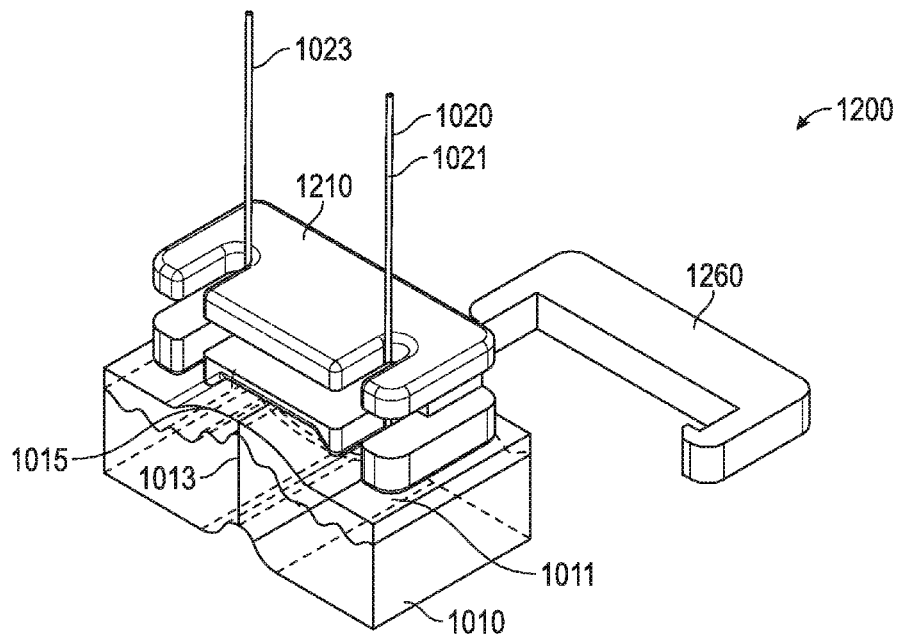
FIGS. 13C and 13D are perspective views of the second embodiment of the suture securing device shown in use, positioned on a patient's skin and securing a simple interrupted suture.
Figure 13D:
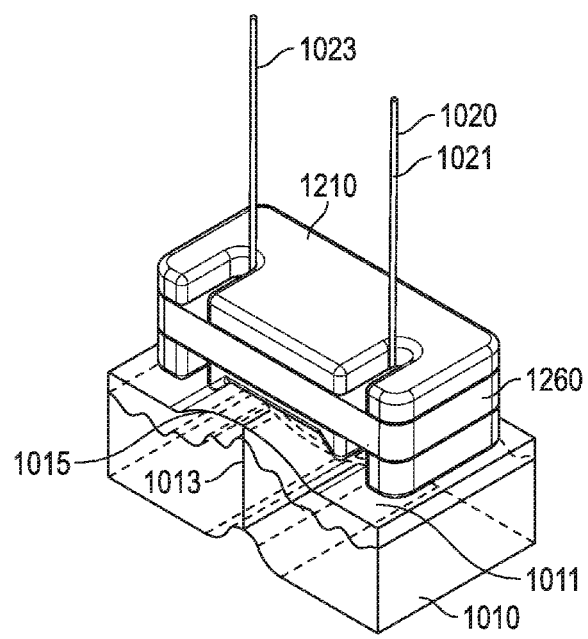
Figure 13E:
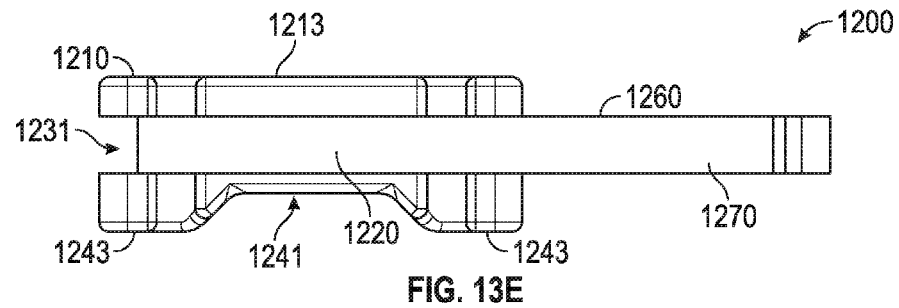
FIGS. 13E through 13J show front, back, top, bottom, and first and second side views of the second embodiment of the suture securing device in the open configuration, respectively.
Figure 13F:
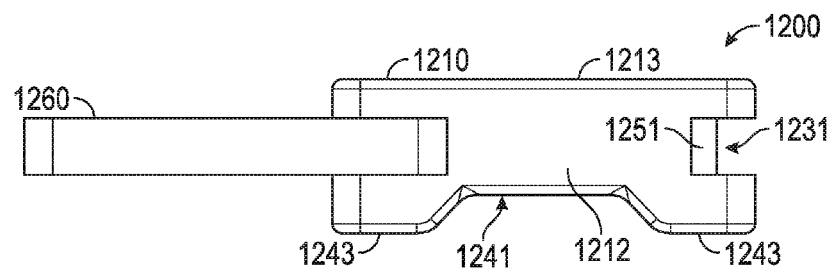
Figure 13G:
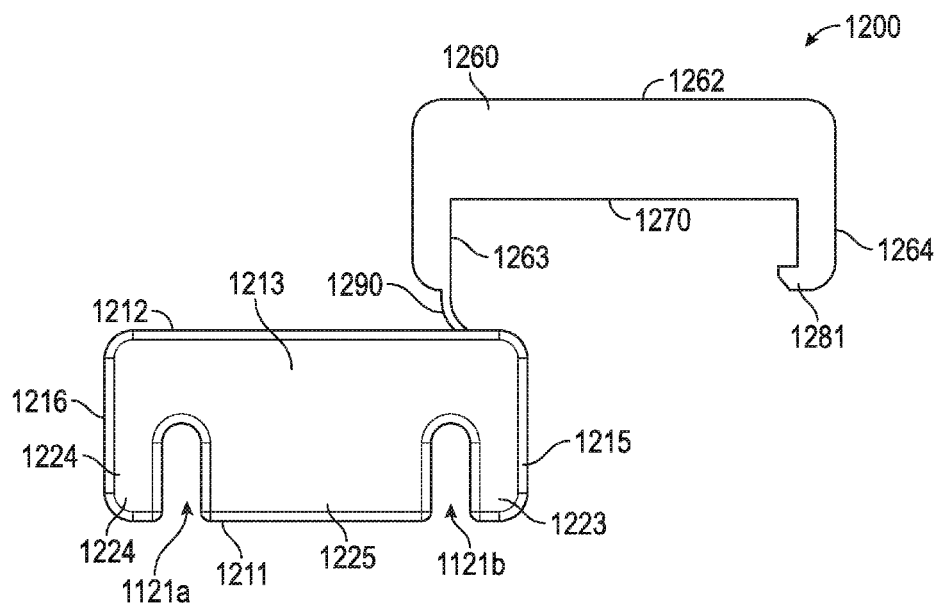
Figure 13H:
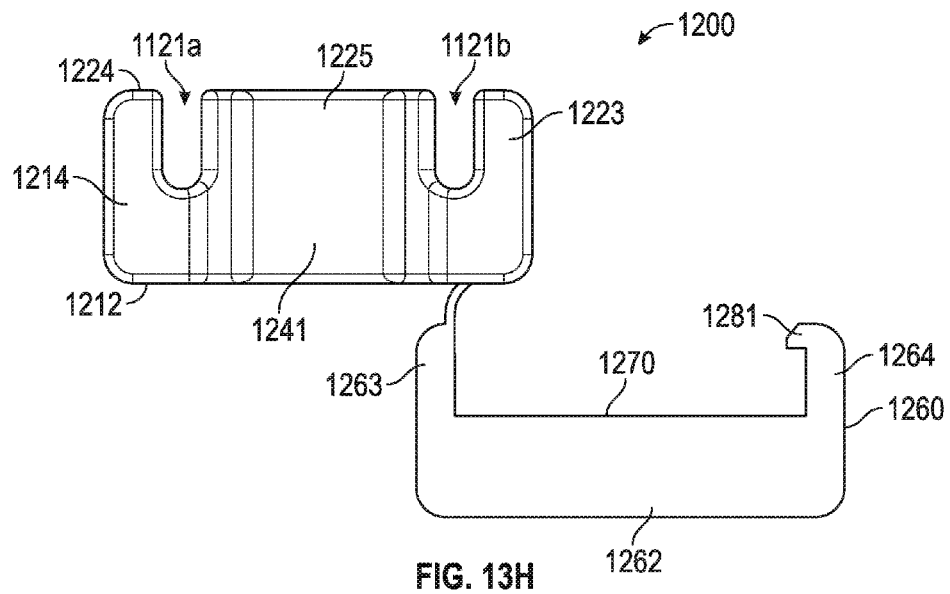
Figure 13I:
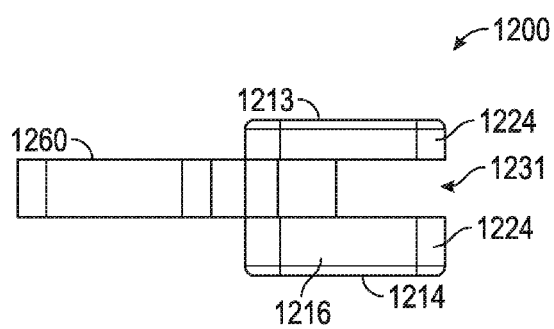
Figure 13J:
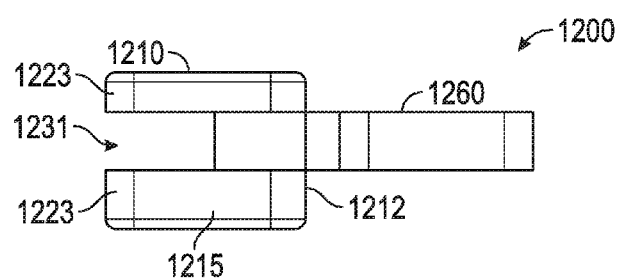
Figure 13K:
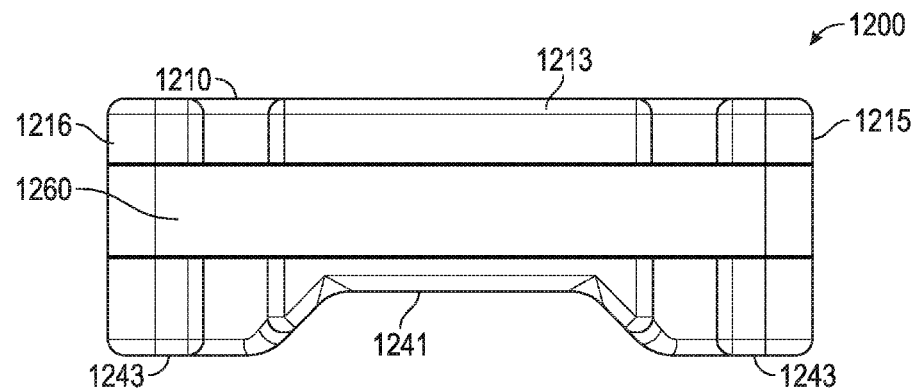
Figure 13L:
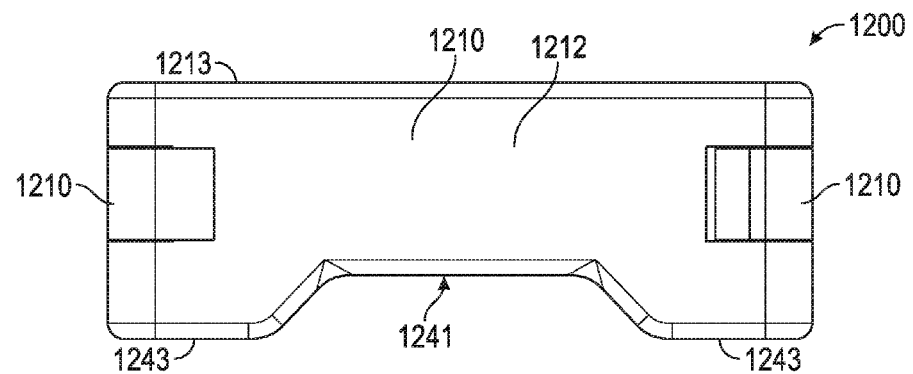
Figure 13M:
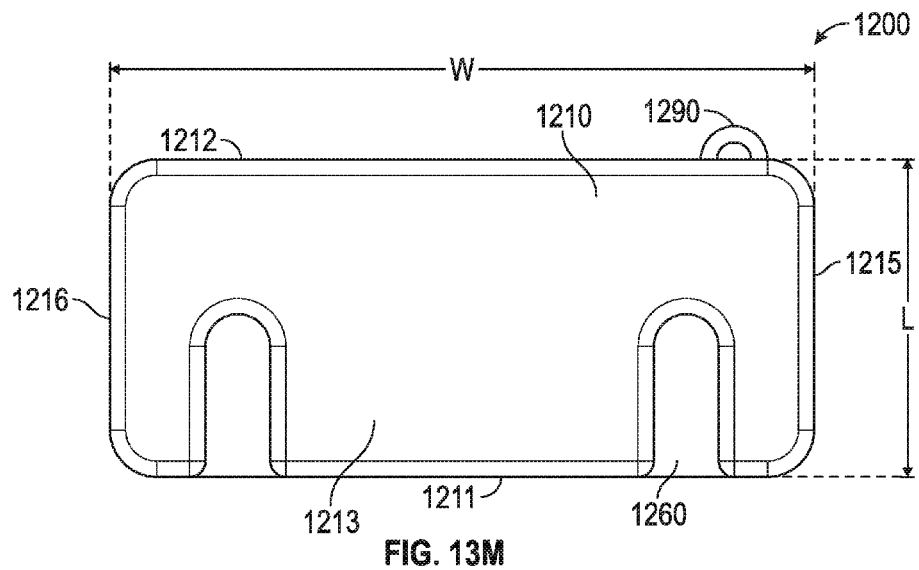
Figure 13N:
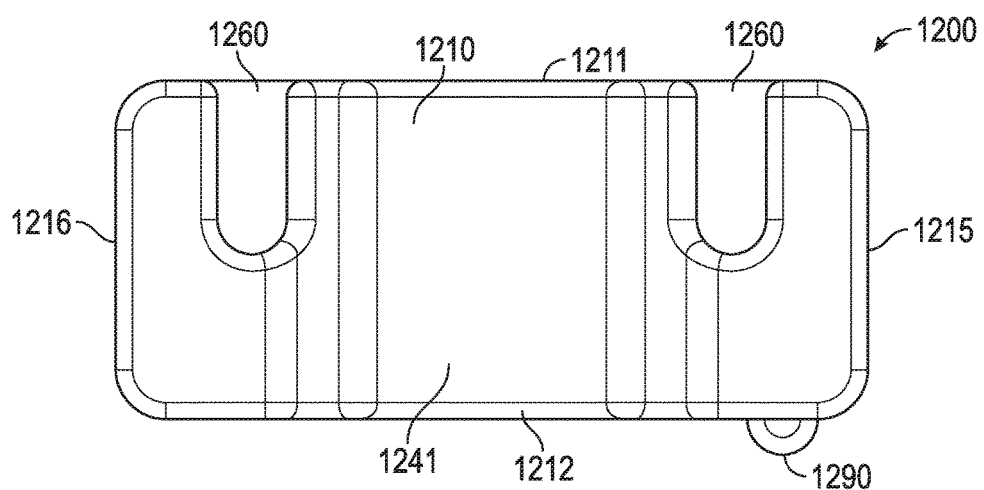
Figure 13O:
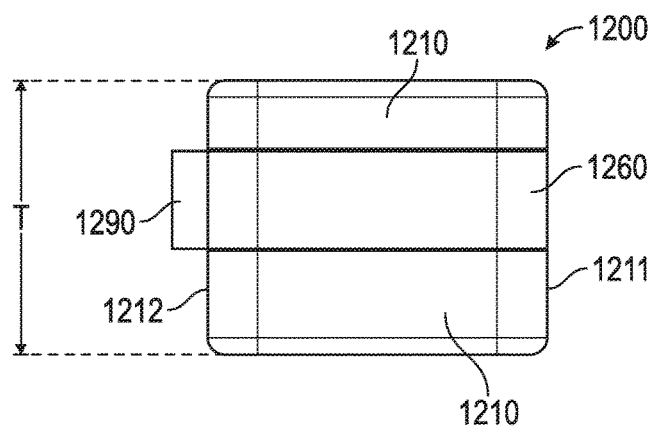
Figure 13P:
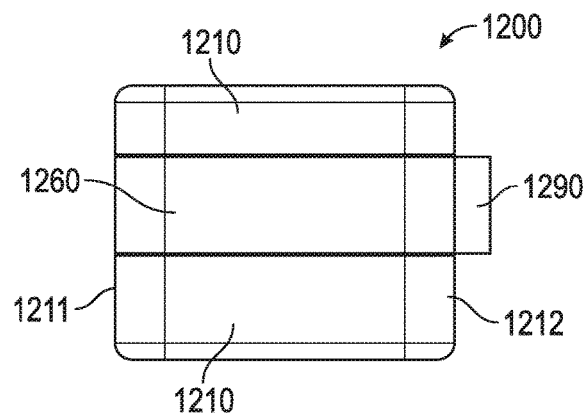

FIGS. 13A through 13P illustrate various views of a second embodiment of a suture securing device 1200 for securing a simple interrupted suture 1020. FIGS. 13A and 13B are perspective views of the second embodiment of the suture securing device 1200 in an open configuration and a closed configuration, respectively. FIGS. 13C and 13D are perspective views of the second embodiment of the suture securing device 200 shown in use, positioned on a patient's skin 1010 and securing a simple interrupted suture 1020. FIGS. 13E through 13J show front, back, top, bottom, and first and second side views of the second embodiment of the suture securing device 1200 in the open configuration, respectively. FIGS. 13K through 13P show front, back, top, bottom, and first and second side views of the second embodiment of the suture securing device 1200 in the closed configuration, respectively.

In the following description, and throughout this disclosure, similarly numbered elements are intended to be similarly configured, unless context dictates otherwise. For example, arm 1260 of the suture securing device 1200 may be similarly configured to the similarly numbered arm 1160 of the suture securing device 1100. For simplicity, similar elements of subsequent will not always be elaborated in detail when similar elements of previous embodiments have already been described. Differences between similarly numbered elements may be pointed out specifically in the text or shown in the figures. It is not intended that similarly numbered elements be exactly the same across different embodiments. As one example, body 1110 of suture securing device 1100 includes a front opening 1121, while, as will be described in greater detail below, the body 1210 of suture securing device 1200 includes individual slots 1221*a*, 1221*b*. However, in other respects, the body 1210 may be substantially similar to the body 1110.

Similar to the first embodiment of the suture securing device 1100 of FIG. 12A, the second embodiment of the suture securing device 1200 includes a body 1210 configured to be positioned across a patient's wound or incision 1013 and an arm 1260 attached to the body 1210 by a hinge 1290. However, in the second embodiment, the body 1210 includes individual slots 1211*a*, 1221*b* extending through the front of the body 1210 for receiving the external strands 1021, 1023 of the suture 1020. The hinge 1290 allows the suture securing device 1200 to be transitioned between an open configuration and a closed configuration as with the first embodiment.

As noted above, the suture securing device 1200 includes a body 1210 and an arm 1260. The body 1210 and the arm 1260 are connected by a hinge 1290. The hinge 1290 can be seen in, for example, FIGS. 13G and 13M. The hinge 1290 is configured to allow the arm 1260 to rotate relative to the body 1210, for example between the open configuration and the closed configuration. In the illustrated embodiment, the hinge 1290 is connected to the body 1210 on a back surface 1212 of the body 1210. However, in some embodiments, the hinge 1290 may connect to the body 1210 on other surfaces and/or locations of the body 1210. In some embodiments, the hinge 1290 may be a living or compliant hinge. A living or compliant hinge may be integrally formed with the body 1210 and/or the arm 1260. In some embodiments, a mechanical hinge may be used.

The body 1210 includes a first gripping surface 1220, and the arm 1260 includes a second gripping surface 1270. The first gripping surface 1220 and the second gripping surface 1270 are positioned on the body 1210 and the arm 1260, respectively, such that, when the suture securing device 1200 is in the closed configuration, the first gripping surface 1220 contacts the second gripping surface 1270. In the closed configuration, the suture 1020 can be securely held between the first and second gripping surfaces 1220, 1270. In some embodiments, the gripping surfaces 1220, 1270 include the same material as the body 1210 and/or arm 1260. In other embodiments, the gripping surfaces 1220, 1270 can be formed of a different material with a greater friction coefficient than that of the body 1210 and/or arm 1260, for example, rubber, latex, nitrile, etc. In some embodiments, the gripping surfaces 1220, 1270 can be smooth, textured, or include other features that increase the ability of the suture securing device 1200 to retain the suture 1020. For example, one of the gripping surfaces 1220, 1270 may include one or more ridges or protrusions extending therefrom, while the other of the gripping surfaces 1220, 1270 may include corresponding grooves or recesses that are configured in size, shape, and position to mate with the corresponding ridges or protrusions.

In the illustrated embodiment, the body 1210 (or the suture securing device when in the closed configuration) is generally shaped as a rectangular prism. The body 1210 includes a front surface 1211, a back surface 1212, a top surface 1213, a bottom surface 1214, a first side surface 1215, and a second side surface 1216. Although many of these surfaces are illustrated as planar, this need not be the case in all embodiments. Similarly, although many of these surfaces are illustrated as positioned orthogonally relative to adjacent surfaces, this need not be the case in all embodiments. Various other shapes for the body 1210 are possible.

As seen, for example, in FIG. 13G, the body 1210 includes two individual slots 1221*a*, 1221*b*. Each of the two individual slots 1221*a*, 1221*b* extends generally into the body 1210 from the front surface 1211 partway toward the back surface 1212. Each of the two individual slots 1221*a*, 1221*b* also extends entirely through the body 1210 from the top surface 1213 to the bottom surface 1214. On opposite side surfaces 1215, 1216 of the body 1210, the two individual slots 1221*a*, 1221*b* are defined by members 1223 and 1224 which extend outwardly from the body 1210. A member 1225 extends outwardly from the body 1210 in between the two individual slots 1221*a*, 1221*b*. Thus, with the two individual slots 1221*a*, 1221*b* and the members 1223, 1224, 1225 the body 1210 may be described as having a E-shape, as best seen in the top and bottom views of FIGS. 13G and 13H. In some instances, the two individual slots 1221*a*, 1221*b* may be used to help position the suture securing device 1200 relative to the suture 1020. For example, with the suture securing device 1200 in the open position, the suture securing device 1200 can be positioned such that each of the external portions 1021, 1023 of the suture 1020 are positioned within one of the two individual slots 1221*a*, 1221*b*, as shown in FIG. 13C. The two individual slots 1221*a*, 1221*b* and members 1223, 1224, 1225 may help to maintain the suture securing device 1200 and suture 1020 in position until the suture securing device is transitioned to the closed configuration. In other words, the body 1210 may have a substantially E-shaped profile when viewed from the top or bottom, and each of the external portions 1021, 1023 of the suture 1020 may be positioned within the openings of the E (in other words, the two individual slots 1221*a*, 1221*b*).

As best seen in the front and back views of FIGS. 13E, 13F, 13K, and 13L, the bottom surface 1214 of the body 1210 includes an eversion recess 1241. The eversion recess 1241 may be configured as an indentation or opening extending into the body 1210 from the bottom surface 1214. The eversion recess 1241 may also be considered as a channel extending through the body 1210 from the front surface 1211 to the back surface 1212. A longitudinal axis of the eversion recess 1241 may be configured so as to be aligned with an incision or wound 1013 when the suture securing device 1200 is in use. The eversion recess 1241 creates a space below the suture securing device 1200 to accommodate skin eversion 1015 (as seen in FIGS. 11A and 11B) that may be present at the wound or incision closure. In some embodiments, the eversion recess 1241 may be omitted.

The bottom surface 1214 may be considered to have feet 1243 on opposite sides of the eversion recess 1241. The feet 1243 may be the portions of the suture securing device 1200 that contact the surface 1011 of the patient's skin 1010. In some embodiments, the feet 1243 and/or bottom surface 1214 may include a treated undersurface having adhesive, anti-bacterial, medicaments, and/or other agents for transfer to the patient's skin underlying the suture securing device to aid in positioning and/or retention of the suture securing device 200, assist in healing, and/or reduce scarring, among other purposes.

The body 1210 also includes a channel 1231 configured to receive the arm 1260 in the closed configuration. The channel 1231 is formed as an opening which extends partway into the body 1210 from the front surface 1211 and the first and second side surfaces 1215, 1216. The channel 1231 is likely best seen in FIGS. 13E, 13F, 13I, and 13J. As shown, the channel 1231 is positioned between the top surface 1213 and the bottom surface 1214 and generally runs parallel to each. As shown in the side views of FIGS. 13I and 13J, the channel 1231 bisects the members 1223, 1224 and 1225, dividing each into two separate protrusions. The first gripping surface 1220 is positioned within the body 1210 and at least partially defines the end of the channel 1231 in one direction: for example, the first gripping surface 1220 defines the end or depth of the channel 1231 extending into the body 1210 from the front surface 1211. In the illustrated embodiment, the channel 1231 is configured such that, in the closed configuration, the arm 1260 is substantially received within the body 1210 as shown, for example, in FIGS. 13B, 13D and 13K through 13P. Accordingly, the depth of the channel 1231 extending from the front surface 1211 and the first and second side surfaces 1215, 1216 may be chosen to correspond to the dimensions and shape of the arm 1260 as will be described in greater detail below. Similarly, the thickness of the channel 1231 may be chosen to correspond to the thickness of the arm 1260. In the illustrated embodiment, the depth of the channel 1231 extending into the body 1210 from the front surface 1211 is greater than the depth of the two individual slots 1221*a*, 1221*b*. Thus, a cross-sectional shape bisecting the body 210 between the first and second side surfaces 1215, 1216 at either of the two individual slots 1221*a*, 1221*b* may also be substantially C-shaped. In some embodiments, the arm 1260 is received within the opening of the C. In the closed configuration this may cause the suture 1020 to serpentine through the body 1210, following this C-shape. This may further help to retain the suture 1020 within the suture securing device 1200 in the closed configuration. In some embodiments, the channel 1231 may be omitted or may be configured to only partially receive the arm 1260 within the body 1210.

In the illustrated embodiment, the arm 1260 includes a front member 1262 and two side members 1263 and 1264, as seen, for example, in FIG. 13G. The front member 1262 is configured to extend across the width of the suture securing device 1200. The front member 1262 also includes the second gripping surface 1270. The side members 1263 and 1264 extend as protrusions from the front member 1262 on opposite ends of the arm 260. Accordingly, in the illustrated embodiment, the arm 1260 is substantially C-shaped, and the second gripping surface 1270 is positioned within the interior of the C. The shape of the arm 1260 may be configured so as to fit within the channel 1231 of the body 1210 described above, such that the arm 1260 may be substantially completely positioned within the body 1210 in the closed configuration. In this way, the arm 1260 may be configured to mate with the body 1210. It will be appreciated, however, that other shapes for the arm 260 are possible and within the scope of this disclosure.

In the illustrated embodiment, the hinge 1290 attaches to the arm at a first of the side members 1263 of the arm 1260. The second of the side members 1264 includes an engagement structure 1281 configured to correspond to and engage with a corresponding engagement structure 1251 of the body 1210. The engagement structures 1251, 1281 may cooperate to secure the arm 1260 to the body 1210 in the closed configuration as described above.

The suture securing device 1200 may be formed partially or entirely from any sturdy and resilient material, such as plastic resin, for example, polypropylene, polyethylene, acrylonitrile butadiene styrene (ABS), high impact polystyrene (HIPS), poly vinyl chloride (PVC), polycarbonate, thermoplastic elastomers, Polybutylene terephthalate, ethylene vinyl acetate, nylon and low-density polyethylene, linear low-density polyethylene, etc. In some embodiments, the body 1210, arm 1260, and hinge 1290 may be formed as a single unitary part, while in other embodiments, these parts may be formed separately and then joined together.

The suture securing device 1200 may have a width W, thickness T, and length L as illustrated in FIGS. 13M and 13O. The width W, thickness T, and length L may be similar to those described above.

The suture securing device 1200 secures the external portions 1021, 1023 of the suture between first and second gripping surfaces 1220, 1270 in a manner similar to that described above in reference to the suture securing device 1100. The principal difference being that the body 210 is configured with the two individual slots 1221*a*, 1221*b*, each of which receives on of the external portions 1021, 1023 of the suture 1020. Accordingly, the suture securing device 1200 provides similar benefits to those identified above, including securing a suture 1020 without requiring a knot to be tied and preventing a suture 1020 from becoming ingrown.

Figure 14A:
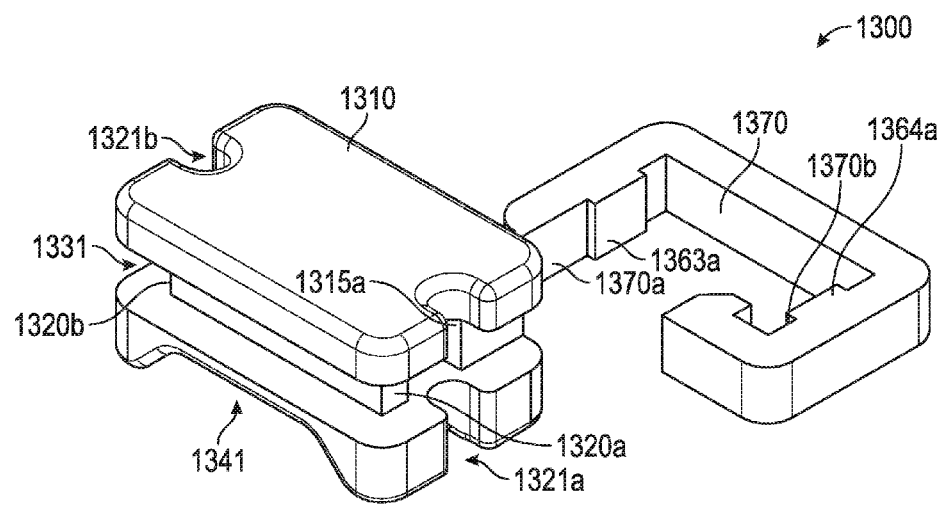
FIGS. 14A through 14P illustrate various views of a third embodiment of a suture securing device for securing a simple interrupted suture. Similar to the second embodiment of FIG. 13A, the third embodiment includes a body with individual slots extending through the body for receiving the external strands of the suture. However, in the third embodiment, the individual slots extend through opposite sides of the body.
Figure 14B:
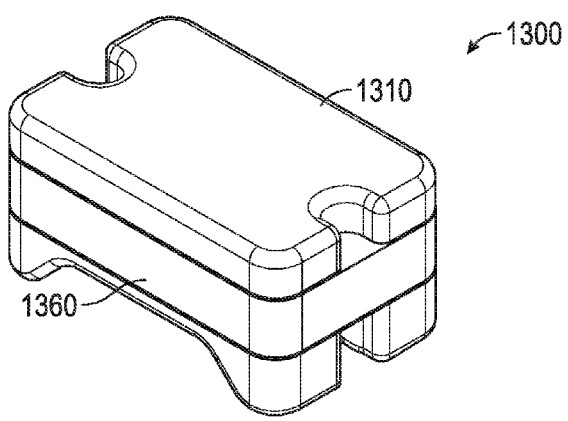
Figure 14C:
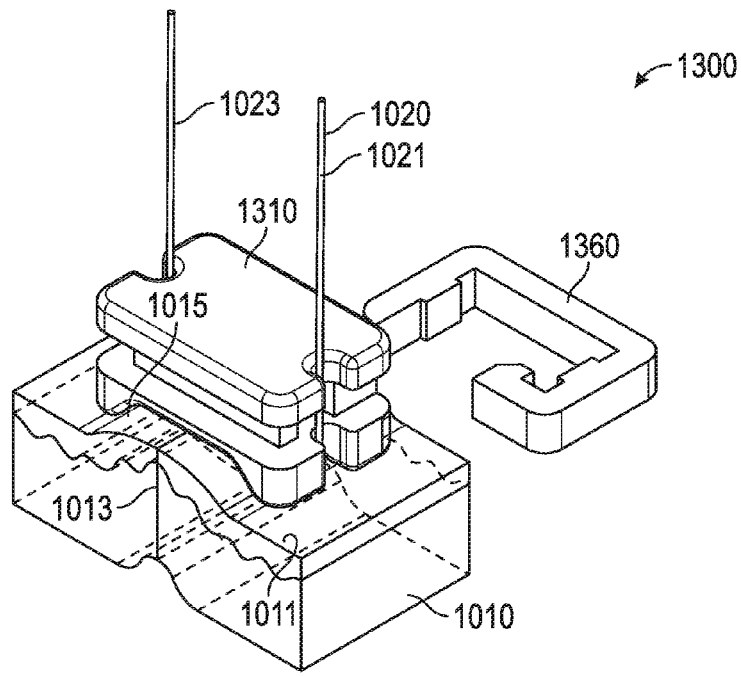
FIGS. 14C and 14D are perspective views of the third embodiment of the suture securing device shown in use, positioned on a patient's skin and securing a simple interrupted suture.
Figure 14D:
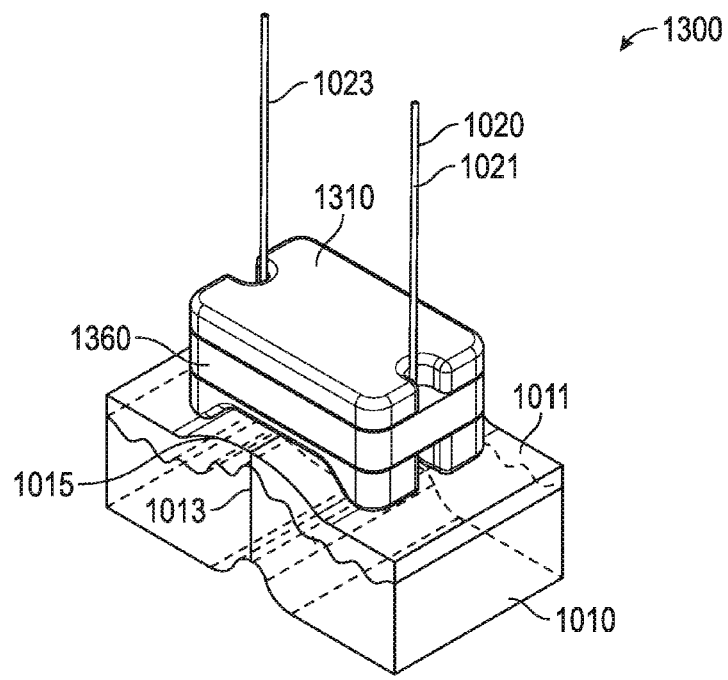
Figure 14E:
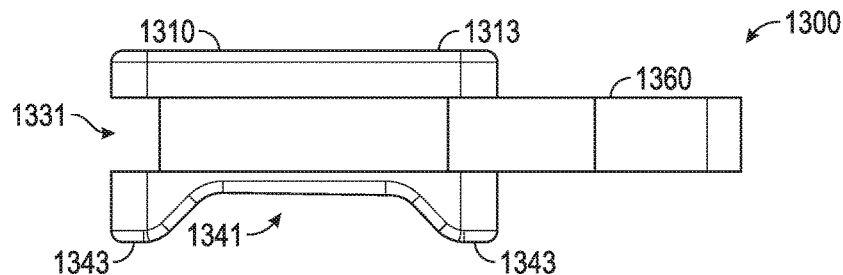
FIGS. 14E through 14J show front, back, top, bottom, and first and second side views of the third embodiment of the suture securing device in the open configuration, respectively.
Figure 14F:
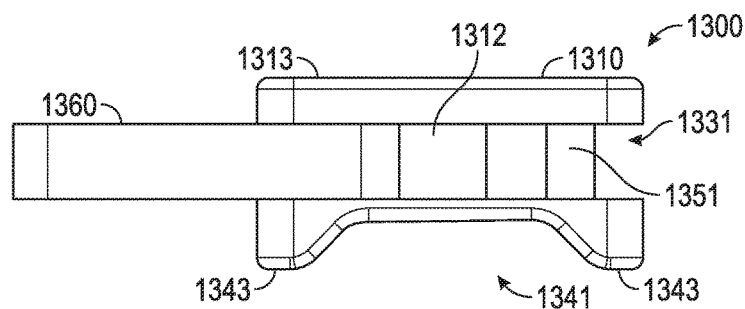
Figure 14G:
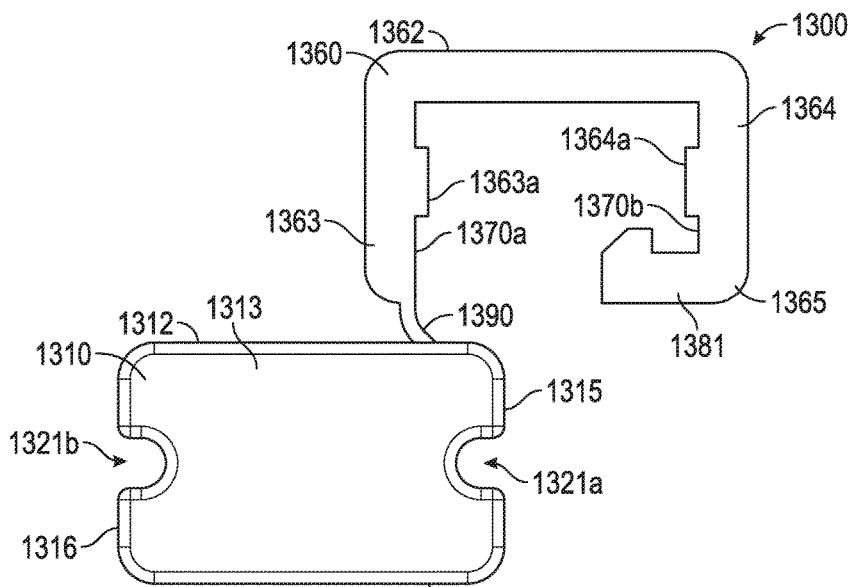
Figure 14H:
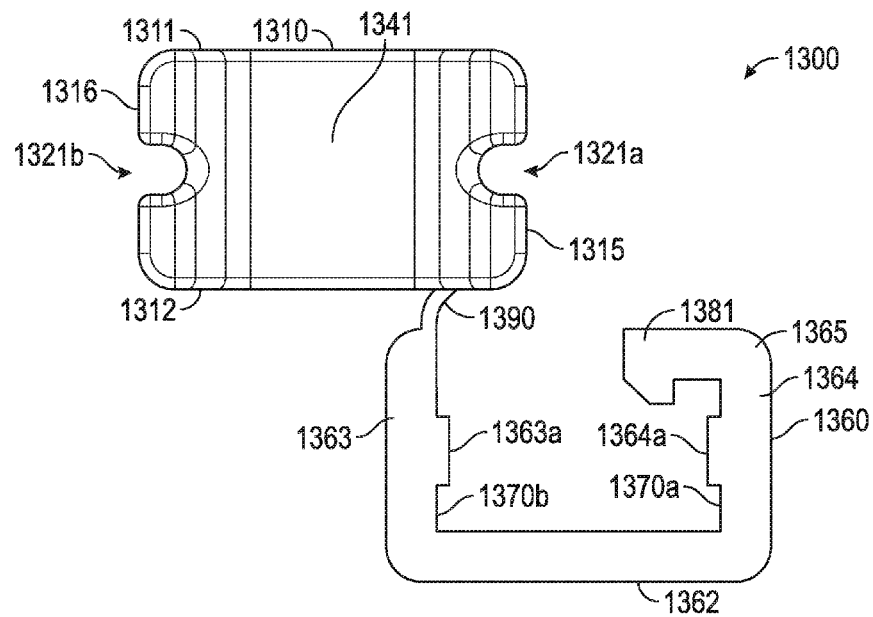
Figure 14I:
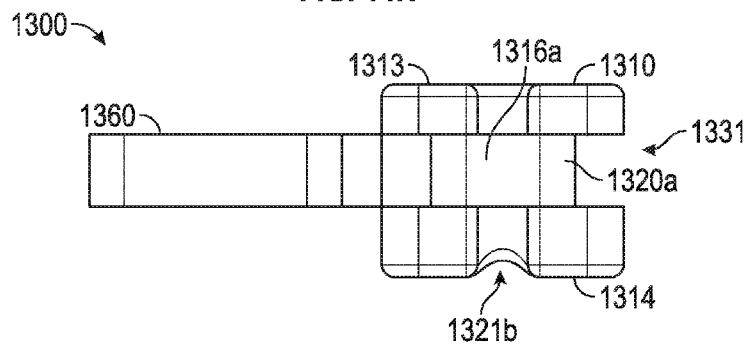
Figure 14J:
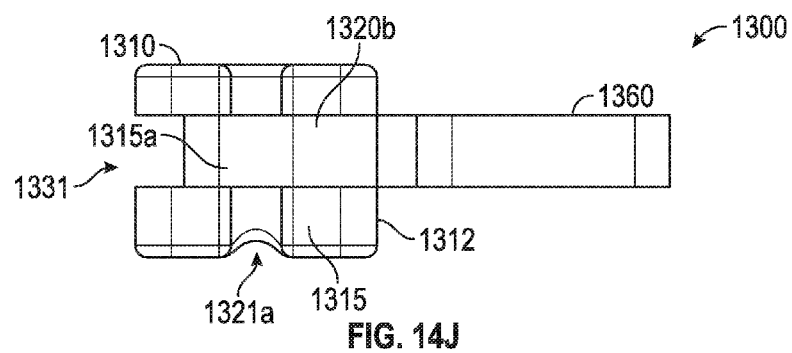
Figure 14K:
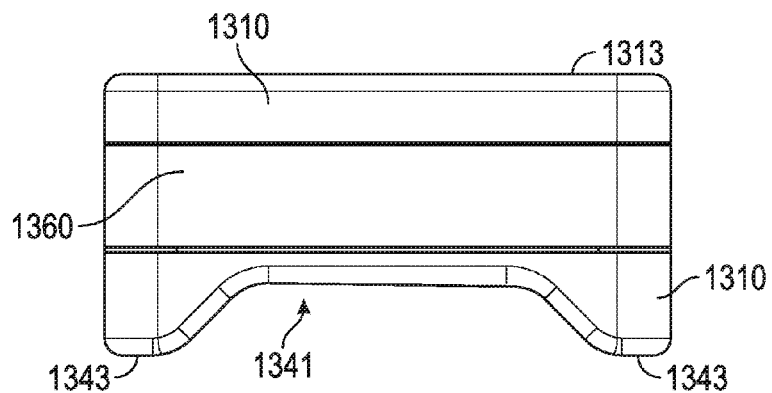
Figure 14L:
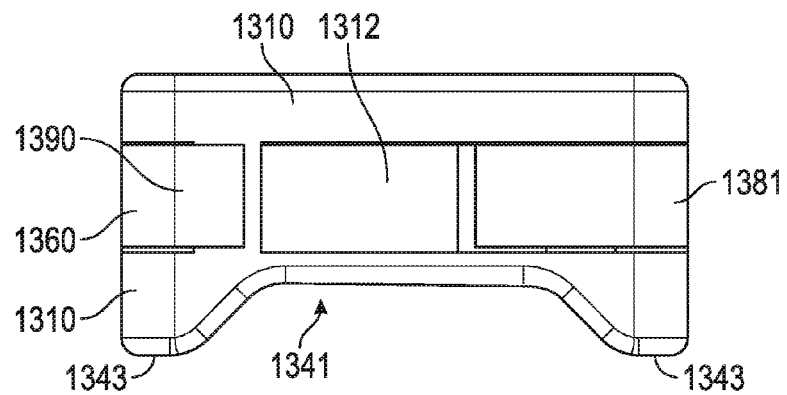
Figure 14M:
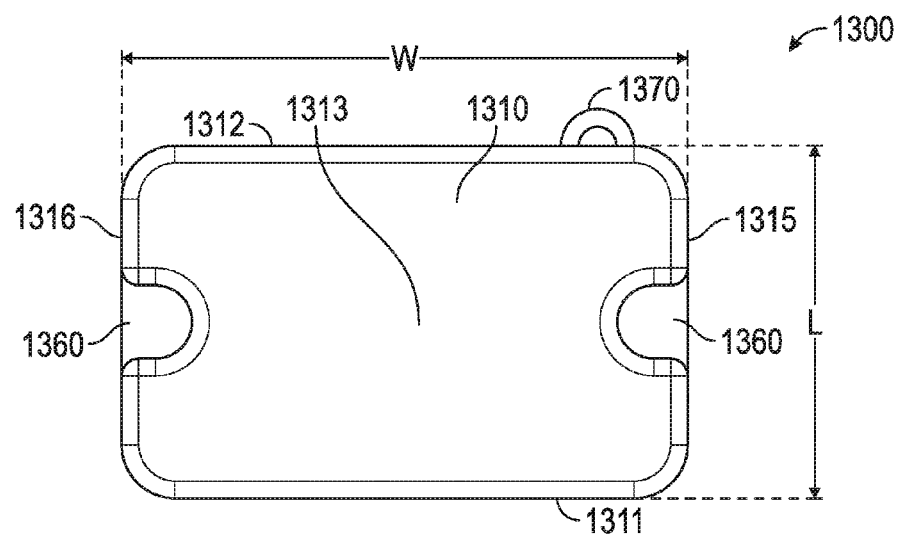
Figure 14N:
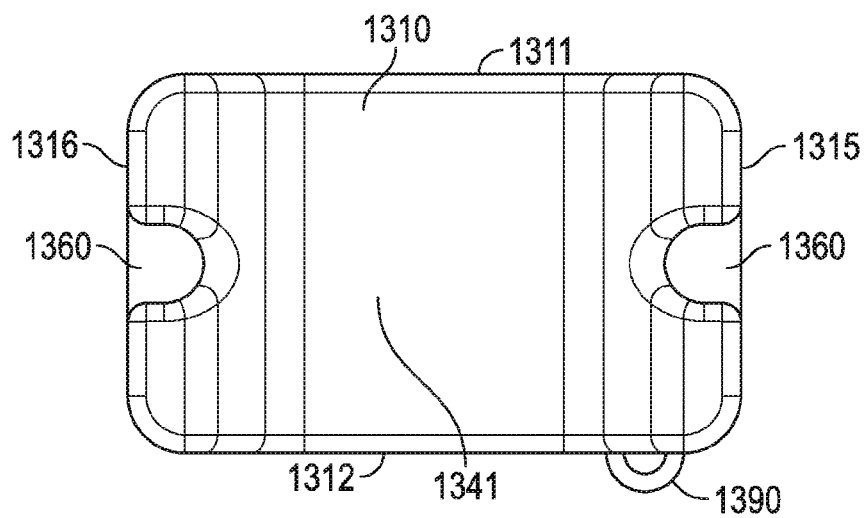
Figure 14O:
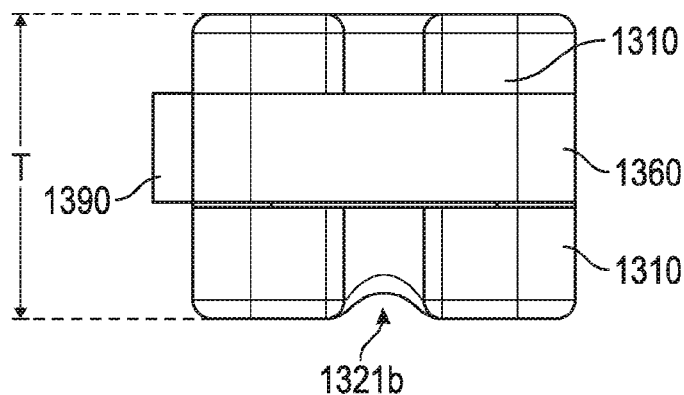
Figure 14P:
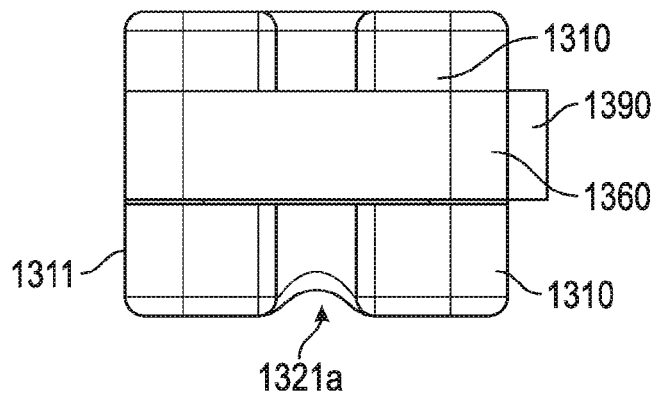

FIGS. 14A through 14P illustrate various views of a third embodiment of a suture securing device 1300 for securing a simple interrupted suture 1020. FIGS. 14A and 14B are perspective views of the third embodiment of the suture securing device 1300 in an open configuration and a closed configuration, respectively. FIGS. 14C and 14D are perspective views of the third embodiment of the suture securing device 1300 shown in use, positioned on a patient's skin 1010 and securing a simple interrupted suture 1020. FIGS. 14E through 14J show front, back, top, bottom, and first and second side views of the third embodiment of the suture securing device 1300 in the open configuration, respectively. FIGS. 14K through 14P show front, back, top, bottom, and first and second side views of the third embodiment of the suture securing device 1300 in the closed configuration, respectively.

In many ways similar to the second embodiment of the suture securing device 1200 of FIG. 13A, the third embodiment of the suture securing device 1300 includes a body 1310 with individual slots 1321*a*, 1321*b* extending through the body 1310 for receiving the external strands 1021, 1023 of the suture 1020. However, in the suture securing device 1300, the individual slots 1321*a*, 1321*b* extend through opposite sides 1315, 1316 of the body 1310, as will be described in greater detail below.

The third embodiment of the suture securing device 1300 includes a body 1310 and an arm 1360. The body 1310 and the arm 1360 are connected by a hinge 1390. The hinge 1390 can be seen in, for example, FIGS. 4G and 4M. The hinge 1390 is configured to allow the arm 1360 to rotate relative to the body 1310, for example between the open configuration and the closed configuration. In the illustrated embodiment, the hinge 1390 is connected to the body 1310 on a back surface 1312 of the body 1310. However, in some embodiments, the hinge 1390 may connect to the body 1310 on other surfaces and/or locations of the body 1310. In some embodiments, the hinge 1390 may be a living or compliant hinge. A living or compliant hinge may be integrally formed with the body 1310 and/or the arm 1360. In some embodiments, a mechanical hinge may be used.

The body 1310 includes first gripping surfaces 1320*a*, 1320*b* located on opposite sides of the body 1310, and the arm 1360 includes second gripping surfaces 1370*a*, 1370*b* located on opposite sides of the arm. The first gripping surfaces 1320*a*, 1320*b* and the second gripping surfaces 1370*a*, 1370*b* are positioned on the body 1310 and the arm 1360, respectively, such that, when the suture securing device 1300 is in the closed configuration, the first gripping surfaces 1320*a*, 1320*b* contact the second gripping surfaces 1370*a*, 1370*b*, respectively. In the closed configuration, the suture 1020 can be securely held between the first and second gripping surfaces 1320*a*, 1320*b*, 1370*a*, 1370*b*, on each side of the body 1310. In some embodiments, the gripping surfaces 1320*a*, 1320*b*, 1370*a*, 1370*b* are formed of the same material as the body 1310 and/or arm 1360. In other embodiments, the gripping surfaces 1320*a*, 1320*b*, 1370*a*, 1370*b* can be formed of a different material with a greater friction coefficient than that of the body 1310 and/or arm 1360, for example, rubber, latex, nitrile, etc. In some embodiments, the gripping surfaces 1320*a*, 1320*b*, 1370*a*, 1370*b* can be smooth, textured, or include other features that increase the ability of the suture securing device 1300 to retain the suture 1020. For example, one of the gripping surfaces 1320*a*, 1320*b*, 1370*a*, 1370*b* may include one or more ridges or protrusions extending therefrom, while the other of the gripping surfaces 1320*a*, 1320*b*, 1370*a*, 1370*b* may include corresponding grooves or recesses that are configured in size, shape, and position to mate with the corresponding ridges or protrusions.

In the illustrated embodiment, the body 1310 (or the suture securing device 1300 when in the closed configuration) is generally shaped as a rectangular prism. The body 1310 includes a front surface 1331, a back surface 1312, a top surface 1313, a bottom surface 1314, a first side surface 1315, and a second side surface 1316. Although many of these surfaces are illustrated as planar, this need not be the case in all embodiments. Similarly, although many of these surfaces are illustrated as positioned orthogonally relative to adjacent surfaces, this need not be the case in all embodiments. Various other shapes for the body 1310 are possible.

As seen, for example, in FIG. 14G, the body 1310 includes two individual slots 1321*a*, 1321*b*. Each of the two individual slots 1321*a*, 1321*b* extends generally into the body 1310 from one of the opposite side surfaces 1315, 1316, respectively. As shown, the two individual slots 1321*a*, 1321*b* extend into the body 1310 toward each other. In the illustrated embodiment, the two individual slots 1321*a*, 1321*b* are aligned with each other, although this need not be the case in all embodiments. Each of the two individual slots 1321*a*, 1321*b* also extends entirely through the body 1310 from the top surface 1313 to the bottom surface 1314. Thus, with the two individual slots 1321*a*, 1321*b*, the body 1310 may be described as having an H-shape, as best seen in the top and bottom views of FIGS. 14G and 14H. In some instances, the two individual slots 1321*a*, 1321*b* may be used to help position the suture securing device 1300 relative to the suture 1020. For example, with the suture securing device 1300 in the open position, the suture securing device 1300 can be positioned such that each of the external portions 1021, 1023 of the suture 1020 are positioned within one of the two individual slots 1321*a*, 1321*b*. In other words, the body 1310 may have a substantially H-shaped profile when viewed from the top or bottom, and each of the external portions 1021, 1023 of the suture 1020 may be positioned within the openings of the H (in other words, the two individual slots 1321*a*, 1321*b* on opposite sides 1315, 1316 of the body 1310).

As best seen in the front and back views of FIGS. 14E, 14F, 14K, and 14L, the bottom surface 1314 of the body 1310 includes an eversion recess 1341. The eversion recess 1341 may be configured as an indentation or opening extending into the body 1310 from the bottom surface 1314. The eversion recess 1341 may also be considered as a channel extending through the body 1310 from the front surface 1331 to the back surface 1312. A longitudinal axis of the eversion recess 1341 may be configured so as to be aligned with an incision or wound 1013 when the suture securing device 1300 is in use. The eversion recess 1341 creates a space below the suture securing device 1300 to accommodate skin eversion 1015 (as seen in FIGS. 11A and 11B) that may be present at the wound or incision closure. In some embodiments, the eversion recess 1341 may be omitted.

The bottom surface 1314 may be considered to have feet 1343 on opposite sides of the eversion recess 1341. The feet 1343 may be the portions of the suture securing device 1300 that contact the surface 1011 of the patient's skin 1010. In some embodiments, the feet 1343 and/or bottom surface 1314 may include a treated undersurface having adhesive, anti-bacterial, medicaments, and/or other agents for transfer to the patient's skin underlying the suture securing device to aid in positioning and/or retention of the suture securing device 1300, assist in healing, and/or reduce scarring, among other purposes.

The body 1310 also includes a channel 1331 configured to receive the arm 1360 in the closed configuration. The channel 1331 is formed as an opening which extends partway into the body 1310 from the front surface 1331, back surface 1312, and the first and second side surfaces 1315, 1316. The channel 1331 is likely best seen in FIGS. 14E, 14F, 14I, and 14J. As shown, the channel 1331 is positioned between the top surface 1313 and the bottom surface 1314 and generally runs parallel to each. The first gripping surfaces 1320*a*, 1320*b* are positioned within the body 1310 and each at least partially define the end of the channel 1331 in one direction: for example, the first gripping surface 1320*a* defines the end or depth of the channel 1331 extending into the body 1310 from the first side surface 1315 and the first gripping surface 1320*b* defines the end or depth of the channel 1331 extending into the body 1310 from the second side surface 1316. In the illustrated embodiment, the channel 1331 is configured such that, in the closed configuration, the arm 1360 is substantially received within the body 1310 as shown, for example, in FIGS. 14B, 14D and 14K through 14P. Accordingly, the depth of the channel 1331 extending from the front surface 1331 and the first and second side surfaces 1315, 1316 may be chosen to correspond to the dimensions and shape of the arm 1360 as will be described in greater detail below. Similarly, the thickness of the channel 1331 may be chosen to correspond to the thickness of the arm 1360.

In the illustrated embodiment, and as best seen in FIGS. 14I and 14J (also partially visible in FIG. 14A) the depth of the channel 1331 extending into the body 1310 from the side surfaces 1315, 1316 may include deeper portions 1315*a*, 1316*a* in the areas of the two individual slots 1321*a*, 1321*b*. These deeper portions 1315*a*, 1316*a* are configured to correspond to and mate with protrusions 1363*a*, 1364*a* which extend from the second gripping surfaces 1370*a*, 1370*b*, respectively, of the arm 1360. In the closed configuration, the deeper portions 1315*a*, 1316*a* mate with corresponding protrusions 1363*a*, 1364*a* to further secure the suture between the first and second gripping surfaces 1320*a*, 1320*b*, 1370*a*, 1370*b*. In some embodiments, the deeper portions 1315*a*, 1316*a* and protrusions 1363*a*, 1364*a* may be omitted. In some embodiments, the channel 1331 may be omitted or may be configured to only partially receive the arm 1360 within the body 1310.

In the illustrated embodiment, the arm 1360 includes a front member 1362, a back member 1365, and two side members 1363, 1364, as seen, for example, in FIG. 4G. The front member 1362 is configured to extend across the width of the suture securing device 1300. The side members 1363, 1364 extend as protrusions from the front member 1362 on opposite ends of the arm 1360. The second gripping surfaces 1360*a*, 1360*b* are located on the side members 1363, 1364. In some embodiments, the protrusions 1363*a*, 1364*a* extend inwardly from the side members 1363, 1364. The shape of the arm 1360 may be configured so as to fit within the channel 1331 of the body 1310 described above, such that the arm 1360 may be substantially completely positioned within the body 1310 in the closed configuration. In this way, the arm 1360 may be configured to mate with the body 1310. It will be appreciated, however, that other shapes for the arm 1360 are possible and within the scope of this disclosure.

In the illustrated embodiment, the hinge 1390 attaches to the arm at a first of the side members 1363 of the arm 1360. The second of the side members 1364 is attached to a back member 1365 which includes an engagement structure 1381 configured to correspond to and engage with a corresponding engagement structure 1351 of the body 1310. The engagement structures 1351, 1381 may cooperate to secure the arm 1360 to the body 1310 in the closed configuration as described above.

The suture securing device 1300 may be formed partially or entirely from any sturdy and resilient material, such as plastic resin, for example, polypropylene, polyethylene, acrylonitrile butadiene styrene (ABS), high impact polystyrene (HIPS), poly vinyl chloride (PVC), polycarbonate, thermoplastic elastomers, Polybutylene terephthalate, ethylene vinyl acetate, nylon and low-density polyethylene, linear low-density polyethylene, etc. In some embodiments, the body 1310, arm 1360, and hinge 1390 may be formed as a single unitary part, while in other embodiments, these parts may be formed separately and then joined together.

The suture securing device 1300 may have a width W, thickness T, and length L as illustrated in FIGS. 14M and 14O. The width W, thickness T, and length L may be similar to those described above.

The suture securing device 1300 secures the external portions 1021, 1023 of the suture between first and second gripping surfaces 1320*a*, 1320*b*, 1370*a*, 1370*b* in a manner similar to that described above in reference to the suture securing device 1300. The principal difference being that the body 1310 is configured with the two individual slots 1321*a*, 1321*b* located on the side surfaces 1315, 1316. Accordingly, the suture securing device 1300 provides similar benefits to those identified above, including securing a suture 1020 without requiring a knot to be tied and preventing a suture 1020 from becoming ingrown.

Figure 15A:
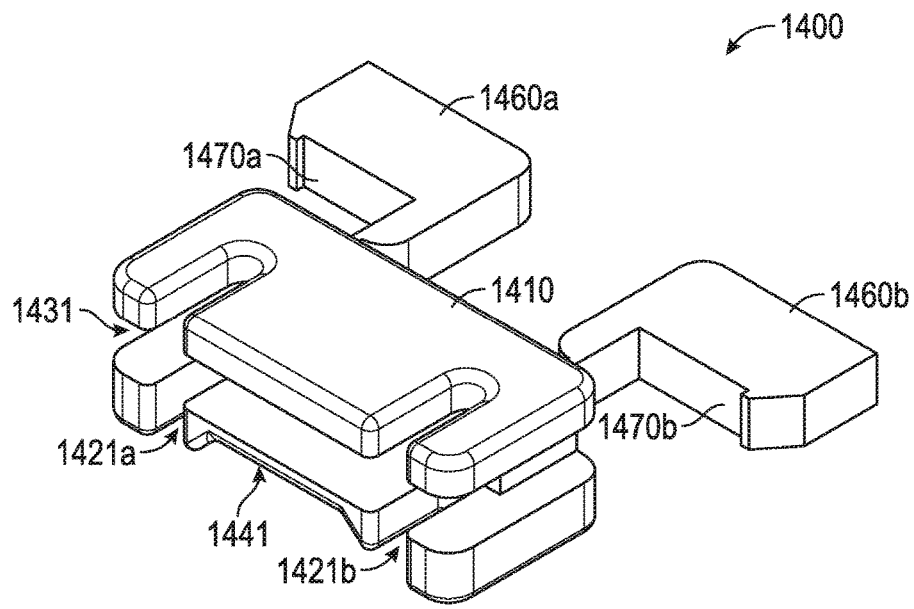
FIGS. 15A through 15P illustrate various views of a fourth embodiment of a suture securing device for securing a simple interrupted suture. The fourth embodiment includes two arms attached to the body by hinges. The hinges allow the suture securing device to be transitioned between an open configuration and a closed configuration. Similar to the second embodiment of FIG. 3A, the body of the fourth embodiment includes individual slots extending through the front of the body for receiving the external strands of the suture.
Figure 15B:
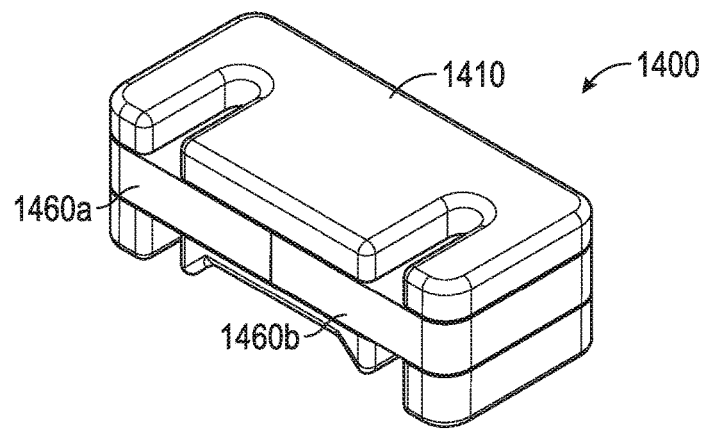
Figure 15C:
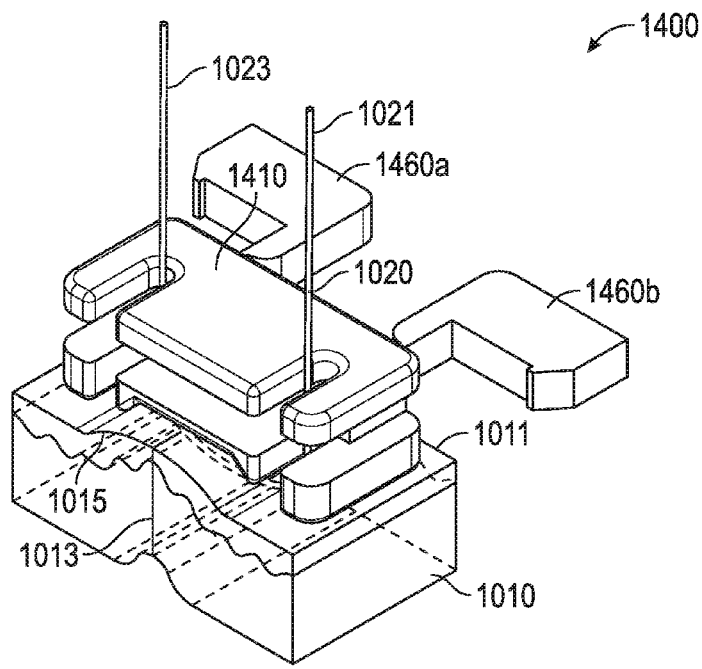
FIGS. 15C and 15D are perspective views of the fourth embodiment of the suture securing device shown in use, positioned on a patient's skin and securing a simple interrupted suture.
Figure 15D:
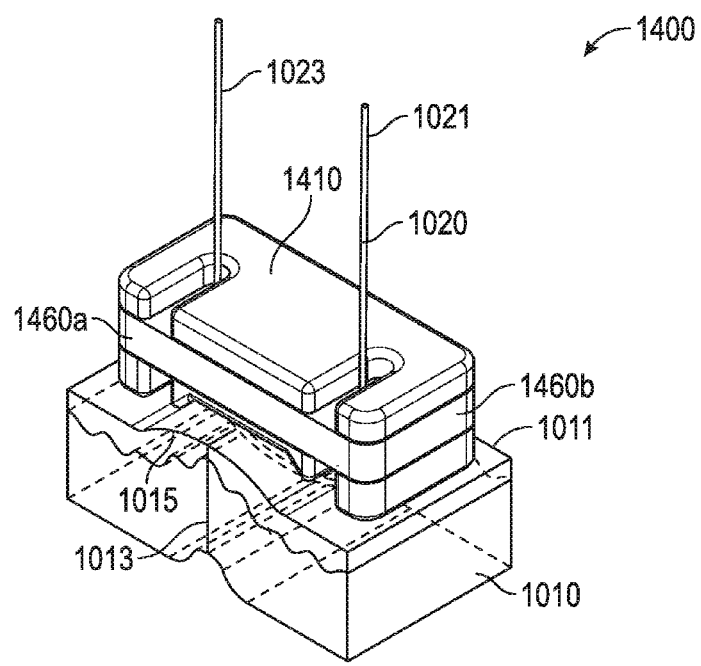
Figure 15E:
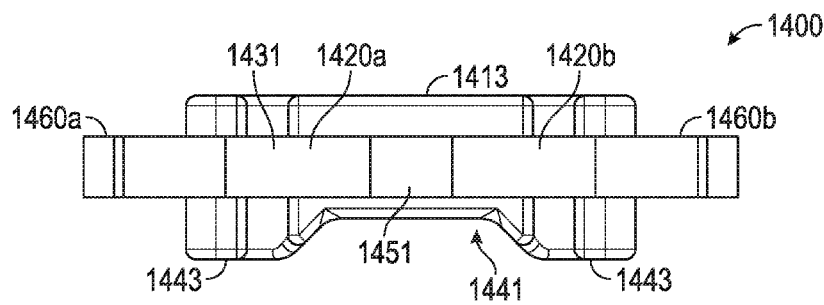
FIGS. 15E through 15J show front, back, top, bottom, and first and second side views of the fourth embodiment of the suture securing device in the open configuration, respectively.
Figure 15F:
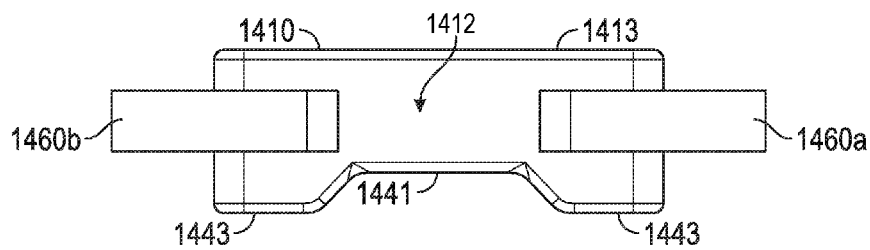
Figure 15G:
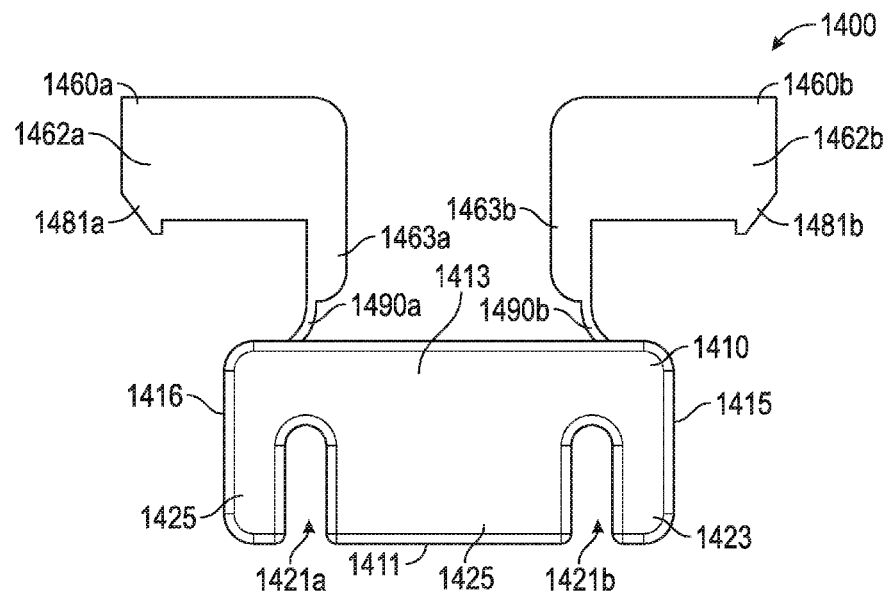
Figure 15H:
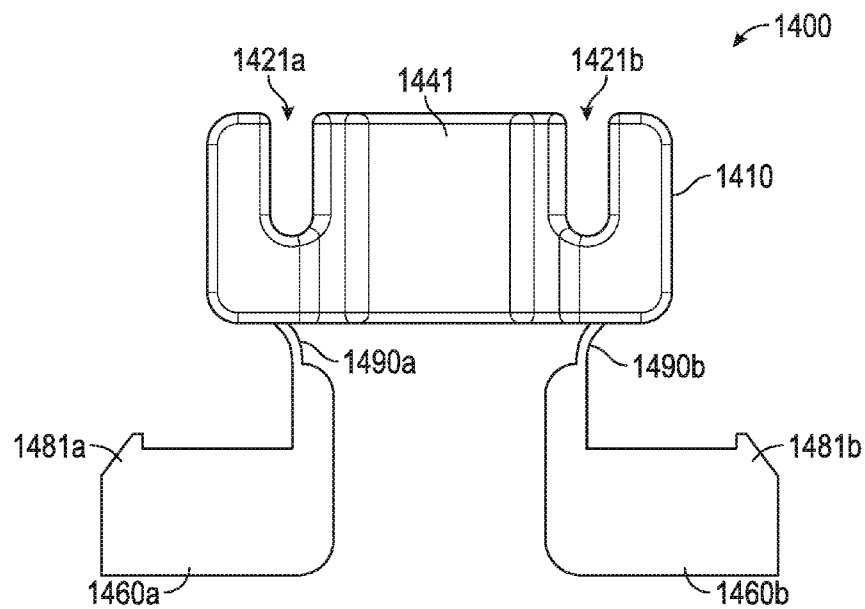
Figure 15I:
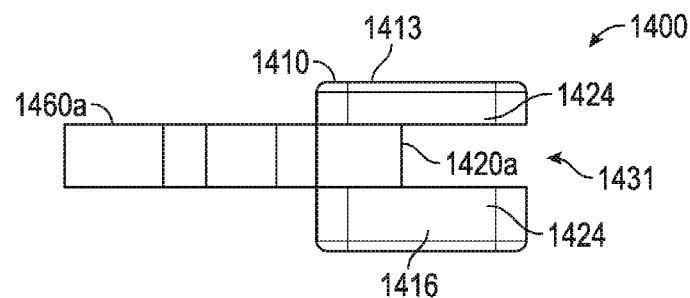
Figure 15J:
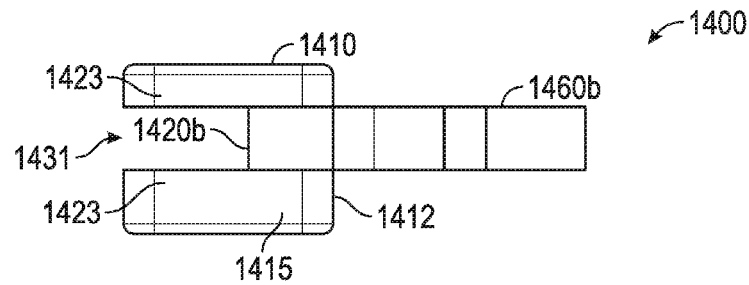
Figure 15K:
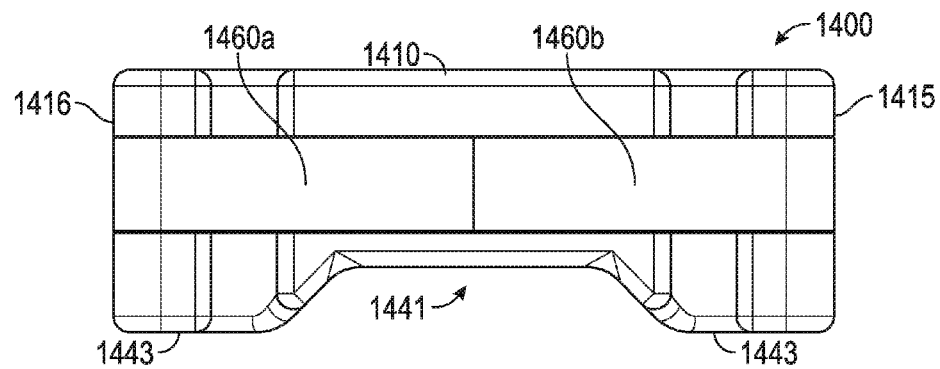
Figure 15L:
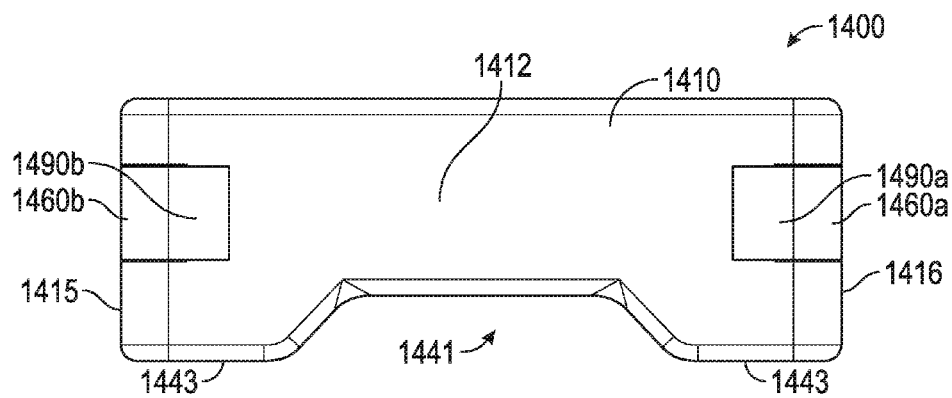
Figure 15M:
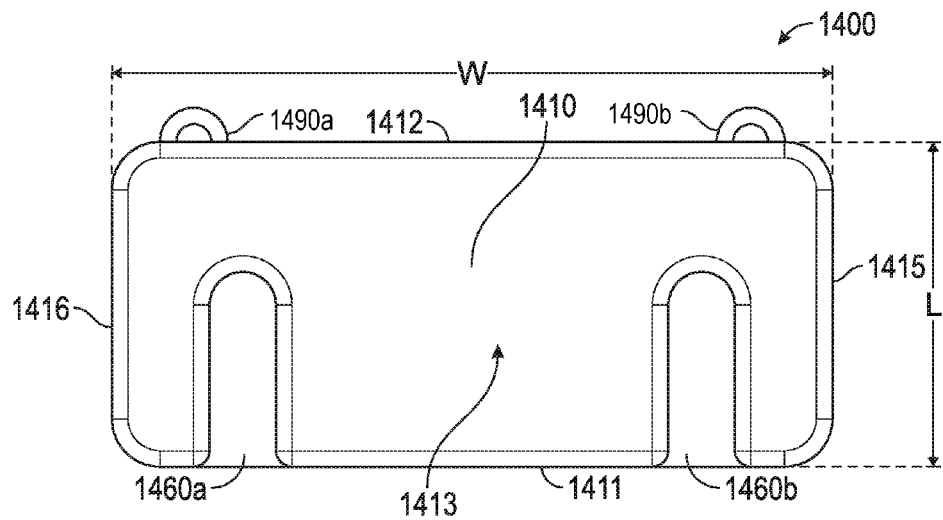
Figure 15N:
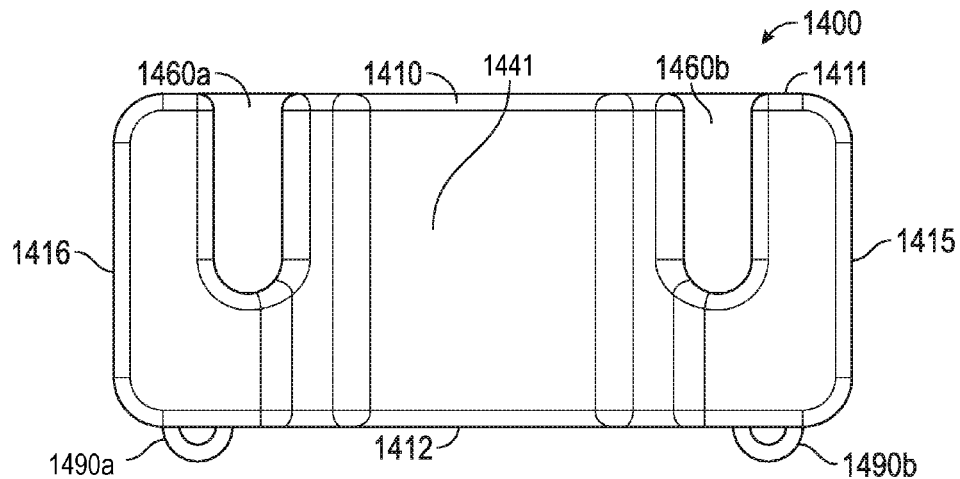
Figure 15O:
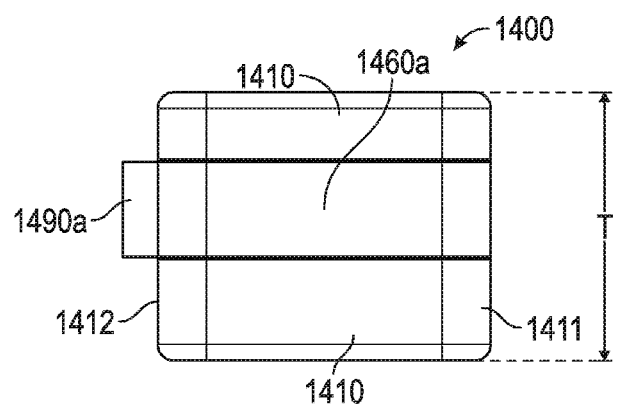
Figure 15P:
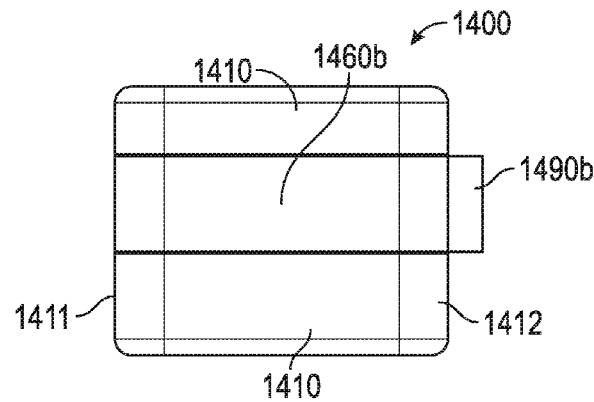

FIGS. 15A through 15P illustrate various views of a fourth embodiment of a suture securing device 1400 for securing a simple interrupted suture 1020. FIGS. 15A and 15B are perspective views of the fourth embodiment of the suture securing device 1400 in an open configuration and a closed configuration, respectively. FIGS. 15C and 15D are perspective views of the fourth embodiment of the suture securing device 1400 shown in use, positioned on a patient's skin 1010 and securing a simple interrupted suture 1020. FIGS. 15E through 15J show front, back, top, bottom, and first and second side views of the fourth embodiment of the suture securing device 1400 in the open configuration, respectively. FIGS. 15K through 15P show front, back, top, bottom, and first and second side views of the fourth embodiment of the suture securing device 1400 in the closed configuration, respectively.

The fourth embodiment includes a body 1410 configured similarly to the body 1110 of the second embodiment of the suture securing device 1200 described above. The fourth embodiment, however, includes two arms 1460*a*, 1460*b* attached to the body 1410 by hinges 1490*a*, 1490*b*. The hinges 1490*a*, 1490*b* allow the suture securing device 1400 to be transitioned between an open configuration and a closed configuration. Also, similar to the second embodiment of FIG. 13A, the body 1410 of the fourth embodiment includes individual slots 1421*a*, 1421*b* extending through the front surface 1411 of the body 1410 for receiving the external strands 1021, 1023 of the suture 1020.

As mentioned above, the suture securing device 1400 includes a body 1410 and two arms 1460*a*, 1460*b*. The body 1410 is connected to each of the arms 1460*a*, 1460*b* by corresponding hinges 1490*a*, 1490*b*. The hinges 1490*a*, 1490*b* can be seen in, for example, FIGS. 15G and 15M. The hinges 1490*a*, 1490*b* are configured to allow the arms 1460*a*, 1460*b* to rotate relative to the body 1410, for example between the open configuration and the closed configuration. In the illustrated embodiment, the hinges 1490*a*, 1490*b* are connected to the body 1410 on a back surface 1412 of the body 1410. However, in some embodiments, the hinges 1490*a*, 1490*b* may connect to the body 1410 on other surfaces and/or locations of the body 1410. In some embodiments, the hinges 1490*a*, 1490*b* may be living or compliant hinges. The living or compliant hinges may be integrally formed with the body 1410 and/or the arms 1460*a*, 1460*b*. In some embodiments, mechanical hinges may be used.

The body 1410 includes a first gripping surface 1420, and each of the arms 1460*a*, 1460*b* includes a second gripping surface 1470a, 1470b, respectively. The first gripping surface 1420 and the second gripping surfaces 1470a, 1470b are positioned on the body 1410 and the arms 1460a, 1460b, respectively, such that, when the suture securing device 1400 is in the closed configuration, a portion of the first gripping surface 1420 contacts each of the second gripping surfaces 1470a, 1470b. In the closed configuration, the suture 1020 can be securely held between the first and second gripping surfaces 1420, 1470a, 1470b. In some embodiments, the gripping surfaces 1420, 1470a, 1470b include the same material as the body 1410 and/or arms 1460a, 1460b. In other embodiments, the gripping surfaces 1420, 1470a, 1470b can be formed of a different material with a greater friction coefficient than that of the body 1410 and/or arms 1460a, 1460b, for example, rubber, latex, nitrile, etc. In some embodiments, the gripping surfaces 1420, 1470a, 1470b can be smooth, textured, or include other features that increase the ability of the suture securing device 1400 to retain the suture 1020. For example, one of the gripping surfaces 1420, 1470a, 1470b may include one or more ridges or protrusions extending therefrom, while the other of the gripping surfaces 1420, 1470a, 1470b may include corresponding grooves or recesses that are configured in size, shape, and position to mate with the corresponding ridges or protrusions.

In the illustrated embodiment, the body 1410 (or the suture securing device when in the closed configuration) is generally shaped as a rectangular prism. The body 1410 includes a front surface 1411, a back surface 1412, a top surface 1413, a bottom surface 1414, a first side surface 1415, and a second side surface 1416. Although many of these surfaces are illustrated as planar, this need not be the case in all embodiments. Similarly, although many of these surfaces are illustrated as positioned orthogonally relative to adjacent surfaces, this need not be the case in all embodiments. Various other shapes for the body 1410 are possible.

As seen, for example, in FIG. 15G, the body 1410 includes two individual slots 1421a, 1421b. Each of the two individual slots 1421a, 1421b extends generally into the body 1410 from the front surface 1411 partway toward the back surface 1412. Each of the two individual slots 1421a, 1421b also extends entirely through the body 1410 from the top surface 1413 to the bottom surface 1414. On opposite side surfaces 1415, 1416 of the body 1410, the two individual slots 1421a, 1421b are defined by members 1423 and 1424 which extend outwardly from the body 1410. A member 1425 extends outwardly from the body 1410 in between the two individual slots 1421a, 1421b. Thus, with the two individual slots 1421a, 1421b and the members 1423, 1424, 1425 the body 1410 may be described as having a E-shape, as best seen in the top and bottom views of FIGS. 15G and 15H. In some instances, the two individual slots 1421a, 1421b may be used to help position the suture securing device 1400 relative to the suture 1020. For example, with the suture securing device 1400 in the open position, the suture securing device 1400 can be positioned such that each of the external portions 1021, 1023 of the suture 1020 are positioned within one of the two individual slots 1421a, 1421b, as shown in FIG. 15C. The two individual slots 1421a, 1421b and members 1423, 1424, 1425 may help to maintain the suture securing device 1400 and suture 1020 in position until the suture securing device is transitioned to the closed configuration. In other words, the body 1410 may have a substantially E-shaped profile when viewed from the top or bottom, and each of the external portions 1021, 1023 of the suture 1020 may be positioned within the openings of the E (in other words, the two individual slots 1421a, 1421b).

As best seen in the front and back views of FIGS. 15E, 15F, 15K, and 15L, the bottom surface 1414 of the body 1410 includes an eversion recess 1441. The eversion recess 1441 may be configured as an indentation or opening extending into the body 1410 from the bottom surface 1414. The eversion recess 1441 may also be considered as a channel extending through the body 1410 from the front surface 1411 to the back surface 1412. A longitudinal axis of the eversion recess 1441 may be configured so as to be aligned with an incision or wound 1013 when the suture securing device 1400 is in use. The eversion recess 1441 creates a space below the suture securing device 1400 to accommodate skin eversion 1015 (as seen in FIGS. 11A and 11B) that may be present at the wound or incision closure. In some embodiments, the eversion recess 1441 may be omitted.

The bottom surface 1414 may be considered to have feet 1443 on opposite sides of the eversion recess 1441. The feet 1443 may be the portions of the suture securing device 1400 that contact the surface 1011 of the patient's skin 1010. In some embodiments, the feet 1443 and/or bottom surface 1414 may include a treated undersurface having adhesive, anti-bacterial, medicaments, and/or other agents for transfer to the patient's skin underlying the suture securing device to aid in positioning and/or retention of the suture securing device 1400, assist in healing, and/or reduce scarring, among other purposes.

The body 1410 also includes a channel 1431 configured to receive the arms 1460a, 1460b in the closed configuration. The channel 1431 is formed as an opening which extends partway into the body 1410 from the front surface 1411 and the first and second side surfaces 1415, 1416. The channel 1431 is likely best seen in FIGS. 15E, 15F, 15I, and 15J. As shown, the channel 1431 is positioned between the top surface 1413 and the bottom surface 1414 and generally runs parallel to each. As shown in the side views of FIGS. 15I and 15J, the channel 1431 bisects the members 1423, 1424 and 1425, dividing each into two separate protrusions. The first gripping surface 1420 is positioned within the body 1410 and at least partially defines the end of the channel 1431 in one direction: for example, the first gripping surface 1420 defines the end or depth of the channel 1431 extending into the body 1410 from the front surface 1411. In the illustrated embodiment, the channel 1431 is configured such that, in the closed configuration, the arms 1460b, 1460 are substantially received within the body 1410 as shown, for example, in FIGS. 15B, 15D and 15K through 15P. Accordingly, the depth of the channel 1431 extending from the front surface 1411 and the first and second side surfaces 1415, 1416 may be chosen to correspond to the dimensions and shape of the arms 1460a, 1460b as will be described in greater detail below. Similarly, the thickness of the channel 1431 may be chosen to correspond to the thickness of the arms 1460a, 1460b. In the illustrated embodiment, the depth of the channel 1431 extending into the body 1410 from the front surface 1411 is greater than the depth of the two individual slots 1421a, 1421b. Thus, a cross-sectional shape bisecting the body 1410 between the first and second side surfaces 1415, 1416 at either of the two individual slots 1421a, 1421b may also be substantially C-shaped. In some embodiments, the arms 1460a, 1460b are received within the opening of the C. In the closed configuration this may cause the suture 1020 to serpentine through the body 1410, following this C-shape. This may further help to retain the suture 1020 within the suture securing device 1400 in the closed configuration. In some embodiments, the channel 1431 may be omitted or may be configured to only partially receive the arms 1460a, 1460b within the body 1410.

In the illustrated embodiment, the each of the arms 1460a, 1460b includes a front member 1462a, 1462b and side members 1463a, 1463b as seen, for example, in FIG. 15G. The front members 1462a, 1462b are each configured to extend across one-half the width of the suture securing device 1400. The front members 1462a, 1462b also include the second gripping surfaces 1470a, 1470b. The side members 1463a, 1463b extend as protrusions from the front members 1462a, 1462b of each arm 1460a, 1460b. The shape of the arms 1460a, 1460b may be configured so as to fit within the channel 1431 of the body 1410 described above, such that the arms 1460a, 1460b may be substantially completely positioned within the body 1410 in the closed configuration. In this way, the arms 1460a, 1460b may be configured to mate with the body 1410. It will be appreciated, however, that other shapes for the arms 1460a, 1460b are possible and within the scope of this disclosure.

In the illustrated embodiment, the hinges 1490a, 1490b are attached to the arms 1460a, 1460b at the side members 1463a, 1463b, respectively. The free end of each of the front members 1462a, 1462b includes an engagement structure 1481a, 1481b configured to correspond to and engage with a corresponding engagement structure 1451 of the body 1410. The engagement structures 1451, 1481a, 1481b may cooperate to secure the arms 1460a, 1460b to the body 1410 in the closed configuration as described above. In the illustrated embodiment, a single engagement structure 1451 is formed as a recess in the body 1410 and configured to receive the engagement structures 1481a, 1481b of both arms 1460a, 1460b. In some embodiments, the engagement structure 1451 on the body 1410 may include multiple recesses, each configured to receive one of the engagement structures 1481a, 1481b of the arms 1460a, 1460b.

The suture securing device 1400 may be formed partially or entirely from any sturdy and resilient material, such as plastic resin, for example, polypropylene, polyethylene, acrylonitrile butadiene styrene (ABS), high impact polystyrene (HIPS), poly vinyl chloride (PVC), polycarbonate, thermoplastic elastomers, Polybutylene terephthalate, ethylene vinyl acetate, nylon and low-density polyethylene, linear low-density polyethylene, etc. In some embodiments, the body 1410, arms 1460a, 1460b, and hinges 1490a, 1490b may be formed as a single unitary part, while in other embodiments, these parts may be formed separately and then joined together.

The suture securing device 1400 may have a width W, thickness T, and length L as illustrated in FIGS. 15M and 15O. The width W, thickness T, and length L may be similar to those described above.

The suture securing device 1400 secures the external portions 1021, 1023 of the suture 1020 between first and second gripping surfaces 1420, 1470a, 1470b in a manner similar to that described above in reference to the suture securing device 1200. The principal difference being that the suture securing device 1400 is configured with the two arms 1460a, 1460b. Accordingly, the suture securing device 1400 provides similar benefits to those identified above, including securing a suture 1020 without requiring a knot to be tied and preventing a suture 1020 from becoming ingrown. Additionally, because the arms 1460a, 1460b secure the external portions 1021, 1023 of the suture 1020 individually, the suture securing device 1400 allows a user to secure the external portions 1021, 1023 of the suture at separate times. For example, a first external portion 1021 may be secured, the suture may be tensioned, and then the second external portion 1023 may be secured.

Figure 16A:
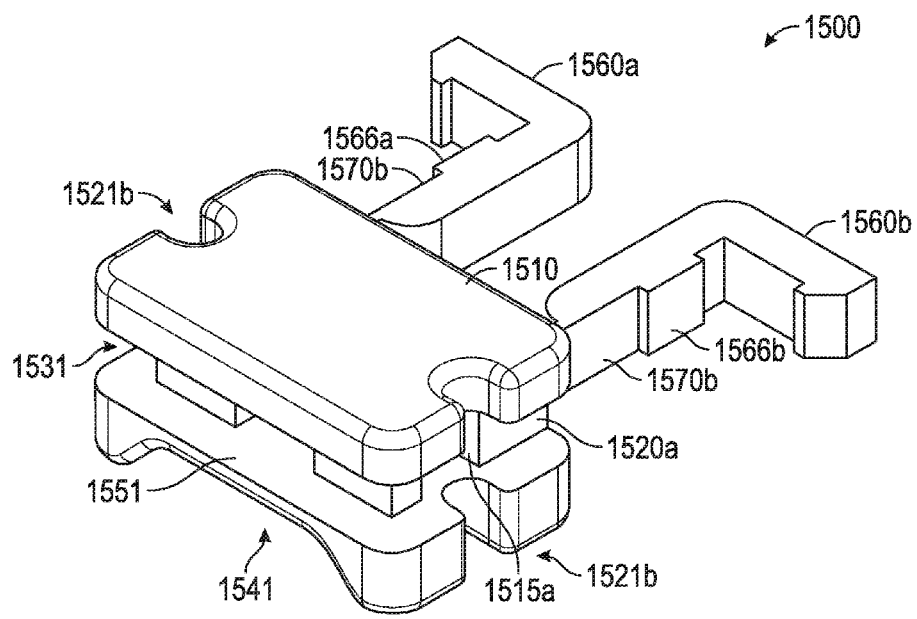
FIGS. 16A through 16P illustrate various views of a fifth embodiment of a suture securing device for securing a simple interrupted suture. The fifth embodiment includes a body configured similarly to that of the third embodiment of FIG. 14A. However, similar to the fourth embodiment of FIG. 15A, the fifth embodiment includes two arms, each attached by a hinge and configured to secure an external portion of simple interrupted suture in one of the slots of the body in a closed position.
Figure 16B:
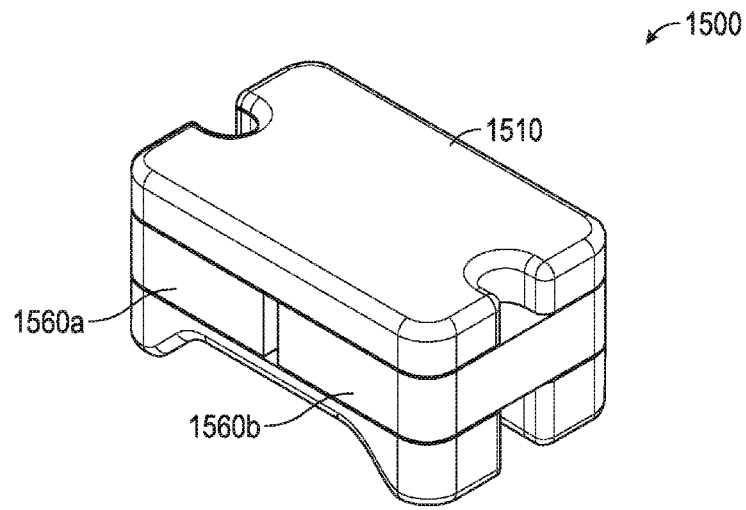
Figure 16C:
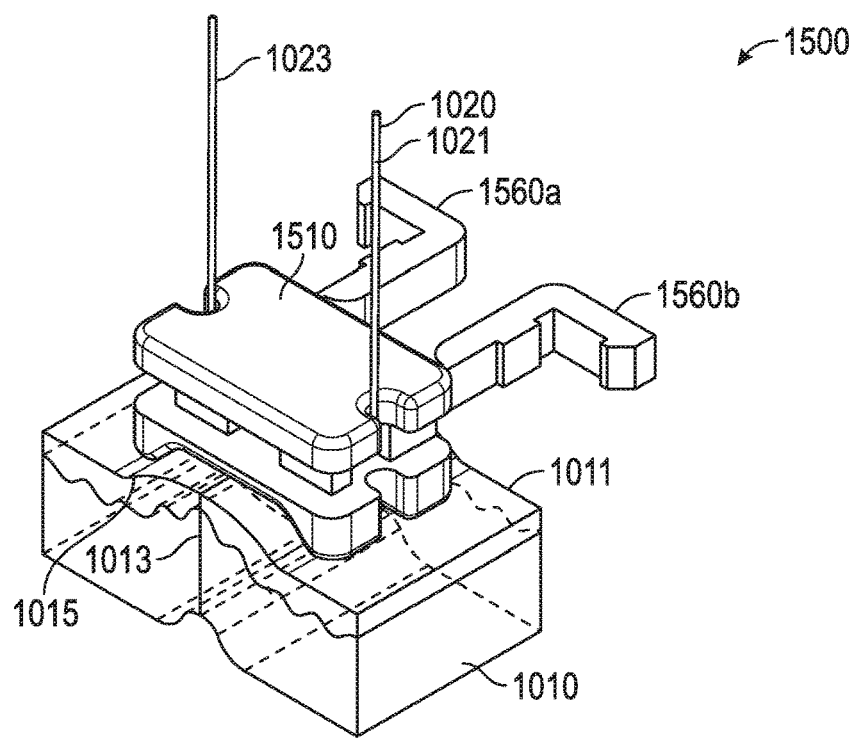
FIGS. 16C and 16D are perspective views of the fifth embodiment of the suture securing device shown in use, positioned on a patient's skin and securing a simple interrupted suture.
Figure 16D:
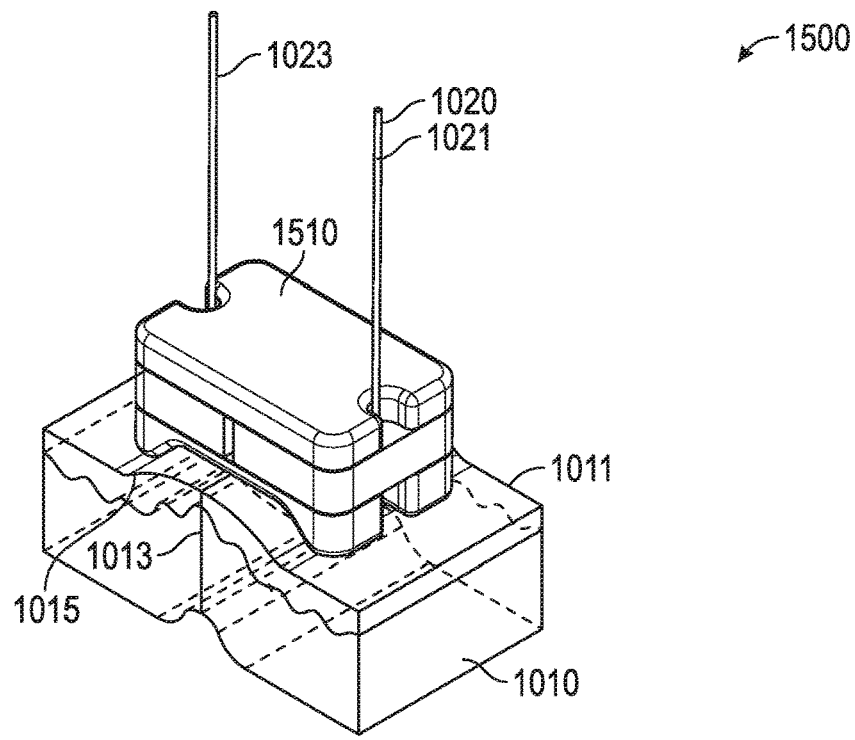
Figure 16E:
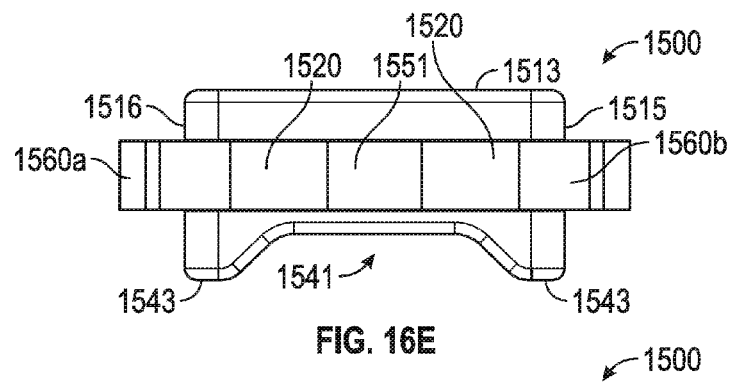
FIGS. 16E through 16J show front, back, top, bottom, and first and second side views of the fifth embodiment of the suture securing device in the open configuration, respectively.
Figure 16F:
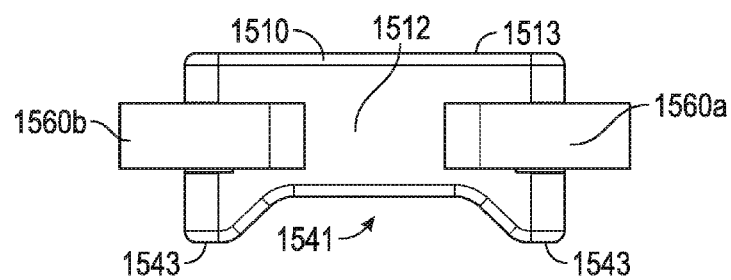
Figure 16G:
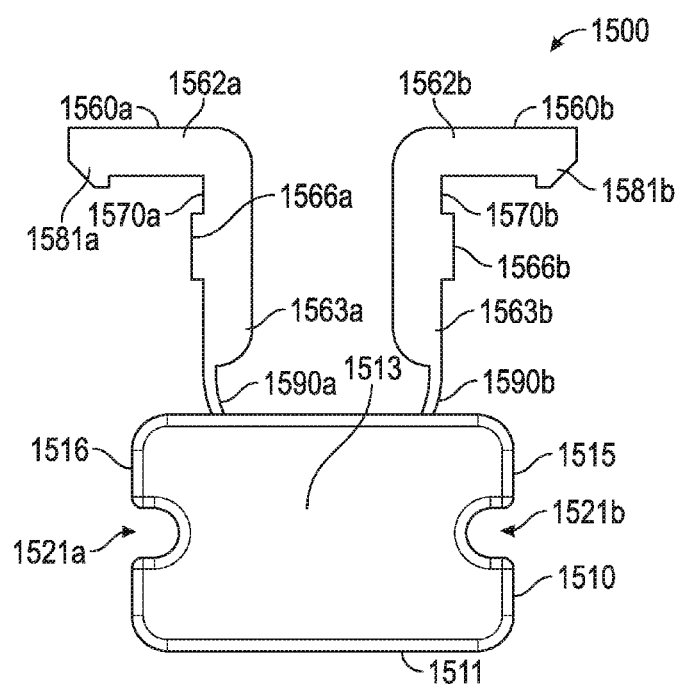
Figure 16H:
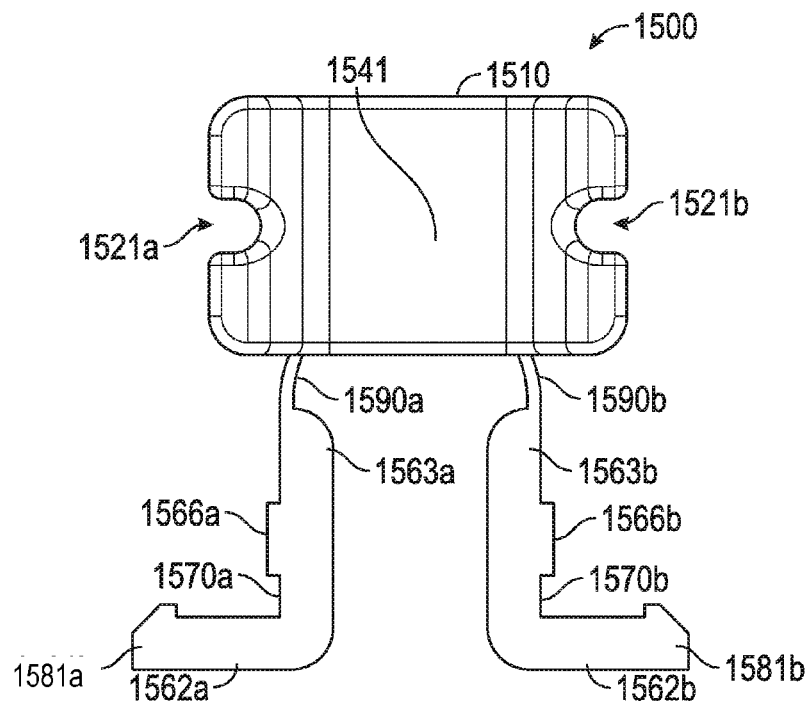
Figure 16I:
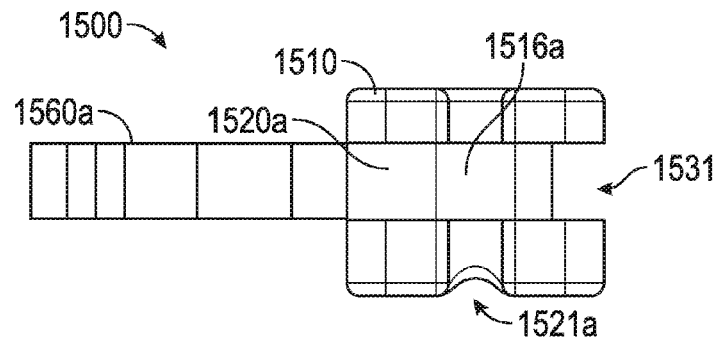
Figure 16J:
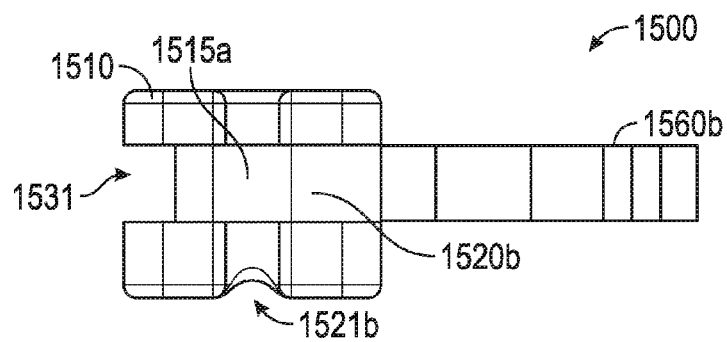
Figure 16K:
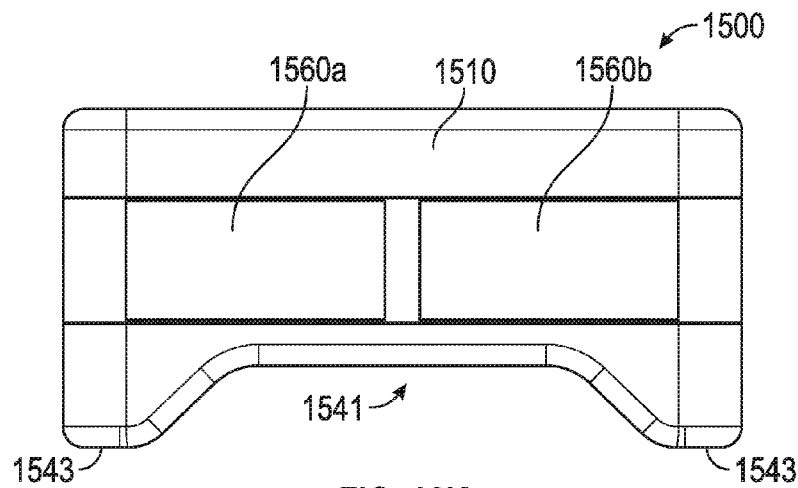
Figure 16L:
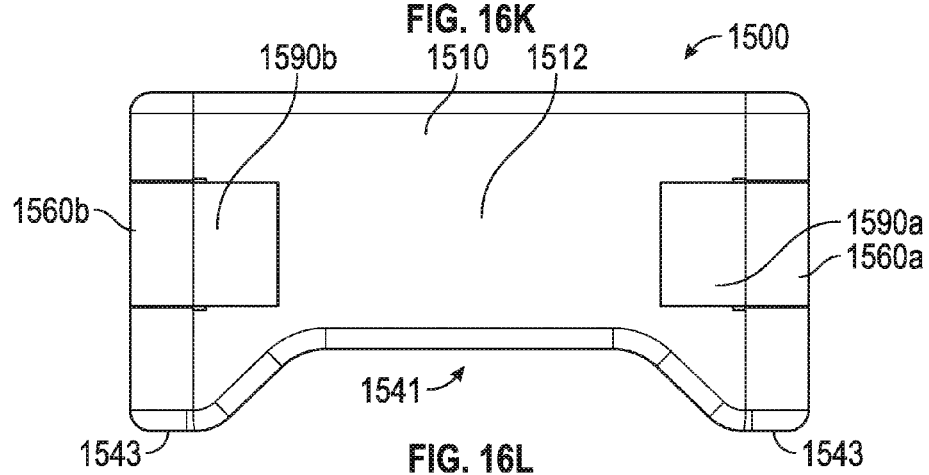
Figure 16M:
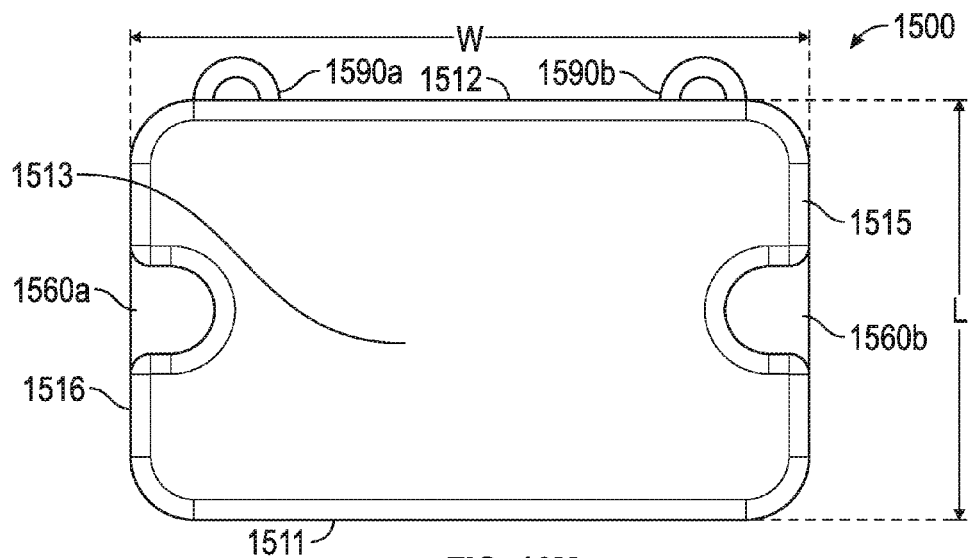
Figure 16N:
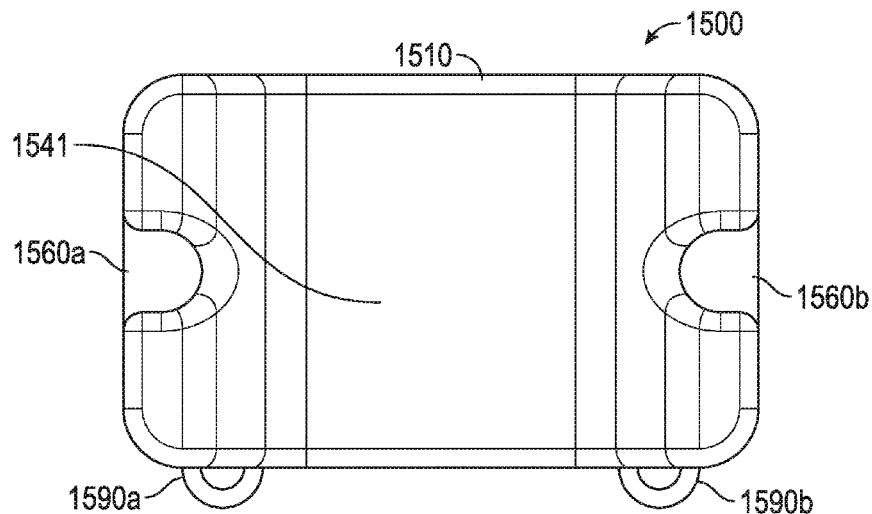
Figure 16O:
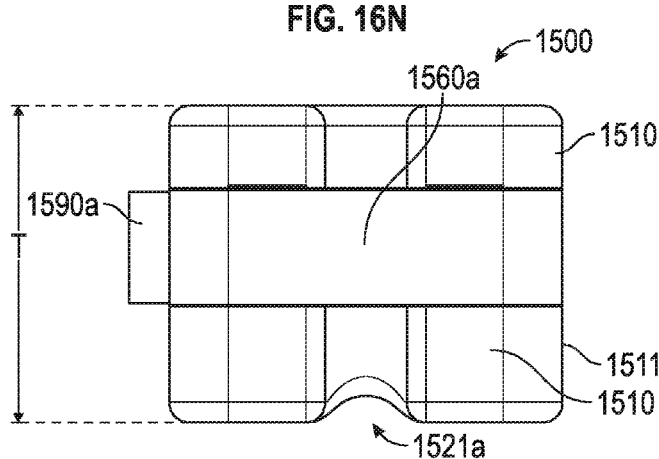
Figure 16P:
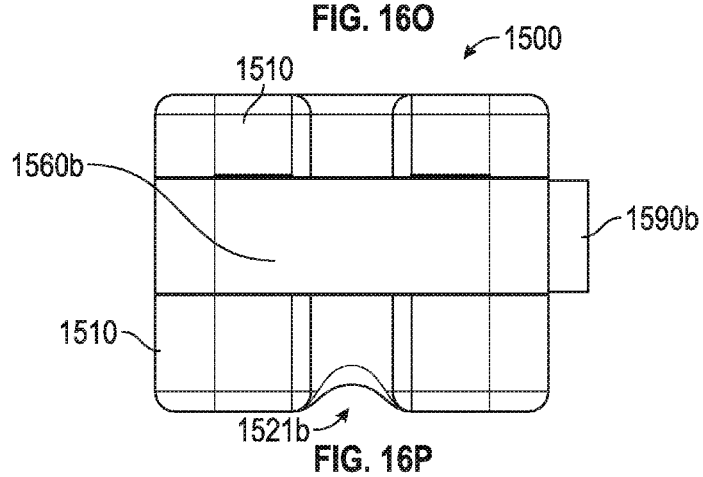

FIGS. 16A through 16P illustrate various views of a fifth embodiment of a suture securing device 1500 for securing a simple interrupted suture 1020. FIGS. 16A and 16B are perspective views of the fifth embodiment of the suture securing device 1500 in an open configuration and a closed configuration, respectively. FIGS. 16C and 16D are perspective views of the fifth embodiment of the suture securing device 1500 shown in use, positioned on a patient's skin 1010 and securing a simple interrupted suture 1020. FIGS. 16E through 16J show front, back, top, bottom, and first and second side views of the fifth embodiment of the suture securing device 1500 in the open configuration, respectively. FIGS. 16K through 16P show front, back, top, bottom, and first and second side views of the fifth embodiment of the suture securing device 1500 in the closed configuration, respectively.

In many ways, the fifth embodiment of the suture securing device 1500 is similar to that of the third embodiment of the suture securing device 1300 of FIG. 14A. Specifically, like the third embodiment, the suture securing device 1500 includes a body 1510 with two individual slots 1521a, 1521b configured on opposite sides 1515, 1516 for receiving the external portions 1021, 1023 of a simple interrupted suture 1020. However, similar to the fourth embodiment of the suture securing device 1400 of FIG. 15A, the fifth embodiment includes two arms 1560a, and 1560b, each attached by a hinge 1590a, 1590b. The features of the fifth embodiment will now be described in greater detail.

The suture securing device 1500 includes a body 1510 and two arms 1560a, 1560b. The body 1510 is connected to each of the arms 1560a, 1560b by corresponding hinges 1590a, 1590b. The hinges 1590a, 1590b can be seen in, for example, FIGS. 16G and 16M. The hinges 1590a, 1590b are configured to allow the arms 1560a, 1560b to rotate relative to the body 1510, for example between the open configuration and the closed configuration. In the illustrated embodiment, the hinges 1590a, 1590b are connected to the body 1510 on a back surface 1512 of the body 1510. However, in some embodiments, the hinges 1590a, 1590b may connect to the body 1510 on other surfaces and/or locations of the body 1510. In some embodiments, the hinges 1590a, 1590b may be living or compliant hinges. The living or compliant hinges may be integrally formed with the body 1510 and/or the arms 1560a, 1560b. In some embodiments, mechanical hinges may be used.

The body 1510 includes first gripping surfaces 1520a, 1520b, and each of the arms 1560a, 1560b includes second gripping surface 1570a, 1570b, respectively. The first gripping surfaces 1520a, 1520b and the second gripping surfaces 1570a, 1570b are positioned on the body 1510 and the arms 1560a, 1560b, respectively, such that, when the suture securing device 1500 is in the closed configuration, each of the first gripping surfaces 1520a, 1520b contacts one of the second gripping surfaces 1570a, 1570b. In the closed configuration, the suture 1020 can be securely held between the first and second gripping surfaces 1520a, 1520b, 1570a, 1570b. In some embodiments, the gripping surfaces 1520a, 1520b, 1570a, 1570b each are formed of the same material as the body 1510 and/or arms 1560a, 1560b. In other embodiments, the gripping surfaces 1520a, 1520b, 1570a, 1570b can be formed or comprised of a different material with a greater friction coefficient than that of the body 1510 and/or arms 1560a, 1560b, for example, rubber, latex, nitrile, etc. In some embodiments, the gripping surfaces 1520a, 1520b, 1570a, 1570b can be smooth, textured, or include other features that increase the ability of the suture securing device 1500 to retain the suture 1020. For example, one of the gripping surfaces 1520*a*, 1520*b*, 1570*a*, 1570*b* may include one or more ridges or protrusions extending therefrom, while the other of the gripping surfaces 1520*a*, 1520*b*, 1570*a*, 1570*b* may include corresponding grooves or recesses that are configured in size, shape, and position to mate with the corresponding ridges or protrusions.

In the illustrated embodiment, the body 1510 (or the suture securing device when in the closed configuration) is generally shaped as a rectangular prism. The body 1510 includes a front surface 1511, a back surface 1512, a top surface 1513, a bottom surface 1514, a first side surface 1515, and a second side surface 1516. Although many of these surfaces are illustrated as planar, this need not be the case in all embodiments. Similarly, although many of these surfaces are illustrated as positioned orthogonally relative to adjacent surfaces, this need not be the case in all embodiments. Various other shapes for the body 1510 are possible.

As seen, for example, in FIG. 16G, the body 1510 includes two individual slots 1521*a*, 1521*b*. Each of the two individual slots 1521*a*, 1521*b* extends generally into the body 1510 from one of the opposite side surfaces 1515, 1516, respectively. As shown, the two individual slots 1521*a*, 1521*b* extend into the body 1510 toward each other. In the illustrated embodiment, the two individual slots 1521*a*, 1521*b* are aligned with each other, although this need not be the case in all embodiments. Each of the two individual slots 1521*a*, 1521*b* also extends entirely through the body 1510 from the top surface 1513 to the bottom surface 1514. Thus, with the two individual slots 1521*a*, 1521*b*, the body 1510 may be described as having an H-shape, as best seen in the top and bottom views of FIGS. 16G and 16H. In some instances, the two individual slots 1521*a*, 1521*b* may be used to help position the suture securing device 1500 relative to the suture 1020. For example, with the suture securing device 1500 in the open position, the suture securing device 1500 can be positioned such that each of the external portions 1021, 1023 of the suture 1020 are positioned within one of the two individual slots 1521*a*, 1521*b*. In other words, the body 1510 may have a substantially H-shaped profile when viewed from the top or bottom, and each of the external portions 1021, 1023 of the suture 1020 may be positioned within the openings of the H (in other words, the two individual slots 1521*a*, 1521*b* on opposite sides 1515, 1516 of the body 1510).

As best seen in the front and back views of FIGS. 16E, 16F, 16K, and 16L, the bottom surface 1514 of the body 1510 includes an eversion recess 1541. The eversion recess 1541 may be configured as an indentation or opening extending into the body 1510 from the bottom surface 1514. The eversion recess 1541 may also be considered as a channel extending through the body 1510 from the front surface 1511 to the back surface 1512. A longitudinal axis of the eversion recess 1541 may be configured so as to be aligned with an incision or wound 1013 when the suture securing device 1500 is in use. The eversion recess 1541 creates a space below the suture securing device 1500 to accommodate skin eversion 1015 (as seen in FIGS. 11A and 11B) that may be present at the wound or incision closure. In some embodiments, the eversion recess 1541 may be omitted.

The bottom surface 1514 includes feet 1534 on opposite sides of the eversion recess 1541. The feet 1534 may be the portions of the suture securing device 1500 that contact the surface 1011 of the patient's skin 1010. In some embodiments, the feet 1534 and/or bottom surface 1514 may include a treated undersurface having adhesive, anti-bacterial, medicaments, and/or other agents for transfer to the patient's skin underlying the suture securing device to aid in positioning and/or retention of the suture securing device 1500, assist in healing, and/or reduce scarring, among other purposes.

The body 1510 also includes a channel 1531 configured to receive the arm 1560 in the closed configuration. The channel 1531 is formed as an opening which extends partway into the body 1510 from the front surface 1511, back surface 1512, and the first and second side surfaces 1515, 1516. The channel 1531 is likely best seen in FIGS. 16E, 16F, 16I, and 16J. As shown, the channel 1531 is positioned between the top surface 1513 and the bottom surface 1514 and generally runs parallel to each. The first gripping surfaces 1520*a*, 1520*b* are positioned within the body 1510 and each at least partially define the end of the channel 1331 in one direction: for example, the first gripping surface 1520*a* defines the end or depth of the channel 1531 extending into the body 1510 from the first side surface 1515 and the first gripping surface 1520*b* defines the end or depth of the channel 1531 extending into the body 1510 from the second side surface 1516. In the illustrated embodiment, the channel 1531 is configured such that, in the closed configuration, the arm 1560 is substantially received within the body 1510 as shown, for example, in FIGS. 16B, 16D and 16K through 16P. Accordingly, the depth of the channel 1531 extending from the front surface 1511 and the first and second side surfaces 1515, 1516 may be chosen to correspond to the dimensions and shape of the arms 1560*a*, 1560*b* as will be described in greater detail below. Similarly, the thickness of the channel 1531 may be chosen to correspond to the thickness of the arms 1560*a*, 1560*b*.

In the illustrated embodiment, and as best seen in FIGS. 16I and 16E (also partially visible in FIG. 16A) the depth of the channel 1531 extending into the body 1510 from the side surfaces 1515, 1516 may include deeper portions 1515*a*, 1516*a* in the areas of the two individual slots 1521*a*, 1521*b*. These deeper portions 1515*a*, 1516*a* are configured to correspond to and mate with protrusions 1566*a*, 1566*b* which extend from the second gripping surfaces 1570*a*, 1570*b*, respectively, of the arms 1560*a*, 1560*b*. In the closed configuration, the deeper portions 1515*a*, 1516*a* mate with corresponding protrusions 1566*a*, 1566*b* to further secure the suture 1020 between the first and second gripping surfaces 1520*a*, 1520*b*, 1570*a*, 1570*b*. In some embodiments, the deeper portions 1515*a*, 1516*a* and protrusions 1566*a*, 1566*b* may be omitted. In some embodiments, the channel 1531 may be omitted or may be configured to only partially receive the arm 1560 within the body 1510.

In the illustrated embodiment, each of the arms 1560*a*, 1560*b* includes a front member 1562*a*, 1562*b* and a side members 1563*a*, 1563*b* as seen, for example, in FIG. 16G. The front members 1562*a*, 1562*b* are each configured to extend across one-half the width of the suture securing device 1500. The front members 1562*a*, 1562*b* also include the second gripping surfaces 1570*a*, 1570*b*. The side members 1563*a*, 1563*b* extend as protrusions from the front members 1562*a*, 1562*b* of each arm 1560*a*, 1560*b*. The shape of the arms 1560*a*, 1560*b* may be configured so as to fit within the channel 1531 of the body 1510 described above, such that the arms 1560*a*, 1560*b* may be substantially completely positioned within the body 1510 in the closed configuration. In this way, the arms 1560*a*, 1560*b* may be configured to mate with the body 1510. It will be appreciated, however, that other shapes for the arms 1560*a*, 1560*b* are possible and within the scope of this disclosure.

In the illustrated embodiment, the hinges 1590a, 1590b are attached to the arms 1560a, 1560b at the side members 1563a, 1563b, respectively. The free end of each of the front members 1562a, 1562b includes an engagement structure 1581a, 1581b configured to correspond to and engage with a corresponding engagement structure 1551 of the body 1510. The engagement structures 1551, 1581a, 1581b may cooperate to secure the arms 1560a, 1560b to the body 1510 in the closed configuration as described above. In the illustrated embodiment, a single engagement structure 1551 is formed as a recess in the body 1510 and configured to receive the engagement structures 1581a, 1581b of both arms 1560a, 1560b. In some embodiments, the engagement structure 1551 on the body 1510 may include multiple recesses, each configured to receive one of the engagement structures 1581a, 1581b of the arms 1560a, 1560b.

The suture securing device 1500 may be formed partially or entirely from any sturdy and resilient material, such as plastic resin, for example, polypropylene, polyethylene, acrylonitrile butadiene styrene (ABS), high impact polystyrene (HIPS), poly vinyl chloride (PVC), polycarbonate, thermoplastic elastomers, Polybutylene terephthalate, ethylene vinyl acetate, nylon and low-density polyethylene, linear low-density polyethylene, etc. In some embodiments, the body 1510, arms 1560a, 1560b, and hinges 1590a, 1590b may be formed as a single unitary part, while in other embodiments, these parts may be formed separately and then joined together.

The suture securing device 1500 may have a width W, thickness T, and length L as illustrated in FIGS. 16M and 16O. The width W, thickness T, and length L may be similar to those described above.

The suture securing device 1500 secures the external portions 1021, 1023 of the suture between first and second gripping surfaces 1520a, 1520b, 1570a, 1570b in a manner similar to that described above in reference to the suture securing device 1500. The principal difference being suture securing device 1500 includes two arms 1560a, 1560b. Accordingly, the suture securing device 1500 provides similar benefits to those identified above, including securing a suture 1020 without requiring a knot to be tied and preventing a suture 1020 from becoming ingrown. Additionally, because the arms 1560a, 1560b secure the external portions 1021, 1023 of the suture 1020 individually, the suture securing device 1500 allows a user to secure the external portions 1021, 1023 of the suture at separate times. For example, a first external portion 1021 may be secured, the suture may be tensioned, and then the second external portion 1023 may be secured.

Figure 17A:
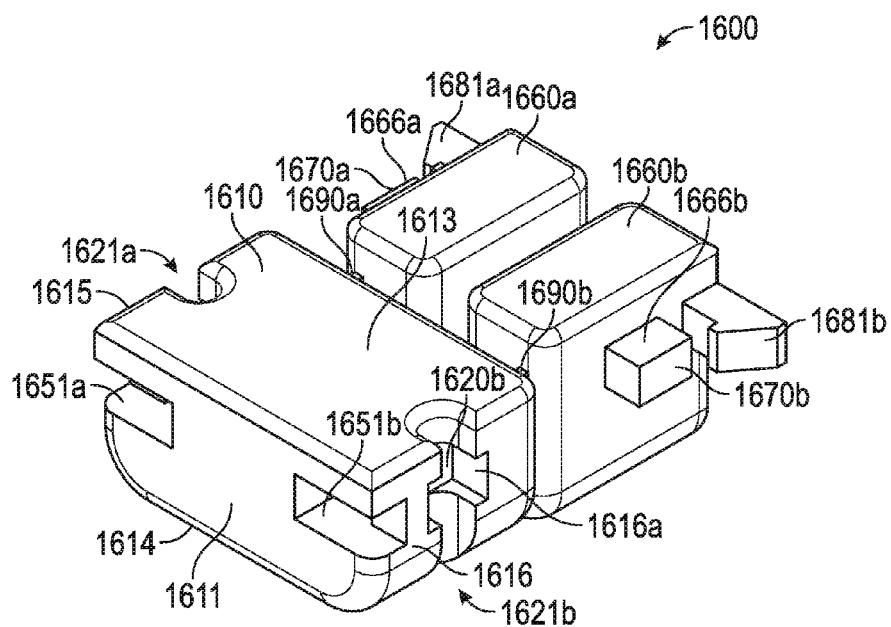
FIGS. 17A through 17P illustrate various views of a sixth embodiment of a suture securing device for securing a simple interrupted suture. The sixth embodiment includes a body with two slots configured to receive external portions of a simple interrupted suture and two arms attached to the body by hinges. In use, the arms contact the patient's skin while the body is raised between the arms to create a space for skin eversion.
Figure 17B:
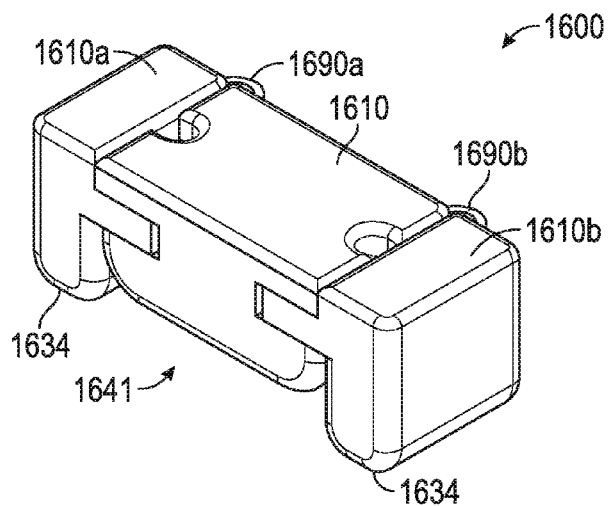
Figure 17C:
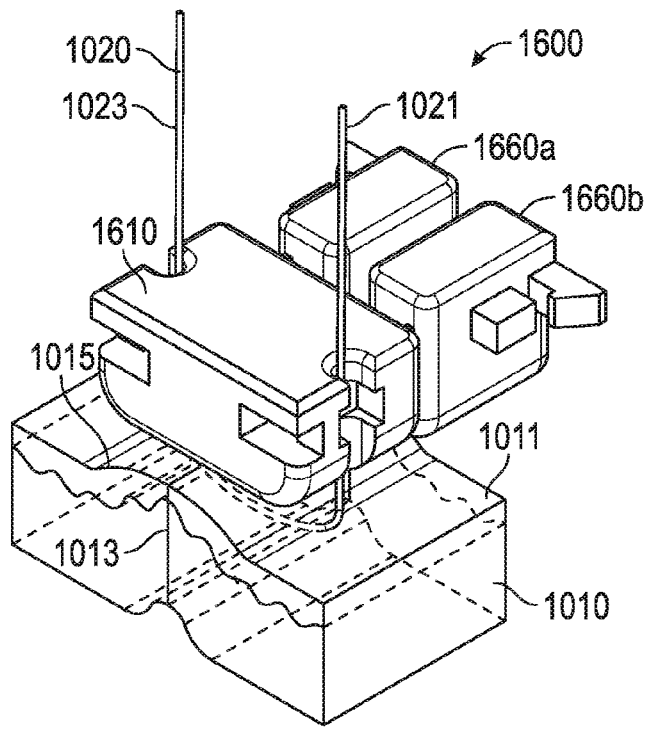
FIGS. 17C and 17D are perspective views of the sixth embodiment of the suture securing device shown in use, positioned on a patient's skin and securing a simple interrupted suture.
Figure 17D:
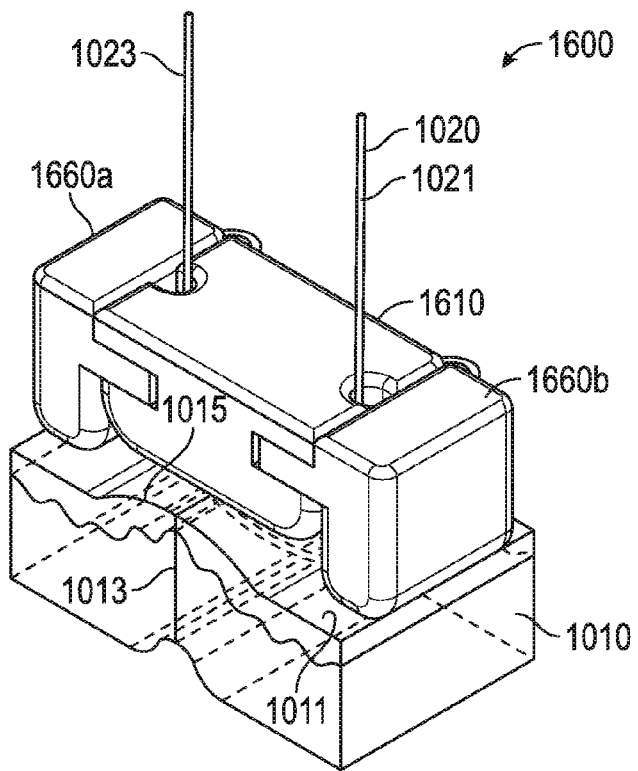
Figure 17E:
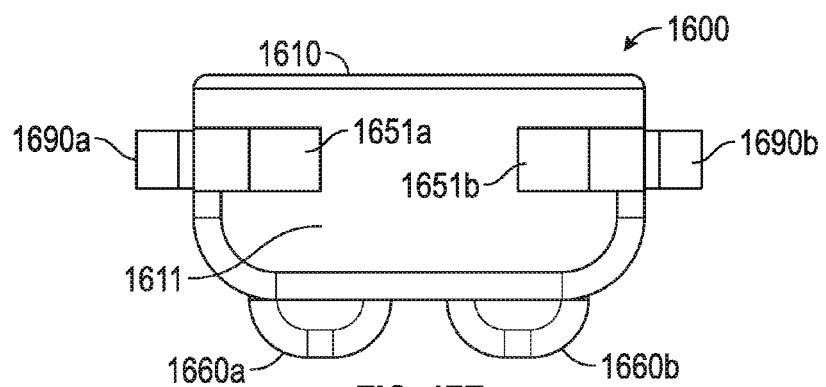
FIGS. 17E through 17J show front, back, top, bottom, and first and second side views of the sixth embodiment of the suture securing device in the open configuration, respectively.
Figure 17F:
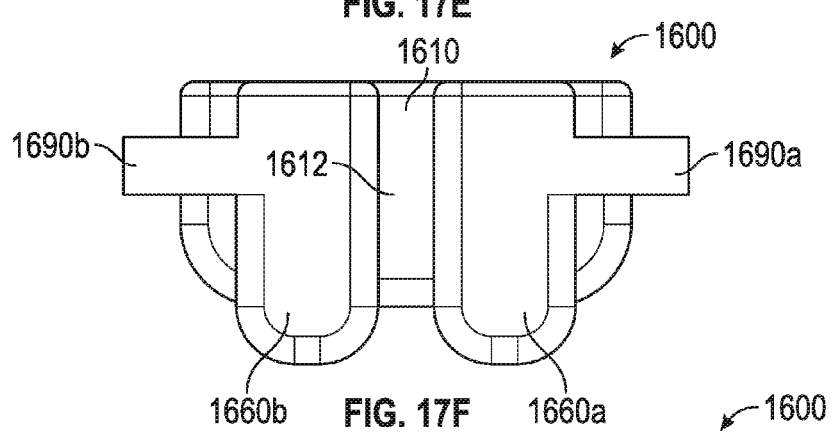
Figure 17G:
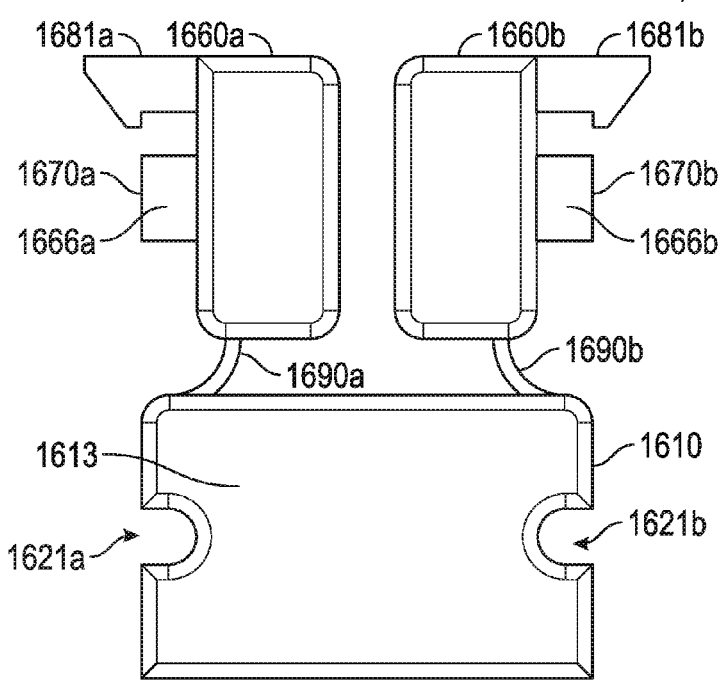
Figure 17H:
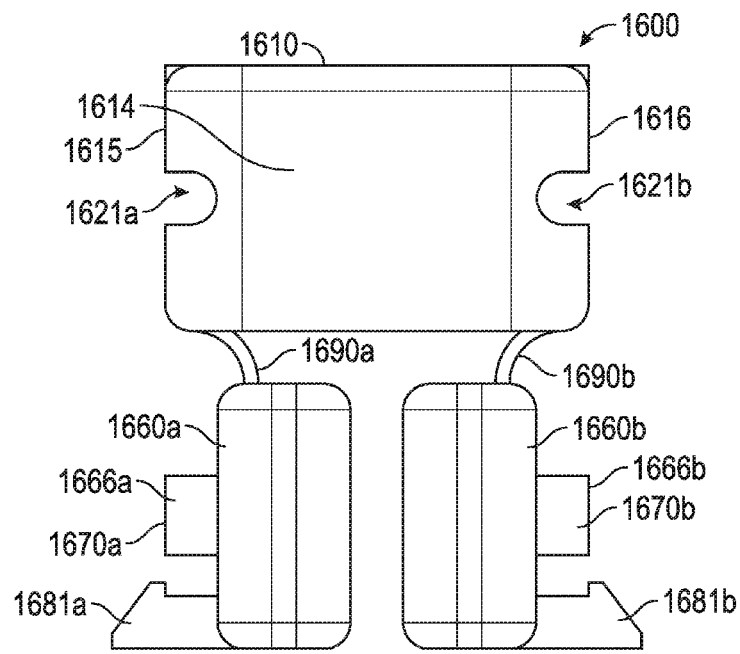
Figure 17I:
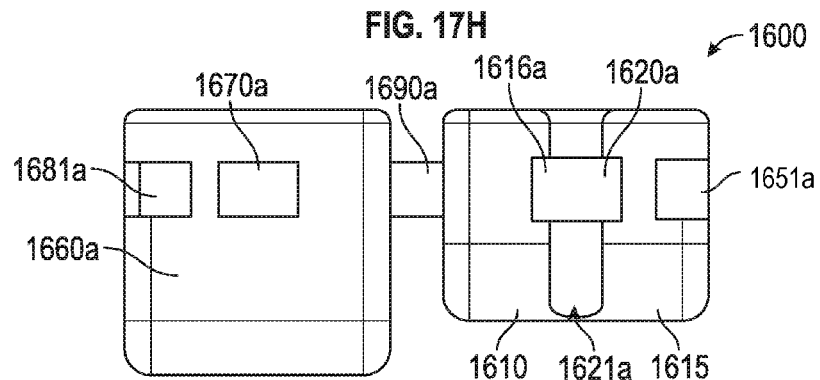
Figure 17J:
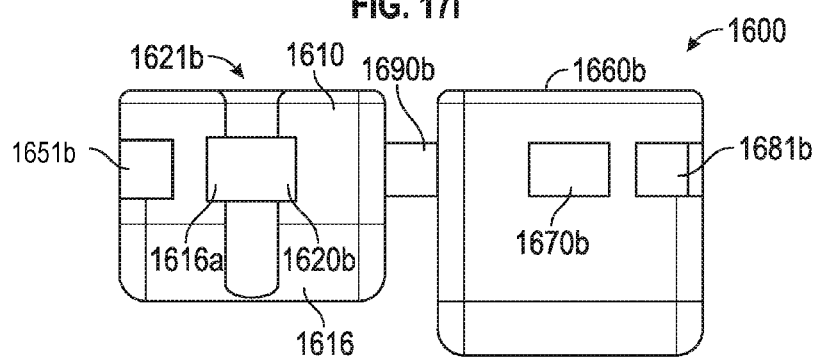
Figure 17K:
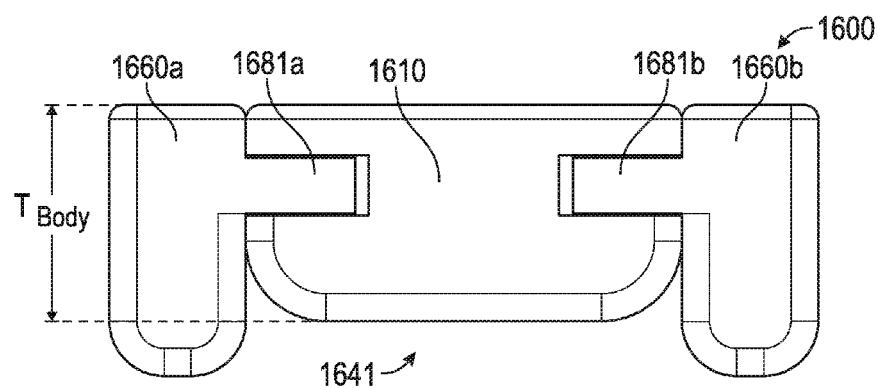
Figure 17L:
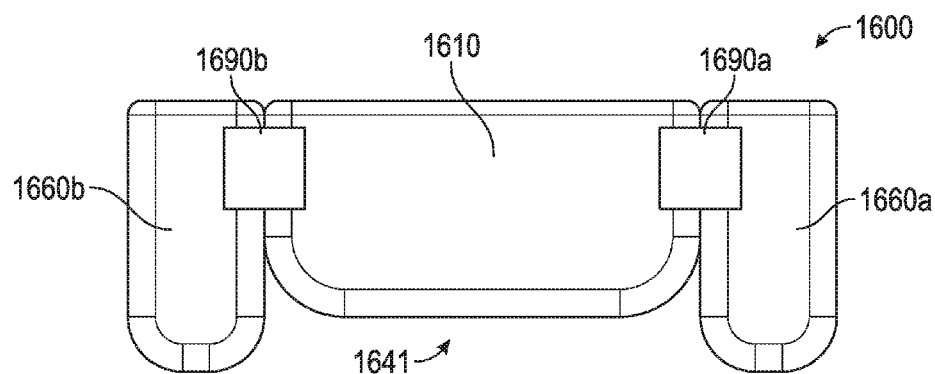
Figure 17M:
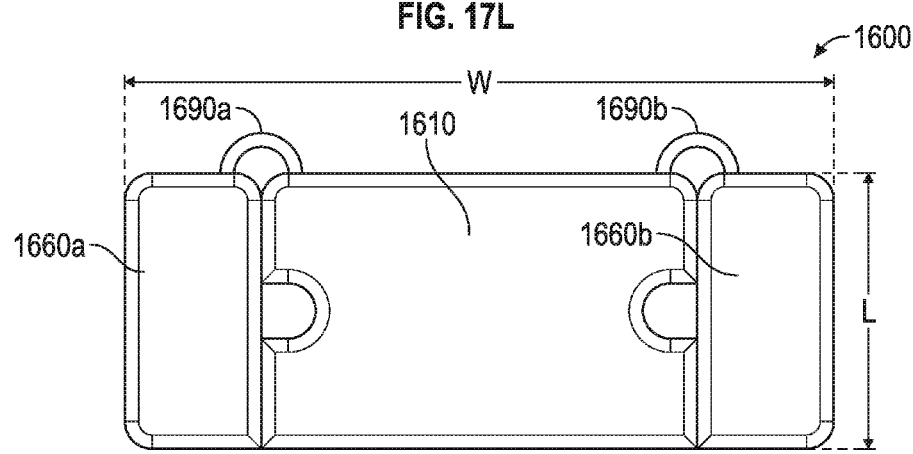
Figure 17N:
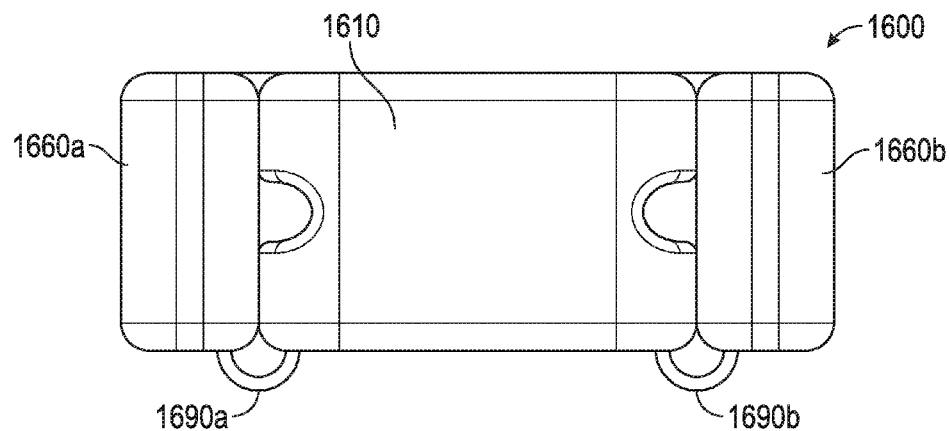
Figure 17O:
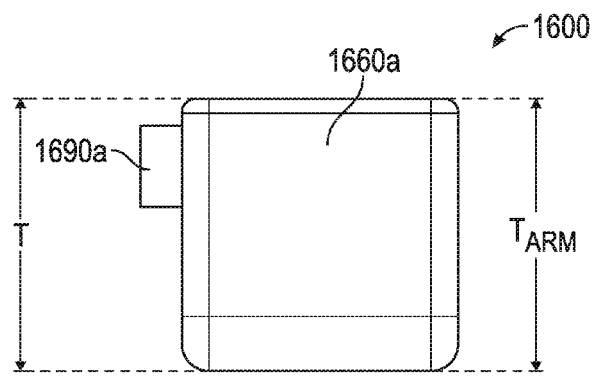
Figure 17P:
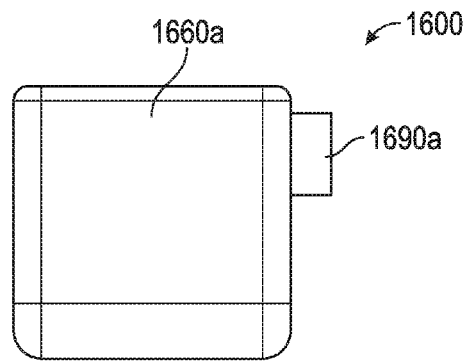

FIGS. 17A through 17P illustrate various views of a sixth embodiment of a suture securing device 1600 for securing a simple interrupted suture 1020. FIGS. 17A and 17B are perspective views of the sixth embodiment of the suture securing device 1600 in an open configuration and a closed configuration, respectively. FIGS. 17C and 17D are perspective views of the sixth embodiment of the suture securing device 1600 shown in use, positioned on a patient's skin 1010 and securing a simple interrupted suture 1020. FIGS. 17E through 17J show front, back, top, bottom, and first and second side views of the sixth embodiment of the suture securing device 1600 in the open configuration, respectively. FIGS. 17K through 17P show front, back, top, bottom, and first and second side views of the sixth embodiment of the suture securing device 1600 in the closed configuration, respectively.

In many ways, the sixth embodiment of the suture securing device 1600 is similar to that of the fifth embodiment of the suture securing device 1500 of FIG. 16A. Specifically, like the fifth embodiment, the suture securing device 1600 includes a body 1610 with two individual slots 1621a, 1621b and two arms 1660a, 1660b configured on opposite sides 1615, 1616 of the body 1610 for receiving the external portions 1021, 1023 of a simple interrupted suture 1020. However, unlike the fifth embodiment of the suture securing device 1500 which includes an eversion recess 1541 formed in the body 1510, in the suture securing device 1600 the eversion recess 1641 is formed by shortening the thickness of the body 1610 and/or increasing the thickness of the arms 1660a, 1660b, such that, in use, the arms 1660a, 1660b contact the surface 1011 of the patient's skin 1010 and the body 1610 is suspended over the wound 1013 and/or wound eversion 1015, between the two arms 1660a, 1160b. This arrangement will be described in greater detail below.

The suture securing device 1600 includes a body 1610 and two arms 1660a, 1660b. The body 1610 is connected to each of the arms 1660a, 1660b by corresponding hinges 1690a, 1690b. The hinges 1690a, 1690b can be seen in, for example, FIGS. 17G and 17M. The hinges 1690a, 1690b are configured to allow the arms 1660a, 1660b to rotate relative to the body 1610, for example between the open configuration and the closed configuration. In the illustrated embodiment, the hinges 1690a, 1690b are connected to the body 1610 on a back surface 1612 of the body 1610. However, in some embodiments, the hinges 1690a, 1690b may connect to the body 1610 on other surfaces and/or locations of the body 1610. In some embodiments, the hinges 1690a, 1690b may be living or compliant hinges. The living or compliant hinges may be integrally formed with the body 1610 and/or the arms 1660a, 1660b. In some embodiments, mechanical hinges may be used. As shown in the figures, the thickness of the arms 1660a, 1660b is greater than the thickness of the body 1610. In the illustrated embodiment, the body the top surface 1613 of the body 1610 is aligned with the top surfaces of the arms, such that (due to its smaller thickness) an eversion channel 1641 is formed below the body 1610 and between the two arms 1660a, 1660b. The eversion channel 1641 is described in greater detail below.

The body 1610 includes first gripping surfaces 1620a, 1620b, and each of the arms 1660a, 1660b includes a second gripping surface 1670a, 1670b, respectively. The first gripping surfaces 1620a, 1620b and the second gripping surfaces 1670a, 1670b are positioned on the body 1610 and the arms 1660a, 1660b, respectively, such that, when the suture securing device 1600 is in the closed configuration, each of the first gripping surfaces 1620a, 1620b contacts a corresponding second gripping surface 1670a, 1670b. In the closed configuration, the suture 1020 can be securely held between the first and second gripping surfaces 1620a, 1620b, 1670a, 1670b. In some embodiments, the gripping surfaces 1620a, 1620b, 1670a, 1670b include the same material as the body 1610 and/or arms 1660a, 1660b. In other embodiments, the gripping surfaces 1620a, 1620b, 1670a, 1670b can be formed of a different material with a greater friction coefficient than that of the body 1610 and/or arms 1660a, 1660b, for example, rubber, latex, nitrile, etc. In some embodiments, the gripping surfaces 1620a, 1620b, 1670a, 1670b can be smooth, textured, or include other features that increase the ability of the suture securing device 1600 to retain the suture 1020. For example, one of the gripping surfaces 1620a, 1620b, 1670a, 1670b may include one or more ridges or protrusions extending therefrom, while the other of the gripping surfaces 1620a, 1620b, 1670a, 1670b may include corresponding grooves or recesses that are configured in size, shape, and position to mate with the corresponding ridges or protrusions.

In the illustrated embodiment, the body 1610 (or the suture securing device when in the closed configuration) is generally shaped as a rectangular prism. The body 1610 includes a front surface 1611, a back surface 1612, a top surface 1613, a bottom surface 1614, a first side surface 1615, and a second side surface 1616. Although many of these surfaces are illustrated as planar, this need not be the case in all embodiments. Similarly, although many of these surfaces are illustrated as positioned orthogonally relative to adjacent surfaces, this need not be the case in all embodiments. Various other shapes for the body 1610 are possible.

As seen, for example, in FIG. 17G, the body 1610 includes two individual slots 1621a, 1621b. Each of the two individual slots 1621a, 1621b extends generally into the body 1610 from one of the opposite side surfaces 1615, 1616, respectively. As shown, the two individual slots 1621a, 1621b extend into the body 1610 toward each other. In the illustrated embodiment, the two individual slots 1621a, 1621b are aligned with each other, although this need not be the case in all embodiments. Each of the two individual slots 1621a, 1621b also extends entirely through the body 1610 from the top surface 1613 to the bottom surface 1614. Thus, with the two individual slots 1621a, 1621b, the body 1610 may be described as having an H-shape, as best seen in the top and bottom views of FIGS. 17G and 17H. In some instances, the two individual slots 1621a, 1621b may be used to help position the suture securing device 1600 relative to the suture 1020. For example, with the suture securing device 1600 in the open position, the suture securing device 1600 can be positioned such that each of the external portions 1021, 1023 of the suture 1020 are positioned within one of the two individual slots 1621a, 1621b. In other words, the body 1610 may have a substantially H-shaped profile when viewed from the top or bottom, and each of the external portions 1021, 1023 of the suture 1020 may be positioned within the openings of the H (in other words, the two individual slots 1621a, 1621b on opposite sides 1615, 1616 of the body 1610).

As best seen in the front and back views of FIGS. 17E, 17F, 17K, and 17L, the bottom surface 1614 of the body 1610 is raised higher than the bottom surface of the arms 1660a, 1660b to form an eversion recess 1641 between the arms 1660a, 1660b and below the body 1610. The eversion recess 1641 may thus be considered as a channel extending through the suture securing device 1600 from the front surface 1611 to the back surface 1612. A longitudinal axis of the eversion recess 1641 may be configured so as to be aligned with an incision or wound 1013 when the suture securing device 1600 is in use. The eversion recess 1641 creates a space below the suture securing device 1600 to accommodate skin eversion 1015 (as seen in FIGS. 11A and 11B) that may be present at the wound or incision closure. In some embodiments, the eversion recess 1641 may be omitted. That is, in some embodiments, the body 1610 and the arms 1660a, 1660b may be equally thick.

The bottom surfaces of the arms 1660a, 1660b may include feet 1634. The feet 1634 may be the portions of the arms 1660a, 1660b that contact the surface 1011 of the patient's skin 1010. In some embodiments, the feet 1634 and/or bottom surface 1614 may include a treated undersurface having adhesive, anti-bacterial, medicaments, and/or other agents for transfer to the patient's skin underlying the suture securing device to aid in positioning and/or retention of the suture securing device 1600, assist in healing, and/or reduce scarring, among other purposes.

The arms 1660a, 1660b and hinges 1690a, 1690b are configured such that, in the closed configurations, the arms 1660a, 1660b are positioned on opposite sides 1615, 1616 of the body 1610. The individual slots 1621a, 1621b extend into the opposite sides 1615, 1616 of the body. The first gripping surfaces 1620a, 1620b are positioned within the body 1610 and each at least partially define an end of each individual slot 1621a, 1621b. In the illustrated embodiment, and as best seen in FIGS. 16I and 16E (also partially visible in FIG. 16A) the depth of the individual slots 1621a, 1621b extending into the body 1610 from the side surfaces 1615, 1616 may include deeper portions 1615a, 1616a. These deeper portions 1615a, 1616a are configured to correspond to and mate with protrusions 1666a, 1666b which extend from the arms 1660a, 1660b, respectively. The first gripping surfaces 1620a, 1620b may be positioned within the deeper portions 1615a, 1616a. The second gripping surfaces 1670a, 1670b may be positioned at the ends of the protrusions 1666a, 1666b. In the closed configuration, the deeper portions 1615a, 1616a mate with corresponding protrusions 1666a, 1666b to further secure the suture 1020 between the first and second gripping surfaces 1620a, 1620b, 1670a, 1670b. In some embodiments, the deeper portions 1615a, 1616a and protrusions 1666a, 1666b may be omitted.

In the illustrated embodiment, the hinges 1690a, 1690b are attached to the arms 1660a, 1660b. The arms 1660a, 1660b also include an engagement structure 1681a, 1681b configured to correspond to and engage with corresponding engagement structures 1651a, 1651b of the body 1610. The engagement structures 1651a, 1651b, 1681a, 1681b may cooperate to secure the arms 1660a, 1660b to the body 1510 in the closed configuration as described above.

The suture securing device 1600 may be formed partially or entirely from any sturdy and resilient material, such as plastic resin, for example, polypropylene, polyethylene, acrylonitrile butadiene styrene (ABS), high impact polystyrene (HIPS), poly vinyl chloride (PVC), polycarbonate, thermoplastic elastomers, Polybutylene terephthalate, ethylene vinyl acetate, nylon and low-density polyethylene, linear low-density polyethylene, etc. In some embodiments, the body 1610, arms 1660a, 1660b, and hinges 1690a, 1690b may be formed as a single unitary part, while in other embodiments, these parts may be formed separately and then joined together.

The suture securing device 1600 may have a width W, total thickness T, and length L as illustrated in FIGS. 17M and 17O. The width W, total thickness T, and length L may be similar to those described above.

The suture securing device 1600 secures the external portions 1021, 1023 of the suture between first and second gripping surfaces 1620a, 1620b, 1670a, 1670b in a manner similar to that described above in reference to the suture securing device 1500. The principal difference being suture securing device 1600 includes a thinner body 1610 between the two arms 1660a, 1660b, forming the eversion recess 1641. Accordingly, the suture securing device 1600 provides similar benefits to those identified above, including securing a suture 1020 without requiring a knot to be tied and preventing a suture 1020 from becoming ingrown. Additionally, because the arms 1660a, 1660b secure the external portions 1021, 1023 of the suture 1020 individually, the suture securing device 1600 allows a user to secure the external portions 1021, 1023 of the suture at separate times. For example, a first external portion 1021 may be secured, the suture may be tensioned, and then the second external portion 1023 may be secured.

Figure 18A:
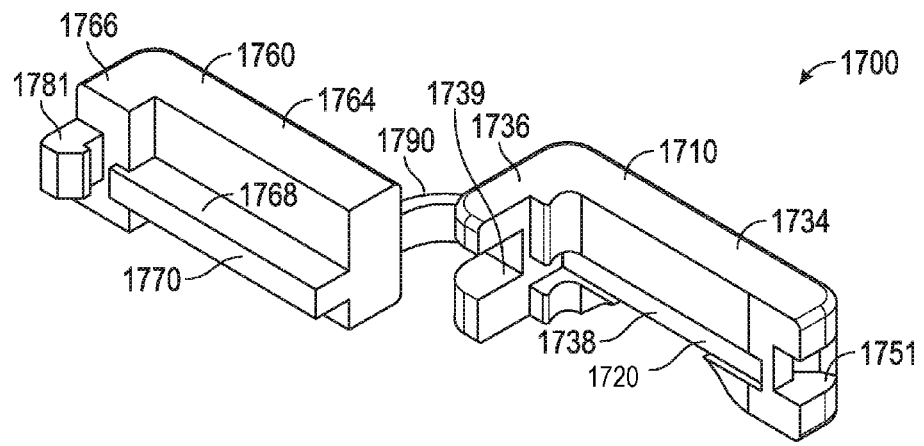
FIGS. 18A through 18P illustrate various views of a seventh embodiment of a suture securing device for securing simple interrupted suture. The seventh embodiment includes a body and an arm attached to the body by a hinge. The body and the hinge are similarly sized such that, in use, a portion of each contacts the patient's skin.
Figure 18B:
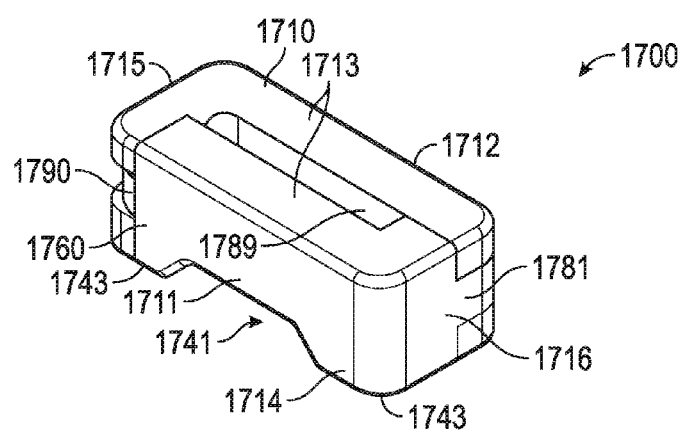
Figure 18C:
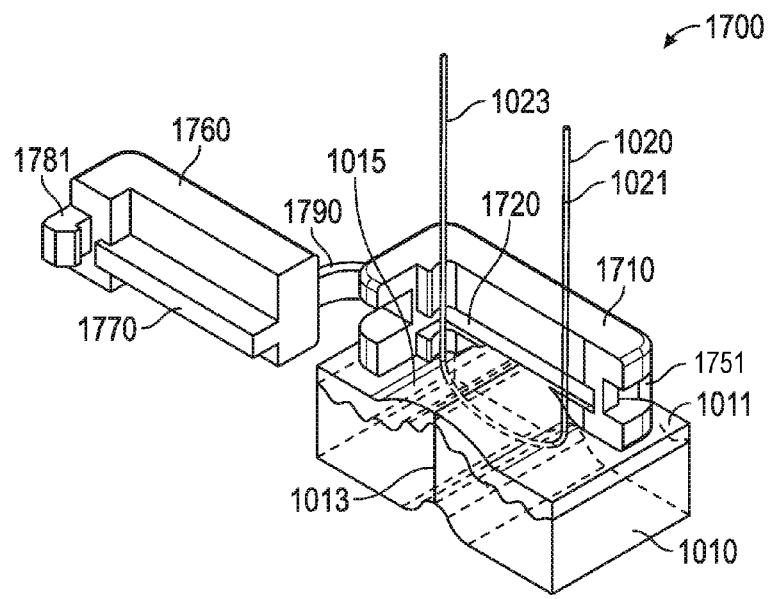
FIGS. 18C and 18D are perspective views of the seventh embodiment of the suture securing device shown in use, positioned on a patient's skin and securing a simple interrupted suture.
Figure 18D:
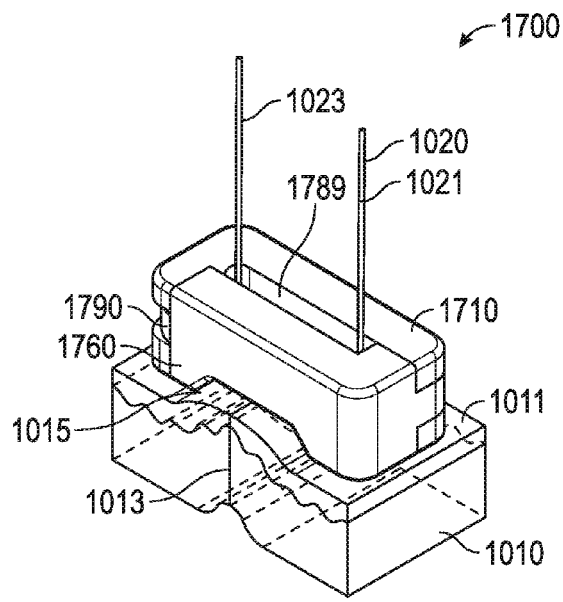
Figure 18E:
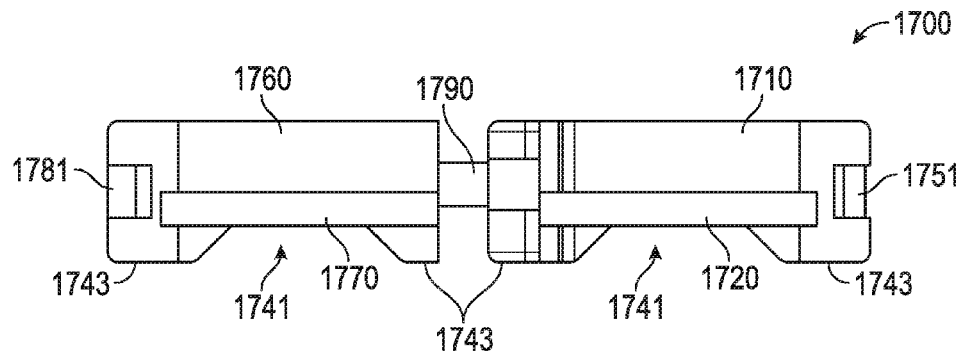
FIGS. 18E through 18J show front, back, top, bottom, and first and second side views of the seventh embodiment of the suture securing device in the open configuration, respectively.
Figure 18F:
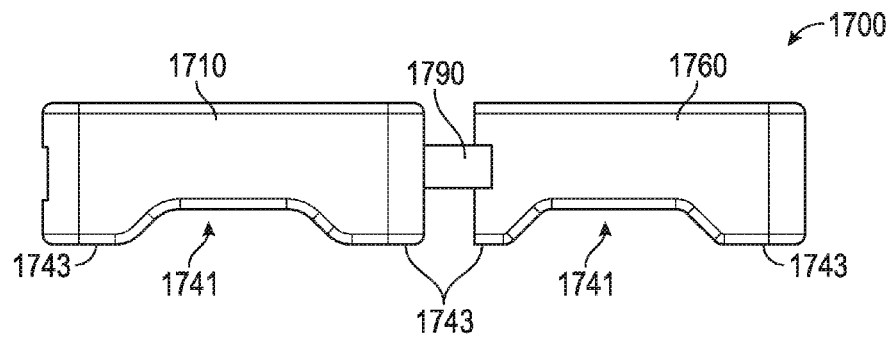
Figure 18G:
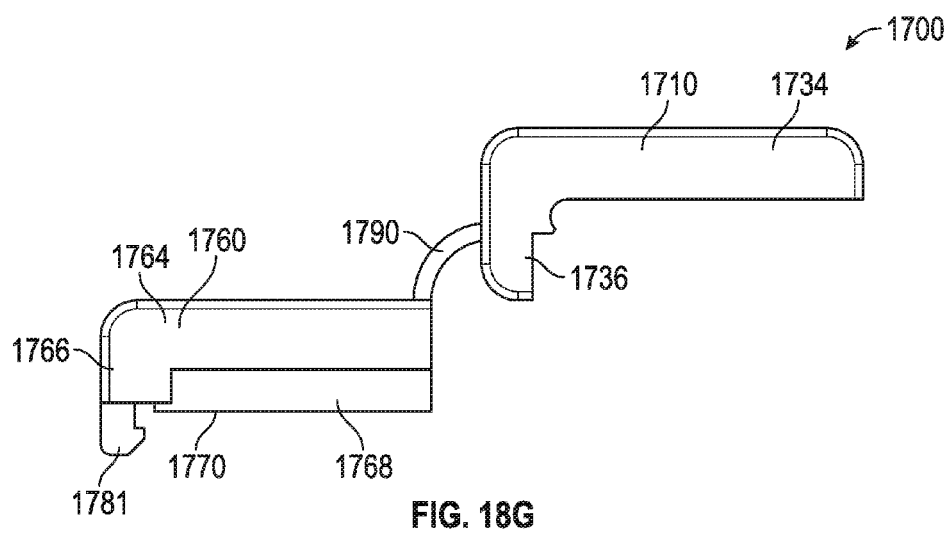
Figure 18H:
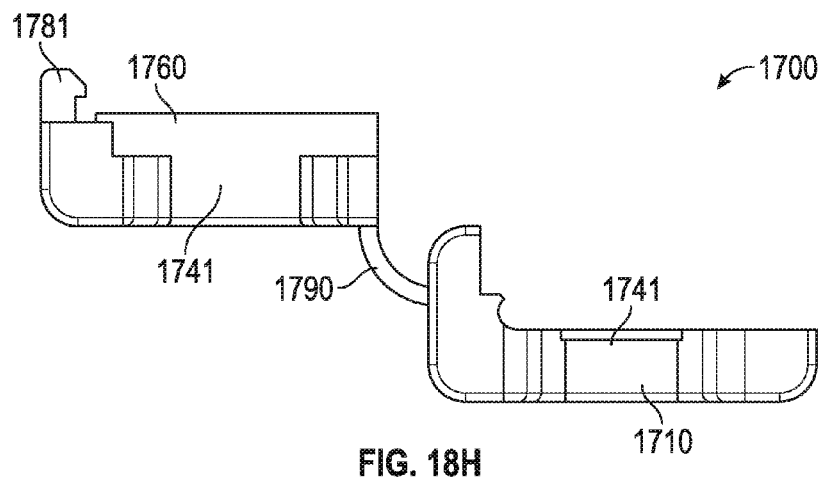
Figure 18I:
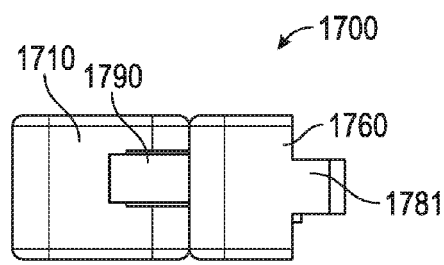
Figure 18J:
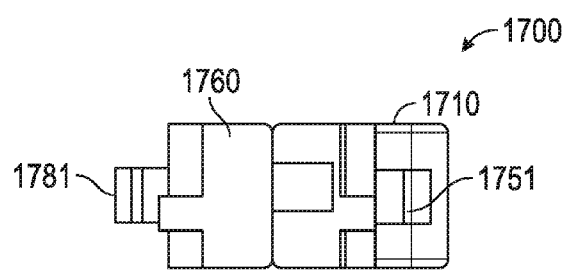
Figure 18K:
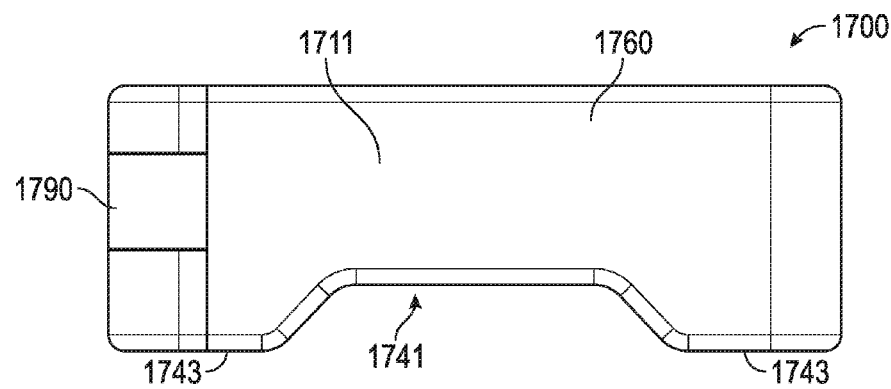
Figure 18L:
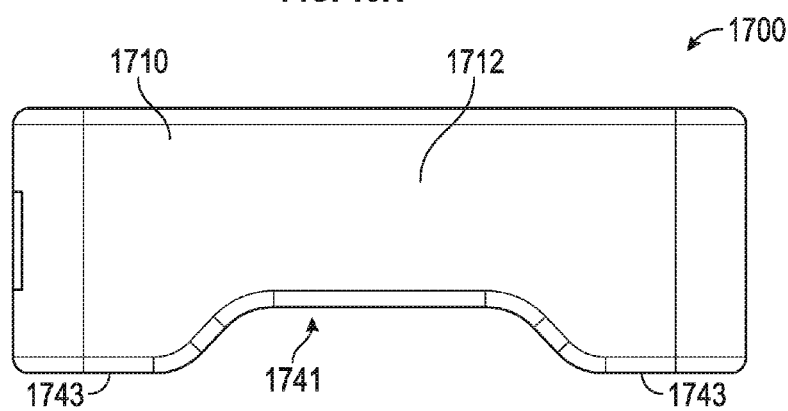
Figure 18M:
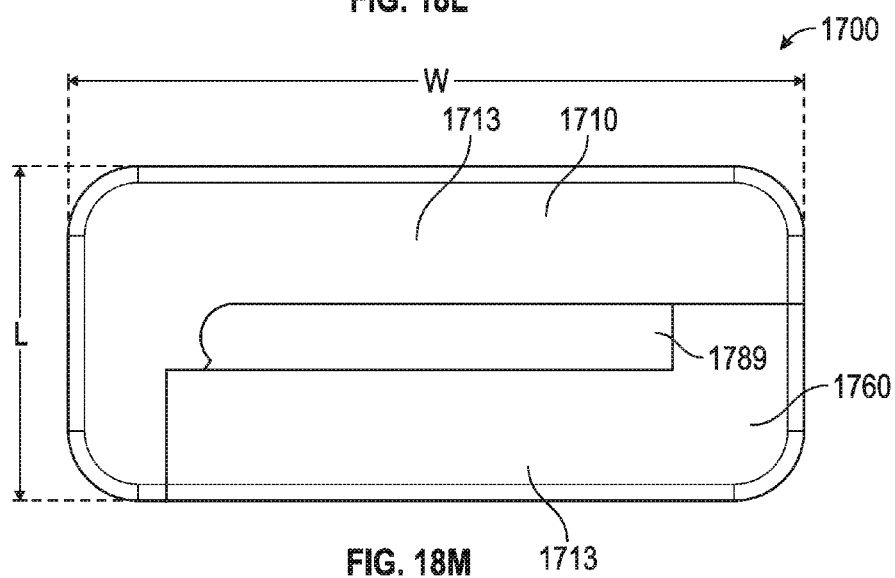
Figure 18N:
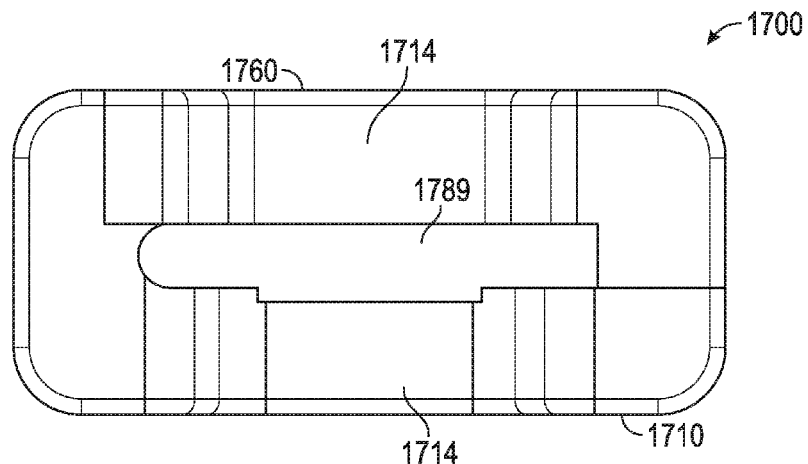
Figure 18O:
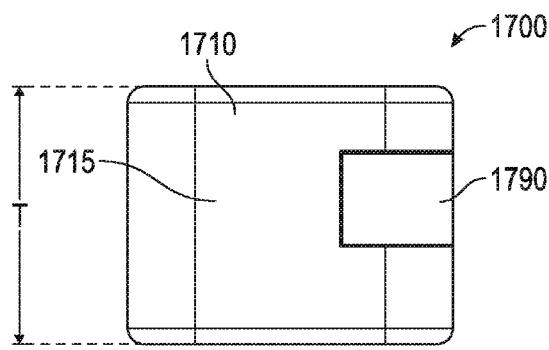
Figure 18P:
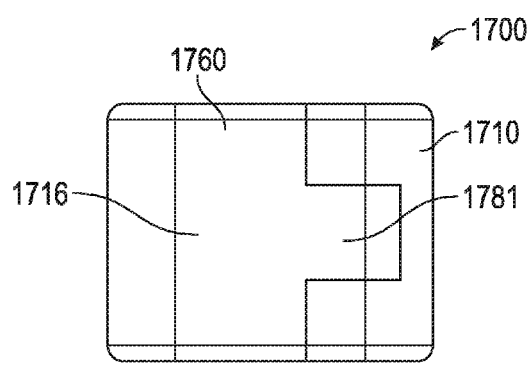

FIGS. 18A through 18P illustrate various views of a seventh embodiment of a suture securing device 1700 for securing a simple interrupted suture 1020. The seventh embodiment includes a body 1710 configured to be positioned across a patient's wound or incision 1013 and an arm 1760 attached to the body 1710 by a hinge 1790. The hinge 1790 allows the suture securing device 1700 to be transitioned between an open configuration and a closed configuration. In the open configuration the suture securing device 1700 can be positioned around exposed the portions 1021, 1023 of the suture 1020. In the closed configuration, the suture 1020 is secured between the arm 1710 and the body 1710. FIGS. 18A and 18B are perspective views of the seventh embodiment of the suture securing device 1700 in an open configuration and a closed configuration, respectively. FIGS. 18C and 18D are perspective views of the seventh embodiment of the suture securing device 1700 shown in use, positioned on a patient's skin 1010 and securing a simple interrupted suture 1020. FIGS. 18E through 18J show front, back, top, bottom, and first and second side views, respectively, of the seventh embodiment of the suture securing device 1700 in the open configuration. FIGS. 18K through 18P show front, back, top, bottom, and first and second side views, respectively, of the first embodiment of the suture securing device 1700 in the closed configuration.

As noted above, the suture securing device 1700 includes a body 1710 and an arm 1760. The body 1710 and the arm 1760 are connected by a hinge 1790. The hinge 1790 can be seen in, for example, FIGS. 18A, 18G, and 18M. The hinge 1790 is configured to allow the arm 1760 to rotate relative to the body 1710, for example between the open configuration and the closed configuration. In the illustrated embodiment, the hinge 1790 is connected to the body 1710 on a back surface 1712 of the body 1710. However, in some embodiments, the hinge 1790 may connect to the body 1710 on other surfaces and/or locations of the body 1710. In some embodiments, the hinge 1790 may be a living or compliant hinge. A living or compliant hinge may be integrally formed with the body 1710 and/or the arm 1760. In some embodiments, a mechanical hinge may be used.

The body 1710 includes a first gripping surface 1720, and the arm 1760 includes a second gripping surface 1770. The first gripping surface 1720 and the second gripping surface 1770 are positioned on the body 1710 and the arm 1760, respectively, such that, when the suture securing device 1700 is in the closed configuration, the first gripping surface 1720 contacts the second gripping surface 1770. In the closed configuration, the suture 1020 can be securely held between the first and second gripping surfaces 1720, 1770. For example, in use, suture securing device 1700 can be positioned on the patient's skin 1010 in the open configuration so that the external portions 1021, 1023 of the suture 1020 are adjacent to the first gripping surface 1720, as shown in FIG. 18C. The suture securing device 1700 can then be transitioned to the closed configuration by rotating the arm 1760 toward the body 1710 until the second gripping surface 1770 of the arm 1760 contacts the first gripping surface 1720 of the body 1710. As shown in FIG. 18D, in this configuration, the external portions 1021, 1023 of the suture 1020 are thus captured between the first gripping surface 1720 and the second gripping surface 1770, and the suture 1020 is secured. In some embodiments, the gripping surfaces 1720, 1770 each include the same material as the body 1710 and/or arm 1760. In other embodiments, the gripping surfaces 1720, 1770 can each be formed of a different material with a greater friction coefficient than that of the body 1710 and/or arm 1760, for example, rubber, latex, nitrile, etc. In some embodiments, the gripping surfaces 1720, 1770 can be smooth, textured, or include other features that increase the ability of the suture securing device 1700 to retain the suture 1020. For example, one of the gripping surfaces 1720, 1770 may include one or more ridges or protrusions extending therefrom, while the other of the gripping surfaces 1720, 1770 may include corresponding grooves or recesses that are configured in size, shape, and position to mate with the corresponding ridges or protrusions.

In the closed configuration, the suture securing device 1700 is generally shaped as a rectangular prism. As illustrated in FIGS. 18B and 18K-18P The suture securing device 1700 includes a front surface 1711, a back surface 1712, a top surface 1713, a bottom surface 1714, a first side surface 1715, and a second side surface 1716. For example, a top surface 1713 of the suture securing device 1700 includes a portion of a top surface of the body 1710 and a portion of the top surface of the arm 1760. The first side surface 1715 may include a side of the body 1710 and the opposite second side surface may include a side of the arm 1760. In reference to the seventh embodiment of the suture securing device 1700, these surfaces are described as being the outer surfaces of the suture securing device 1700 in the closed configuration. Although many of these surfaces are illustrated as planar, this need not be the case in all embodiments. Similarly, although many of these surfaces are illustrated as positioned orthogonally relative to adjacent surfaces, this need not be the case in all embodiments. Various other shapes for the suture securing device 1700 are possible.

In the suture securing device 1700, the body 1710 may be configured substantially in an L-shape, including a width portion 1734 and a length portion 1736. The width portion 1734 may extend across the wound or incision 1013 and include the first gripping surface 1720. The first gripping surface 1720 may be positioned within a channel 1738 (as seen in FIG. 18A) formed on a face of the body 1710. The length portion 1736 is connected to the width portion 1734 at a first end of the length portion 1736. In some embodiments, the width portion 1734 is substantially orthogonal to the length portion 1736, so as to form the L-shape of the body. The length portion 1736 may include a notch 1739 (as seen in FIG. 18A) configured to receive the hinge 1790 in the closed configuration. In some embodiments, the notch 1739 may be omitted. The arm 1760 may also be formed substantially in an L-shape. The L-shape of the arm 1760 may be complimentary to the L-shape of the body 1710, such that the two fit together to form the rectangular prism shape of the suture securing device 1700 in the closed configuration. The arm 1760 includes a width portion 1764 and a length portion 1766. The width portion 1764 and the length portion 1766 may be substantially orthogonal to each other. The width portion 1764 may include a protrusion 1768 extending from a face thereof. The second gripping surface 1770 may be positioned at the end of the protrusion 1768. The protrusion 1768 may be configured to mate with the channel 1738 in the closed configuration, such that the first gripping surface 1720 contacts the second gripping surface 1770. In the closed configuration, the arm 1760 compliments the body 1710 and a slot 1789 (as seen in FIGS. 18B, 18D, 18M, and 18N) is formed therebetween. The slot 1789 may be defined between the width portion 1734, 1764 of the arm 1710 and body 1760, respectively, and the length portions 1736, 1766 of the arm 1710 and body 1760. When viewed from above or below, the slot 1789 may not extend completely through the suture securing device because of the protrusion 1768 of the arm 1760 extending into the channel 1738 of the body 1710.

As best seen in the front and back views of FIGS. 18E, 18F, 18K, and 18L, the bottom surface 1114 of the suture securing device 1700 (including the body 1710 and the arm 1760) includes an eversion recess 1741. The eversion recess 1741 may be configured as an indentation or opening extending into the suture securing device 1700 from the bottom surface 1714, a portion of which is formed in the body 1710 and the arm 1760. The eversion recess 1741 may also be considered as a channel extending through the suture securing device 1700 from the front surface 1711 to the back surface 1712. A longitudinal axis of the eversion recess 1741 may be configured so as to be aligned with an incision or wound 1013 when the suture securing device 1700 is in use. The eversion recess 1741 creates a space below the suture securing device 1700 to accommodate skin eversion 1015 (as seen in FIGS. 11A and 11B) that may be present at the wound or incision closure. For example, as shown in FIGS. 18C and 18D, the suture securing device 1100 may be positioned across a wound or incision 1013, so that the bottom surface 1714 of the suture securing device 1700 rests on the surface 1011 of the patient's skin 1010 on opposite sides of the wound or incision 1013. The eversion recess 1741 may be positioned substantially directly above the wound or incision 1013 so as to accommodate skin eversion 1015. In some embodiments, the eversion recess 1741 may be omitted.

The bottom surface 1714 may be considered to have feet 1743 on opposite sides of the eversion recess 1741. The feet 1743 may be the portions of the suture securing device 1700 that contact the surface 1011 of the patient's skin 1010. A portion of the feet 1734 may be formed in each of the body 1710 and the arm 1760. In some embodiments, the feet 1743 and/or bottom surface 1714 may include a treated undersurface having adhesive, anti-bacterial, medicaments, and/or other agents for transfer to the patient's skin underlying the suture securing device to aid in positioning and/or retention of the suture securing device 1100, assist in healing, and/or reduce scarring, among other purposes.

In the illustrated embodiment, the hinge 1190 attaches to the arm 1760 at a first end of the arm 1760. The opposite end of the arm 1760 includes an engagement structure 1781 configured to correspond to and engage with a corresponding engagement structure 1751 of the body 1710. The engagement structures 1751, 1781 may cooperate to secure the arm 1760 to the body 1710 in the closed configuration. In some embodiments, the arm 1760 can be permanently locked into the closed configuration with the body 1710 after mating the engagement structures 1751, 1781. In other embodiments, the engagement structures 1751, 1781 can be configured to releasably engage, such that the arm 1760 can releasably engage the body 1710 and the suture securing device 1700 can be alternatively and repeatedly transitioned between the open and closed configuration. Releasable engagement of the engagement structures 1751, 1781 may allow for repositioning and/or tensioning adjustment of the suture 1020 over time. In the illustrated embodiment, the engagement structure 1781 on the arm 1760 includes a hooked structure, and the engagement structure 1751 of the body 1710 includes a notched recess. The suture securing device 1700 can thus be secured in the closed configuration by catching the hooked structure within the recess. The hooked structure and the recess may be configured for a compliant snap fit. That is, the hooked member, the side member 1764, or side of the recess may be configured to deform slightly to allow for engagement and/or disengagement. In some embodiments, these features may be reversed, such that the arm 1760 includes the recess and the body 1710 includes the hooked structure. Further, other possible engagement structures 1751, 1781 are possible and within the scope of this disclosure.

The suture securing device 1700 may be formed partially or entirely from any sturdy and resilient material, such as plastic resin, for example, polypropylene, polyethylene, acrylonitrile butadiene styrene (ABS), high impact polystyrene (HIPS), poly vinyl chloride (PVC), polycarbonate, thermoplastic elastomers, Polybutylene terephthalate, ethylene vinyl acetate, nylon and low-density polyethylene, linear low-density polyethylene, etc. In some embodiments, the body 1710, arm 1760, and hinge 1790 may be formed as a single unitary part, while in other embodiments, these parts may be formed separately and then joined together.

The suture securing device 1700 may have a width W, thickness T, and length L as illustrated in FIGS. 18M and 18O. The width W, thickness T, and length L may be similar to those previously described.

The suture securing device 1700 secures the external portions 1021, 1023 of the suture between first and second gripping surfaces 1720, 1770. Accordingly, the suture securing device 1700 may be used to secure a suture 1020 without requiring the external portions 1021, 1023 to be tied into a knot. Additionally, as best seen in FIGS. 18C and 18D, the suture securing device 1700 secures the external portions 1021, 1023 of the suture 1020 in a position at which they extend substantially orthogonally to the surface 1011 of the patient's skin 1010. Thus, the suture securing device reduces or eliminates the need for any portion of the suture 1020 rest directly on the surface of the skin as is common with convention suture securing techniques like knot tying. This may eliminate or reduce the likelihood that the suture 1020 will become ingrown as the wound or incision heals. Further, because the likelihood that the suture 1020 will be become ingrown is reduced when the suture securing device 1100 is used, the suture 1020 can remain in place for longer than conventional knot-tied sutures.

FIGS. 19A-27D show various embodiments of suture securing devices configured for use with simple interrupted sutures that include a body and one or more insertable clips. As will be described in greater detail below, in some embodiments, the one or more clips are insertable into the body from the front (or back), top (or bottom) and or opposite sides of the body. Further, in some embodiments, the clip surrounds the body (for example, as shown in FIG. 19B), while in other embodiments the body surrounds the clip (for example, as in FIG. 26A). These principles may be modified, combined, and/or otherwise used with any of the other suture securing devices described throughout.

Figure 19A:
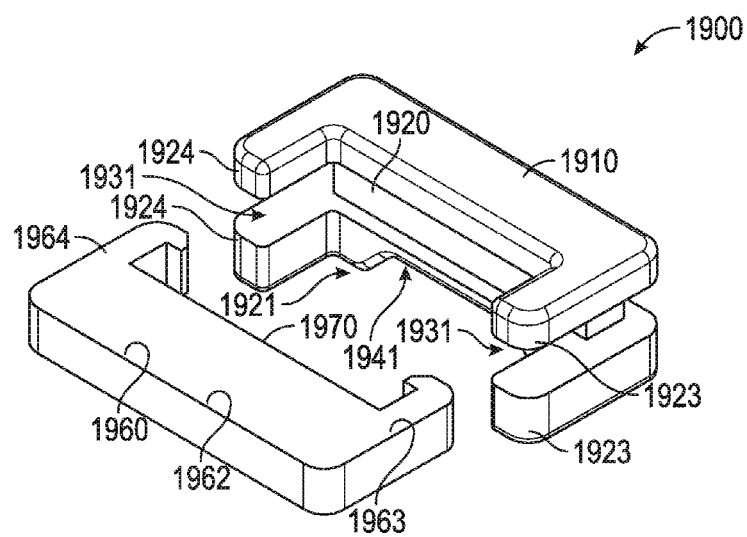
FIGS. 19A through 19P illustrate various views of an eighth embodiment of a suture securing device for securing a simple interrupted suture. The eighth embodiment includes a body and an insertable clip. The clip is inserted into the front of the body to secure the suture.
Figure 19B:
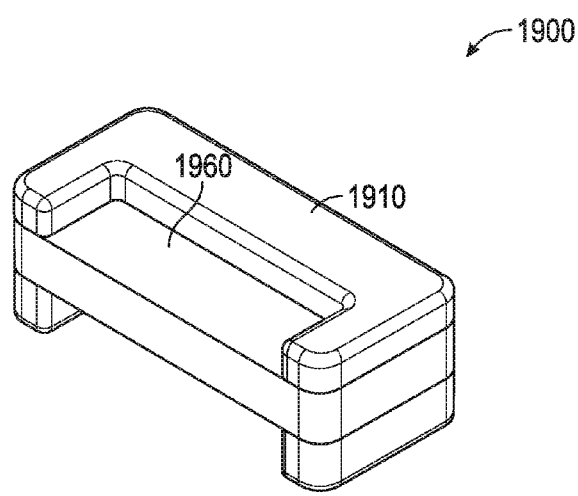
Figure 19C:
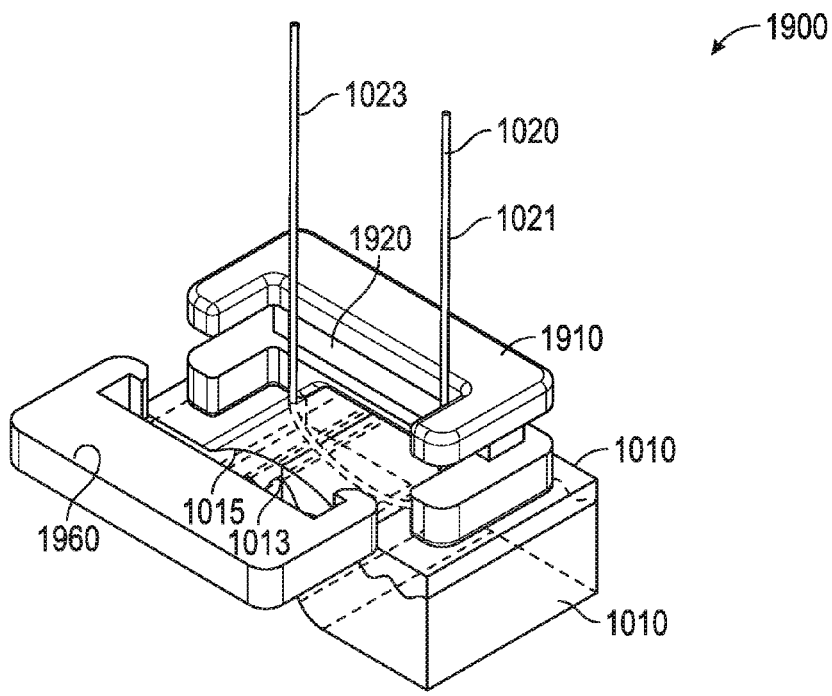
FIGS. 19C and 19D are perspective views of the eighth embodiment of the suture securing device shown in use, positioned on a patient's skin and securing a simple interrupted suture.
Figure 19D:
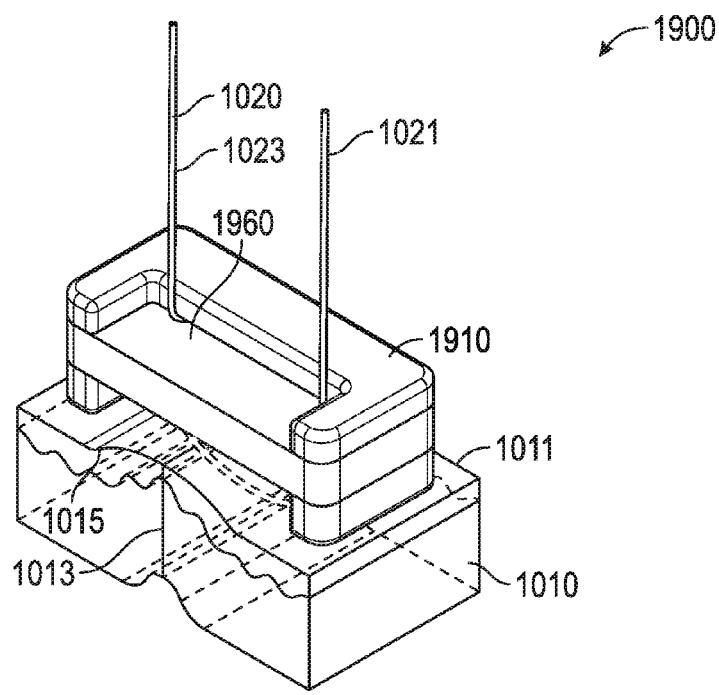
Figure 19H:
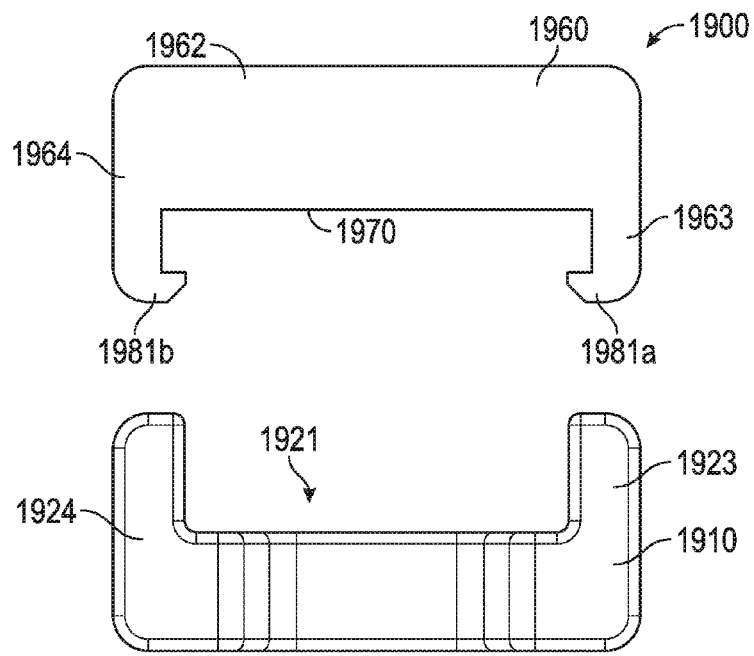
Figure 19I:
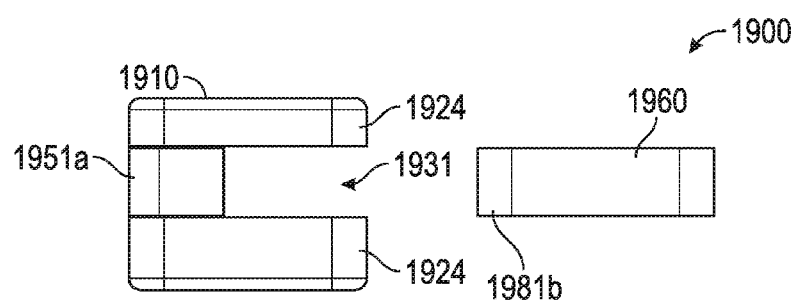
Figure 19J:
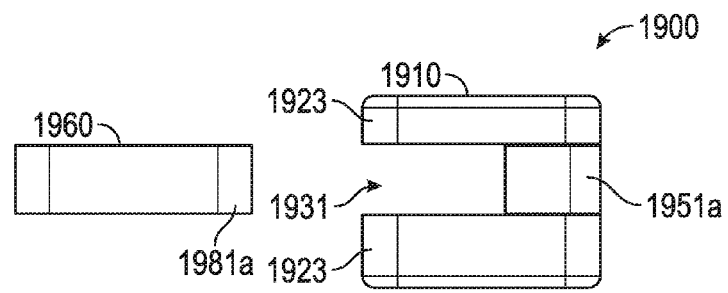
Figure 19K:
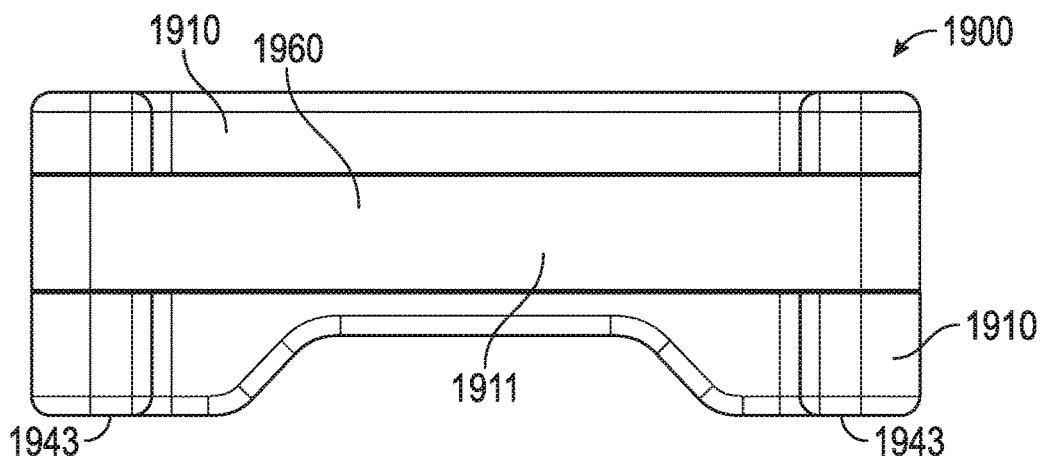
Figure 19L:
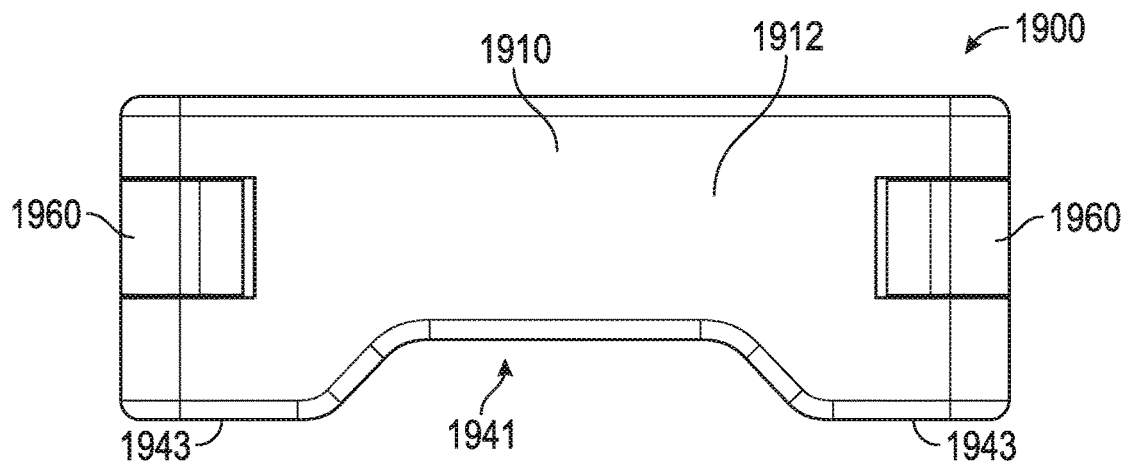
Figure 19M:
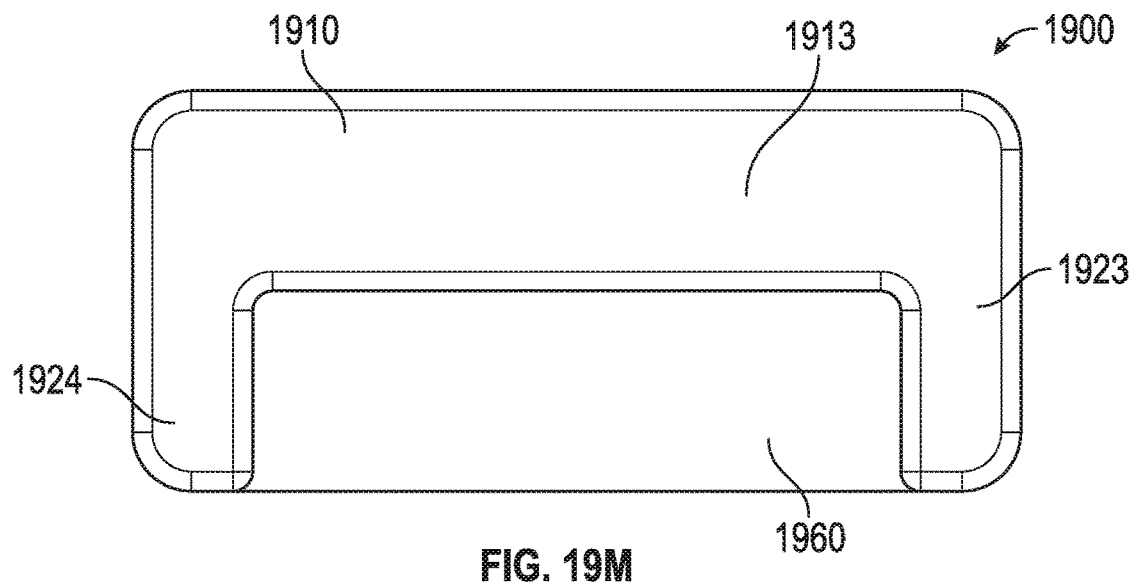
Figure 19N:
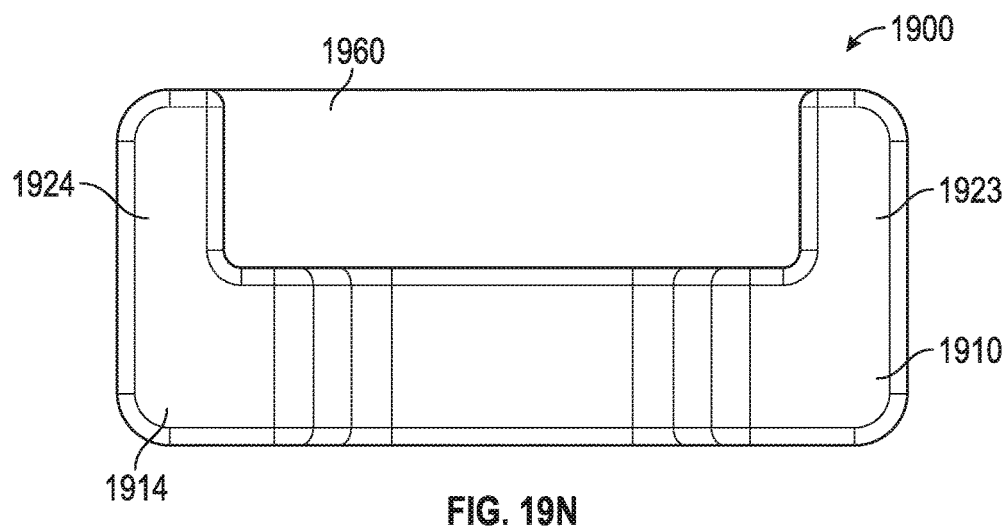
Figure 19O:
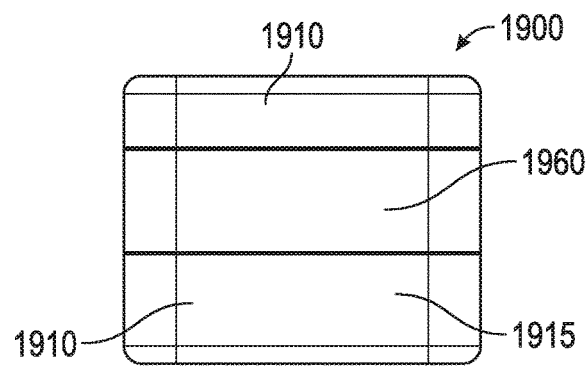
Figure 19P:
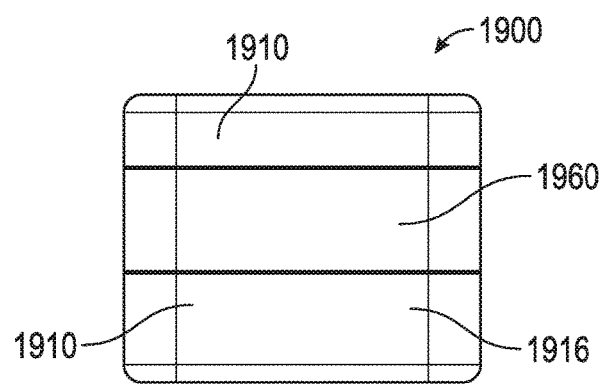

FIGS. 19A through 19P illustrate various views of an eighth embodiment of a suture securing device 1900 for securing simple interrupted suture 1020. The eighth embodiment includes a body 1910 and an insertable clip 1960. The clip 1960 is inserted into the front of the body 1910 to secure the suture 1020. FIGS. 19A and 19B are perspective views of the eighth embodiment of the suture securing device 1900 in an open configuration and a closed configuration, respectively. FIGS. 19C and 19D are perspective views of the eighth embodiment of the suture securing device 1900 shown in use, positioned on a patient's skin 1010 and securing a simple interrupted suture 1020. FIGS. 19E through 19J show front, back, top, bottom, and first and second side views of the eighth embodiment of the suture securing device 1900 in the open configuration, respectively.

FIGS. 19K through 19P show front, back, top, bottom, and first and second side views of the eighth embodiment of the suture securing device 1900 in the closed configuration, respectively. In many aspects, the suture securing device 1900 is similar to the suture securing device 1100 of FIG. 12A, however, the arm 1160 of the suture securing device 1100 has been replaced by a clip 1960 in the suture securing device 1900.

The suture securing device 1900 includes a body 1910 and an insertable clip 1960. In an open configuration, the body 1910 and the clip 1960 are not connected (as shown, for example, in FIG. 19A). In a closed configuration, the clip 1960 is inserted into the body 1910 (as shown, for example, in FIG. 19B). As will be described in greater detail below, the suture securing device 1900 may be positioned on a patient's skin 1010 proximal to a suture 1020 in the open configuration, and then transitioned to the closed configuration (by inserting the clip 1960 into the body 1910) to secure the suture 1020. In the closed configuration, the suture 1020 is secured between the clip 1960 and the body 1910.

The body 1910 includes a first gripping surface 1920 (as seen in FIG. 19A), and the clip 1960 includes a second gripping surface 1970 (as seen in FIGS. 19A and 19G). The first gripping surface 1920 and the second gripping surface 1970 are positioned on the body 1910 and the clip 1960, respectively, such that, when the suture securing device 1900 is in the closed configuration, the first gripping surface 1920 contacts the second gripping surface 1970. In the closed configuration, the suture 1020 can be securely held between the first and second gripping surfaces 1920, 1970. For example, in use, body 1910 can be positioned on the patient's skin 1010 in the open configuration so that the external portions 1021, 1023 of the suture 1020 are adjacent to the first gripping surface 1920, as shown in FIG. 19C. The suture securing device 1900 can then be transitioned to the closed configuration by inserting the clip 1960 into the body 1910 until the second gripping surface 1970 of the clip 1960 contacts the first gripping surface 1920 of the body 1910. As shown in FIG. 12D, in this configuration, the external portions 1021, 1023 of the suture 1020 are thus captured between the first gripping surface 1920 and the second gripping surface 1970, and the suture 1020 is secured. In some embodiments, the gripping surfaces 1920, 1970 include the same material as the body 1910 and/or clip 1960. In other embodiments, the gripping surfaces 1920, 1970 can be formed or comprised of a different material with a greater friction coefficient than that of the body 1910 and/or clip 1960, for example, rubber, latex, nitrile, etc. In some embodiments, the gripping surfaces 1920, 1970 can be smooth, textured, or include other features that increase the ability of the suture securing device 1900 to retain the suture 1020. For example, one of the gripping surfaces 1920, 1970 may include one or more ridges or protrusions extending therefrom, while the other of the gripping surfaces 1920, 1970 may include corresponding grooves or recesses that are configured in size, shape, and position to mate with the corresponding ridges or protrusions.

In the illustrated embodiment, the suture securing device 1900, in the closed configuration, is generally shaped as a rectangular prism (as best seen in FIGS. 19K-19P). The body 1910 includes a front surface 1911, a back surface 1912, a top surface 1913, a bottom surface 1914, a first side surface 1915, and a second side surface 1916. Although many of these surfaces are illustrated as planar, this need not be the case in all embodiments. Similarly, although many of these surfaces are illustrated as positioned orthogonally relative to adjacent surfaces, this need not be the case in all embodiments. Various other shapes for the body 1910 are possible.

As seen, for example, in FIG. 19G, the body 1910 includes a front opening 1921. The front opening 1921 extends generally into the body 1910 from the front surface 1911 partway toward the back surface 1912. The front opening 1921 also extends entirely through the body 1910 from the top surface 1913 to the bottom surface 1914. On opposite side surfaces 1915, 1916 of the body 1910, the front opening is defined by members 1923 and 1924 which extend outwardly from the body 1910. Thus, with the front opening 1921 and the members 1923 and 1924, the body 1910 may be described as having a C-shape, as best seen in the top and bottom views of FIGS. 19G and 19H. In some instances, the front opening 1921 may be used to help position the suture securing device 1900 relative to the suture 1020. For example, with the suture securing device 1900 in the open position, the suture securing device 1900 can be positioned such that the external portions 1021, 1023 of the suture are positioned within the front opening 1921, as shown in FIG. 19C. The front opening 1921 and members 1923, 1924 may help to maintain the suture securing device 1900 and suture 1020 in position until the clip 1960 is inserted. In other words, the body 1910 may have a substantially C-shaped profile when viewed from the top or bottom, and the external portions 1021, 1023 of the suture 1020 may be positioned within the opening of the C (in other words, front opening 1921).

As best seen in the front and back views of FIGS. 19E, 19F, 19K, and 19L, the bottom surface 1914 of the suture securing device 1900 includes an eversion recess 1941. The eversion recess 1941 is formed in the body 1910. The eversion recess 1941 may be configured as an indentation or opening extending into the body 1910 from the bottom surface 1914. The eversion recess 1941 may also be considered as a channel extending through the body 1910 from the front surface 1911 to the back surface 1912. A longitudinal axis of the eversion recess 1941 may be configured so as to be aligned with an incision or wound 1013 when the suture securing device 1900 is in use. The eversion recess 1941 creates a space below the suture securing device 1900 to accommodate skin eversion 1015 (as seen in FIGS. 11A and 11B) that may be present at the wound or incision closure. For example, as shown in FIGS. 12C and 12D, the suture securing device 1900 may be positioned across a wound or incision 1013, so that the bottom surface 1914 of the suture securing device 1900 rests on the surface 1011 of the patient's skin 1010 on opposite sides of the wound or incision 1013. The eversion recess 1941 may be positioned substantially directly above the wound or incision 1013 so as to accommodate skin eversion 1015. In some embodiments, the eversion recess 1941 may be omitted.

The body 1910 is configured such that the bottom surface 1914 includes feet 1943 on opposite sides of the eversion recess 1941. The feet 1943 may be the portions of the suture securing device 1900 that contact the surface 1011 of the patient's skin 1010. In some embodiments, the feet 1943 and/or bottom surface 1914 may include a treated undersurface having adhesive, anti-bacterial, medicaments, and/or other agents for transfer to the patient's skin underlying the suture securing device to aid in positioning and/or retention of the suture securing device 1900, assist in healing, and/or reduce scarring, among other purposes.

The body 1910 also includes a channel 1931 configured to receive the clip 1960 in the closed configuration. The channel 1931 is formed as an opening which extends partway into the body 1910 from the front surface 1911 and the first and second side surfaces 1915, 1916. The channel 1931 is likely best seen in FIGS. 19A, 19C, 19I, and 19J. As shown, the channel 1931 is positioned between the top surface 1913 and the bottom surface 1914 and generally runs parallel to each. As shown in the side views of FIGS. 19I and 19J, the channel 1931 bisects the members 1923, 1924, dividing each into two separate protrusions on each side of the suture securing device 1900. The first gripping surface 1920 is positioned within the body 1910 and at least partially defines the end of the channel 1931 in one direction: for example, the first gripping surface 1920 defines the end or depth of the channel 1931 extending into the body 1910 from the front surface 1911. In the illustrated embodiment, the channel 1931 is configured such that, in the closed configuration, the clip 1960 is substantially received within the body 1910 as shown, for example, in FIGS. 19B, 19D and 19K through 19P. Accordingly, the depth of the channel 1931 extending from the front surface 1911 and the first and second side surfaces 1915, 1916 may be chosen to correspond to the dimensions and shape of the clip 1960 as will be described in greater detail below. Similarly, the thickness of the channel 1931 may be chosen to correspond to the thickness of the clip 1960. In the illustrated embodiment, the depth of the channel 1931 extending into the body 1910 from the front surface 1911 is greater than the depth of the front opening 1921. Thus, a cross-sectional shape bisecting the body 1910 between the first and second side surfaces 1915, 1916 may also be substantially C-shaped. In some embodiments, the clip is received within the opening of the C. In the closed configuration this may cause the suture 1020 to serpentine through the body 1910, following this C-shape. This may further help to retain the suture 1020 within the suture securing device 1900 in the closed configuration. In some embodiments, the channel 1931 may be omitted or may be configured to only partially receive the clip 1960 within the body 1910.

In the illustrated embodiment, the clip 1960 includes a front member 1962 and two side members 1963 and 1964, as seen, for example, in FIG. 19G. The front member 1962 is configured to extend across the width of the suture securing device 1900. The front member 1962 also includes the second gripping surface 1970. The side members 1963 and 1964 extend as protrusions from the front member 1962 on opposite ends of the clip 1960. Accordingly, in the illustrated embodiment, the clip 1960 is substantially C-shaped, and the second gripping surface 1970 is positioned within the interior of the C. The shape of the clip 1960 may be configured so as to fit within the channel 1931 of the body 1910 described above, such that the clip 1960 may be substantially completely positioned within the body 1910 in the closed configuration. Accordingly, the front portion 1962 can be sized so as to fit within the channel 1931 extending into the body 1910 from the front surface 1911 of the body 1910. The front portion may further be configured such that the second gripping surface 1970 contacts the first gripping surface 1920 in the closed configuration. Similarly, the side members 1962, 1963 may be sized so as to fit within the channel 1931 extending into the side surfaces 1915, 1916 of the body 1910. In this way, the clip 1960 may be configured to mate with the body 1910. It will be appreciated, however, that other shapes for the clip 1960 are possible and within the scope of this disclosure.

In the illustrated embodiment, the clip 1960 includes engagement structures 1981a, 1981b at the free ends of the first and second side members 1963, 1964, respectively. The engagement structures 1981a, 1981b are configured to correspond to and engage with a corresponding engagement structures 1951a, 1951b on opposite sides of the body 1910. The engagement structures 1951, 1981 may cooperate to secure the clip 1960 to the body 1910 in the closed configuration. In some embodiments, the clip 1960 can be permanently locked into the closed configuration with the body 1910 after mating the engagement structures 1951a, 1951b, 1981a, 1981b. In other embodiments, the engagement structures can be configured to releasably engage, such that the clip 1960 can releasably engage the body 1910 and the suture securing device can be alternatively and repeatedly transitioned between the open and closed configuration. Releasable engagement of the engagement structures may allow for repositioning and/or tensioning adjustment of the suture 1020 over time. In the illustrated embodiment, the engagement structures on the clip 1960 include a hooked structure, and the engagement structures of the body 1910 include a recess. The suture securing device 1900 can thus be secured in the closed configuration by catching the hooked structure within the recess. The hooked structure and the recess may be configured for a compliant snap fit. That is, the hooked members, the side members 1963, 1964, or side of the recesses may be configured to deform slightly to allow for engagement and/or disengagement. In some embodiments, these features may be reversed, such that the clip 1960 includes the recesses and the body 1910 includes the hooked structures. Further, other possible engagement structures 1951, 1981 are possible and within the scope of this disclosure.

The suture securing device 1900 may be formed partially or entirely from any sturdy and resilient material, such as plastic resin, for example, polypropylene, polyethylene, acrylonitrile butadiene styrene (ABS), high impact polystyrene (HIPS), poly vinyl chloride (PVC), polycarbonate, thermoplastic elastomers, Polybutylene terephthalate, ethylene vinyl acetate, nylon and low-density polyethylene, linear low-density polyethylene, etc. In some embodiments, the body 1910 and the clip 1960 may be made of the same material or different materials.

The suture securing device 1900 may have a width W, thickness T, and length L as illustrated in FIGS. 19M and 19O. In some embodiments, the width W may be between 1 mm to 15 mm. In some embodiments, the thickness T may be between 0.5 mm to 10 mm. In some embodiments, the length L may be between 5 mm to 60 mm. However, these ranges are merely provided as examples and may be adjusted to adapt the suture securing device 1900 for any particular application.

As previously described, the suture securing device 1900 secures the external portions 1021, 1023 of the suture between first and second gripping surfaces 1920, 1970. Accordingly, the suture securing device 1900 may be used to secure a suture 1020 without requiring the external portions 1021, 1023 to be tied into a knot. Additionally, the suture securing device 1900 reduces or eliminates the need for any portion of the suture 1020 rest directly on the surface of the skin as is common with convention suture securing techniques like knot tying.

Figure 20A:
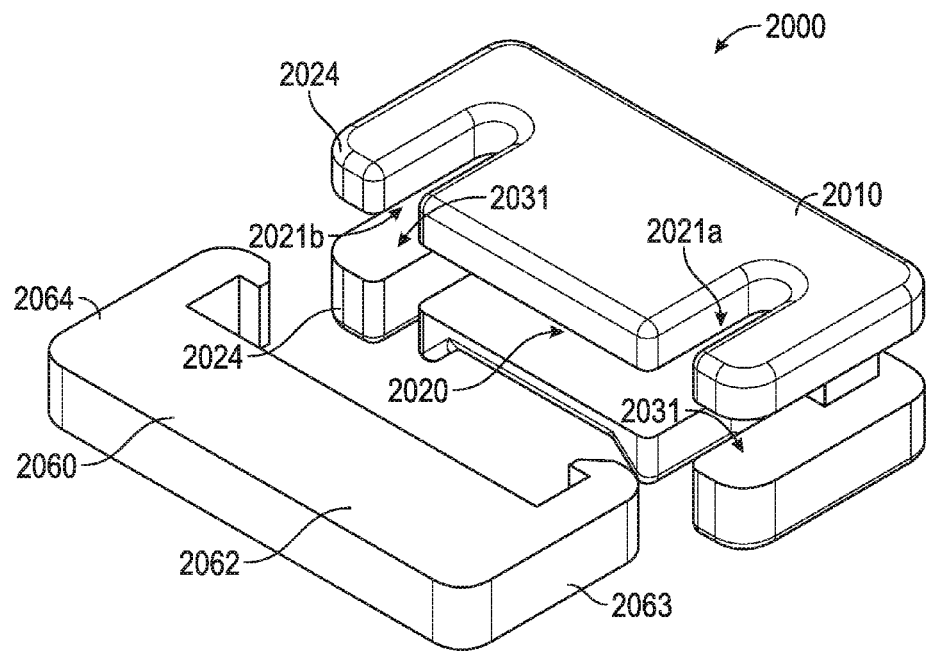
FIGS. 20A through 20P illustrate various views of a ninth embodiment of a suture securing device for securing a simple interrupted suture. The ninth embodiment includes a body and an insertable clip. The body includes two individual slots on the front of the body to secure the external portions of the suture. The clip is inserted into the front of the body.
Figure 20B:
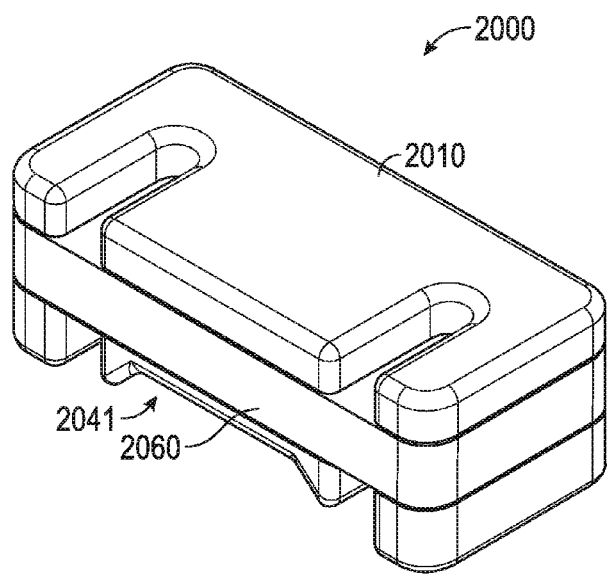
Figure 20C:
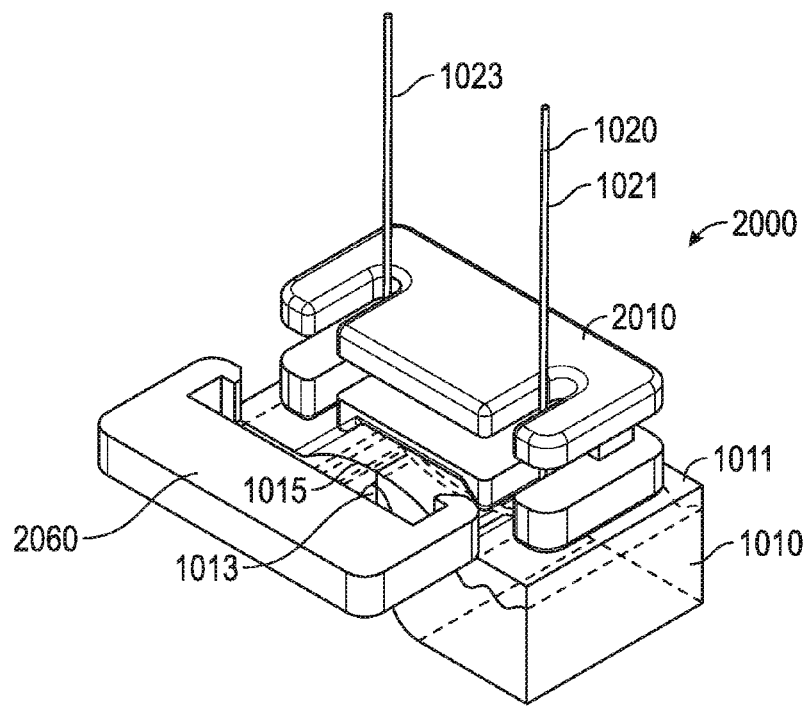
FIGS. 20C and 20D are perspective views of the ninth embodiment of the suture securing device shown in use, positioned on a patient's skin and securing a simple interrupted suture.
Figure 20D:
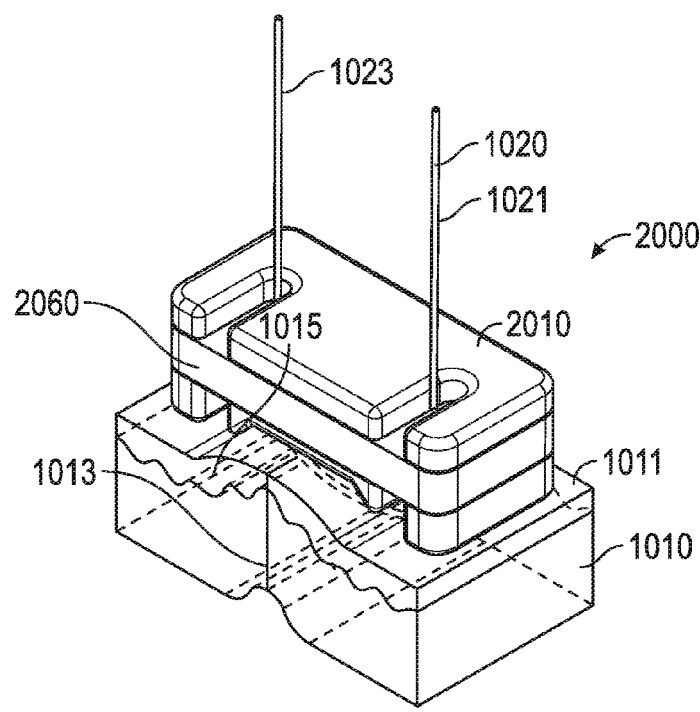
Figure 20E:
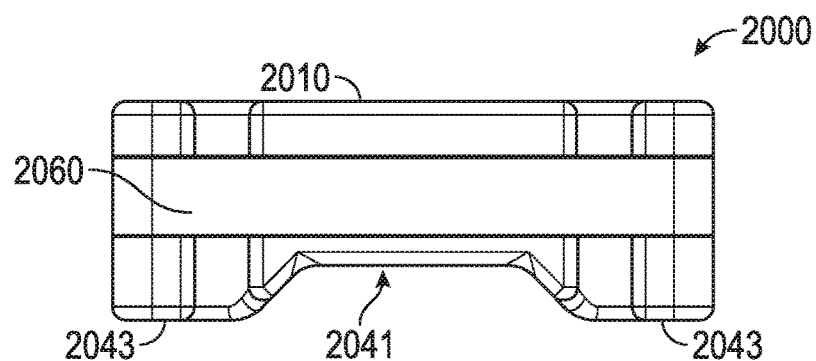
FIGS. 20E through 20J show front, back, top, bottom, and first and second side views of the ninth embodiment of the suture securing device in the open configuration, respectively.
Figure 20F:
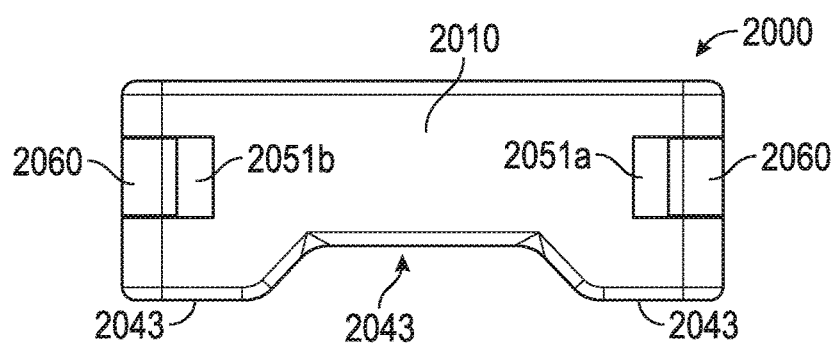
Figure 20G:
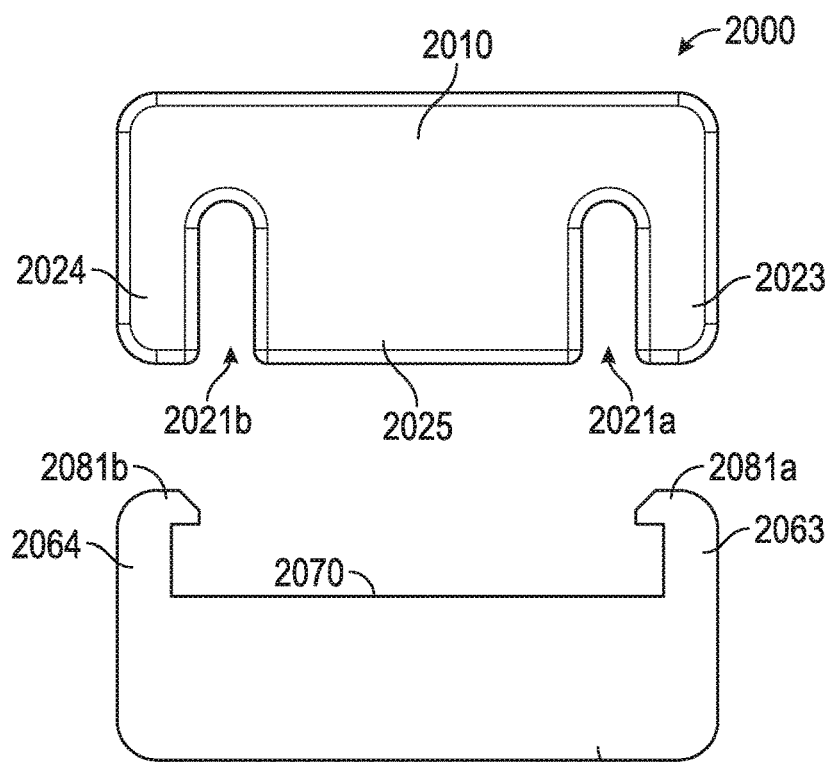
Figure 20H:
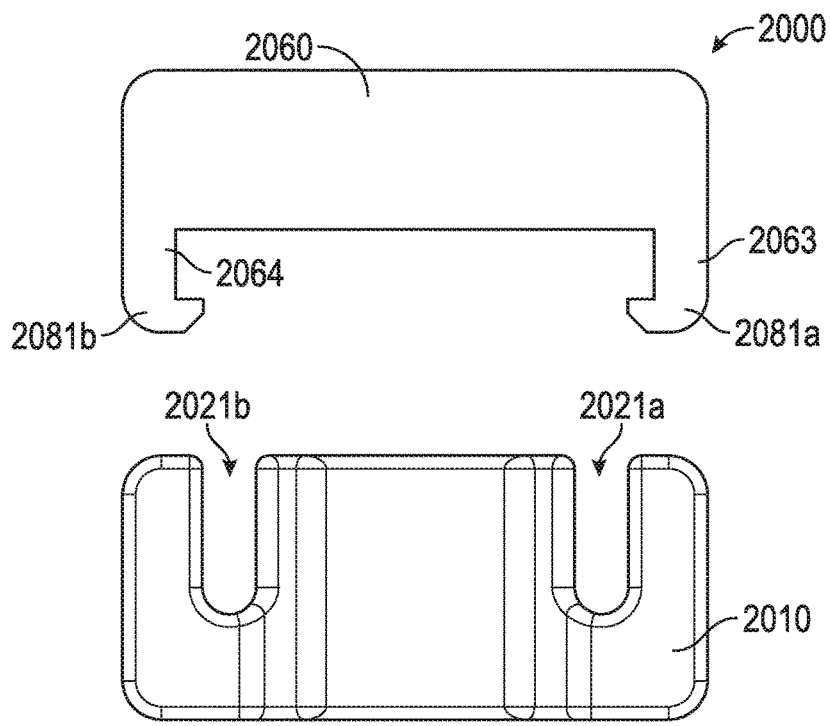
Figure 20I:
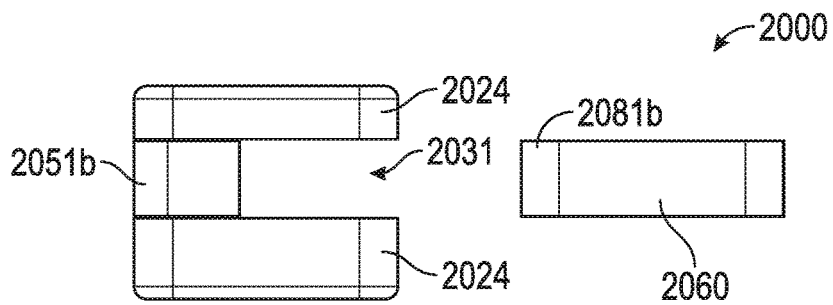
Figure 20J:
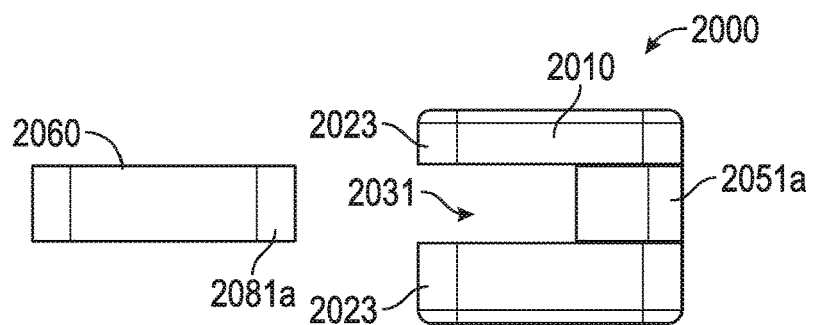
Figure 20K:
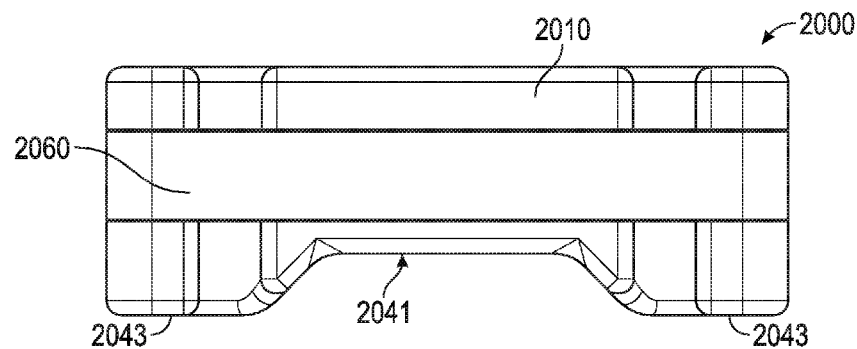
Figure 20L:
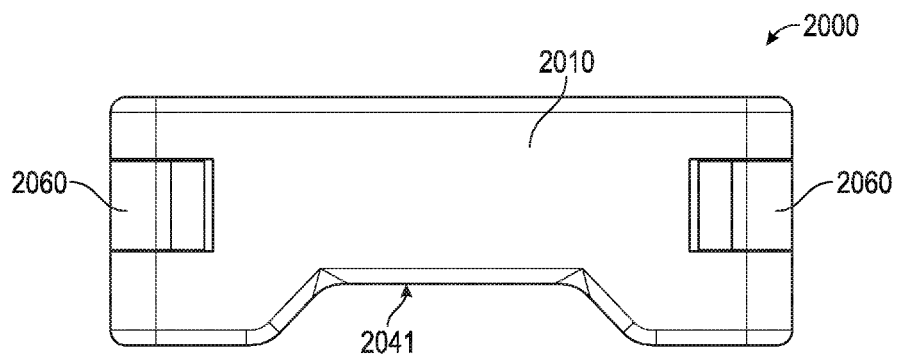
Figure 20M:
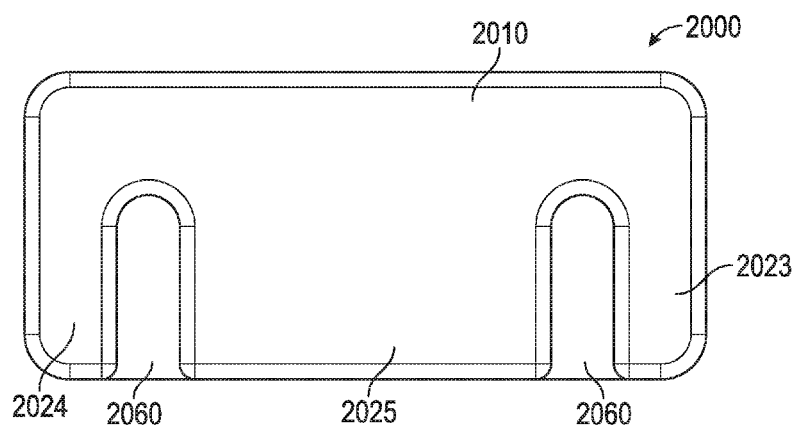
Figure 20N:
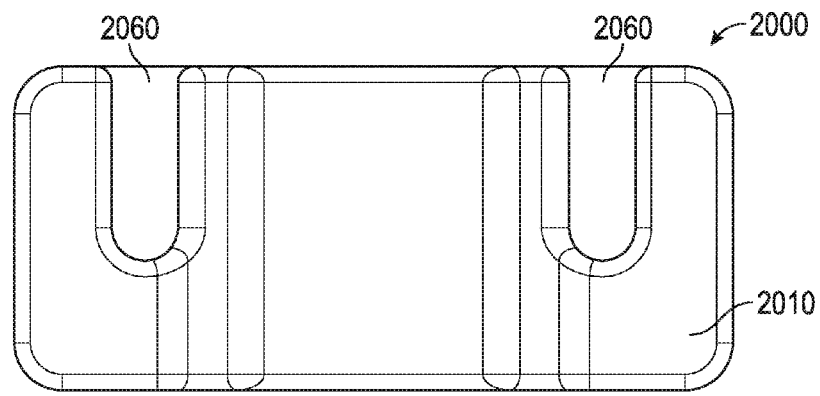
Figure 20O:
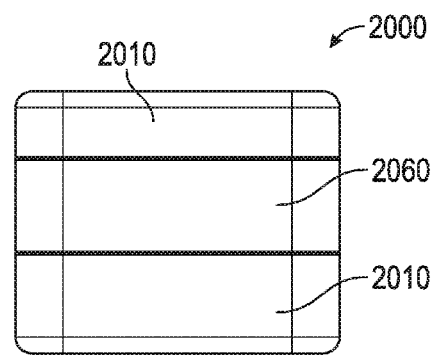
Figure 20P:
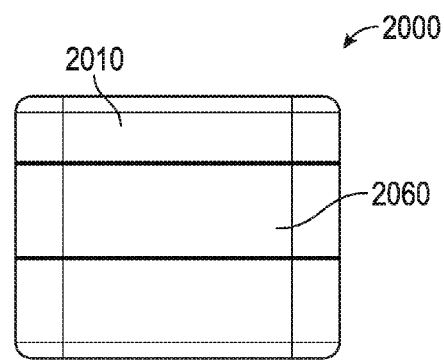

FIGS. 20A through 20P illustrate various views of a ninth embodiment of a suture securing device 2000 for securing simple interrupted suture 1020. The ninth embodiment includes a body 2010 and an insertable clip 2016. The body 2010 includes two individual slots 2021a, 2021b on the front of the body 2010 to secure the external portions 1021, 1023 of the suture 1020. The clip 2060 is inserted into the front of the body 2010. FIGS. 20A and 20B are perspective views of the ninth embodiment of the suture securing device 2000 in an open configuration and a closed configuration, respectively. FIGS. 20C and 20D are perspective views of the ninth embodiment of the suture securing device 2000 shown in use, positioned on a patient's skin 1010 and securing a simple interrupted suture 1020. FIGS. 20E through 20J show front, back, top, bottom, and first and second side views of the ninth embodiment of the suture securing device 2000 in the open configuration, respectively. FIGS. 20K through 20P show front, back, top, bottom, and first and second side views of the ninth embodiment of the suture securing device 2000 in the closed configuration, respectively.

In many aspects, the suture securing device 2000 is similar to the suture securing device 1900 of FIG. 19A. For example, the clip 2060 is substantially similar to the clip 1960. The principle difference between the suture securing device 2000 and the suture securing device 1900 is that the body 2010 includes two individual slots 2021a, 2021b, as opposed to the front space 1921. For example, as seen, in FIG. 20G, the body 2010 includes two individual slots 2021a, 2021b. Each of the two individual slots 2021a, 2021b extends generally into the body 2010 from the front surface 2011 partway toward the back surface 2012. Each of the two individual slots 2021a, 2021b also extends entirely through the body 2010 from the top surface 2013 to the bottom surface 2014. On opposite side surfaces 2015, 2016 of the body 2010, the two individual slots 2021a, 2021b are defined by members 2023 and 2024 which extend outwardly from the body 2010. A member 2025 extends outwardly from the body 2010 in between the two individual slots 2021a, 2021b. Thus, with the two individual slots 2021a, 2021b and the members 2023, 2024, 2025 the body 2010 may be described as having a E-shape, as best seen in the top and bottom views of FIGS. 20G and 20H. In some instances, the two individual slots 2021a, 2021b may be used to help position the suture securing device 2000 relative to the suture 1020. For example, with the suture securing device 2000 in the open position, the suture securing device 2000 can be positioned such that each of the external portions 1021, 1023 of the suture 1020 are positioned within one of the two individual slots 2021a, 2021b, as shown in FIG. 20C. The two individual slots 2021a, 2021b and members 2023, 2024, 2025 may help to maintain the suture securing device 2000 and suture 1020 in position until the suture securing device is transitioned to the closed configuration. In other words, the body 2010 may have a substantially E-shaped profile when viewed from the top or bottom, and each of the external portions 1021, 1023 of the suture 1020 may be positioned within the openings of the E (in other words, the two individual slots 2021a, 2021b).

The function and advantages of the suture securing device 2000 are substantially similar to that previously described in reference to suture securing device 1900 and will not be repeated here.

Figure 21A:
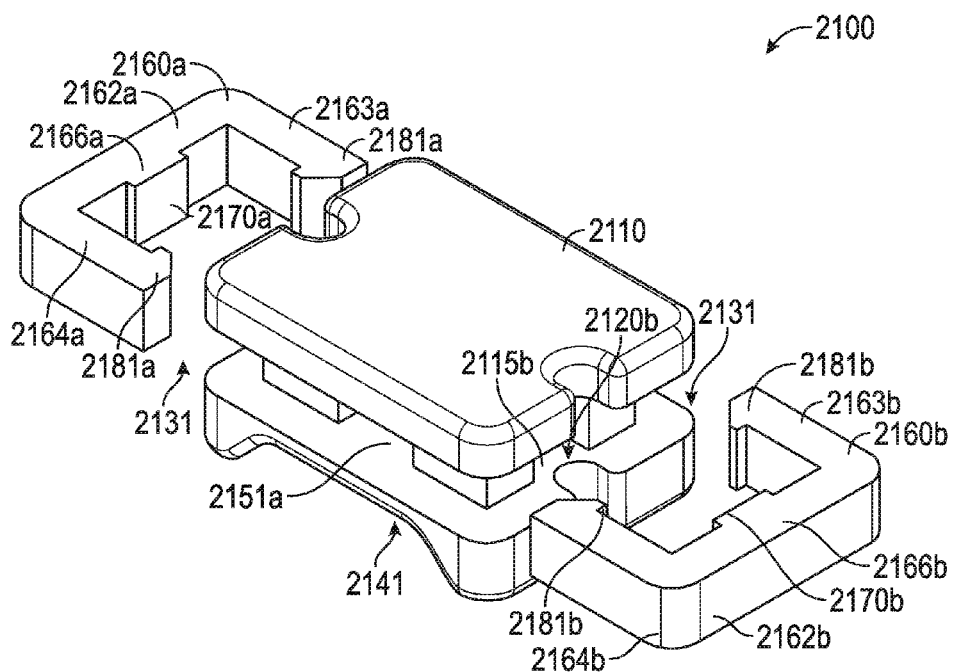
FIGS. 21A through 21P illustrate various views of a tenth embodiment of a suture securing device for securing a simple interrupted suture. The tenth embodiment includes a body and two insertable clips. The body includes two individual slots on opposite sides of the body to secure the external portions of the suture. The clips are inserted into opposite sides of the body.
Figure 21B:
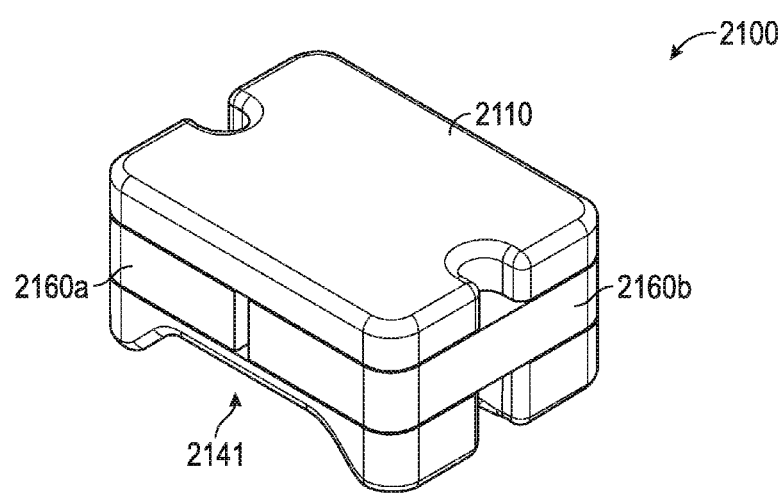
Figure 21C:
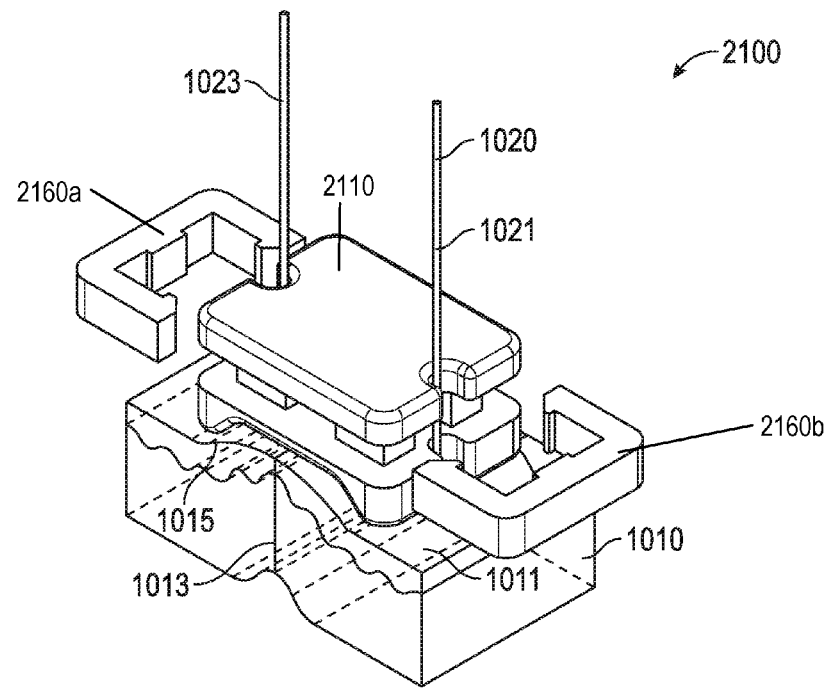
FIGS. 21C and 21D are perspective views of the tenth embodiment of the suture securing device shown in use, positioned on a patient's skin and securing a simple interrupted suture.
Figure 21D:
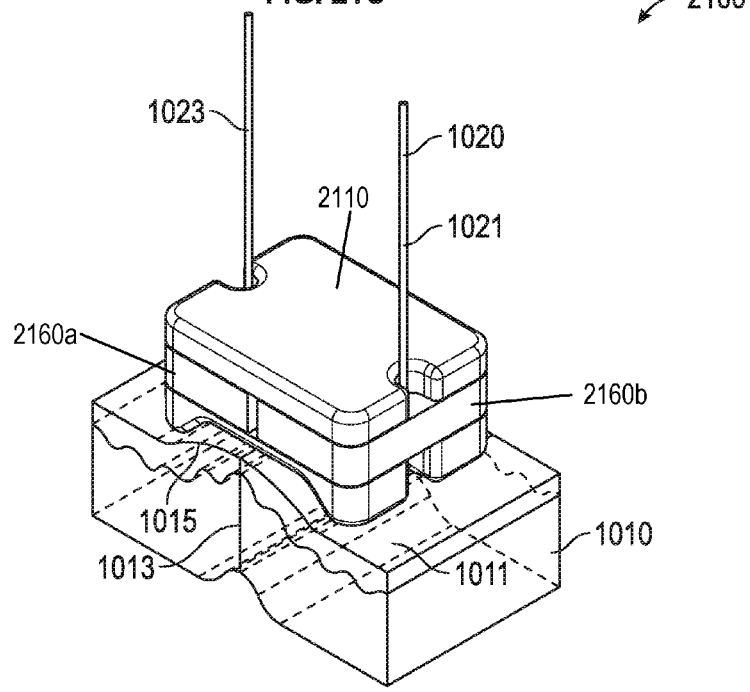
Figure 21E:
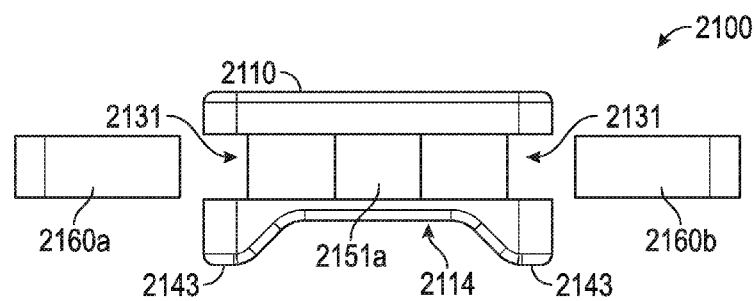
FIGS. 21E through 21J show front, back, top, bottom, and first and second side views of the tenth embodiment of the suture securing device in the open configuration, respectively.
Figure 21F:
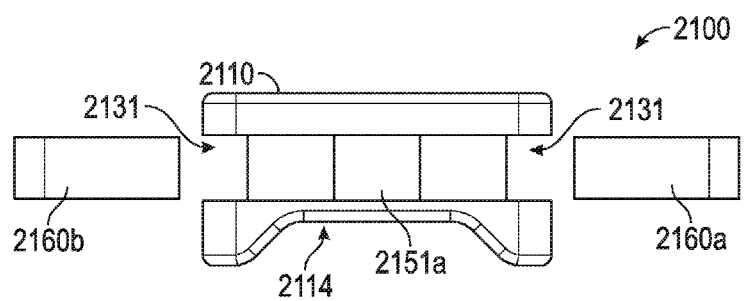
Figure 21G:
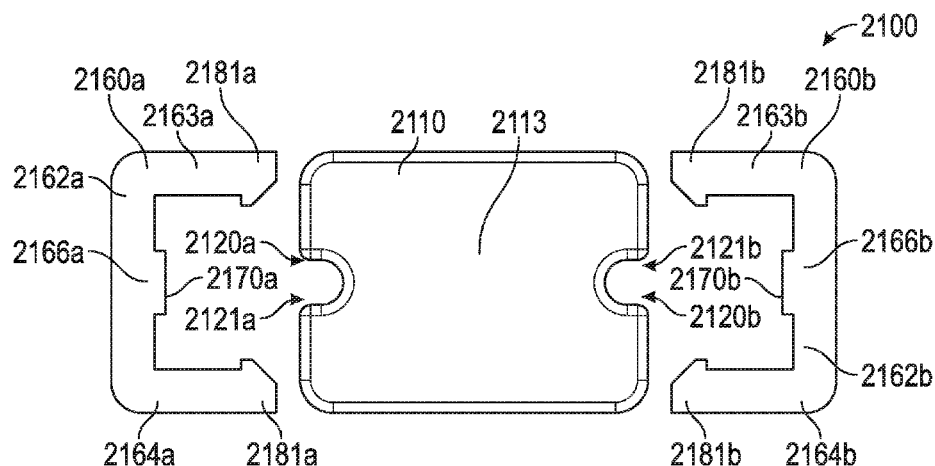
Figure 21H:
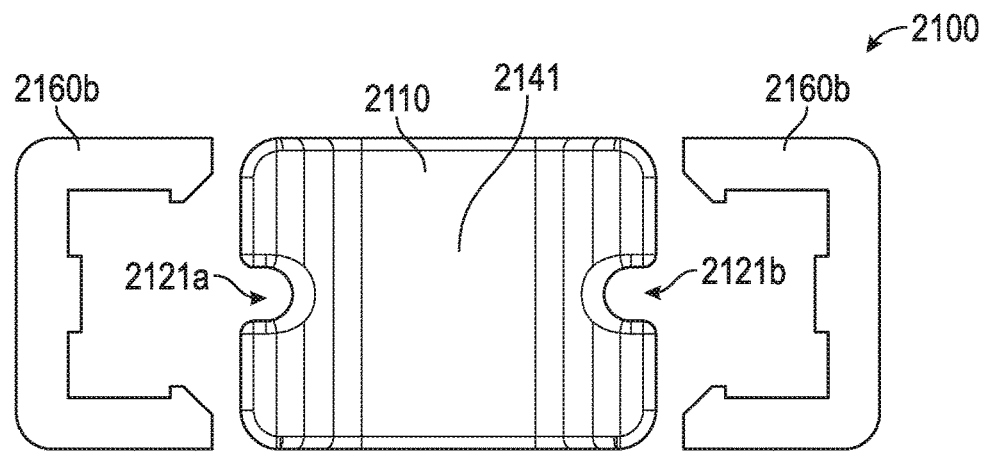
Figure 21I:
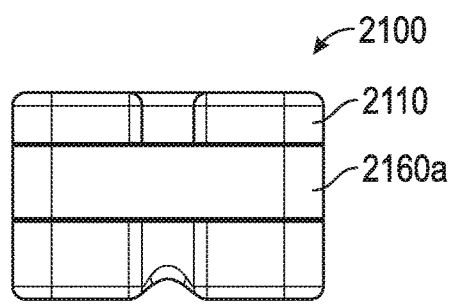
Figure 21J:
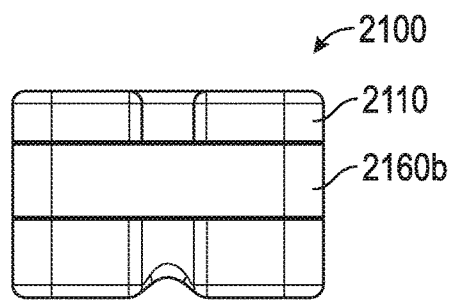
Figure 21K:
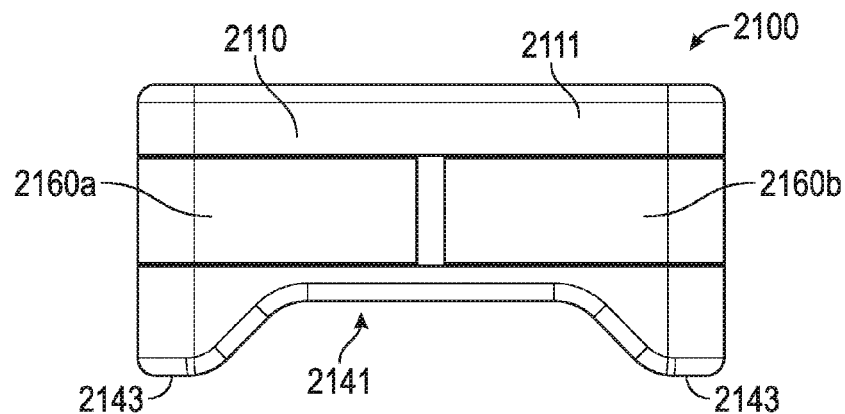
Figure 21L:
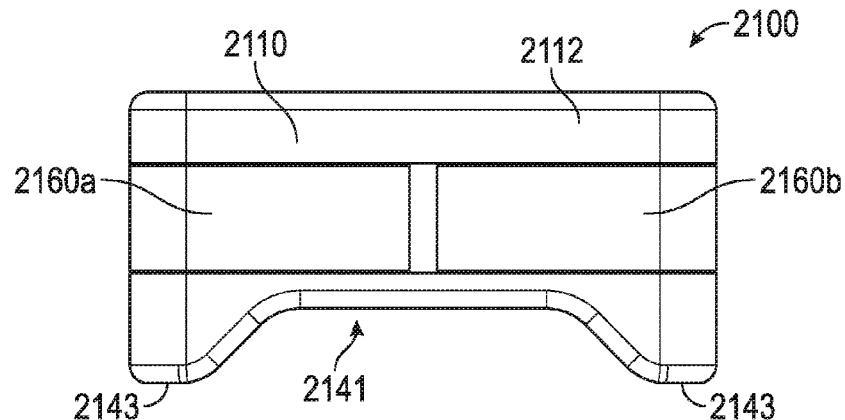
Figure 21M:
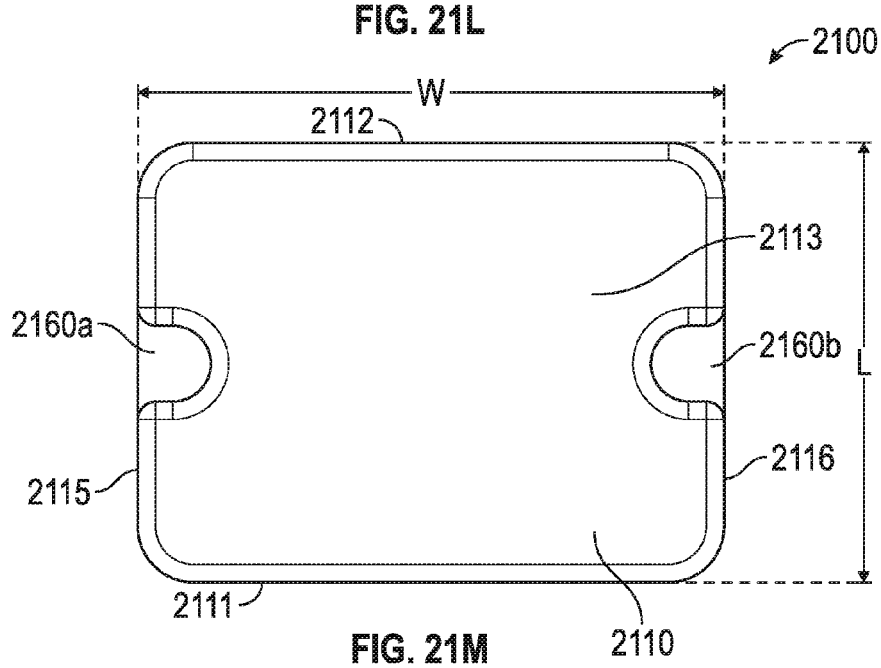
Figure 21N:
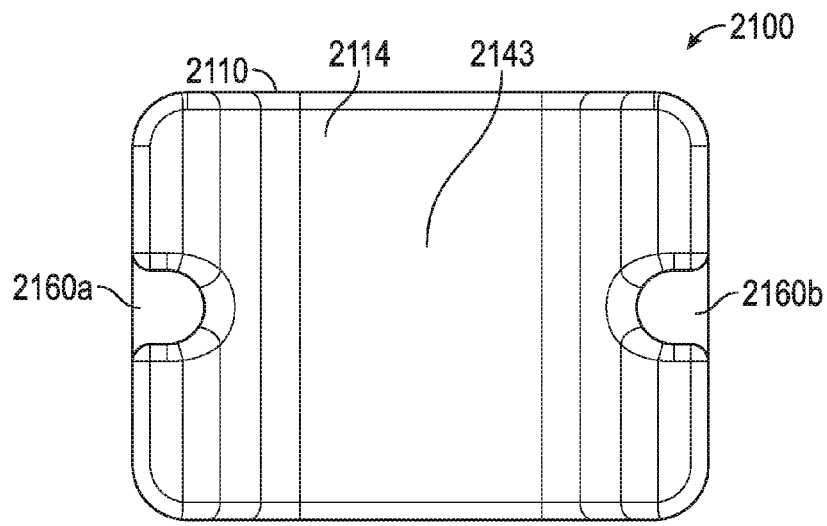
Figure 21O:
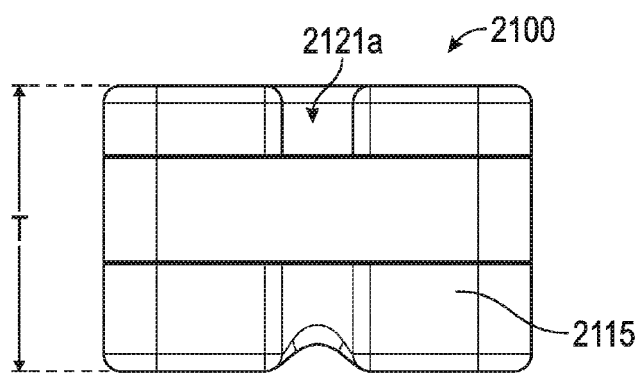
Figure 21P:
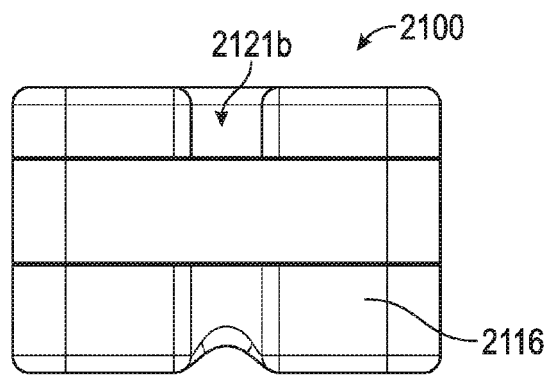

FIGS. 21A through 21P illustrate various views of a tenth embodiment of a suture securing device 2100 for securing simple interrupted suture 1020. The tenth embodiment includes a body 2110 and two insertable clips 2160a, 2160b. The body 2110 also includes two individual slots 2121a, 2121b on opposite sides of the body 2110 to secure the external portions of the suture 1020. The clips 2160a, 2160b are inserted into opposite sides 2115, 2116 of the body 2110. FIGS. 21A and 21B are perspective views of the tenth embodiment of the suture securing device 2100 in an open configuration and a closed configuration, respectively. FIGS. 21C and 21D are perspective views of the tenth embodiment of the suture securing device 2100 shown in use, positioned on a patient's skin and securing a simple interrupted suture 1010. FIGS. 21E through 21J show front, back, top, bottom, and first and second side views of the tenth embodiment of the suture securing device 2100 in the open configuration, respectively. FIGS. 21K through 21P show front, back, top, bottom, and first and second side views of the tenth embodiment of the suture securing device 2100 in the closed configuration, respectively.

As noted, the body 2110 includes first gripping surfaces 2120a, 2120b, and each of the clips 2160a, 2160b includes second gripping surface 2170a, 2170b, respectively. The first gripping surfaces 2120a, 2120b and the second gripping surfaces 2170a, 2170b are positioned on the body 2110 and the clips 2160a, 2160b, respectively, such that, when the suture securing device 2100 is in the closed configuration, each of the first gripping surfaces 2120a, 2120b contacts each of the second gripping surfaces 2170a, 2170b. In the closed configuration, the suture 1020 can be securely held between the first and second gripping surfaces 2120a, 2120b, 2170a, 2170b. In some embodiments, the gripping surfaces 2120a, 2120b, 2170a, 2170b each include or are formed of the same material as the body 2110 and/or clips 2160a, 2160b. In other embodiments, the gripping surfaces 2120a, 2120b, 2170a, 2170b can be formed of a different material with a greater friction coefficient than that of the body 2110 and/or clips 2160a, 2160b, for example, rubber, latex, nitrile, etc. In some embodiments, the gripping surfaces 2120a, 2120b, 2170a, 2170b can be smooth, textured, or include other features that increase the ability of the suture securing device 2100 to retain the suture 1020. For example, one of the gripping surfaces 2120a, 2120b, 2170a, 2170b may include one or more ridges or protrusions extending therefrom, while the other of the gripping surfaces 2120a, 2120b, 2170a, 2170b may include corresponding grooves or recesses that are configured in size, shape, and position to mate with the corresponding ridges or protrusions.

In the illustrated embodiment, each of the clips 2160a, 2160b includes a front member 2162a, 2162b, first side members 2163a, 2163b, and second side members 2164a, 2164b as seen, for example, in FIG. 21G. The front members 2162a, 2162b are each configured to extend across the length of the suture securing device 2100. The front members 2162a, 2162b also include second gripping surfaces 2170a, 2170b. The second gripping surfaces may be positioned at the ends of protrusions 2166a, 2166b which extend from the front members 2162a, 2162b. The first side members 2163a, 2163b and second side members 2164a, 2164b also extend as orthogonal protrusions from opposite sides of the front members 2162a, 2162b of each clips 2160a, 2160b. Engagement structures 2181a and 2181b are positioned at free ends of each of the first side members 2163a, 2163b and the second side members 2163a, 2164b. The shape of the clips 2160a, 2160b may be configured so as to fit within a channel 2131 of the body 2110 described below, such that the clips 2160a, 2160b may be substantially completely positioned within the body 2110 in the closed configuration. In this way, the clips 2160a, 2160b may be configured to mate with the body 2110. It will be appreciated, however, that other shapes for the clips 2160a, 2160b are possible and within the scope of this disclosure. Further, in some embodiments, the clips may be designed to be inserted into the body from the front and/or back, rather than the sides.

In many respects, the body 2110 of the suture securing device 2100 is substantially similar to the body 1510 of the suture securing device 1500 previously described in reference to FIG. 16A. For example, the body 2110 (or the suture securing device when in the closed configuration) is generally shaped as a rectangular prism. The body 2110 includes a front surface 2111, a back surface 2112, a top surface 2113, a bottom surface 2114, a first side surface 2115, and a second side surface 2116. Although many of these surfaces are illustrated as planar, this need not be the case in all embodiments. Similarly, although many of these surfaces are illustrated as positioned orthogonally relative to adjacent surfaces, this need not be the case in all embodiments. Various other shapes for the body 2110 are possible.

As seen, for example, in FIG. 21G, the body 2110 includes two individual slots 2121a, 2121b. Each of the two individual slots 2121a, 2121b extends generally into the body 2110 from one of the opposite side surfaces 2115, 2116, respectively. As shown, the two individual slots 2121a, 2121b extend into the body 2110 toward each other. In the illustrated embodiment, the two individual slots 2121a, 2121b are aligned with each other, although this need not be the case in all embodiments. Each of the two individual slots 2121a, 2121b also extends entirely through the body 2110 from the top surface 2113 to the bottom surface 2114. Thus, with the two individual slots 2121a, 2121b, the body 2110 may be described as having an H-shape, as best seen in the top and bottom views of FIGS. 21G and 21H. In some instances, the two individual slots 2121a, 2121b may be used to help position the suture securing device 2100 relative to the suture 1020. For example, with the suture securing device 2100 in the open position, the suture securing device 2100 can be positioned such that each of the external portions 1021, 1023 of the suture 1020 are positioned within one of the two individual slots 2121a, 2121b. In other words, the body 2110 may have a substantially H-shaped profile when viewed from the top or bottom, and each of the external portions 1021, 1023 of the suture 1020 may be positioned within the openings of the H (in other words, the two individual slots 2121a, 2121b on opposite sides 2115, 2116 of the body 2110).

As best seen in the front and back views of FIGS. 21E, 21F, 21K, and 21L, the bottom surface 2114 of the body 2110 includes an eversion recess 2114 similar to those previously described. The bottom surface 2114 also includes feet 2134 on opposite sides of the eversion recess 2114. The feet 2134 may be the portions of the suture securing device 2100 that contact the surface 1011 of the patient's skin 1010. In some embodiments, the feet 2134 and/or bottom surface 2114 may include a treated undersurface having adhesive, anti-bacterial, medicaments, and/or other agents for transfer to the patient's skin underlying the suture securing device to aid in positioning and/or retention of the suture securing device 2100, assist in healing, and/or reduce scarring, among other purposes.

The body 2110 also includes a channel 2131 configured to receive the clips 2160a, 2160b in the closed configuration. The channel 2131 is formed as an opening which extends partway into the body 2110 from the front surface 2111, back surface 2112, and the first and second side surfaces 2115, 2116. In the illustrated embodiment, the channel 2131 extends entirely around the body 2110, although this need not be the case in all embodiments. The channel 2131 is likely best seen in FIGS. 21A, 16C, 16E, and 16F. As shown, the channel 2131 is positioned between the top surface 2113 and the bottom surface 2114 and generally runs parallel to each. The first gripping surfaces 2120a, 2120b may be positioned the channel 2131. In the illustrated embodiment, the channel 2131 is configured such that, in the closed configuration, the clips 2160a, 2160b are substantially received within the body 2110 as shown, for example, in FIGS. 21B, 21D and 21K through 21P. Accordingly, the depth of the channel 2131 extending from the front surface 2111, the first and second side surfaces 2115, 2116, and the back surface 2112 may be chosen to correspond to the dimensions and shape of the clips 2160a, 2160b as will be described in greater detail below. Similarly, the thickness of the channel 2131 may be chosen to correspond to the thickness of the clips 2160a, 2160b.

In the illustrated embodiment, and as best seen in FIG. 21A the depth of the channel 2131 extending into the body 2110 from the side surfaces 2115, 2116 may include deeper portions 2115a, 2116a in the areas of the two individual slots 2121a, 2121b. The deeper portions 2115a, 2116a may include the first gripping surfaces 2120a, 2120b. These deeper portions 2115a, 2116a are configured to correspond to and mate with protrusions 2166a, 2166b which extend from the second gripping surfaces 2170a, 2170b, respectively, of the clips 2160a, 2160b. In the closed configuration, the deeper portions 2115a, 2116a mate with corresponding protrusions 2166a, 2166b to further secure the suture 1020 between the first and second gripping surfaces 2120a, 2120b, 2170a, 2170b. In some embodiments, the deeper portions 2115a, 2116a and protrusions 2166a, 2166b may be omitted. In some embodiments, the channel 2131 may be omitted or may be configured to only partially receive the clips 2160a, 2160b within the body 2110.

Additional features of the suture securing clip 2100 are shown in the figures and may be substantially similar to similarly numbered features shown and described in reference to other embodiments.

FIGS. 22A-25B show various embodiments of suture securing devices that include a body and one or more clips that are insertable into a top surface of the body. These embodiments may include features similar to those previously described in reference to previously described embodiments. Description of these features may not be repeated here. Further, the features of these embodiments may be modified and/or combined with other embodiments described herein. For example, these embodiments may be modified to include a hinge that attaches the clip to the body.

Figure 22A:
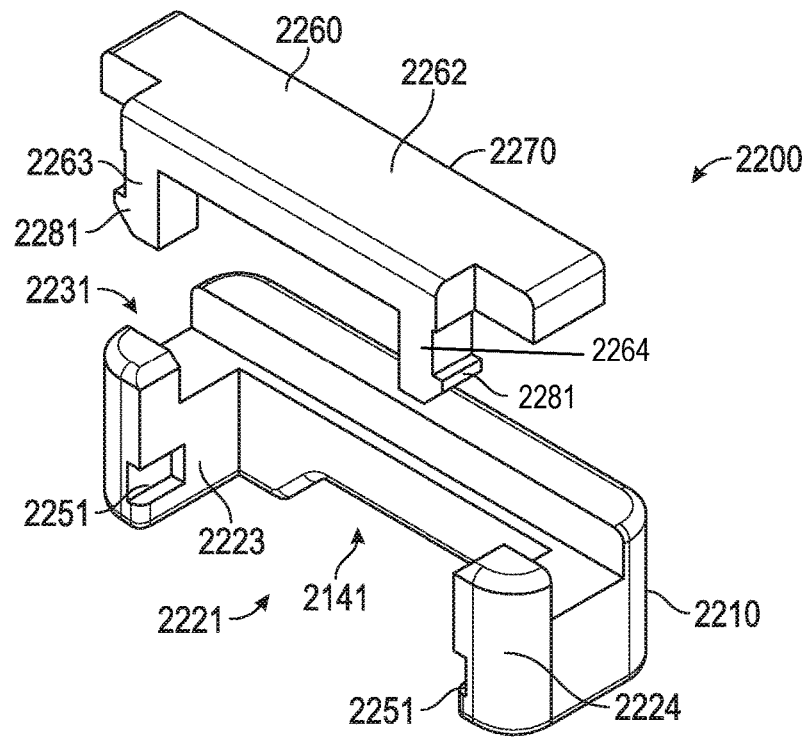
FIGS. 22A-22D show various views of an eleventh embodiment of a suture securing device that includes a clip insertable into a top surface of a body to secure a simple interrupted suture. The body includes a front space that receives external portions of a suture to be secured.
Figure 22B:
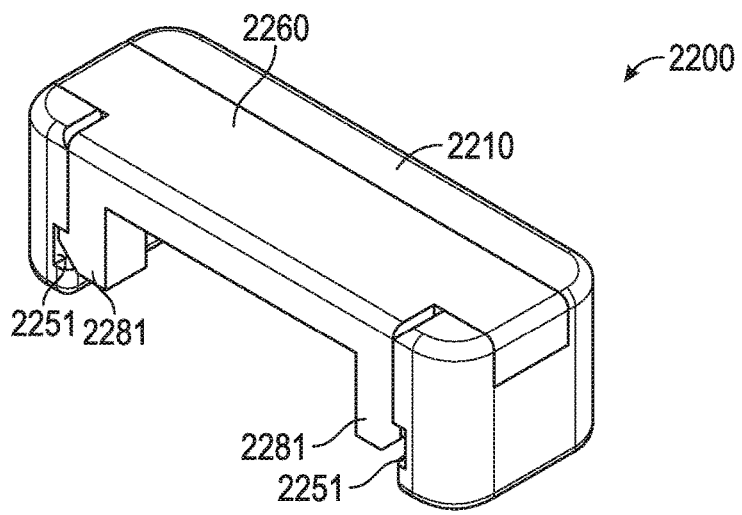
Figure 22C:
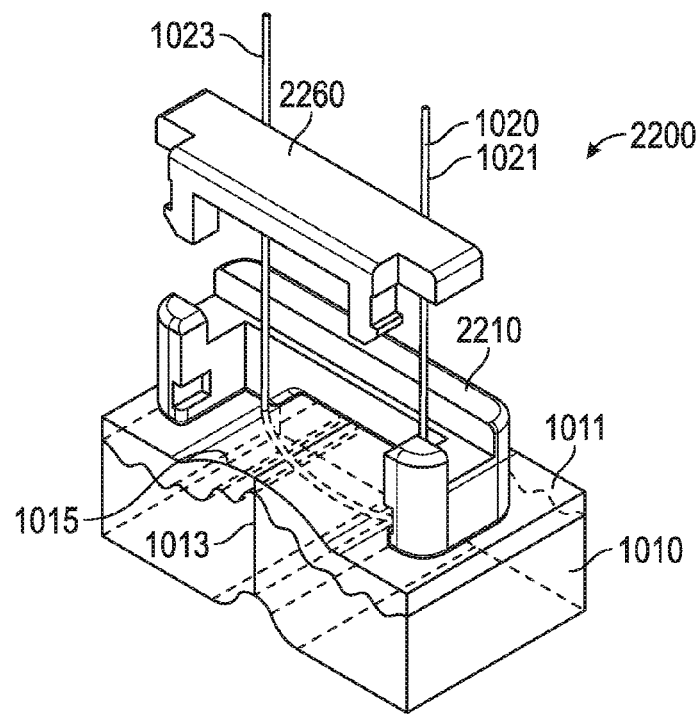
Figure 22D:
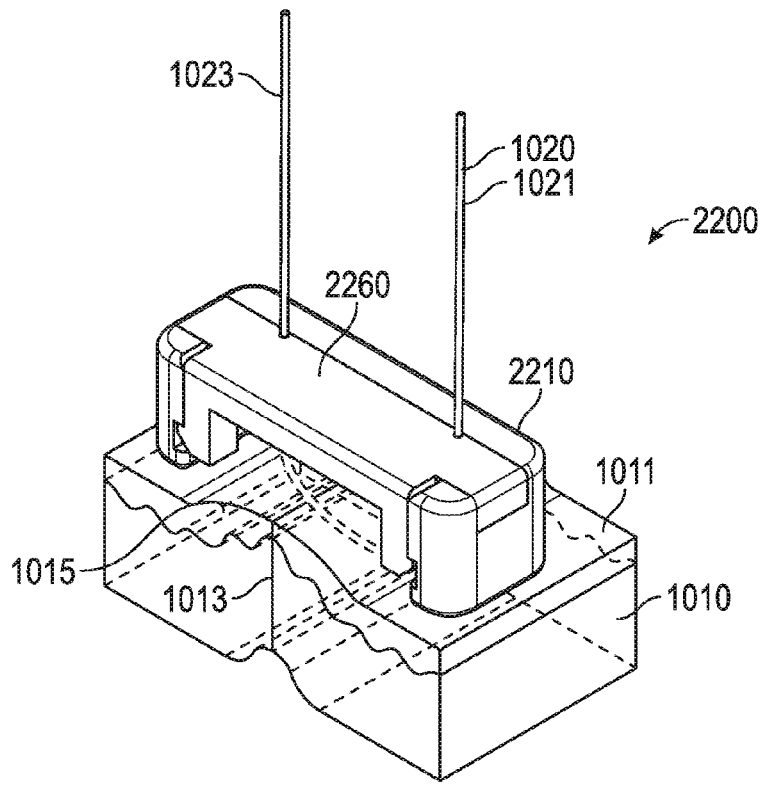

FIGS. 22A-22D show various views of an eleventh embodiment of a suture securing device 2200 that includes a clip 2260 insertable into a top surface of a body 2210 to secure a simple interrupted suture 1020. The body 2210 includes a front space 2221 that receives external portions 1021, 1023 of a suture 1020 to be secured. FIGS. 22A and 22B show perspective views the eleventh embodiment of the suture securing device 2200 in an open and closed configuration, respectively. FIGS. 22C and 22B show perspective views the eleventh embodiment of the suture securing device 2200 in use with a simple interrupted suture 1020, in the open and closed configuration, respectively.

The body 2210 includes a first gripping surface 2220 and the clip 2260 includes a second gripping surface 2270. In the closed configuration, the external portions 1021, 1023 of a simple interrupted suture 1010 are secured between the first and second gripping surface 2220, 2270.

The body 2210 includes a front opening 2221. The front opening 2221 extends generally into the body 2210 from a front surface of the body 2210 partway toward a back surface. The front opening 2221 also extends entirely through the body 2210 from a top surface to a bottom surface. On opposite side surfaces of the body 2210, the front opening is defined by members 2223, 2224, which extend outwardly from the body 2210. Thus, with the front opening 2221 and the members 2223 and 2224, the body 2210 may be described as having a C-shape. In some instances, the front opening 2221 may be used to help position the suture securing device 2200 relative to the suture 1020. For example, with the suture securing device 200 in the open position, the suture securing device 2200 can be positioned such that the external portions 1021, 1023 of the suture are positioned within the front opening 1121, as shown in FIG. 22C. The front opening 2221 and members 2223, 2224 may help to maintain the suture securing device 2200 and suture 1020 in position until the suture securing device 2200 is transitioned to the closed configuration by inserting the clip. In other words, the body 2210 may have a substantially C-shaped profile when viewed from the top or bottom, and the external portions 1021, 1023 of the suture 1020 may be positioned within the opening of the C (in other words, front opening 2221).

The clip 2260 includes a top member 2262. The top member 2262 extends across the width of the suture securing device 2200. In some embodiments, the top member 2262 may extend completely or incompletely across the width of the suture securing device 2200. In the illustrated embodiment, the top member 2262 extends partway across the length of the suture securing device 2200. That is, in the closed configuration (FIG. 22B), the top surface of the suture securing device 2200 includes a portion of a top surface of the body 2210 and a portion of the top surface of the clip 2260. In some embodiments, the clip may extend entirely across the length of the suture securing 2200. In the illustrated embodiment, two clipping arms 2263, 2264 extend downwardly from the top member 2262. In some embodiments, one, two, three, or more clipping arms may be included. An engagement structure 2281 may be positioned at the free end of each of the clipping arms 2263, 2264. The engagement structures 2281 of the clip 2260 may engage with corresponding engagement structures 2251 of the body 2210. In some embodiments, the engagement structures 2251 of the body are recesses formed in the members 2223, 2224 of the body 2210.

The body 2210 may include a channel 2231 formed in a top surface thereof configured to receive the clip 2210 in the closed configuration. Accordingly, the shape of the channel 2231 may be configured to mate with the corresponding shape of the clip 2260.

Figure 23A:
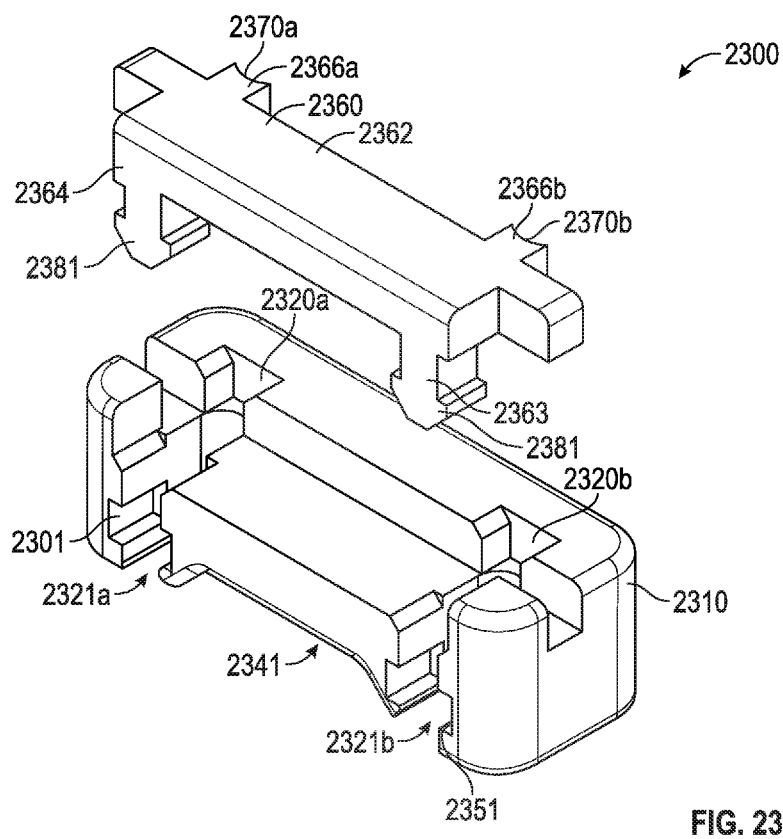
FIGS. 23A and 23B show perspective views of a twelfth embodiment of suture securing device for securing a simple interrupted suture in an open configuration and a closed configuration, respectively. The twelfth embodiment includes two individual slots in the front of the body for receiving the external portions of suture.
Figure 23B:
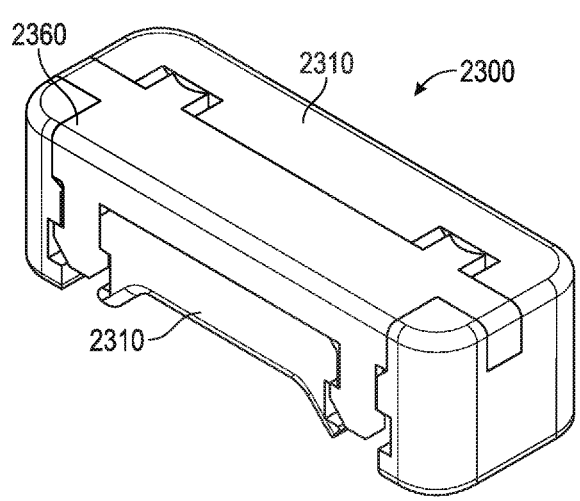

FIGS. 23A and 23B show perspective views of a twelfth embodiment of suture securing device 2300 for securing a simple interrupted suture in an open configuration and a closed configuration, respectively. The twelfth embodiment includes two individual slots 2321*a*, 2321*b* in the front of the body 2310 for receiving the external portions of suture.

The body 2310 includes first gripping surfaces 2320*a*, 2320*b* and the clip 2360 includes second gripping surfaces 2370*a*, 2370*b*. In the closed configuration, the external portions of a simple interrupted suture are secured between the first and second gripping surface 2320*a*, 2320*b*, 2370*a*, 2370*b*.

As noted above, the body 2310 includes two individual slots 2321*a*, 2321*b*. The individual slots 2321*a*, 2321*b* extend generally into the body 2310 from a front surface of the body 2310 partway toward a back surface. The two individual slots 2321*a*, 2321*b* also extend entirely through the body 2310 from a top surface to a bottom surface. On opposite side surfaces of the body 2310, the two individual slots 2321*a*, 2321*b* are defined by members 2323 and 2324 which extend outwardly from the body 2310. A member 2325 extends outwardly from the body 2310 in between the two individual slots 2321*a*, 2321*b*. Thus, with the two individual slots 2321*a*, 2321*b* and the members 2323, 2324, 2325 the body 2210 may be described as having an E-shape. In some instances, the two individual slots 2321*a*, 2321*b* may be used to help position the suture securing device 2300 relative to the suture. For example, with the suture securing device 2300 in the open position, the suture securing device 2300 can be positioned such that the external portions of the suture are positioned within the two individual slots 2321*a*, 2321*b*. The two individual slots 2321*a*, 2321*b* and members 2323, 2324, 2325 may help to maintain the suture securing device 2300 and suture in position until the suture securing device 2300 is transitioned to the closed configuration by inserting the clip 2360. In other words, the body 2310 may have a substantially E-shaped profile when viewed from the top or bottom, and the external portions of the suture may be positioned within the openings of the E (in other words, the two individual slots 2321*a*, 2321*b*).

The clip 2360 includes a top member 2362. The top member 2362 extends across the width of the suture securing device 2300. In some embodiments, the top member 2362 may extend completely or incompletely across the width of the suture securing device 2300. In the illustrated embodiment, the top member 2362 extends partway across the length of the suture securing device 2300. That is, in the closed configuration (FIG. 23B), the top surface of the suture securing device 2300 includes a portion of a top surface of the body 2310 and a portion of the top surface of the clip 2360. In some embodiments, the clip may extend entirely across the length of the suture securing 2300. In the illustrated embodiment, two clipping arms 2363, 2364 extend downwardly from the top member 2362. In some embodiments, one, two, three, or more clipping arms may be included. An engagement structure 2381 may be positioned at the free end of each of the clipping arms 2363, 2364. The engagement structures 2381 of the clip 2360 may engage with corresponding engagement structures 2351 of the body 2310. In some embodiments, the engagement structures 2351 of the body are recesses formed in the members 2323, 2324, 2325 of the body 2310. In the illustrated embodiment, the second gripping surfaces 2370*a*, 2370*b* are positioned at the ends of protrusions 2366*a*, 2366*b* which extend laterally from the top member 2362.

The body 2310 may include a channel 2331 formed in a top surface thereof configured to receive the clip 2310 in the closed configuration. Accordingly, the shape of the channel 2331 may be configured to mate with the corresponding shape of the clip 2360. For example, the channel 2331 may be shaped to receive the protrusions 2366*a*, 2366*b* and the top member 2362 of the clip 2360.

Figure 24A:
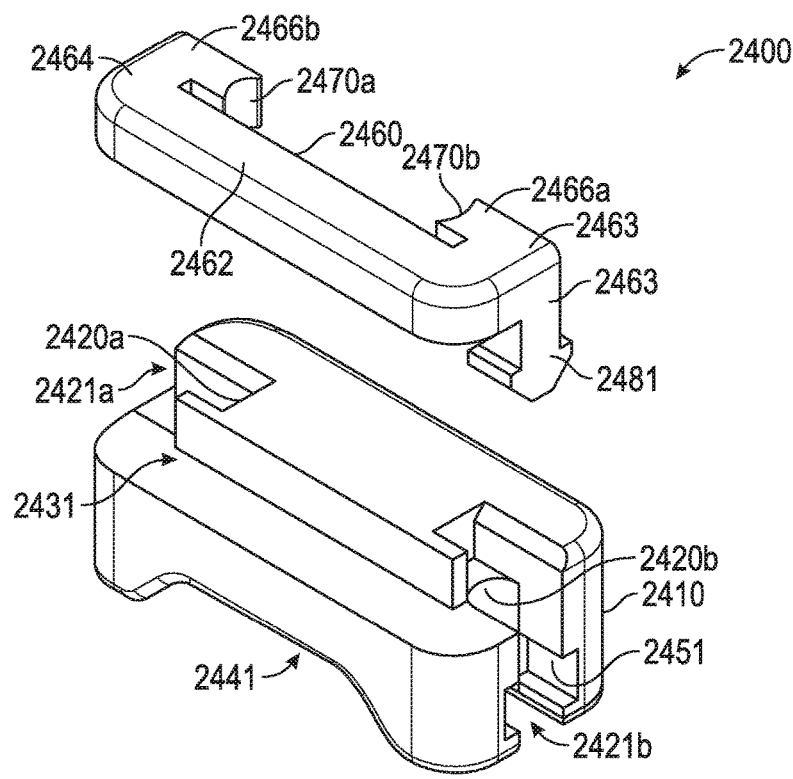
FIGS. 24A and 24B show perspective views of a thirteenth embodiment of suture securing device for securing a simple interrupted suture in an open configuration and a closed configuration, respectively. The twelfth embodiment includes two individual slots in opposite sides the body for receiving the external portions of suture.
Figure 24B:
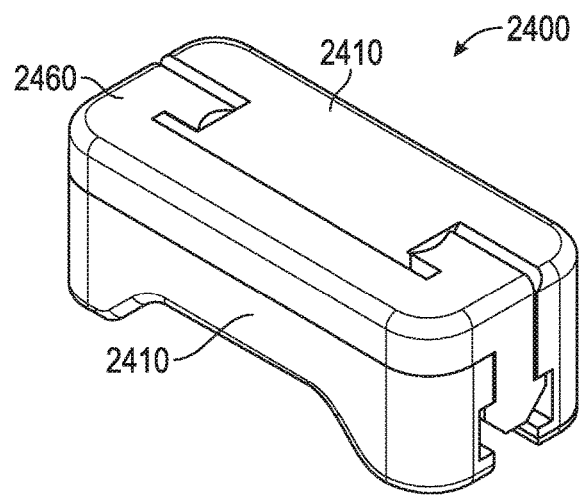

FIGS. 24A and 24B show perspective views of a thirteenth embodiment of suture securing device 2400 for securing a simple interrupted suture in an open configuration and a closed configuration, respectively. The twelfth embodiment includes two individual slots 2421*a*, 2421*b* in opposite sides the body 2410 for receiving the external portions of suture.

The body 2410 includes a first gripping surfaces 2420*a*, 2420*b* and the clip 2460 includes second gripping surfaces 2470*a*, 2470*b*. In the closed configuration, the external portions of a simple interrupted suture are secured between the first and second gripping surface 2420*a*, 2420*b*, 2470*a*, 2470*b*.

As noted above, the body 2410 includes two individual slots 2421*a*, 2421*b*. The individual slots 2421*a*, 2421*b* extend generally into the body 2410 from a front surface of the body 2410 partway toward a back surface. The two individual slots 2421*a*, 2421*b* also extend entirely through the body 2410 from a top surface to a bottom surface. Thus, with the two individual slots 2421*a*, 2421*b* the body 2410 may be described as having an H-shape. In some instances, the two individual slots 2421a, 2421b may be used to help position the suture securing device 2400 relative to the suture. For example, with the suture securing device 2400 in the open position, the suture securing device 2400 can be positioned such that the external portions of the suture are positioned within the two individual slots 2421a, 2421b. In other words, the body 2410 may have a substantially E-shaped profile when viewed from the top or bottom, and the external portions of the suture may be positioned within the openings of the E (in other words, the two individual slots 2421a, 2421b).

The clip 2460 includes a top member 2462. In the illustrated embodiment, the top member includes a C-shape. The top member 2462 extends across the width of the suture securing device 2400. In some embodiments, the top member 2462 may extend completely or incompletely across the width of the suture securing device 2400. In the illustrated embodiment, the top member 2462 extends partway across the length of the suture securing device 2400. That is, in the closed configuration (FIG. 24B), the top surface of the suture securing device 2400 includes a portion of a top surface of the body 2410 and a portion of the top surface of the clip 2460. In some embodiments, the clip may extend entirely across the length of the suture securing 2400. In the illustrated embodiment, a clipping arm 2463 extends downwardly from the top member 2462. In some embodiments, one, two, three, or more clipping arms may be included. An engagement structure 2481 may be positioned at the free end of the clipping arm 2463. The engagement structure 2481 of the clip 2460 may engage with a corresponding engagement structure 2451 of the body 2410. In some embodiments, the engagement structure 2451 of the body is a recess formed in the body 2410. In the illustrated embodiment, the second gripping surfaces 2470a, 2470b are positioned at the ends of protrusions 2466a, 2466b which extend laterally from the top member 2462.

The body 2410 may include a channel 2431 formed in a top surface thereof configured to receive the clip 2410 in the closed configuration. Accordingly, the shape of the channel 2431 may be configured to mate with the corresponding shape of the clip 2460. For example, the channel 2431 may be shaped to receive the protrusions 2466a, 2466b and the top member 2462 of the clip 2460. For example, in the illustrated embodiment, the channel 2431 is C-shaped, to match the C-shape of the clip 2460.

Figure 25A:
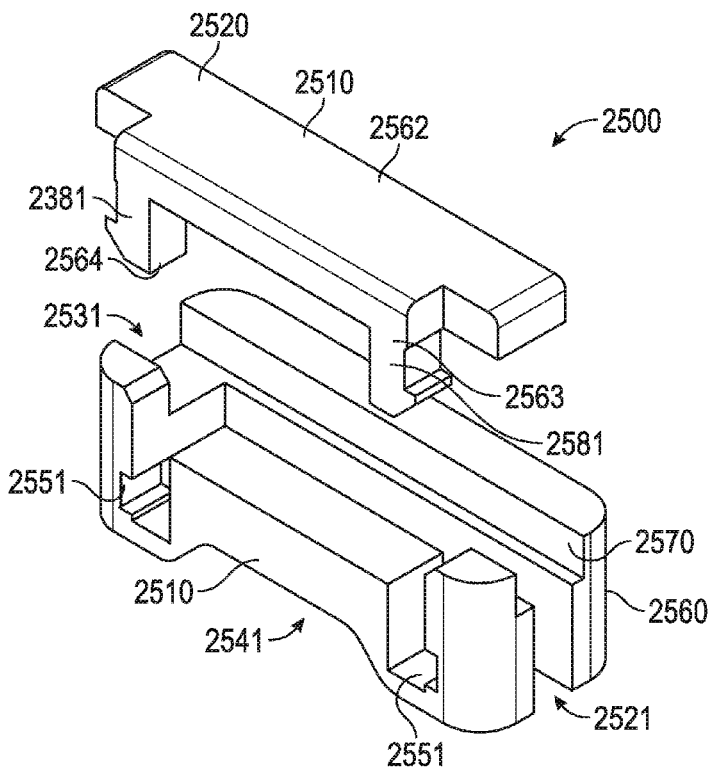
FIGS. 25A and 25B show perspective views of a thirteenth embodiment of suture securing device for securing a simple interrupted suture in an open configuration and a closed configuration, respectively. The thirteenth embodiment includes a slot extending into the side of the body for receiving the external portions of suture.
Figure 25B:
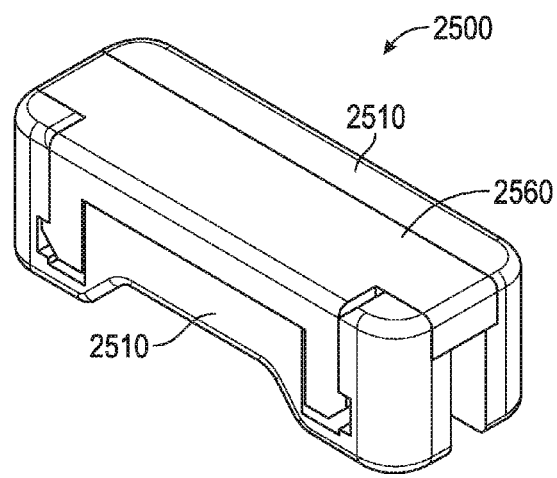

FIGS. 25A and 25B show perspective views of a thirteenth embodiment of suture securing device for securing a simple interrupted suture in an open configuration and a closed configuration, respectively. The thirteenth embodiment includes a slot extending into the side of the body for receiving the external portions of suture.

The body 2510 includes a first gripping surface 2520 and the clip 2560 includes a second gripping surface 2570. In the closed configuration, the external portions of a simple interrupted suture are secured between the first and second gripping surface 2520, 2570.

As noted above, the body 2510 includes a slot 2521 that extends generally into the body 2510 from a side surface of the body 2510 partway toward an opposite side surface. The slot 2521 also extends entirely through the body 2510 from a top surface to a bottom surface. Thus, with the slot 2521, the body 2510 may be described as having a C-shape. In some instances, the slot 2521 may be used to help position the suture securing device 2500 relative to the suture. For example, with the suture securing device 2500 in the open position, the suture securing device 2500 can be positioned such that the external portions of the suture are positioned within the slot 2521.

The clip 2560 includes a top member 2562. The top member 2562 extends across the width of the suture securing device 2500. In some embodiments, the top member 2562 may extend completely or incompletely across the width of the suture securing device 2500. In the illustrated embodiment, the top member 2562 extends partway across the length of the suture securing device 2500. That is, in the closed configuration (FIG. 25B), the top surface of the suture securing device 2500 includes a portion of a top surface of the body 2510 and a portion of the top surface of the clip 2560. In some embodiments, the clip may extend entirely across the length of the suture securing 2500. In the illustrated embodiment, two clipping arms 2563, 2564 extend downwardly from the top member 2562. In some embodiments, one, two, three, or more clipping arms may be included. An engagement structure 2581 may be positioned at the free end of each of the clipping arms 2563, 2564. The engagement structures 2581 of the clip 2560 may engage with corresponding engagement structures 2551 of the body 2510. In some embodiments, the engagement structures 2551 of the body are recesses formed the body 2510.

The body 2510 may include a channel 2331 formed in a top surface thereof configured to receive the clip 2510 in the closed configuration. Accordingly, the shape of the channel 2331 may be configured to mate with the corresponding shape of the clip 2560.

Figure 26A:
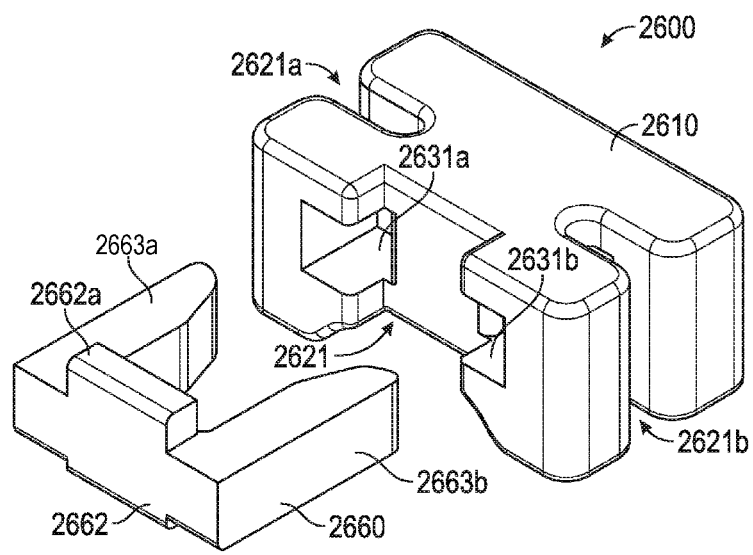
Figure 26B:
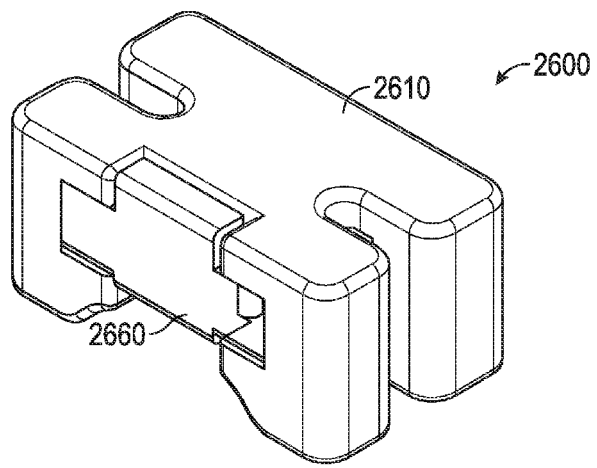

FIGS. 26A-D illustrate another embodiment of a suture securing device 2600 configured for use with a simple interrupted suture. The suture securing device 2600 includes a clip 2660 that is insertable into a body 2610. The body 2610 surrounds the clip 2660. FIGS. 26A and 26B are perspective views of the suture securing device 2600 in an open configuration and a closed configuration, respectively. FIGS. 26C and 26D are cross-sectional views of the suture securing device 2600 in the open and closed configurations, respectively.

The body 2610 includes two individual slots 2621a, 2621b. Each of the two individual slots 2621a, 2621b extends generally into the body 2610 from one of the opposite side surfaces of the body 2610, respectively. As shown, the two individual slots 2621a, 2621b extend into the body 2610 toward each other. In the illustrated embodiment, the two individual slots 2621a, 2621b are aligned with each other, although this need not be the case in all embodiments. Each of the two individual slots 2621a, 2621b also extends entirely through the body 2610 from the top surface 2613 to the bottom surface 2614. Thus, with the two individual slots 2621a, 2621b, the body 2610 may be described as having an H-shape. In some instances, the two individual slots 2621a, 2621b may be used to help position the suture securing device 2600 relative to the suture. For example, with the suture securing device 2600 in the open position, the suture securing device 2600 can be positioned such that each of the external portions 1021, 1023 of the suture 1020 are positioned within one of the two individual slots 2621a, 2621b. In other words, the body 2610 may have a substantially H-shaped profile when viewed from the top or bottom, and each of the external portions 1021, 1023 of the suture 1020 may be positioned within the openings of the H (in other words, the two individual slots 2621a, 2621b on opposite sides of the body).

The body also includes two channels 2631a, 2631b that extend through the body 2610. Each channel 2631a, 2631b may be formed as a hole extending into the body 2610. In the illustrated embodiment, the channels 2631a, 2631b extend entirely through the body 2610 (as shown in FIG. 26C), although this need not be the case in all embodiments. Inside surface of the channels 2631a, 2631b may include first gripping surfaces 2620a, 2620b. Also in the illustrated embodiment, the channels 2631a, 2631b extend into the body 2610 from a front surface of the body, although in other embodiments, the channels may extend into the body from a different surface (for example, top, back, or side surfaces). A front space 2621 may also be formed on the body 2610. The front space 2621 may be formed as a recess extending partway into the body 2610. The front space 2621 may be positioned between the channels 2631a, 2631b as shown in the figures. The purpose of the channels 2631a, 2631b and the front space 2621 will be described below.

The clip 2660 includes a width member 2662 and two arms 2663a, 2663b. The arms 2663a, 2663b extend orthogonally from the width member 2662 at opposite ends of the width member 2663. The arms 2663a, 2663b may be sized so as to fit within the channels 2631a, 2631b, respectively. Inside surface of the arms 2663a, 2663b may include second gripping surfaces 2670a, 2670b. The width member 2662 may also include larger section 2662a configured in size and shape to fit within the front space 2621 when the clip 2660 is inserted into the body 2610.

In use, the body 2610 is positioned on the patient's skin such that the external portions of a suture are positioned within the individual slots 2621a, 2621b. The clip 2660 is then inserted to the body 2610 (as shown in FIGS. 26B and 26D). The external portions of the suture are secured between the first and second gripping surfaces 2620a, 2620b, 2670a, 2670b. In some embodiments, the clip 2660 and/or the body 2610 may include engagement structures to secure the clip 2660 into the body 2610. The suture securing device 2600 may include additional features, for example, the eversion recess, described throughout this application.

Figure 27A:
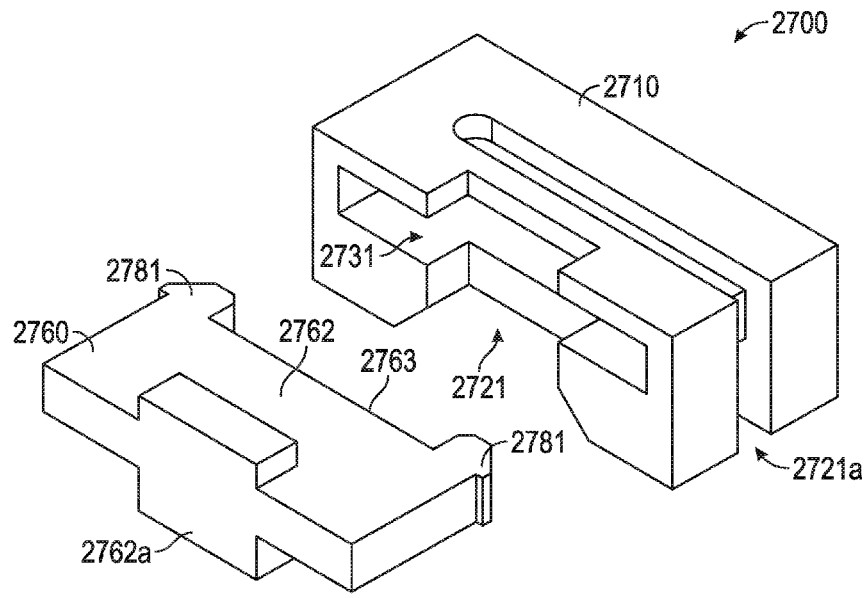
FIGS. 27A-D illustrate another embodiment of a suture securing device configured for use with a simple interrupted suture. The suture securing device includes a clip that is insertable into a body. The body surrounds the clip.
Figure 27B:
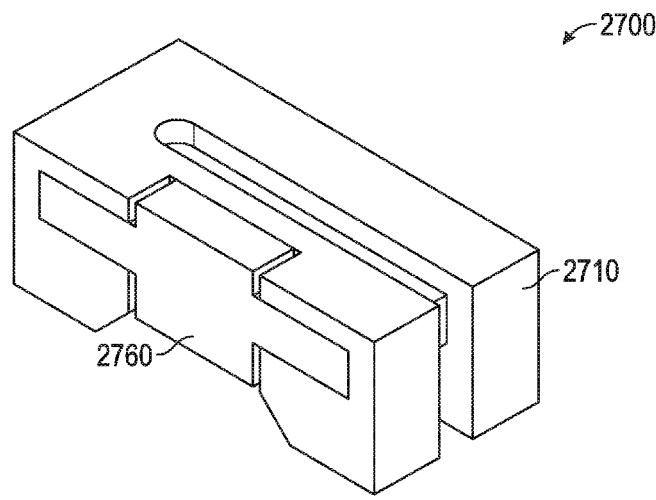
Figure 27C:
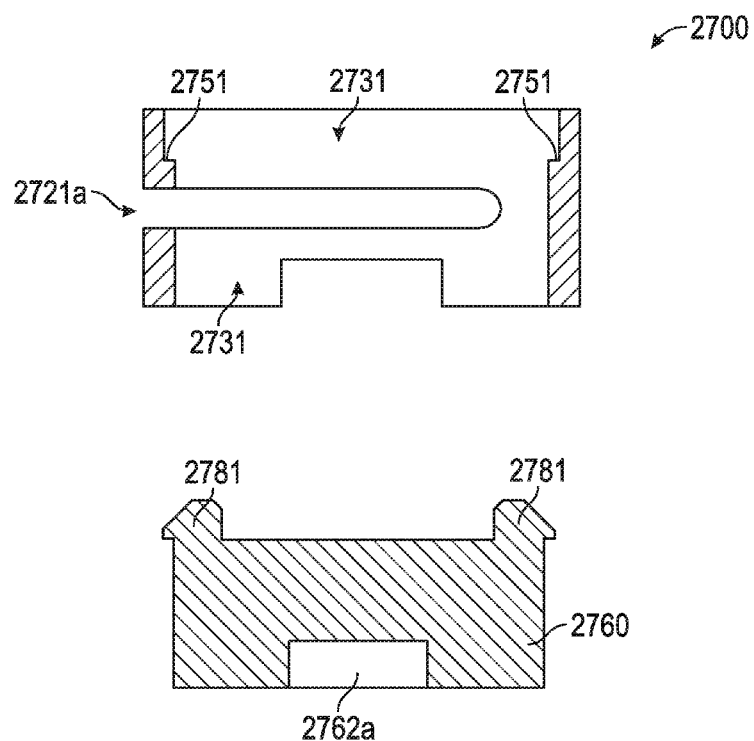
Figure 27D:
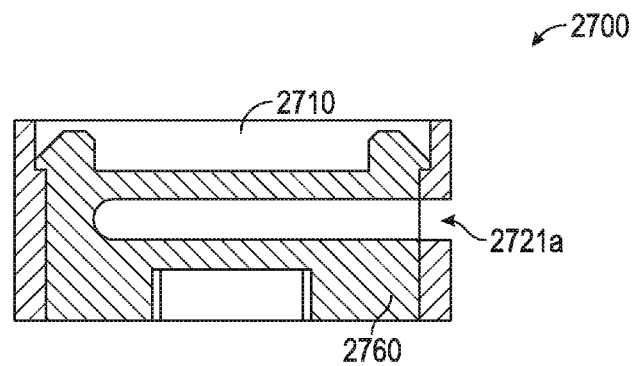

FIGS. 27A-D illustrate another embodiment of a suture securing device 2700 configured for use with a simple interrupted suture. The suture securing device 2700 includes a clip 2760 that is insertable into a body 2710. The body 2710 surrounds the clip 2760. FIGS. 27A and 27B are perspective views of the suture securing device 2700 in an open configuration and a closed configuration, respectively. FIGS. 27C and 27D are cross-sectional views of the suture securing device 2700 in the open and closed configurations, respectively.

The suture securing device 2700 is similar to the suture securing device 2600 previously described. However, the suture securing device 2700 includes a single slot 2721a extending into a side surface of the body 2710. The slot extends deeply enough into the body to accommodate the two external portions of a simple interrupted suture. The body 2710 also include a single channel 2731 extending through the body 2710 from the front surface to the back surface. The channel 2731 may be configured as a hole extending through the body 2710. The channel 2731 may be configured to receive the clip 2760.

The clip 2762 includes a main portion 2762. When inserted into the body 2710, a front surface 2763 of the main portion 2762 may extend beyond the slot 2721a. Thus, a suture positioned within the slot 2721a is forced by the clip 2760 to deform around the front surface 2763. This may secure the suture as it is caught between the clip 2760 and the body 2710. The clip may also include a larger portion 2762a configured to be received within a front space 2721 on the body 2710. The body 2710 and the clip 2760 include engagement structures 2751, 2781 configured to secure the clip 2760 to the body 2710.

The suture securing device 2700 may include other features describe elsewhere in this application, for example, the eversion recess previously described.

FIGS. 28A through 32 illustrate various embodiments of suture securing devices configured for use with horizontal mattress sutures. Although the following disclosure describes these embodiments in reference to horizontal mattress sutures, these embodiments may be used (or modified for use) with other suturing techniques, for example, vertical mattress suturing or simple interrupted suturing. Further, the features shown in each of these embodiments may be combined with features shown or described in reference to any other embodiment described herein. These suture securing devices, in some embodiments, may include a width W between 1 mm to 15 mm, a thickness T between 0.5 mm to 10 mm, and a length L between 5 mm to 60 mm. However, these ranges are merely provided as examples and may be adjusted to adapt the suture securing device 1100 for any particular application.

Figure 28A:
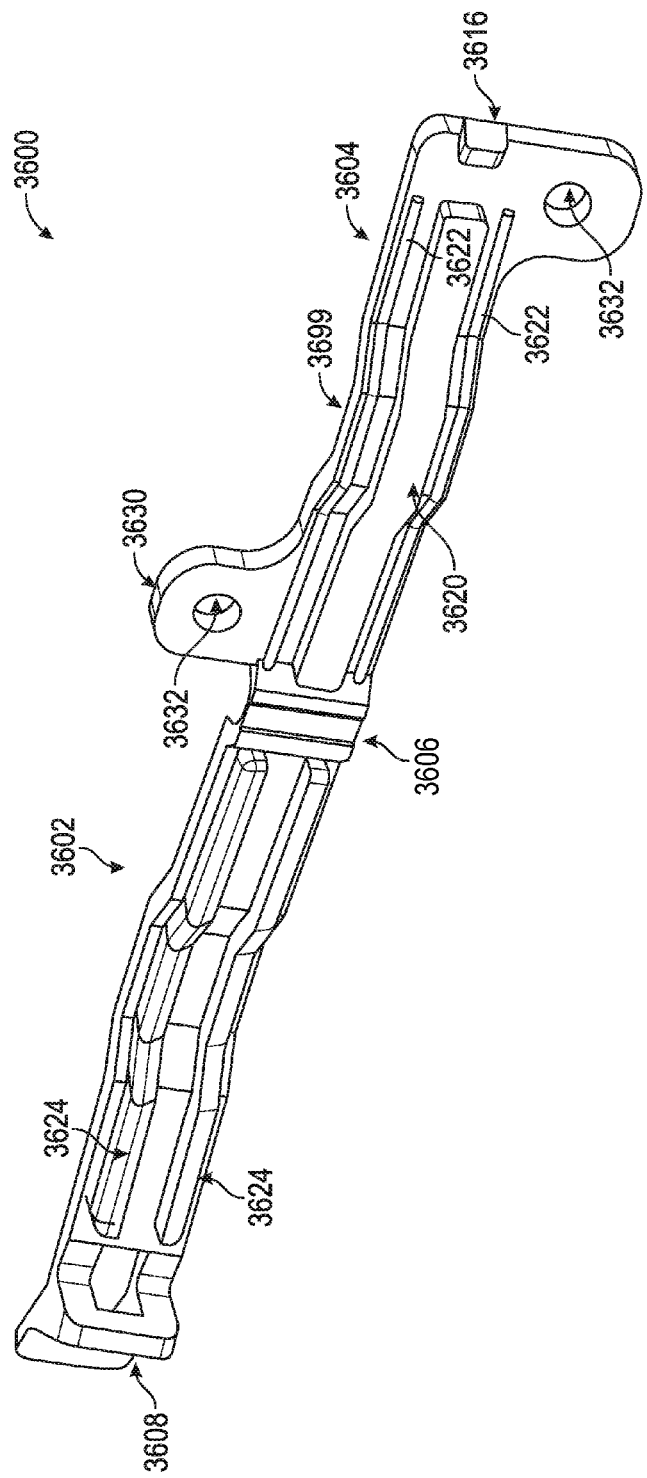
FIG. 28A is a front perspective view of an embodiment of a suture securing device configured for use with a horizontal mattress suture.
Figure 28B:
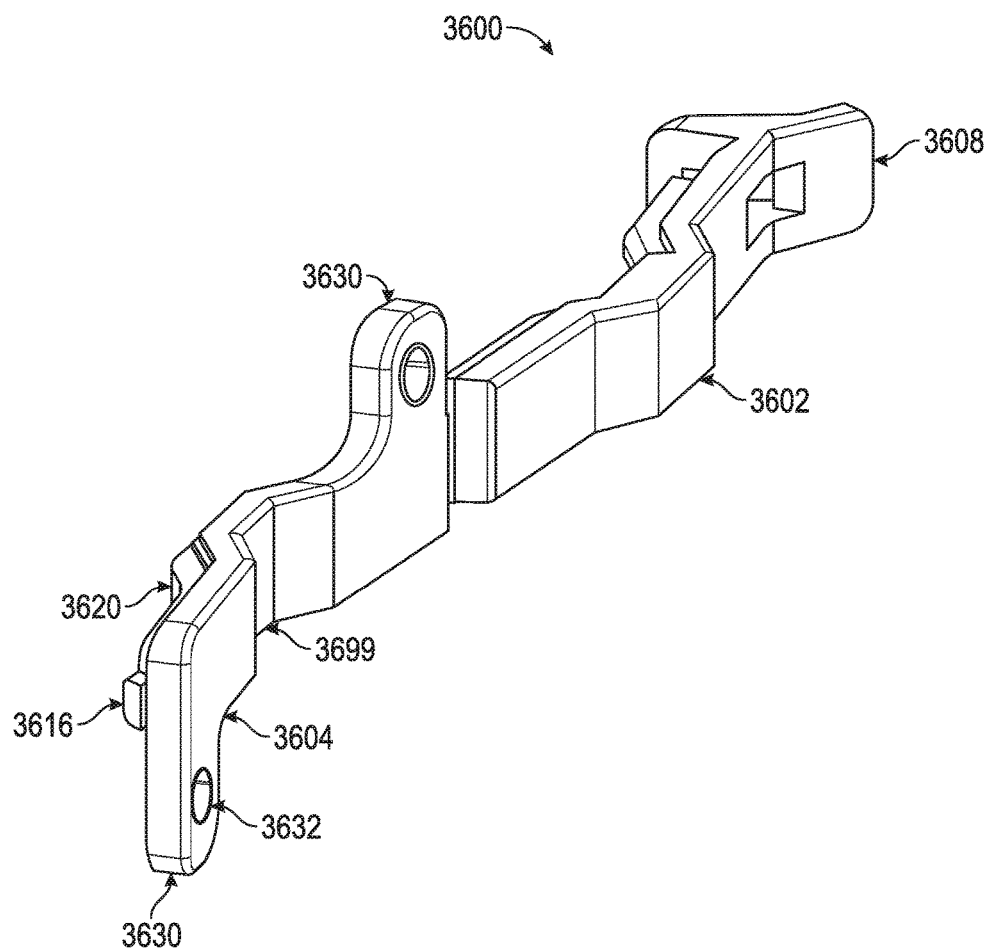
FIG. 28B is a back perspective view of the suture securing device of FIG. 28A.
Figure 28C:
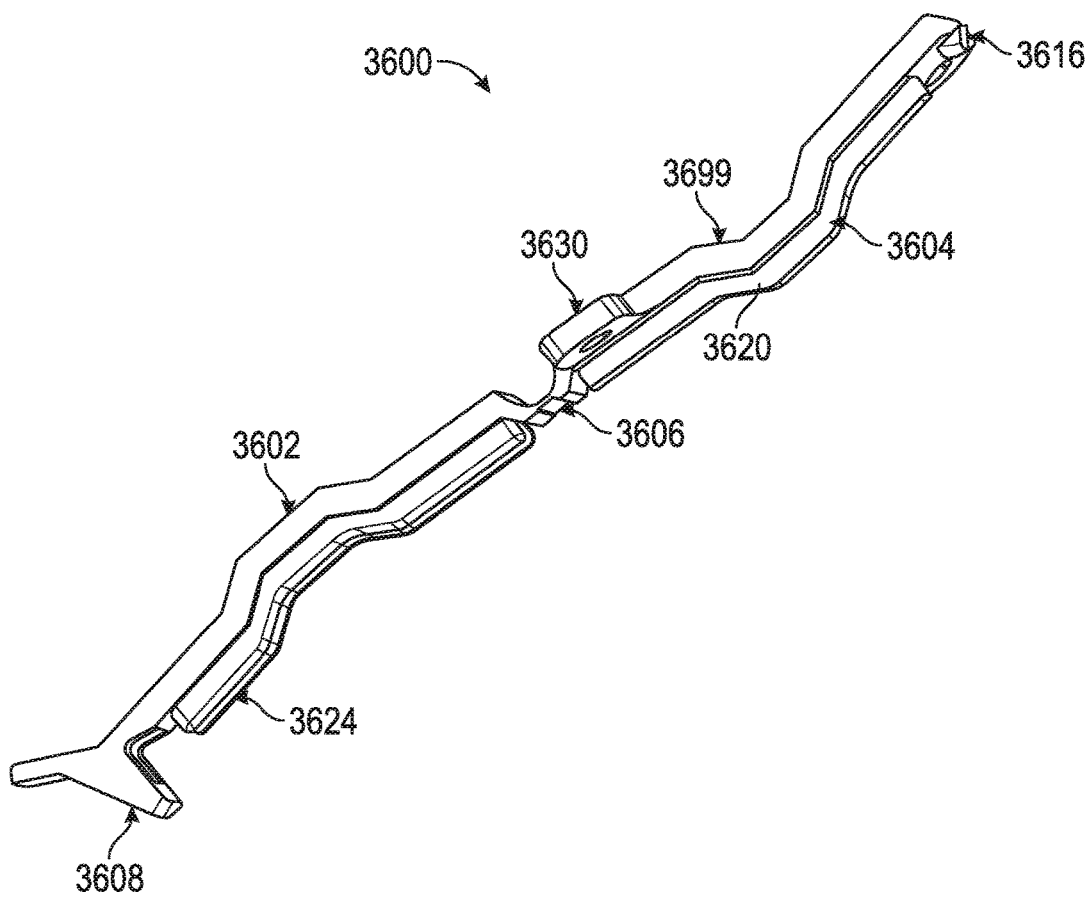
FIG. 28C is a side perspective view of the suture securing device of FIG. 28A.
Figure 28D:
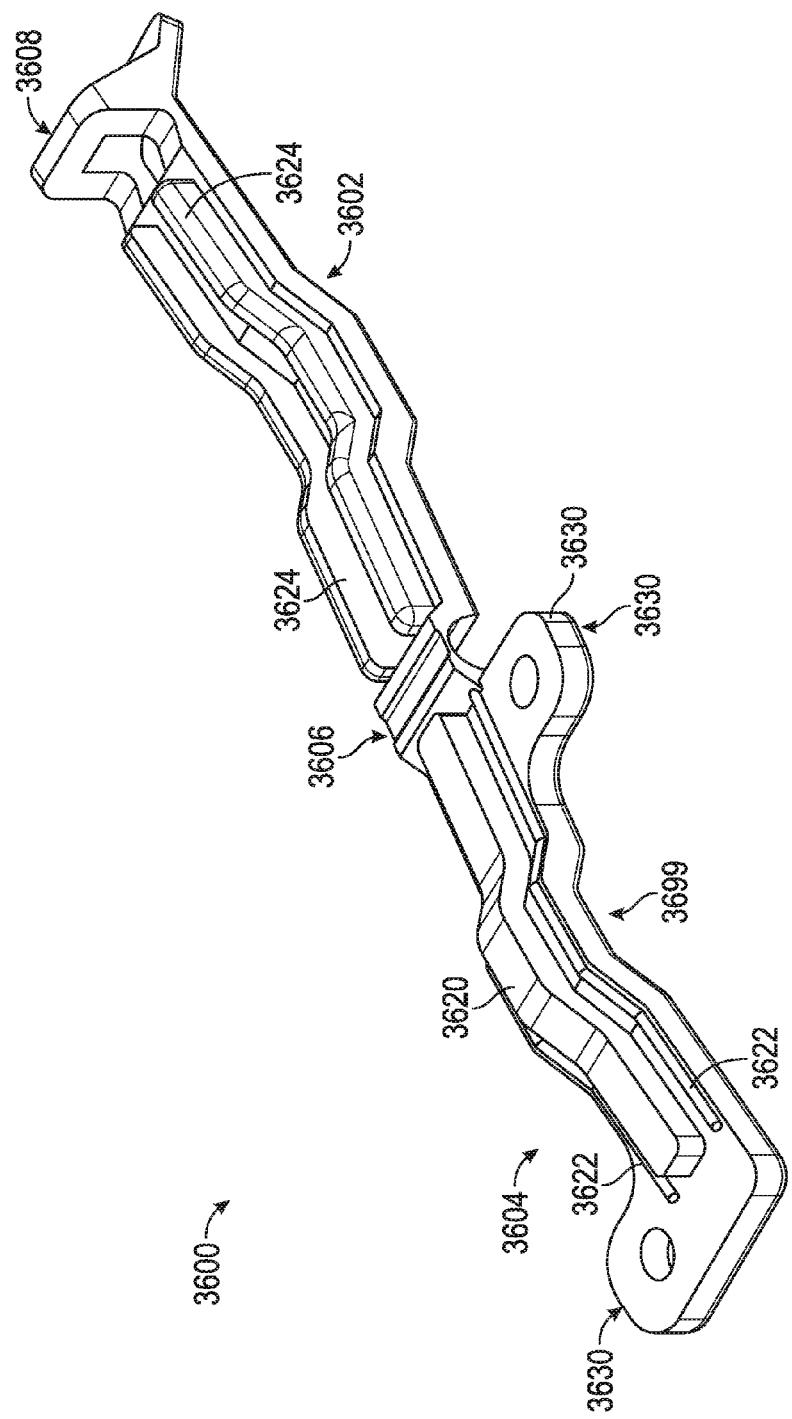
FIG. 28D is a side perspective view of the suture securing device of FIG. 28A.

FIG. 28A-28D illustrate various views of an embodiment of a suture securing device 3600 configured for use with a horizontal mattress suture. FIG. 28A is a front perspective view, FIG. 28B is a back perspective view, FIG. 28C is a side perspective view, and FIG. 28D is a side perspective view. As shown in these figures, the suture securing device 3600 includes an arm 3602 attached to a base 3604 via a hinge 3606. In the figures, the hinge 3606 is illustrated in an open position. When the hinge 3606 is in a closed position the arm 3602 folds over the base 3604. As will be described in greater detail below in reference to FIG. 32, in use, external portions of a horizontal mattress suture may be secured between the arm 3602 and the base 3604 when the hinge 3606 is in the closed position. The arm 3602 includes two ridges 3624 and an engagement mechanism 3608. The base 3604 includes a first surface having a first bulge 3620 and two grooves 3622 on either side of the bulge 3620. The base 3604 also includes an engagement structure 3616 and tabs 3630. The tabs 3630 each include a hole 3632. In some embodiments, the hole 3632 may be used to receive a suture thread. When the hinge 3606 is in the closed position the two ridges 3624 engage on either side of the bulge 3620 and with the two grooves 3622, respectively. Further, when the hinge 3606 is in a closed position the engagement mechanism 3608 of the arm 3602 will engage with the engagement mechanism 3616 of the base 3604.

Figure 32:
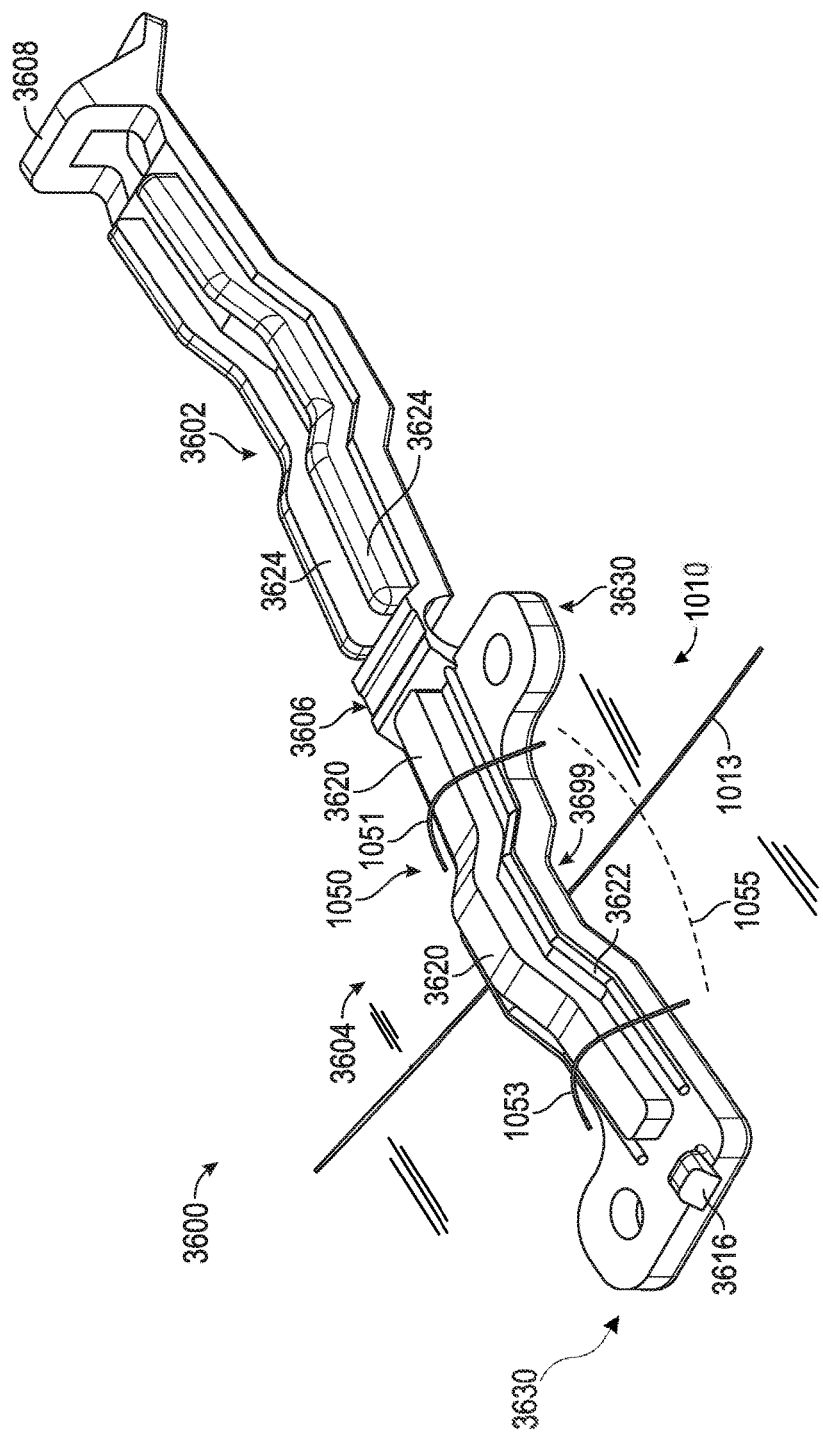
FIG. 32 illustrates an embodiment of a suture securing device in use with a horizontal mattress suture.

FIG. 28B is a back perspective view of the suture securing device 3600 of FIG. 28A. A second surface of the base 3604 includes an eversion recess 3699. The eversion recess 3699 may be a trench that is configured to interact and mate with the raised surface of a healing wound. In other words, after sutures are properly applied to a wound, either edge of the healing wound will be placed and held together such that a convex bulge is made (in other words, wound eversion). The convex bulge will mate with the eversion recess 3699 of the suture lock 3600. Thus, with the suture securing device 3600, the eversion recess 3699 is positioned to be substantially parallel to the direction of the wound when coupled to a mattress suture (as shown in FIG. 32).

The suture securing device 3600 may be formed partially or entirely from any sturdy and resilient material, such as plastic resin, for example, polypropylene, polyethylene, acrylonitrile butadiene styrene (ABS), high impact polystyrene (HIPS), poly vinyl chloride (PVC), polycarbonate, thermoplastic elastomers, Polybutylene terephthalate, ethylene vinyl acetate, nylon and low-density polyethylene, linear low-density polyethylene, etc. In some embodiments, the body 3604, arm 3602, and hinge 3606 may be formed as a single unitary part, while in other embodiments, these parts may be formed separately and then joined together.

Figure 29A:
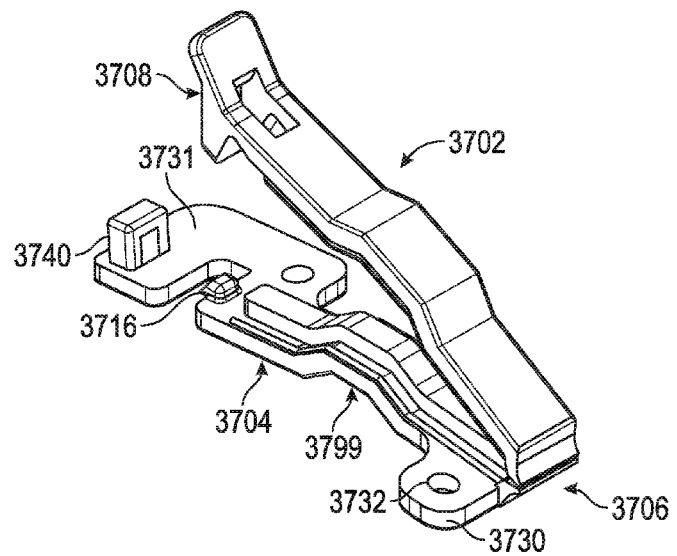
FIGS. 29A and 29B are top perspective and front views of another embodiment of a suture securing device configured for use with a horizontal mattress suture.
Figure 29B:
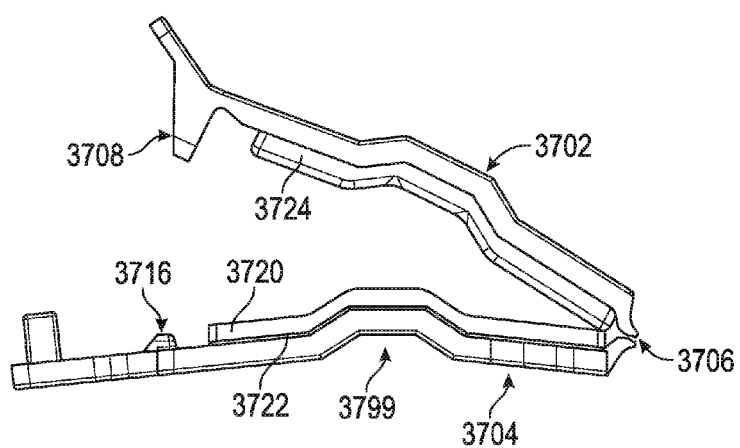

FIGS. 29A and 29B are top perspective and front views of another embodiment of a suture securing device 3700 configured for use with a horizontal mattress suture. The suture securing device 3700 may be substantially similar to the suture securing device 3600 described above. However, the suture securing device 3700 also includes features which allow attachment of accessories.

The suture securing device 3700 includes an arm 3702 attached to a base 3704 by hinge 3706. The arm 3702 includes two ridges 3724 and an engagement mechanism 3708. The base 3704 includes a first surface having a first bulge 3720 and two grooves 3722 on either side of the bulge 3720. The base 3804 also includes an engagement structure 3716 and a first tab 3730. Each of these features may be substantially similar to the similarly described features of the suture securing device 3600.

The suture securing device 3700 also includes a second tab 3731 which includes a feature 3740 that can be used to secure accessories to the suture securing device. The features 3740 is a female adapter that may be used to interlock the suture securing device 3700 with another suture securing device or other type of device. Interlocking will be discussed in greater detail below in reference to suture securing device 3900.

Figure 30A:
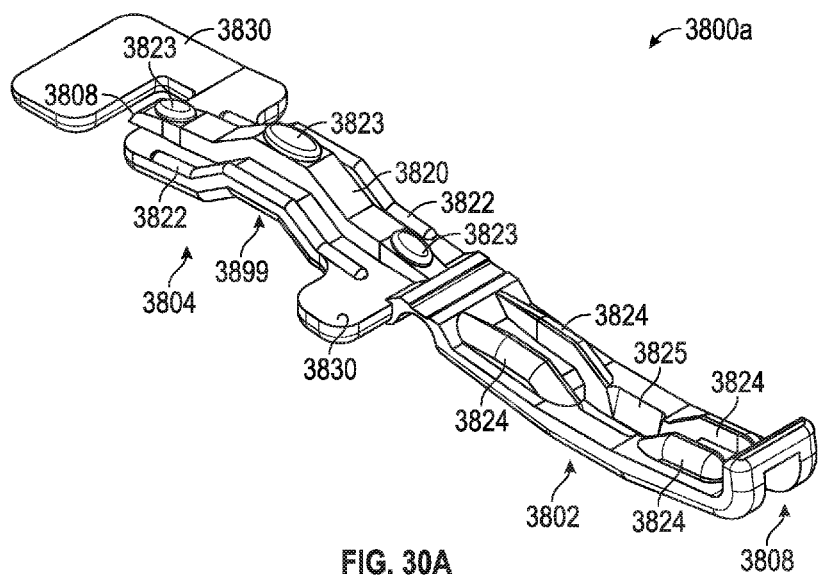
FIGS. 30A and 30B illustrate additional securement features that may be included in some embodiments of suture securing devices.
Figure 30B:
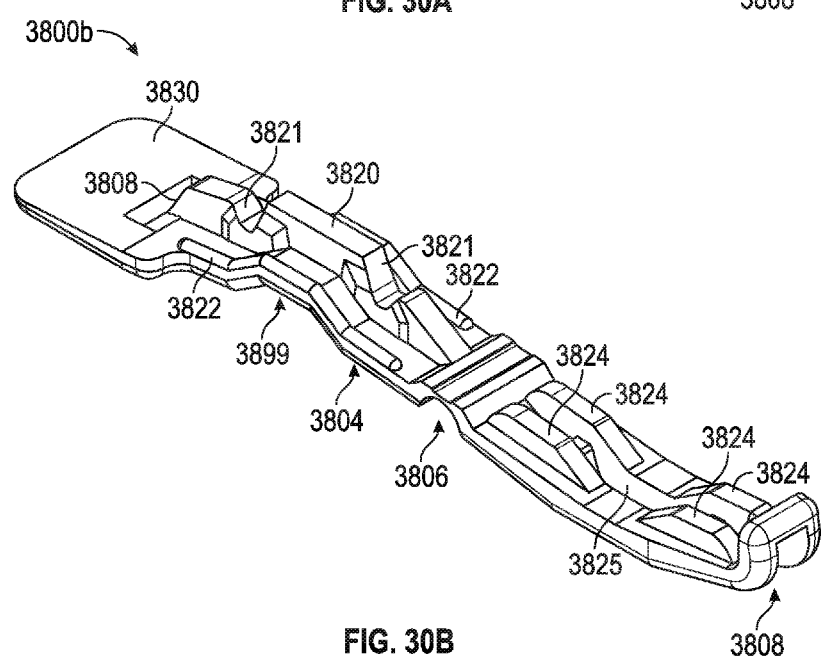

FIGS. 30A and 30B illustrate additional securement features that may be included in some embodiments of suture securing devices. FIGS. 30A and 30B illustrate additional embodiments of a suture securing device 3800a, 3800b, respectively, configured for use with a horizontal mattress suture. In many respects the suture securing device 3800a, 3800b are similar to the suture securing device 3600 described above. For example, each of the suture securing device 3800a, 3800b includes an arm 3802 attached to a base 3804 by hinge 3806. The arm 3802 includes two ridges 3824 and an engagement mechanism 3808. The base 3804 includes a first surface having a first bulge 3820 and two grooves 3822 on either side of the bulge 3820. The base 3804 also includes an engagement structure 3816 and a first tab 3830. Each of these features may be substantially similar to the similarly described features of the suture securing device 3600. However, each of the suture securing device 3800a, 3800b include additional securement features which will now be described. These embodiments also include the eversion recess 3899. As with the previously described embodiments, the eversion recess 3899 helps create wound eversion.

Referring to FIG. 30A, the bulge 3620 on the arm 3804 further includes nubs 3823 extending from a top surface thereof. Although three nubs 3823 are illustrated, other numbers of nubs are possible, for example, one, two, four, five, six, etc. In some embodiments, these nubs prevent the surgeon from using those areas of the device and may further serve to reduce closing forces of the device. In some instances, the nubs 3823 may be used to secure a suture in a manner similar to that described above in reference to teeth 252. Further, the arm 3802 may be configured with one or more recesses 3825 configured to receive and mate with the nubs 3823 when the hinge 3804 is in the closed position. The one or more recesses 3825 may be positioned between the ridges 3824. In some instances, there is a corresponding recess 3825 for each nub 3823. In some instances, a recess 3825 is configured as a channel and configured to accept more than one nub 3824.

Referring to FIG. 30B, the bulge 3820 may include one or more notches 3821. Although the suture securing device 3800b is illustrated with two notches 3821, other numbers may be used, for example, one, three, four, five, etc. In some embodiments, these notches are intended to direct the suture strands into the clamping areas of the device. One or more recesses 3825 may be included between the ridges 3824 of the arm. The one or more recesses 3825 may be configured in size and shape to mate with and receive the bulge 3820 and include a corresponding shape to confirm with the notches 3821.

Figure 30C:
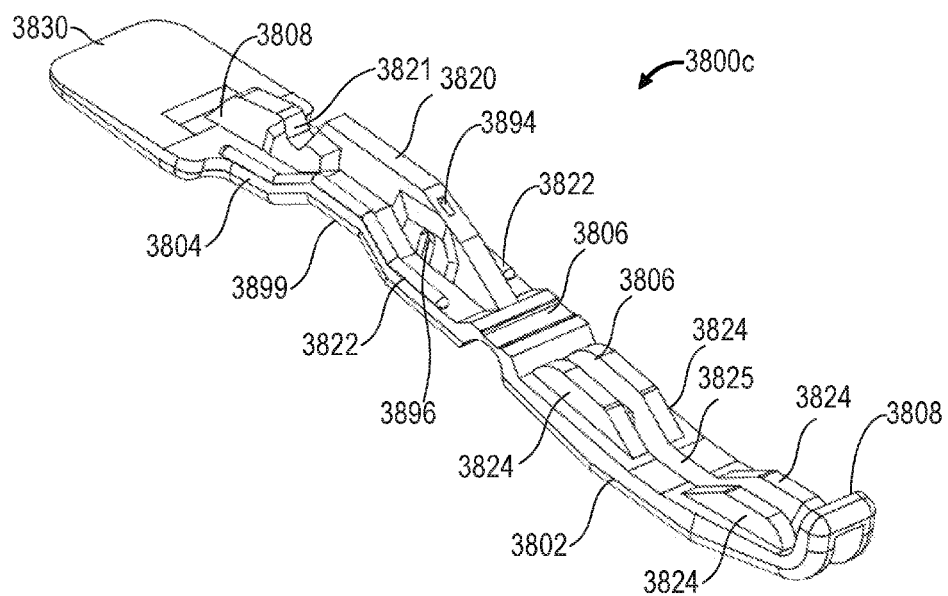
FIGS. 30C and 30D illustrate perspective and side views, respectively, of an additional embodiment of a suture securing device configured for use with a mattress suture that includes a hole which may be used to help orient the device.
Figure 30D:
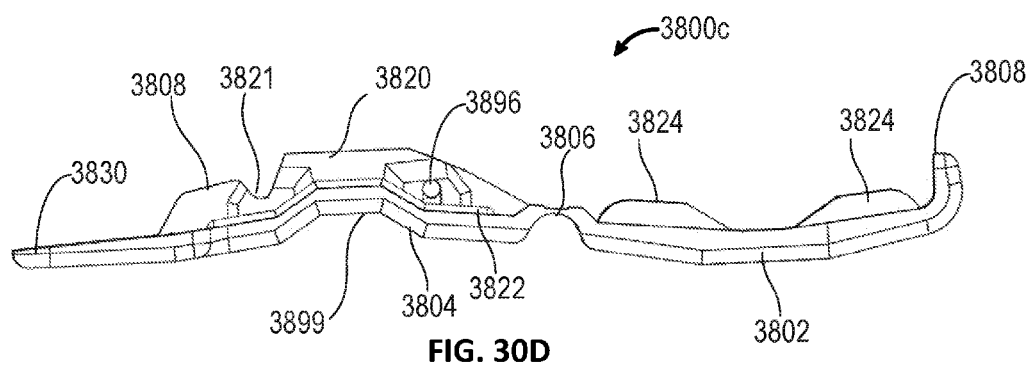

FIGS. 30C and 30D illustrate perspective and side views, respectively, of an additional embodiment of a suture securing device 3800c configured for use with a mattress suture that includes a hole 3896 which may be used to help orient the device. In many ways, suture securing device 3800c is similar to suture securing devices 3800a, 3800b discussed above in reference to FIGS. 30A and 30B. For example, suture securing device 3800c includes an arm 3802 attached to a base 3804 by hinge 3806. The arm 3802 includes ridges 3824 with a lateral recess 3825 positioned therebetween and an engagement mechanism 3808. The base 3804 includes a first surface having a bulge 3820 and two grooves 3822 on either side of the bulge 3820, the grooves 3288 spaced laterally away from the budge 3820. The base 3804 also includes an engagement structure 3816 and a first tab 3830. The hinge 3806 can be rotated such that the arm 3802 is positioned substantially on top of the base 3804. In this position, the bulge 3820 is received in the recess 3825 between the ridges 3824. A suture thread may be retained between the arm 3802 and the base 3806 in this position, and retention of the suture may be increased as the suture thread bends around the various features of the arm 3802 and the base 3804. Each of these features may be substantially similar to the similarly described features of the suture securing devices 3800a, 3800b, 3600. Additionally, suture securing device 3800c also includes the eversion recess 3899. As with the previously described embodiments, the eversion recess 3899 helps create wound eversion.

The suture securing device 3800c includes several additional features, including a hole 3896 and a notch 3821, both formed in the bulge 3820. As best seen in the side view of FIG. 30D, the hole 3896 extends laterally through the bulge 3820 on a first side of the eversion recess. In some embodiments, the axis of the hole 3896 is configured to be parallel to the surface of the patient's skin and or the direction of the wound when the suture securing device 3800c is in place, although this need not be the case in all embodiments. In some embodiments, a user applying the suture securing device 3800c would pass a portion of the suture thread through the hole 3896 during use. For example, the user may do first pass of suture (as in typical mattress suture), then thread the needle and attached suture thread through the hole 3896 before making the second pass. On tightening the suture, the suture securing device 3800c would then self-position because of the thread passing through the hole 3896. The portion of the suture thread passing through the hole 3896 is secured in the closed position by a friction fit between the bulge 3820, recess 3825, and ridges 3825. The opposite end of the suture is secured between the arm 3802 and the base 3804 as with the previously described embodiments.

As shown in FIGS. 30C and 30D, the illustrated embodiment also includes a notch 3821 on the opposite side of the eversion recess 3899. As above, the notch 3821 may be used to receive a portion of the suture. In some embodiments, the position of the hole 3896 and the notch 3821 may be reversed. That is, in some embodiments, the notch 3821 can be positioned on the hinge side of the eversion recess. In some embodiments, the notch 3821 can be omitted. In some embodiments, the notch 3821 may be replaced by an additional hole. In some embodiments, a suture securing device may include more one, two, or more than two holes extending through the bulge 3820.

As seen in FIG. 30C, an additional opening 3894 may be formed in the top surface of the bulge 3820. Similar openings may also be formed in the bottom surface of the base 3804. The openings 3894 may be used during manufacturing to help form the hole 3896, such that the suture securing device 3800c can be molded as a single piece, without requiring later drilling of the hole. The openings 3894 are formed by inserts in the mold (which extend from opposite sides of the mold) to form the hole 3896. In some embodiments, the openings 3894 may be omitted.

Figure 31A:
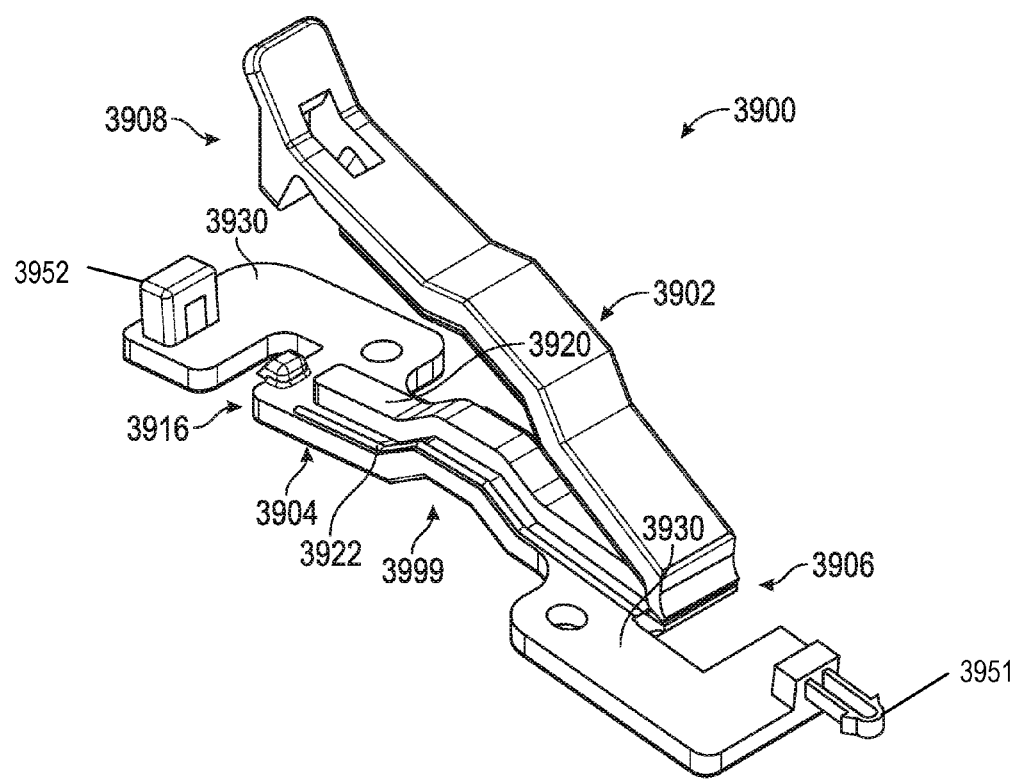
FIGS. 31A through 31B illustrate an additional embodiment of a suture securing device configured for securing a horizontal mattress suture.
Figure 31B:
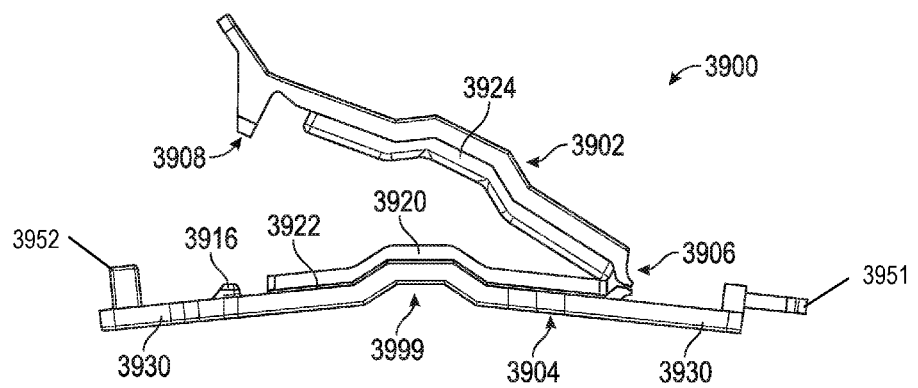

FIGS. 31A through 31B illustrate an additional embodiment of a suture securing device 3900 configured for securing a horizontal mattress suture. The suture securing device 3900 is further configured to interlock with one or more additional suture securing devices 3900. For example, the suture securing device 3900 may include a male adapter 3951 on one end and a female adapter 3952 on the opposite end. Multiple suture securing devices 3900 may then be interlocked together by connecting the male adapter 3951 to the female adapter 3952 of an adjacent device. In the illustrated embodiment, the male and female adapters 3951, 3952 are oriented to connect the suture securing devices end to end. In this configuration, the suture securing devices may be aligned on opposite sides of a wound, parallel to the wound. The suture securing devices may be secured to the skin with tape or sutures (for example, a suture passing through the holes in the tab of the device). In another embodiment, the male and female adapters may be oriented to connect the devices side by side. This may allow devices to be placed across a wound and connected to adjacent devices which are also placed across the wound. In many respects the suture securing device 3900 is similar to the suture securing device 3600 described above. For example, the suture securing device 3900 includes an arm 3902 attached to a base 3904 by hinge 3906. The arm 3802 includes two ridges 3924 and an engagement mechanism 3908. The base 3904 includes a first surface having a first bulge 3920 and two grooves 3922 on either side of the bulge 3920. The base 3904 also includes an engagement structure 3916 and tabs 3930. Each of these features may be substantially similar to the similarly described features of the suture securing device 3600.

FIG. 32 illustrates an embodiment of the suture securing device 3600 of FIG. 28A in use with a horizontal mattress suture 1050. A horizontal mattress stich is performed which includes a first perpendicular loop 1055, extending below the skin and across the wound (illustrated with dashed lines to represent that the suture is below the surface of the skin), a first parallel loop 1051, extending over the base 3604 and parallel to the wound 1013, a second parallel loop (not visible in the figure), extending back across the wound and below the skin, and a second parallel loop 1053, extending across base 3604. Either of the parallel loops may be formed by the two free ends of the thread (not shown) and may or may not be tied in a knot. As shown, each of the parallel loops 1051, 1053 extend over the base 3604 and parallel to the wound 1013.

The hinge 3606 may then be closed by folding the arm 3602 on top of the base 3604. Corresponding engagement structures 3608, 3616 on the arm 3602 and base 3604 may lockingly engage the arm 3602 to the base 3604. The parallel loops 1051, 1053 of the suture 1050 are secured between the arm 3602 and the base 3604, thus locking the suture 1050 in place. Further, the engagement between the bulge 3620 and ridges 3624 may further increase the ability of the suture securing device 3600 to retain and secure the suture 1050.

As further seen in FIG. 32, the eversion recess 3699 is positioned generally above the wound 1013. Accordingly, the eversion recess 3699 creates a space for and facilitates wound eversion. In some embodiments, the wound contacts the surface of the eversion recess 3699, although this may not be the case in all embodiments. The bottom surface of the suture securing device 3600 as well as the eversion recess 3699 may include a treated undersurface having adhesive, anti-bacterial, medicaments, and/or other agents for transfer to the patient's skin underlying the suture securing device to aid in positioning and/or retention of the suture securing device 3600, assist in healing, and/or reduce scarring, among other purposes.

In some embodiments, the previously described suture securing devices, such as suture securing device 3600, may be used to secure vertical mattress sutures. This may be accomplished by positioning the suture securing device such that it runs parallel to the wound. A second suture securing device can also be included on the opposite side of the wound, again running parallel to the wound. Each suture securing device may receive a single loop or vertical mattress suture, or more than one loop from more than one vertical mattress suture. When used with a vertical mattress suture, the eversion recess may be omitted, as the device may not extend across the wound. However, in some embodiments, the devices on each side of the wound may be connected by a bridging member that may include an eversion recess.

FIGS. 33A-35 illustrate various embodiments of suture securing devices configured for use with subcutaneous sutures. In general, one of these devices can be included at each exposed end of subcutaneous suture to secure the suture. As noted throughout this disclosure, the features of these embodiments may be combined and/or modified for use with any of the other embodiments described herein.

Figure 33A:
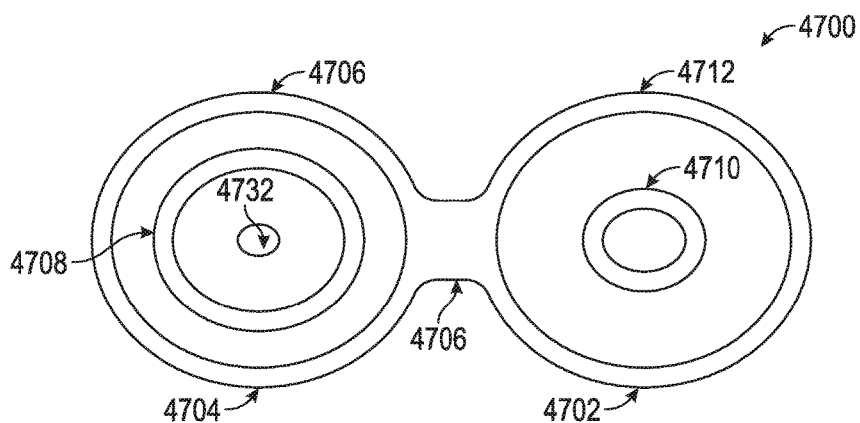
FIG. 33A is a top view of an embodiment of a suture securing device configured for use with a subcutaneous suture.
Figure 33B:
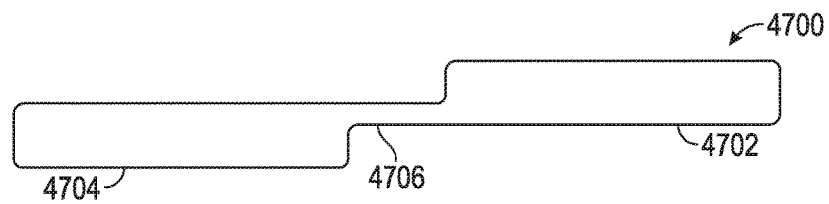
FIG. 33B is a side view of the suture securing device of FIG. 33A.

FIG. 33A is a top view of an embodiment of a suture securing device 4700 configured for use with a subcutaneous suture. FIG. 33B is a side view of the suture securing device 4700 of FIG. 33A. The suture securing device 4700 includes a first piece 4702 connected to a second piece 4704 via a hinge 4706. The first piece 4702 may be considered an arm and the second piece 4704 may be considered a base. The hinge 4706 may be a living or compliant hinge. The hinge 4706 connects to a bottom portion of the first piece 4702 and a top portion of the second piece 4704. In some embodiments, the hinge 4706 may be omitted, such that the first piece 4702 is not permanently connected to the second piece 4704. The first piece 4702 includes a substantially circular protrusion 4710 from a first surface of the first piece 4702. The first piece 702 also includes a substantially circular outer ring 4712 around the perimeter of the first surface of the first piece 4702. The second piece 704 includes a substantially circular outer ring 4706 around the perimeter of the first surface of the second piece 4704. The second piece 4704 also includes a substantially circular protrusion 4708 within the outer ring 4706 and a hole 4732 in the center of the substantially circular protrusion 4708. The hole 4732 allows for an external portion of a subcutaneous suture to protrude through. The hinge 4706 includes an open position and a closed position. FIG. 33A illustrates the hinge 4706 in an open position. When the hinge 4706 is in a closed position, an outer perimeter of the substantially circular protrusion 4710 from the first piece 4702 will engage with an inner portion of the substantially circular protrusion 4708 to lock the suture securing device 4700 and hold the hinge 4706 in a closed position. This closed position will lock a subcuticular suture.

In use, an exposed portion of a subcutaneous suture extends upward from the surface of a patient's skin and through the hole 4732. The suture securing device 4700 is transition to the close position and the exposed portion of the suture thread is captured between the first piece 4702 and the second piece 4704. A bottom surface of the second piece 4704 rests on the surface of the patient's skin, and may include a treated undersurface having adhesive, anti-bacterial, medicaments, and/or other agents for transfer to the patient's skin underlying the suture securing device to aid in positioning and/or retention of the suture securing device 1100, assist in healing, and/or reduce scarring, among other purposes The suture securing device 3700 may be formed partially or entirely from any sturdy and resilient material, such as plastic resin, for example, polypropylene, polyethylene, acrylonitrile butadiene styrene (ABS), high impact polystyrene (HIPS), poly vinyl chloride (PVC), polycarbonate, thermoplastic elastomers, Polybutylene terephthalate, ethylene vinyl acetate, nylon and low-density polyethylene, linear low-density polyethylene, etc. In some embodiments, the first piece 4702, the second piece 4704, and hinge 4706 may be formed as a single unitary part, while in other embodiments, these parts may be formed separately and then joined together.

Figure 34A:
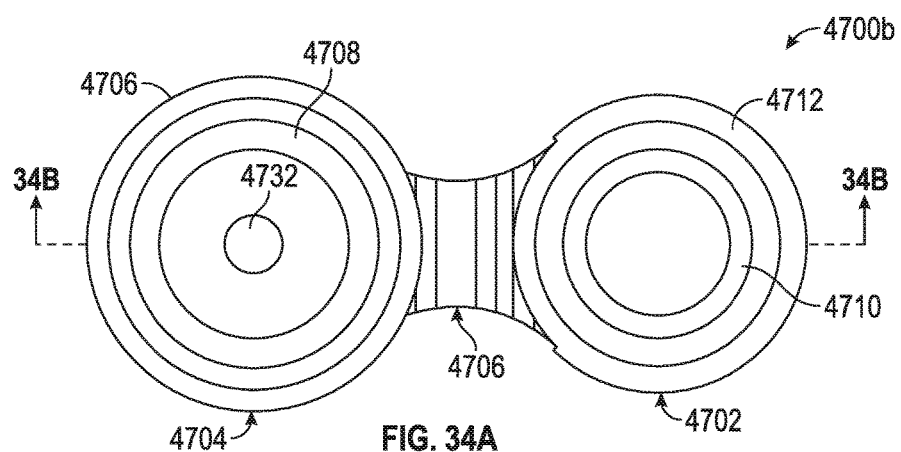
FIG. 34A is a top view of another embodiment of a suture securing device configured for use with a subcutaneous suture.
Figure 34B:
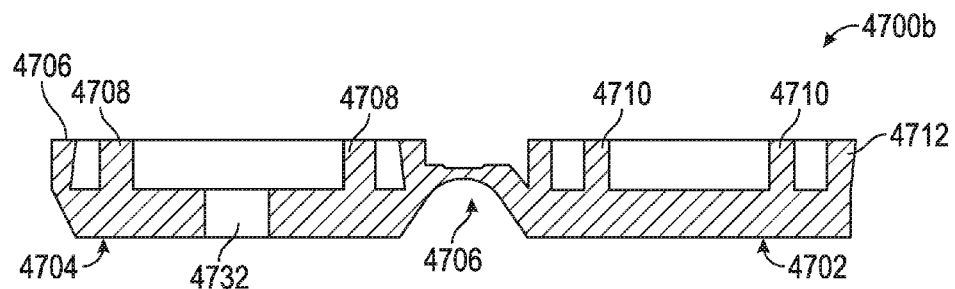
FIG. 34B is a cross-sectional view of the suture securing device of FIG. 34A.

FIG. 34 is a top view of another embodiment of a suture securing device 4700*b* configured for use with a subcutaneous suture. FIG. 34B is a cross-sectional view of the suture securing device 4700 of FIG. 34A. The suture securing device 4700*b* is similar to the suture securing device 4700 and includes a first piece 4702 connected to a second piece 4704 via a hinge 4706. The first piece 4702 may be considered an arm and the second piece 4704 may be considered a base. The hinge 4706 may be a living or compliant hinge. The first piece 4702 includes a substantially circular protrusion 4710 from a first surface of the first piece 4702. The first piece 702 also includes a substantially circular outer ring 4712 around the perimeter of the first surface of the first piece 4702. The second piece 704 includes a substantially circular outer ring 4706 around the perimeter of the first surface of the second piece 4704. The second piece 4704 also includes a substantially circular protrusion 4708 within the outer ring 4706 and a hole 4732 in the center of the substantially circular protrusion 4708. The hole 4732 allows for an external portion of a subcutaneous suture to protrude through. As shown in FIG. 34B, the hinge 4706 connects to a middle portion of the first piece 4702 and a middle portion of the second piece 4704.

Figure 35:
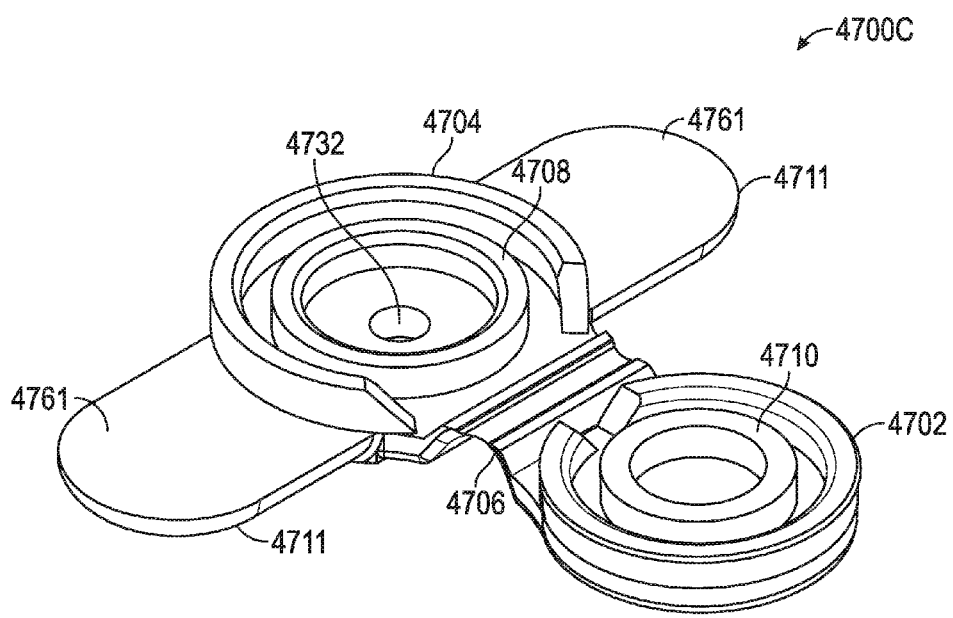
FIG. 35 is a perspective view of a suture securing device configured for use with a subcutaneous suture that includes tabs.

FIG. 35 is a perspective view of a suture securing device 4700*c* configured for use with a subcutaneous suture that includes tabs. The suture securing device 4700*c* is substantially similar to the suture securing device 4700*b* previously described. However, the suture securing device 4700*c* further includes tabs 4761 extending outwardly from the second piece 4704. The tabs 4761 are generally positioned so at to be parallel with and contact the surface of a patient's skin during use of the device. Although two tabs 4761 are shown, other numbers and arrangements of the tabs are possible.

In another aspect, a method for securing a mattress suture is disclosed. The method includes positioning a suture securing device proximal to a wound, the suture securing device comprising a base connected to an arm by a hinge and having an open configuration and a closed configuration; forming a mattress suture, an external portion of the mattress suture passing over a portion of the base; capturing the external portion of the mattress suture between the body and the arm by transitioning the suture securing device from the open configuration to the closed configuration such that the external portion of the mattress suture is secured between the arm and the base.

In some embodiments, positioning the suture securing device proximal to a wound includes positioning the base of the suture securing device such that it extends across the wound, and the mattress suture may be a horizontal mattress suture. The base may include an eversion recess positioned over the wound, and capturing the external portion of the horizontal mattress suture may include capturing a first external portion of the horizontal mattress suture on a first side of the eversion recess and capturing a second external portion of the horizontal mattress suture on a second side of the eversion recess.

In some embodiments, positioning the suture securing device proximal to a wound comprises positioning the base parallel to the wound on a first side of the wound, and the mattress suture may be a vertical mattress suture.

In some embodiments, the mattress suture is secured without requiring the tying of a knot. The method may also include securing the suture securing device to a patient's skin. Securing the suture securing device to a patient's skin may include using a suture, adhesive, or tape. The method may also include maintaining the suture securing device in position for greater than two weeks.

In another aspect, a method for securing a simple interrupted suture is described. The method includes positioning a suture securing device across an incision. The suture securing device may include a body connected to an arm by a hinge and having an open configuration and a closed configuration. The method further includes capturing an external portion of a thread of a simple interrupted suture between the body and the arm by, with the suture securing device in the open configuration, inserting the external portion of the thread into an opening formed in the body, and transitioning the suture securing device from the open configuration to the closed configuration such that the external portion of the thread is secured between the arm and the body.

In some embodiments, the external portion of a thread comprises a first external portion and the method further includes capturing an second external portion of the thread of the simple interrupted suture between the body and the arm by, with the suture securing device in the open configuration, inserting the second external portion of the thread into an opening formed in the body. The method may also include positioning the body of the suture securing device between the first external portion of the thread and the second external portion of the thread. The method may also include positioning the body of the suture securing device generally on a single side of a line extending between the first external portion of the thread and the second external portion of the thread. In some embodiments, the simple interrupted suture is secured without requiring the tying of a knot. The method may also include securing the suture securing device to a patient's skin. Securing the suture securing device to a patient's skin may include using a suture, adhesive, or tape. The method may also include maintaining the suture securing device in position for greater than two weeks.

Each of the suture securing device examples described above provide a mechanism for securing sutures without requiring that the medical practitioner tie suture knots. Further, suture strands and/or knots are elevated away from the skin of the patient and limit pressure on the skin, increase skin perfusion, and aid in wound and/or incision healing. Furthermore, as the sutures and knots are elevated away from the skin, "in grown" sutures can be prevented. Further still, the sutures can be selectively secured and released and the suture securing devices can be selectively interconnected and disconnected. In some examples, additional devices, such as medical devices can be attached to the suture securing devices. In other examples, including an elevated undersurface on the base, blood flow to the wound and/or incision can be maximized to assist in healing.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. Applicant reserves the right to submit claims directed to combinations and sub-combinations of the disclosed inventions that are believed to be novel and non-obvious. Inventions embodied in other combinations and sub-combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

What is claimed is:

1. A system for wound closure, comprising:
a suture interface device, comprising:
a base having a bottom surface including two flat legs, at least a portion of the two flat legs configured to contact a surface of a patient when in use, and an eversion recess formed in the bottom surface, where said eversion recess is an indentation concave feature that creates a space below the bottom surface and is configured to suspends a portion of the base above the surface of the patient, where said eversion recess is configured to align parallel with an incision to accept a convex bulge of two portions of a wound, and a top surface opposite the bottom surface, the top surface having a raised contour that complements the eversion recess of the bottom surface;
an arm connected to the base by a hinge, the hinge having an open configuration and a closed configuration, wherein in the closed configuration the arm is folded on top of the base, the arm having a contacting surface contacting at least a portion of the top surface of the base when the hinge is in the closed configuration; and
an engagement structure securing the arm to the base when the hinge is in the closed configuration; and
a suture passing over the two flat legs of the base on either side of the eversion recess, the suture forming at least two parallel portions that are spaced apart from one another.

2. The system of claim 1, wherein the base comprises an elongate shape, and includes two parallel and flat skin-contacting portions on either side of the eversion recess, the base being configured to extend across the wound and simultaneously contact a surface of a patient via the skin-contacting portions at locations adjacent to the eversion recess on both sides of the incision such that the eversion recess is suspended above the incision, and wherein the suture is a horizontal mattress suture.

3. The system of claim 2, wherein when the hinge is in the closed configuration, a first external portion of the horizontal mattress suture is secured between the base and the arm on a first side of the eversion recess and a second portion of the horizontal mattress suture is secured between the base and the arm on a second side of the eversion recess.

4. The system of claim 1, wherein the suture is a vertical mattress suture.

5. The system of claim 1, wherein the base further includes a bulge extending from the top surface of the base, wherein the arm further includes two ridges extending substantially in parallel from the contacting surface of the arm, and wherein when the hinge is in the closed configuration the bulge is received between the two ridges.

6. The system of claim 5, further comprising:
at least one nub extending from the top surface of the base; and
at least one recess formed in the contacting surface of the arm, the at least one recess configured to receive the at least one nub in the closed configuration.

7. The system of claim 5, wherein one or more notches are formed in the bulge.

8. The system of claim 5, wherein the base further includes two tracks extending from the top surface on opposite sides of the bulge.

9. The system of claim 5, further comprising a hole extending laterally through the bulge.

10. The system of claim 1, further comprising a first tab extending outwardly from a first end of the base and a second tab extending outwardly from a second end of the base, the second end opposite the first end, and wherein each of the first tab and the second tab include a hole extending therethrough.

11. The system of claim 10, wherein one of the first tab or the second tab includes a male adapter extending therefrom, and the other of the first tab or the second tab includes a female adapter extending therefrom.

12. The system of claim 1, wherein the engagement structure comprises a protrusion formed at a free end of the arm and a corresponding opening formed in the base, the opening positioned on the base such that, in the closed configuration, the protrusion extends into the opening.

13. The system of claim 1, wherein the hinge comprises a living hinge.

14. A system for wound closure comprising:
a suture interface device including:
a base having a top surface, and a bottom surface opposite the top surface, the bottom surface including a contact portion in the form of at least two flat legs configured to contact a surface of a patient, and an indentation adjacent to the flat legs, the indentation being configured to i) align parallel with an incision and, ii) be suspended above the incision to accommodate a convex bulge formed of two portions of a wound into the indentation;
a suture passing over the two flat legs of the base on either side of the indentation, the suture forming at least two parallel loops that are spaced apart from one another;
an arm connected to the base by a hinge, the hinge having an open configuration and a closed configuration, wherein in said closed configuration the arm is folded on top of the base, the arm having a contacting surface wherein said contacting surface contacts at least a portion of the top surface of the base when the hinge is in the closed configuration; and
an engagement structure, wherein said engagement structure is configured to secure the arm to the base when the hinge is in the closed configuration, wherein when the hinge is in the closed configuration, external portions of the suture are secured between the top surface of the base and the contacting surface of the arm.

15. The system of claim 14, wherein the base has a longitudinal axis and is configured to a) extend across two opposing sides of the incision so that the longitudinal axis of the base is perpendicular to the incision and b) simultaneously contact a surface of a patient on both of the two sides of the incision with the indentation aligned with the incision.

16. The system of claim 14, wherein the top surface is elongated, and includes a groove, and a bulge, the bulge and the groove being aligned in parallel with the length of the top surface.

17. The system of claim 16, wherein the bulge includes at least one notch configured to accept the suture.

18. The system of claim 16, wherein the bulge includes at least one hole extending through it, and is configured to orient the suture interface device with the incision.

19. The system of claim 14, wherein at least one hole extends from the top surface to the bottom surface.

20. The system of claim 14, wherein the base further comprises:
a suspended portion adjacent to each of the two legs, wherein the angle between the suspended portion and each leg is obtuse, and
a spaced portion between the suspended portions, the system configured to compress the two portions of the convex bulge together.

21. A system for wound closure comprising:
a suture device including:
a base having a bottom surface configured to contact a patient's surface, and a top surface opposite the bottom surface, the bottom surface including two flat legs configured to contact the patient's surface and a suspended portion disposed between the two flat legs and configured to be spaced from the patient's surface; and
an arm coupled to the base by a hinge so that the suture device is transitionable between an open configuration and a closed configuration; and
a suture passing over each of the two flat legs of the base on either side of the suspended portion, the suture forming at least two parallel loops that are spaced apart from one another.

22. The system of claim 21, wherein the arm includes a raised portion that is aligned with the suspended portion of the base and capable of receiving the suspended portion therein, and the suture passes under the arm at fixed distances spaced from the raised portion.

* * * * *